(12) United States Patent
Rohr et al.

(10) Patent No.: US 7,799,904 B2
(45) Date of Patent: Sep. 21, 2010

(54) GILVOCARCIN GENE CLUSTER, RECOMBINANT PRODUCTION AND USE THEREOF

(75) Inventors: Jurgen Rohr, Georgetown, KY (US); Carsten Fischer, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 667 days.

(21) Appl. No.: 10/866,089

(22) Filed: Jun. 14, 2004

(65) Prior Publication Data

US 2005/0048536 A1 Mar. 3, 2005

Related U.S. Application Data

(60) Provisional application No. 60/477,957, filed on Jun. 13, 2003.

(51) Int. Cl.
| | |
|---|---|
| C12N 15/00 | (2006.01) |
| C12N 15/11 | (2006.01) |
| C12N 15/52 | (2006.01) |
| C12N 5/10 | (2006.01) |
| C12N 1/21 | (2006.01) |

(52) U.S. Cl. .......... 536/23.2; 435/320.1; 435/477; 435/252.3; 536/23.1; 536/23.7

(58) Field of Classification Search .......... None
See application file for complete search history.

(56) References Cited

U.S. PATENT DOCUMENTS

| | | | |
|---|---|---|---|
| 4,360,595 A | 11/1982 | Balitz et al. | |
| 4,461,831 A | 7/1984 | Matson et al. | |
| 4,598,145 A | 7/1986 | Matson et al. | |
| 5,672,491 A | 9/1997 | Khosla et al. | |
| 5,843,718 A | 12/1998 | Khosla et al. | |
| 5,843,735 A | 12/1998 | Lee et al. | |
| 6,030,951 A | 2/2000 | Nakashima et al. | |
| 6,066,721 A | 5/2000 | Khosla et al. | |
| 6,210,930 B1 | 4/2001 | Filippini et al. | |
| 6,297,007 B1* | 10/2001 | Waters et al. | .......... 435/6 |
| 6,303,767 B1 | 10/2001 | Betlach et al. | |
| 6,399,382 B1 | 6/2002 | Khosla et al. | |
| 6,399,583 B1 | 6/2002 | Ylihonko et al. | |
| 7,108,998 B2* | 9/2006 | Farnet et al. | .......... 435/41 |
| 2001/0024810 A1 | 9/2001 | Khosla et al. | |
| 2001/0024811 A1 | 9/2001 | Khosla et al. | |
| 2002/0010328 A1 | 1/2002 | Reeves et al. | |
| 2002/0068332 A1 | 6/2002 | Khosla et al. | |
| 2002/0110874 A1 | 8/2002 | Khosla et al. | |
| 2002/0164747 A1 | 11/2002 | Farnet et al. | |
| 2006/0084141 A1* | 4/2006 | Floss et al. | .......... 435/69.1 |

OTHER PUBLICATIONS

Marti et al, Cloning, Nucleotide Sequence, and Heterologous Expression of the Biosynthetic Gene Cluster for R1128, a Non-steroidal Estrogen Receptor Antagonist, JBC, 2000, vol. 275(43), pp. 33443-33448.*
AF293442, Streptomyces sp R1128 biosynthetic gene cluster, U.S. National Library of Medicine, Bethesda, MD, USA, Nov. 6, 2000, accessed by PTO on Mar. 31, 2007.*
CRII vector map, Invitrogen, downloaded from the web Apr. 2, 2007.*
Lesk et al, Prediction of Protein Function from Protein Sequence and Structure, p. 27 and 28, downloaded Sep. 16, 2007.*
Guo et al, Protein tolerance to random amino acid change, PNAS, 2004, vol. 101 (25), pp. 9205-9210.*
Fischer et al, The complete gene cluster of the antitumor agent gilvocarcin V and its implication for the biosynthesis of the gilvocarcins, J Am Chem Soc. Jul. 2, 2003;125(26):7818-9.*
Fischer et al, The Complete Gene Cluster of the Antitumor Agent Gilvocarcin V and Its Implication for the Biosynthesis of the Gilvocarcins, J. Am. Chem. Soc. 2003, 125, 7818-7819.*

* cited by examiner

*Primary Examiner*—Maria Marvich
(74) *Attorney, Agent, or Firm*—McDermott Will & Emery LLP

(57) ABSTRACT

A nucleic acid molecule encoding the gilvocarcin V gene cluster and subunits thereof. Recombinant vectors and host cells comprising a nucleic acid compound encoding the gilvocarcin V gene cluster or subunits thereof. Host cells comprising recombinant vectors encoding the gilvocarcin polyketide synthase and gilvocarcin post-PKS modifying enzymes from *Streptomyces griseoflavus* can be used to produce gilvocarcin and functional gilvocarcin mutants, analogs and derivatives thereof with application as antibiotics, anticancer agents, immunosuppressants, antivirals, and neuroprotective agents.

7 Claims, 27 Drawing Sheets

Figure 3.

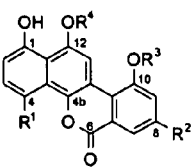

Gilvocarcin-Type Anticancer Drugs

| | R¹ | R² | R³ | R⁴ |
|---|---|---|---|---|
| Gilvocarcin M: | α-D-Fuc | CH₃ | CH₃ | CH₃ |
| Gilvocarcin E: | α-D-Fuc | CH₂CH₃ | CH₃ | CH₃ |
| Gilvocarcin V: | α-D-Fuc | CH=CH₂ | CH₃ | CH₃ |
| Defucosyl-Gilvocarcin V: | H | CH=CH₂ | CH₃ | CH₃ |
| Ravidomycin: | β-D-Rav | CH=CH₂ | CH₃ | CH₃ |
| Deacetyl-Ravidomycin: | DeAc-β-D-Rav | CH=CH₂ | CH₃ | CH₃ |
| Deacetyl-Ravidomycin M: | DeAc-β-D-Rav | CH₃ | CH₃ | CH₃ |
| FE35A: | N,N-MeAc-DeAc-β-D-Rav' | CH=CH₂ | CH₃ | CH₃ |
| FE35B: | N-Ac-β-D-Rav' | CH=CH₂ | CH₃ | CH₃ |
| Chrysomycin A: | β-D-Vir | CH=CH₂ | CH₃ | CH₃ |
| Chrysomycin B: | β-D-Vir | CH₃ | CH₃ | CH₃ |
| BE-12406 A: | H | CH₃ | CH₃ | α-L-Rha |
| BE-12406 B: | H | CH₃ | H | α-L-Rha |

 α-D-Fuc = 6-Deoxy-α-D-galacto-furanose (D-fucose)

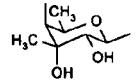 β-D-Vir = 6-Deoxy-3-methyl-β-D-gulo-pyranose (D-virenose)

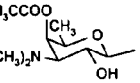 β-D-Rav = 4-Acetyl-3-amino-3,6-dideoxy-3-N,N-dimethylamino-β-D-galactopyranose (D-ravinose)

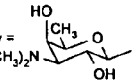 DeAc-β-D-Rav = 3-amino-3,6-dideoxy-3-N,N-dimethylamino-β-D-galactopyranose (deacetyl-D-ravinose)

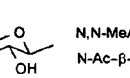 N,N-MeAc-DeAc-β-D-Rav': X = H, Y = Ac, Z = CH₃
N-Ac-β-D-Rav': X = Ac, Y = Ac, Z = H

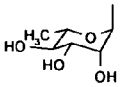 α-L-Rha = 6-Deoxy-α-L-manno-pyranose (L-rhamnose)

Gilvocarcin V  1

Figure 6.
A.
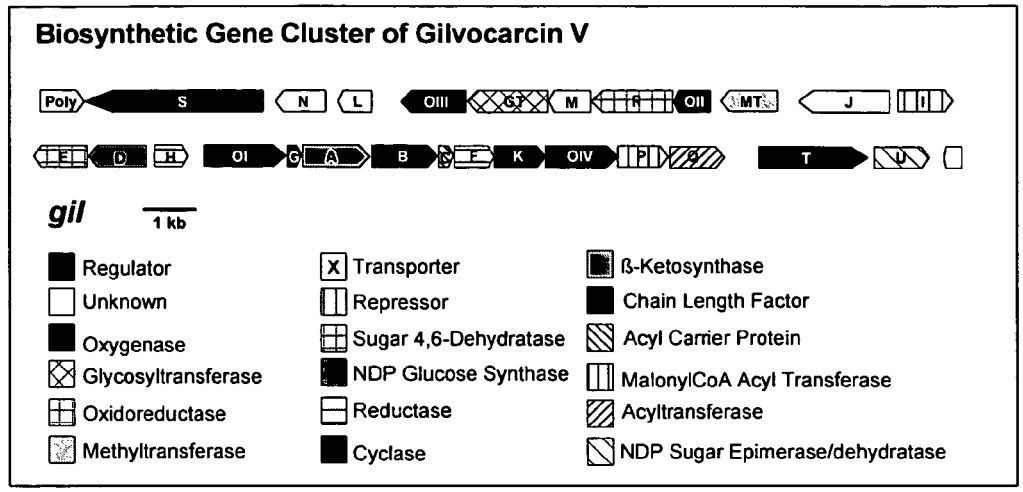
B.
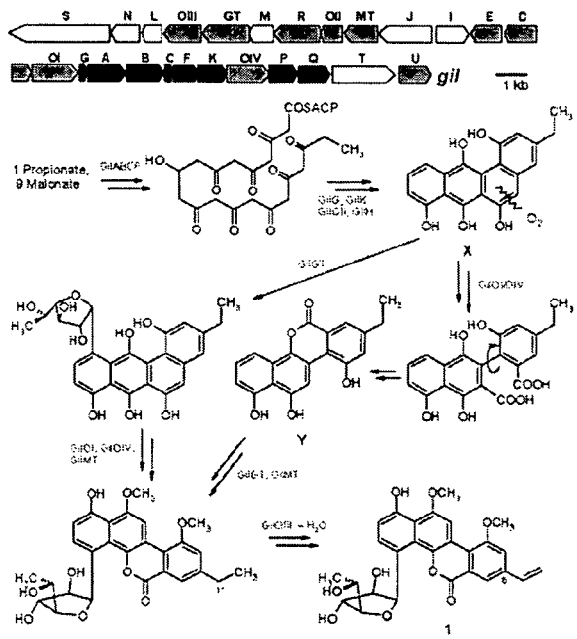

Proposed Biosynthetic Pathway for the GV-sugar moiety

NDP = nucleosyldiphosphate (= activation for glycosyltransfer step)

Figure 9.
(SEQ ID NO:1)

```
        PstI polymerase ->
   1    CTGCAGATCCCCAAGGTCATCCGCCGCGCCGCCGTCGCCGACCCCGGCTGGCGCCTCGTCGTCGC

66    CGACGCCGACCAGATGGAACCGAGGGTGCTGGCGGCCATCTCCCGCGACCCCGGCCTGATGGAGG

131    TGGCCGGCCGGGAGGGCGACCTCTACCAGTCGGTGTCCGACCGCGCCTTCTCCGGCGACCGCGCC

196    CAGGCCAAGCTCGCCGTCCTCGGCGCCGTCTACGGCCAGACCTCCGGCGACGGCCTGAAGAACCT
                                                    SalI
 261    CGCCGCGCTCAGGCGCCGCTTCCCCAAGGCGGTGGCCTACGTCGACGAGGCCGCCCGCGCCGGCG

326    AGGAGGGCCGTCTCGTACGGACCTGGCTGGGCCGCACCTGCCCGCCCGCCGTCCGCCCGACGGAC

391    GACGCGGCGGAGGAGGCCGGCATCCCGCCCGCCCAGGAGGAGCCGGGCCCAGCGGCCCGACCGTG
                                      SmaI                             SmaI
 456    GGCCCCGGAGGCCGAGGCCCGCCCGTGGGTCCCGGGCTACGCCTCGACCGACGCCCGCGCCCGGG

521    GCCGCTTCGCCCGCAACTTCGTGGTCCAGGGCAGCGCCGCCGACTGGGCCCTGCTGCTGCTCGCG

586    GCGCTGCGGAGGACGCTGAGCGGCATGGCGGCCGAACTGGTCTTCTTCCAGCACGACGAGGTGAT

651    CGTGCACTGCCCCGAGGAGGAGGCGGCGACGGTGGCGGAGGCGATCCGGCAGTCCGCCGACCTCG

716    CCGGCCGGCTGACGTTCGGACCGACCCCCGTGCGCTTCCCGTTCACGACGGCGGTCGTGGAGTGC
                        *****
 781    TACGCCGACGCCAAGTGATCAGCTCGCCGGCCGGGCACCGGCCACGAGTCCGCGCAACTCCTCCA

846    CCACGGCCCGCTCGTCCGTGCCGTCCAGCGCGGCGAGCGCCGACCGCCACTGCTCGCGCGCCTCG

911    CCCACCCGCCCCCGCTCGCGCAGCAGCAGACCGTACTGGTGGCGGGCCAGACCACCGGTGTAGCG

976    GTCGGCTCGGGCGTCCGCGCGGCGCAGCAGTTCGGCGCACTCGGCGTCGGCCCGGCCGGCGTGCC

1041    CCAGCAGCCGCAGGGCGCGCACCAGGCCGAGCCGGGTCTGGGACTCTCCGTGCCAGTCGCCGTGC

1106    CCGGCGAGGATGCGCAGGCTCTCCTCGAAGTGCGGCAGGGCGGCGGCCGGTTCACCCAGCCGGAG

1171    GTGGGCGTAGCCGATGTTGCAGTGGGCGGAGTGCCGCACGATCACCGCTCCGATGCGGTCCCCGA

1236    TCACGAGCGAGCGCCGGTGCTGGTCGATCGCCGCGCGCGGATCGGTGTGCTCGTACAGGTTGCCG

1301    AGGTGGCTGAGGGTGACGGCCTCGCCGTAGGGGTCGGCCAACTGCCGCGAGTGGGTGAGGCTCTG

1366    CCGCAGTGCCCGCTCCGACTCCGCGTACCGGCCGAGCCCTTCGAGCAGCAGCCCCGGTGGTTGA
                    BamHI
1431    GGGCGCGCCGGATCCAGGAGACGGCTCCGAGCCGCCGCCAGATCTCCAGCGCGCGGTCGGTGAGG

1496    GCGAGGGCCTCGCCGGTGCGACCGGTCAGGAAGTGCAGCCCCGCCAGATCGCCCAGCGCGCACGC

1561    CTCGGCGGCCTCGTCCCCGAGCCGCCGCGCCACCCGCAGGGCCGCCCGCCCGAGCACCTCCAGCT

1626    CGGGGACCCGGCCGCCGCGCAGGAGGTAGGGGTGGAGCAGGCGGAGGAGTACGGCGATGTGGACG

1691    TCGTGACGGCCCCGGTCACCGCCCCCGCCGGTGCCCTCACCGGCGTACCGCCCGACGAGGGTGAC

1756    GATGTTCTCCAGCTCCCGGTCGCCCCAGGCGAAGGCCGCCCCCGCGTCGTCGAACGGGGGTACGG
```

Figure 9. cont.

```
                     SmaI
1821  ACGCGACGTGAGCGGTGTGCCCGGGCGGCTGGGACGGGGTCGGGCGGCGGCGGTCGTCCTGGTCG

1886  GGGCCGGGTTCGACGATCGCGGTGAGGGCGCGTTCGGCGACGGCGGCGTACCAGCGCAGGGCGGT

1951  CTCGGCGGGGTGCTCGCGCGTGCCGGTCCGAGGGCCGGCGTCCTCGCGGGGTGCGGCGTCCTCGC

2016  GGGGTGCGGCATCCTCGCGGAGTACGGCCTCCTCGCGGGGTGCGGCGCCCTCGCGGGGTGCGGCG

2081  CCCTCGCGGAGTACGGCGCCCTCGCGGAGTACGGCGCCCTCGCGGAGTACGGCGCCCTCGCGGAG

2146  TACGGCATCCTCGCGGAGTACGGCATCCTCGCGGAGTACGGCGTCCTCGCGGAGTGCGGCGTCCT

2211  CGCGGGGCGCGGTCTGCGGACCCGCCGCCGCTCGGGCTCGTTCGCGGGCGAAGTCACGGACCAGG
                                                SalI
2276  TCGTGGGGGACGTAGCGGCCGTACGCGGTCTCCTCCACGAGGGCCACGTCGACGAGCCGGTCCAG

2341  CGCGGCCTCCGCCCGGCGTTCGCCGGTGCCGGTGAGCCGGGCGAGCAGCGGCGCGCCGTAGGCGG

2406  GCAGGTCGAGCGCGCCGATGCGGCACAGGGCGAGGGCGGCGTCGCGGTCCGTCTCACGGTCGGAG

2471  ACGGTGAGCGCGTCGTGCGCGACGGCCAGCGAGCGGCGCACGCTGAGGTCGTCGTACTCCAGGTG

2536  CGGCAACCGGCTGTCGGTGGCGGAGAGCTGACCGGCGAGGTCGTCGGGCGTGAGGGCCCGGCGCG

2601  CGGCGAGCCGGGCCGCGACCACCCGCAGGGCCAGCGGAAGCCGGCCGGTGAGCGCGACGAGCGGG

2666  TGCCCGGCGCCGAGACCGTCCCGGCCGGAGACCGCCCGCAGCAGGGCGGCACTGTCCTCGTCGGA

2731  CAGCGGGCCGAGCGGGACACGGACGGCACCGTCGAGCGTGGTGAGCGGCGAACGGCTGGTGACGA
                     NotI
2796  TCACCGCACAGCCGGGTCCGCCCGGCAGCAGCGGCCGCACCTGCGCGGCGTCCGCGGCGTCGTCC
                                                              NotI
2861  AGCACCAGGAGGGTGCGGGTGGGCGCGAGCAGCGAGCGCAGCAGGGCGGCGGCCGCGTCCGGCCG

2926  TTCGGGGACGGCGCAGGGCTCGGTGCCCAGGTCGCGCAGGAGAGCGCTGAGGGCCTGGGCGGGGG
                                                       SalI
2991  TGAGGGGGGTCATGCCGGGGGTCGTGCCGTGCAGGTTGACGTAGAGCTGACCGTCGACGAAACGT
                                                              KpnI
3056  TCCGCCAGTGTGTGTGCGACCTGGACGGCGAGCGCGCTCTTCCCCACACCAGCGGTACCGCTGAC

3121  GACGACGGCAGGGGCCCGGCGGCGGGCCGGGGGCACGGGTGAGCACACGGATCAGCTCGTCCC

3186  GCACCGCGTCCCGCCCGGTGAAGTGAGCAGGCGCGGGCGGCAGTTGCGCCGGCCTGGGCGGCACA

3251  CCGCCCCCTCCTGCGGCCTCCGCGCACCGACCGTGCTCCTGCCGCTCCCCCTGCCCCCGCAGCAC

3316  CTCCACGTGGGCCTCGCGCACCCCGGCCCCGGTTCGACGCCGAGTTCGTCCGCCAGGCGGGCCC

3381  GCAGATCCCGGTGGACCACCAGCGCCTCCGCCTGACGGCCGGTGCGGTGCAGCGCGAGCATCAGC

3446  TGACGGTGGTACGACTCCCGCAGCGGATGTTCGGCGGCCAGTGCCGCCAGTTCGGGCACGAGATC

3511  GGCCAGGCGCTCGCCGCCCAGGGCCAGTTCGGCGTCGTACCGCCACTCCAGGAGCAGCAGCCGCG

3576  CCTCGCGCAGCCGCCGCACCAGGGCGTAGCCGCCCACTTCCGGGGGCATCCCGGCCAGCGGGTTC
```

Figure 9. cont.

```
                                                                     SmaI
3641    CCCCGCCACAGCGCGAGCGCGGCGGCGCACTCGCGCGCCACCCGCTCCCAGTCCCGGGCGGTGTG

3706    CGCGGCGCGGGCGGCTGCGGTGTGCGCGTCGAAGACCTGGACGTCCACCTCGCCCTCTCCCACCC
            EcoRV              SmaI
3771    GCAGCAGATATCCGGTGGGCACGGTGAGCAGCCGGCCCGGGTCGTCGAGCAGCCGCCGCAACCGG

3836    GCGACGTGATTGTGCAGCGAGGGCAGCGCGGAGACGGGCGGCGCACCGCCCCACAGGGCGTCCTT

3901    CAGCGCCTCGACGGACACGACCCGCCCGGCGTCGAGCAGCAACGCGACGAACAGCGCACGGAGTT
                      SmaI
3966    TGGGACTTCCGGTCACCTGGACGGACCCGGGGCGTCGGGCCCCTCGCCGTCGTACAGCACCGGT
                                                <- gilS
4031    GTTCCCAGCAGTCCGAACCGCAGTCCGCGCCGTGTCACGCCGCACCACTGCCTTCCGGGTGACCG 4096    AACGGACAACCAATGGCCTTATGTTAGCGATCCGTTGGCAAAGTCTGATGTGATCACTACATCGG
        BamHI   SmaI
4161    ATCCGGCCCGGGGTGCGCGCGTAGAACGCGCAGCTCGGGGGAGTGTCGCCGCCGCGGCCCGGTC 4226    CGCACACGAGGGTTCCCGGTCGGACAGAGGTGAACGGCCGGGCCCTCGTTCTCTTCTGCCGCCGC
                               ***
4291    GTTCGCCCTTCGGGTCAGATGACGGGCGGCCGTCCGAGCCGGGTGAGCCGCCACACCGTCCGCCA

4356    GCGCATGGCCCGCCGCTCCCCGGCCGGCTCCCGCAGCCCCTCCGCGAAACCGCCGAACCAGGCGC

4421    GCAGCCCCTGGACCGACCGAGTCCGCAGCAGGGTGAGCAGGACCCACACCCCGAGGTGCACGGGG

4486    ATCAGCGCGAGCGGCAGCCGCCGCCGGGCCAGCCAGACCCGGTTGCGGGCGTTCACCCGGAAGTA

4551    GATCGCGTGCCGGGCCGGCGAGGTCTTGGGGTGCTGGAGCAGCAGGTCGGGCGCGTAGAGGATGC

4616    GCCACCCCGCGTCGGCGGCACGCCAGGCGAGGTCGGTCTCCTCGTGCGCGAAGAAGAACGCGCCG

4681    GGCCAGTCGCCGATCTCGTCGAGCATCGACATCCGCAGCGCGTGCCCGCCCCCGAGGAACCCGGT

4746    GACGTACCCGCCCTTCATCGGGTCCGCCTTTCCGAGCCGGGGCACGTGCCGCTGCTGCGTCTCCC

4811    CCAGCTCGTCGGCGATCCGGAAGCCGACGACGCCGAGCCGGTCGTCCGCCGCGTACAACTCCCCC

4876    ACCCGGCGCAGCACATCGGCGTCCACCAGCAGACCGTCGTCGTCCAGTTCGACGACGACGTCCAC
                                                     SmaI
4941    GTCCCCGAACTCCCGCAGCCGCTCGATCCCCACGTTCCGCCCGCCCGGGCAGCCGAGGTTCTCCG

5006    CCAGCTCGACGGTGGTGACCTCACCGGGCAGGGACAGCCGCCGGGCGAACTCGGGCAGCGGACAG

5071    CCGTTCCCCACGATCACGATCCGCGCGGGCGCCACGTCCTGCTTCGCCACGGACTCCAGCAGCGC
                                                                <- gilN
5136    GTCCACCTCGGCCGGCCGGTTCCCCATGGTCACGACGGCGACGGCGATCCTCGGCGTCCCCATGC
                                                                    SphI
5201    CCTCACCCCACTCCACCCGGCTGCTCCGCTGACGGGCGATGCTAACCGTTCACGGTGAGGACGCA
        SphI
5266    TGCATGACACCCACCACCGCGGCGTACTCCGCCCCCGCCCCACACGAACAGGACACACGTGTCCC
              SmaI
5331    TGGTGCTCGCCCGGGGACGACCGGAGGGGCCCCGTGCGGCAGCCGCGGCCGGCTGCCGCACGGGG
                      ***
5396    GCCGGGAGCGGTCGCCGGTCAGCGGGTGGTGACGAAGGGGCTCTGGTGCGTGTGCGGGGTGGTGA
```

Figure 9. cont.

```
5461    GTTCGTCGAGCATGGCGATCGCGAGGTCGCGGCGCGTCGTCCATGCCCGTCCGCCGGGAAGGTCG
                         SmaI
5526    GCGGTGACCCGCAGCTCGTCGCCCGGGCGTGCCTCGTCGCTGAGCCGGGCGGGACGCATGACCGT

5591    CCACTCCAGGTCGCGGGCTCCGGTGAGGATGTCCTCCATGCGGCGCATGTCCGCGTACAGGGTCC
          SmaI                                                      SmaI
5656    GCCCGGGGCCGTTGCGCAGGATGCCGTAGACCGGCCGCTGCCATCGCACCCCGCCCCGGGTGACC

5721    GGATGTGTCAGGCCGGCGCTCACGACGACCAGGCGCCTGACGTCCGCCGCGCGCATCCCGTCCAC
                SmaI
5786    GACGGCCCGGGCGGACGCCGAGTAGACCGTGACCGGCCTCCAGGAGTACGGCGCTCCCAGGCAGG

5851    ACAGGACGGCGTCGGCGCCCTTGAACACGGACGTCATGTCCGCGACGTCCGTGACGTCCGCCGTT

5916    TCCACGGTCAGCCTCTCCCCCGGAGTGACCGAACCCGGACGCCGGACGACGGCGACGACGTCATG

5981    GCCGGCCGCACAGGCCAGGGCCGTCACCTGCCGTCCGGTCGGGCCGCTTGCACCGAGCACTGCTA
        <- gilL                                      SphI
6046    CTTTCATGCCGTCTCCAGACGATGCGCGGACGATGTACGGACGCATGCGGACGATGTGCGTCGTG 6111    CGGTGGTCGAGAAGGTGCCCCGGTCGGCGCCCTTCCCGAACGACGCCCCATCGTAGGAGTCGCGG
             SmaI                                              SmaI
6176    CGCCCGGCCCCGGGTCCGAGGCCGTGGGCACCGTCGAGAACAGGCCGCCCGGGCGGGGCCGTTGC
                                                                       SmaI
6241    GGCGGGCGCCACGGAGCGGGAGCGCGGGCGGCACGCCGCCGGCTCCCGCCCGCGTTCCCGGGCGG

6306    CACGCCGCCACCCCTCAGGAGGAGCCCTGCCGCGCCGTCCGCGCGGACGTTGCGGGGGCCGTCCT

6371    GGCCAGTTCGAGGGCGCCCATCGGACAGGACCGGATCAACCGCTCCACCTGCCGGACATCGCCGA

6436    ACCCGTCGGCCGCCCCGCTGAGACGGTGATCTGCTGCTCGGGGCTGCGGAAGACGGCCCTGGAC

6501    AACCCCTCGCACTGTTCGTGCAACTCGCACCGCCGGCCGTCGATCCTGACCACCGTCACGTCCTC
                ***
6566    GACGGGCTCAGGCAGTTCGTCCATGGAACGTCACATCCATCCTCTCGATCCCGCGGATGGTGTTG
                                                      SalI
6631    TGCAGCCTCCAGGTCGGCTCCCCCACCTCGATCCTGTCGACGTGACGGACCAGCGCCTCCAGGAG

6696    GCTCTGCCCCTCCAGGCGGGACAGGGCCTGACCGACGCAGGCGTGGATACCGTGCCCGAAACCGA

6761    CGTGCTGGGCCGCGCCCTGCCGGGCGACGTCGAAGGACTCCGGGTCCTTCCAGAACCGCTCGTCA

6826    CGGTTGGCCGAACCGAAGAGGAGGAGGACGCGCGATCCGCGGGGCAGCGCGGCTCCGCCCAGCTC

6891    CGTGTCCTCGGCGACGTAGCGGGTGAACCCGCGCAGCGGCGATTCCAGCCGGATGATCTCGTTGA

6956    AGGCCGACGAGACCAGGGAGGGGTCCTCCCGCAGACGGCGCCACTGGTCCTGGTGCGTGCCGAGC
              SphI
7021    AGCCACAGCATGCTGGAGAGCGCGCTGACGGACGTGTCCATGGACGGGGCGAGGAAGTCACCGAG

7086    CAGTCCGGGCAGCAGCTTGTCCTCGATCTTGCCCTCGCGGGCCTCCGAGACGAGTTCGGCACCCC

7151    AGCTCCCCGGACGCAGATTGCCGGGCTGTGACATCCGGTGGAGGAACTCGCCCATCTCGCCGAGC

7216    AGCGGCAGGCCGGCCCGCGTCCGGTCGTTCAGGGGACCGAAGGCGTTGAATCCGGCGCTGGCCCA
```

Figure 9. cont.

```
7281  CTCCAGGAGCCTTTCCTTCCCCTCGCCCTCCGGCCATCCCAGCAGATCGGGCACCACGGCCAGCG

7346  GGAAGGCGACCGCGAAGTCCTGGACGGCGTCGAACGACTTCCGGGCGACGAGGTCCCGGACAAGA

7411  CGGTCCGCCCAGGACGTGACGTACCCGTTGATGTCGGCCATCGCGCGGGGCTTCAGGTGGCGGGC

7476  CACGAGCCCCCGCACGTAGGCGTGGTACGGCGGGTCGCTGGTGAAGCTACTGCCCTTCTGCGCCT

7541  TGTTCAGGGTGTCGGTCAGACCGACGCCCTCGCCGGACACGAACGTGCCGTGGCGGTGCAGGGCC

7606  GCGTACACCTCGTCGTAGCGGGCGGCGCAGTGCACCTGGTGCGCCGTCAGGTACACCACCGGTGC

7671  CGCGTCGCGCAGCGCACCGTACAGGGGGTACGGGTCGGTTATCGACGCGTCCGTGTACGGATCGA
                                <- gilOIII     ***
7736  GATCGAGGTGGGGGATCGTCGATGTGGAGATCACCGCTTCATCCTTTCCGCGCGAGGAGGTCTTC 7801  GATCAGCGGCACCATGCCCACGGCCGTCGGCGCGGTCGCGCCCTGCTCCGCCAGTCTCCGGGCCC
                BamHI
7866  TGGAGGAGTAGGACGGATCCCCGAGCATCTCCTTGACCACCTGCGTGATCGCCTCCGGGGTGCCC

7931  TCCTCGCGGTAGAGCGTCCGCGCGCACCCGTAGTCCGTGAGGTGCTTCAGCCTCGGGACGAAGGC

7996  CTCGAAGGGGTTGAGGATCAGCTGCGGAGTCGCCGTGTTGATGGCGTTGATGGCCGTCAGTCCGC
                                                                  BamHI
8061  CCGCCGGATGGATGATCACCTCACAGGTCGGGAGGATGGCCTCCAGCGGGATCCAGCCGGCGCGC
        SmaI         PstI
8126  ACCCGGGGGTACTTCTCCTGCAGCCGCTGCCCCTCCGCCTCGCCGATGGCCACGACGACCTCGAC
      XhoI SalI
8191  CTCGAGCTCCAGCAGCCCTTCGACGATGGCCGAGATGCGGTCCATCGCGCCGGGGAAGGCGTACC
          HindIII
8256  GGAAGCTTCCCATCGTCAGGCACACGCGCCCGGCGTCCGGAGCCGTCAGCATCCACGGCTCGATC

8321  GCCCGCTGCATGTTGTGCGGGGTCCAGCGCATGAAGGTGCCGGTCGCCCCGACCAGGCCGGGCGG

8386  GCAGATGTCGATCTTCAGTGAGGGTCGGGCAGTGCGTCCGAGCCGATCCTGGCCAGCTCGTCCG
              XhoI
8451  CCATCTCCTCGAGGAGGTACTCCTCGTAGCCGCCGACGTCGAACAGGTCCCAGGACTGCCGGACG

8516  AAGGGGATGCCGAGGAACCGGGCGGCGATCTCGGCACCGTGTCCCTGGCTCCCCGCGATCAGGAC

8581  GTCGGCGCCCCACGTCCGGGCGACGTCCACCAGGTCGTCGAAGACGTGGCTTCCCTGACGCCCGA

8646  ACCAGTGGCCCAGGTAGGGCATCTCCTGTTCGGGCCGGTGGGGGTACTCGATCGCCGGCTTGCCG
              NotI                            SmaI
8711  CCGGCGGCCGCCTTGATGCTCTCGGTCGTGTGCCCCCGGGCCACCGGGAGGGACGGCAGACCGAT

8776  GCCGGTGACGGCGCCGGACATCTCCTCGAAGGACGCCACCAGGACGTCGTGCCCGGACAACCGGA

8841  GTGCCGAGGCGAGGGGTCCGATGGCGAACGCGCTGGCCGGGCTCGTGCCCGCGGCGTAGAAGAGG

8906  GCCTTCACGCGGCGCCCTCCCGTGACCGGTCCCTTGTCGCGTTCCGCGAAGTAGGCCTCCTTCAG

8971  GCCCACGGTCTCGAAGTCGATGACGGCGAGGCCCGAGGTCAGCAGACGACTCGAACGCAGCTCCC

9036  GGACCAGGTCCAGGTAGTTGTCCATCTCGTCGAAGCCCAGGATGAAGAAACTCTCCGCCTCACGG
```

Figure 9. cont.

```
9101   CCGTACTTGATGGCGCGCACCGGTGTTATCTCCCCGCCCCGCTTCACGAAGGCGCCGATGCTGGG

9166   GAAGACGTGCTCGTGTTCGACCGTGATGCGCTCGTCGAGGGACAACTCGTACCACGGGGTGAGGT
                                          <- gilGT
                                           ***
9231   AGTTGACGACAAGGACGGCGGCGAACTTCATGCCGGGCTCTCCGATCGGGTTGCCTGCGGACGCA
                                 SphI
9296   GTACGGCATGCATGTGCCAGATGTGGGAGACGACGTTCCCGGCTTCGTCCACCATCTGGGCGGCG
           ───────                                                 SalI
9361   AGGTTGTCGGTGGGGGCGTTCACCTCGAAGGTCCGCGGGTCGACCATCTGCGCGACGGCCTCCGG
                                            ───────
           KpnI
9426   CGGCAGCGAGCTGTGGTACCGCGTCGCCTCGATCACCTTGATGTCCCAGTCGGCGCCGAACGCCT
                     ───────
                                      SmaI
9491   CCCGCAACTCCGGTTCGGAGATGCGGCGCGGACCCGGGTAGTCGGGGGTCAGCTCCTTCGAGAAG
                                     ───────
                                                                SacI
9556   GTGAACAGGTGCAGCTCGGCCCCCTCCTTGCACAGGGTCCGCAGGAGCTCCGTGTAGCGCGGCAC
                                                  ───────
9621   CTCCTCCTGCGGCAGCGTGTGGAAGAAGGCGCTGTCCAGGACGGCGTCGTACCGGACACCGGACT
                                                           SalI            SmaI
9686   CCGCGAGGCGGAAGGCGTCGGTCACCTGGAAGTCGACGCTCACGCCGTGGTCCCGGGCCTTGTCG
                                            ───────              ───────
                                             SalI                 SmaI
9751   CGCCCGCACTGGACGGCGACCTCCGAGATGTCGACCGCGGAGACCCGCAGCCCCCGGGAAGCCAG
                                      ───────            ───────
9816   GTAGAGCGCGTTGTCTCCGAGCCCGCAGCCCAGATCGAGCACGTGCCCGCGGAAGCCGCCGCGAT 9881   CACAGATCGCGCGTACGGCCGGCTGCGGGCCGCCGATGTTCCACGGCATGAGGGGGCCTGACTTC
                                                             <- gilM
9946   TCCCCGTCCTGGTAGAGCTTCTCGAAGGGGATCTTCTCCGTGCTGCCCGTTGGCATCGAGCGCCA
                                                              ***
10011  CTCCTCTCAGAGTCCTATGGACATGCTGTGATGGAAGGTGTTCAAGGGGTCCCACGCGCGCTTCG 10076  CCGACCGCAGACGGGCGTAGTTGTCCTTGTAGTACAGGTGGTGCCAGGGCTCCCCGGAGCGGTTG
                                                                   NotI
10141  CGGGCCGGGTCCAGGAGATCCGCGTCGGGGTAGTTGATGTAGCAGCCGTCCGTGCGGCCGCCGGT
                                                                 ───────
10206  GACGGGCACCCCTCCCGTGCCGGCGAAGAACTCCTCGTAGAGCCCGCGCAGCCAGCCGAGGTGCA

10271  GCTCGTCCAGCTCCGCGTCCTGCCAGGCCGAGAACCAGGACGACTTCACGACGGAGTCCCGCTGG

10336  GGGACGGCGGCGTCCGACGGCCCCCGCCGGTTGATCTCTCCCCCGTAGCTGTTGAACATGACGTA

10401  CGAGGCCTGGCCGGGGTGGTCGGCGTGCAGGTGCCGGTGGAGCACCGAGAGCTGCTCGTCGGTGG

10466  GTGCCGCGCGGTGGTAGGCGGACTTGGAGGCGGAGCGGGCGCCCATGACGTCACCGCAGTCGGCC

10531  TGACTCATGTAGCGGGTTCCGGTGAGCCAGCTCATGACACCCCTCGGGGGATGCCCACCACGCC

10596  GGTGCCCTCGGTCAGGGACGCGACGAACCGCGCGAGGATCTCGCCCTCGGGGTCCACGTCGGCGT
                                       PstI
10661  CCTGCTGGACCATCAGCTGCAGGACGCCCGAGCTGACGTGGTTCACGAAGAAGGTGGCGAACAGC
                         ───────
10726  GAGGACTCCGGCGACCCCGGCTCGGAGTGGCGTTCATGCCACTCGAAGAAACGTCTCATCACAGT

10791  GACGAAGGACGTCTCGTCGATCATGGCCCAGGGGAACACCACCTTCTGGACGTGCAGTCGGCCGG

10856  CGGCGCGGGGCAGGCCGACGGGTTCCGTGGCGAGGTGCTCCGGGCTGCGGAACTCGTACGCCGTG
```

Figure 9. cont.

```
                                                            SacI
10921   ACCACGCCGAAGTTGCCGCCGCCACCGCCGGTGTGTGCCCAGAAGAGCTCACCGAGATCGCCGGT
                                                        SalI
10986   GTCGTCGGCCCTCGCCGTCACGAGGCGAACGGTGCGGGACTCGTCGACGACGGCGACCTCCACCG
                        SalI
11051   CGTGCAGGTGGTCGACCACCAGCCCCAGCTGGCGCGACAGCGGCCCGTAACCACCTCCGGCGACC

11116   AGGCCGCCCATGCCGACCGCGGAGCAGGCCCCGAGCGGCAGGGCCGCGTTCCACCGGCGGAACAG
                    SalI
11181   GGCCTTCTGGACCTGGTCGACCGTCGCACCGGAACCGACGCGCACCCCGGCGCCGTCCGCGGCCG

11246   GGCCGATGGCATGGAGGTTGTGCAGGTCCAGGACGAGGTCCCGGCGCGGCGTGCCGACGAAGTCC
                                                                    PstI
11311   TGGCCGCAGTGACCGCCGGACCGGCAGGCGACCCCCCGCCCTTCCGTGACGGCCTTCTGCAGGGA

11376   GGCGACGACGTCGTCCGGCGTGGCGGGGAGGAAGAACTCCTCGGGCTCGACGACGAACCGGTGGT

11441   TGTCCGAGTGCGACAGTTCGATGTACCGCGGGTCCTCGCGGCCCACCGTGAACGGCGGTACGGAA
        <- gilR
            ***
11506   GCGGTCACGACGCGTACCCCTCGACCGACTGGGTGAACACGGTCTCGTAGGTGTTGGACTCCCGC

11571   GAGGTCAGCAGCGCCTTGCCGCGTGCGCGCATCTCCCGGTCGTGCGCCGGGCGTTCCTCCTCGGG

11636   CATGGCGTGGAACGCCTCGTAGGAGGCCGCGTCGTCCCACTGGGCGTAGTTGATGACCATGTCGC
                                KpnI    SmaI
11701   CGTCGAGCGCCCTGAGGATGCTGTGGGACCGGTACCCGGGCACCTGCCGCATCCAGTCGTCCGGC
                        SacI
11766   TTCTCCAGCAGGGACACGAGCTCGCCCTGGTCCTTGGGGTCGCACCCCATCAGGACGATGACGGT

11831   CAGGTCCCCCCGGTCCGGGCCGATCTCCGTGCGGGCGGCACCGTCCTTCGTCTGGACGGACACCA

11896   CCTCGGTCTTCAGCAGGTGCACCGACGTGGTGAGTTCGGTGAAGTAGGGGACCGTGTTGTGCTTG

11961   AAGTTCTCCCCCTCGTACCGCTCCCTCAGGTCGTTGATCGACCGCCACTGTATGTAGTTGGCCGC
                            SalI                SmaI
12026   ACAGGGCCTCGCCACCCCCGCGTGCAGGGTCGACGACCGCCATCCCGGGTAGTTCGCGTTCGCGA

12091   TGATGCCGCGCATGGCGTCCAGGAGGGTCGCCTGCTTCTCCGAGTCGGTGGTGTTGAACAGGTTG
                                                        <- gilOII
12156   AACACGGTCAGGGAGCCGTTCTCGGGCTCGATGATCGGCATGAGGCCTTCCATGAGGTGTCGGAC

12221   GGCCCCGGAGGGCCGGCTGTGGCTGATGGGTTCTGACCTCGGTGACGACGAGGACGCGGGCGGCC

12286   GGCTCTCCGGGCCGCCCGGACCGCCTGTCGGGATGCCCGCCGCACACCCGGCCCGGCGGCCGGCG
            ***
12351   TCACCGGCTGCGGGGAGAGCCCGGTGTACCGGTCTCCCCGAGACCTTCCTTCCTTCGACGACGG

12416   ACTGGAGTCCGGCGCGGCTGACCCCGACCAGCTCGATCCCGACCTCGGCCATCAGGAGCCGGAAC

12481   TCCTCCACGGTGCGCTGTTTGCCTTCGCACAGGAGGAGCATGTCCATGTCCATGAGGGAGATCGC

12546   CTTGTCCGCCGTGTCGTCCAGGCCCGCCACAGCCTCCACGACGGCGATGTGCGCCCCCTCGTGCA

12611   TGGCCTCCGCGATGTTCCTGAGGATGAGACGGGAACGGCCGTCGTCCCAGTCGTGCAGCACGTTG
```

Figure 9. cont.

```
12676   GAGATCATGAACAGGTCGCTGCCCGACGGAACGCCGTCGAAGAAGGAGCCGGACTTCACCGTGAC

12741   GCGGTGGGCCACCGCCGCGTCCGACAGCTCCGGCAGGGACCGCGACACGACGTCCGGCTGGTCGA

12806   AGAGGACGCCGGTCATCTCGGGGTGCTTGCGGAGCACGGCGGCCAGCAGCGCCCCCCTCCCCCCG

12871   CCCACGTCGGTGACACTGCTGAACCGGGAGAAGTCGAACGCCTCGATCACGGGCTGGATGACGCG
                                                              BamHI
12936   CTTGGACAGTTCGGTCATGGCCGAGTTGAAGACGGCCGCGGTGTCGGGATCCGACTCCATGAACT

13001   CCCACACGCCCGAACCGTGCATCGCGGCGAAGGGAGAGCGGCCGGTGCGCACCGCGGTGGCCAGG
                      SalI
13066   TGGGCCCAGGTCGCGCGTTCGGCCGTCGACCCCGTCCACCGCGCGAAGTTGCGCATGGAGCCGTC

13131   GTCGGAGGCCAGGGCCCGGCCCAGCTCCGTCAGCTCCAGCGTGTCGTGCTCGCCCCTCCGCAGCA

13196   GCCCCACGGAGGCGCCGGCGCGGAAGAAGCGCTCCGCGGTGTCGTGCTCCAACCCCAGCCGGACC

13261   GCCAGTTGTGCGGGCGTCAGCCCGCCGGCGGCCAGGCCGTCGGCCACGCCCAGTTCCGCGAACGT

13326   GCTGACGACACCGGCGCGCCAGCCTCCCATCAGGAGGTCGAGGATCTGCACAGCGACGGGTGCCG
                                <- gilMT
13391   ACGGGGGCAGCGATCCCGATGCAGTAATGGTCATGATGTCCCTTCGACTGGTGGACATGCGGGGA 13456   GGTGAGGCACCGCTGCAAGGGCAGTTCGCTCTCGAACACACTTTGTTCGTGATGCCTCACCGGCG
                                      SmaI
13521   CTAGGTATCCTCATGGGATGGTCCCGGGAAGCAGCGCCTGAACTGCGCAGAGTGCTGCCGGACGG

13586   GAGCGGATCGCCCGCCCGCACTCTGCGGCTGGTGGAACGGACGACCGTGCGGAGCCGGGCCGGCA

13651   CGGTCCGGTGGAAGGGCGGCCCTGCGGTGATCCGGGCGGCCCGCCCCGTGCTCCCGGCGTCCCA

13716   CGCTCCGTAGGCGCGGGACGCCGGACACCTCATGATCCCGACGACGGCCCTGTGGGTCCGGCCG
                XhoI                      ***
13781   GCGACGGGGCGCTCCTCGAGGAGCGCGGTGCTACTTCGCGTCCACGTCGGCTTCCTCGGCCCCGC

13846   GGGGAGCGTTCTCCCCTCCCCACTGCTGGGCGTCCCCCTTGGGCCGCGGGATGAGGAAGGTCGCC

13911   AGCATCCCGAGCGCCAGCAGCGCGGCGCAGGTGTAGCCGTTGATCTGGATCGCGTACGACATGGC
                      NotI
13976   GTCGCGGGCGGCGTCGGCGGCGGCCGCCGTGTCCGGGTTCTCACTCAGTCCGGAGATCATCGCGC
                                                                     SalI
14041   CGGCGCTGTCGGAGACCGCCGACGACAGCTCGTTCGCCTCCGGCGCGGGCGTCCCCTGGTCGACG
                                           SalI
14106   AGCCGGTCGGACAGGTCGGAGTCCAGTGCCGTGAAGAAGGTCGACGTCAGAATCGCGATGCCGAG
                                                  BamHI
14171   CGCGGAACCGAGCTGGCGTGCGGCGCTCTGGATGCCGGATCCCTGGCCGGCGTGCCGCGGCGGCA

14236   CGTCCGCCAGGACGACGTTGGTGACCTGCGCCGTAGCGAACCCGACTCCCATGCCGTACAGGAAG

14301   AGGGCGATGCCGATGACCCACCACTGCGAGTCGCTGCTGGCCAGCAGACCGAACATCAGCAGACC
                  XhoI
14366   GACGGCCTCGAGGACGAGGCCGATGCGCACCAGCCCGATGGGGCCGACGTTCTCGGCCATGCCGA

14431   AGCTCGCACCGCTCGCGAAGAAGCTGCCGACCGCGACGACGAAGACGATCAGTCCGGTCTGGAGC
```

Figure 9. cont.

```
                                                                    SphI
14496   ACCGAGTACCCCAGCGTGTACTGGAGCCACAGGGGGAGAACGGCGAGCATGCCGAACTCCGCCAG

14561   CGCGATGATCAGCGTCGCGATGTTGCCCGTGCTGAAGGACTTGATGCCGAACAGCGAGGTGTCCA
                         SmaI                     PstI
14626   TCAGCGGCGCCGTGCCGTCCACCCGGGTGAGCCGGACCTGGCGCTGCAGGAACAGCCCCAGGCAC

14691   ACCACGGAGACGACCAGGGCGACCGGGATGACCGACAGCTCCACCGGGTCGCCGAAGGGACCGAA

14756   GCTCTTGCGCGGGTCCCACCAGCCGTAGTTGCGGCCCTCGATCAGCGCGAAGGCGAGAAGTCCGA
                       SalI
14821   GGCCCAGCACCGACAGCACGCCGCCGACGGCGTCGACCTTGCCCGGCTGCGCGGGGACTGGTCC

14886   AGGAACTTCATGACGCCCGCGATGATCAGCACCACGACGAAGATGTTGATGCCGAACGCCCACCG
                                                      NotI
14951   CCAGGAGAACTCGGCGAGCCAGCCGCCCAGGAGCGGGCCGACCGCGGCGGCCGCACCGATCGTGG

15016   ACCCCCAGATGGCGAAGGCCTTGCCCCGGTCGGCTCCCCGGAAGGACATGTTGAGCAGGGCGAGC

15081   GAGGTCGGCATGATGATCGCGCCGCCGACGCCCTGGGCGAACCGGCTGGCGATCAGGAGTTCCCC

15146   GGAGGGCGCCAGGGCGGCGGCGATGCTCGCCAGCCCGAACACCACGGTGCCGATGAGGAACAGCC

15211   GGCGTGCTCCCACCACGTCCGACAGACGCCCCATCACCAGCAGCAGAGCGGCCAGGATGATCGCG
              BamHI                       XhoI
15276   TAGGACTCCTGGATCCACTGGGCGCCGAAGGCCGAGATCTCGAGGTCGTCGATGATCGGCGGCAT

15341   CACCACGTTGACGATGGTGAAGTCCACGACCACCAGCGACACACCGAGAGAAATGGCGAGCAAGC
                                                             <- gilJ
15406   CCAGCCAGGGGTCCCGGTTGGCCGGTGAGGACCGAGTTGGATTGTCAGACACTGCGTTCATCCGT

15471   CCTATGTGACACACATGGCCCAGTTGGGTCGCCGGGGGCGAGACAAGGGGGTAGGGCGGGGGAGC

15536   CTCCCGCCCCCGGCGCAATGGCACTATGACAGGAGAAGAGGACGGATTCTGACCTCTACTGACAC
                           gilI ->
15601   CGATCCGGAGGGCAATTCTTGATCGCCAACCGCACGTTGGAACTCCTCAGCCTGTTACAGACCCA

15666   GAGGGAGTGGACCGGTGACGGGCTGGCCGAGCGGCTGGGTGTGTCCCCGCGGACCGTCCGGCGCG

15731   ACATCAACCGACTCCGCGAGCTGGGCTACCCCGTCACGGCGACGAAAGGCCCCTCCGGCTCCTAC
                                                    SalI
15796   CGGCTGTCCCGCGGAGCGCGTCTTCCTCCCCTGATAGTCGACGACGAGCAGGCCCTCGCCATCGC
          PstI
15861   CCTGTCCCTGCAGACCGCGCCGGCCTCGGTGACCGGCATGGGAGACGCCACCAAACGTGCGCTGA

15926   ACTCCATCCAGGAACTGTTGCCACCTCATCTGGCCCACCGGCTCGCCACCTTCTCCGTCGAACAG
                                     SalI
15991   ATCGAGAACGCGTGGGAACTCGCTCCGCCGCAGGTCGACCCCTCCCTGCTCGCACAGCTCAGCAG

16056   CGCCGCCCAGCAGCGTGACCTCGTGAGGTTCTCCTACCGCTCCATCCACCACGACTCGATGCAGG
                                                                KpnI
16121   ACGGGGAGGTCCTGGCCGAACCCCACCGGCTCGTCGTCTGGTCGGGACGCTGGTACCTGGTGGCC
                 SacI                        SalI
16186   TACGACCAGCAGCGGAGCTCATGGCACGCCTACCGGGTCGACCGCATCAAGGATCTGGCGCCCAC

16251   CGCCTGGCGCTTCGGCGAGCGGGAGGGTCCCGACGAGGACATCACCCGCTTCGTACAGAACCAGC
```

Figure 9. cont.

```
16316   CCGATCGCGGTGACACCCCGGACACCTGGCCCTGCTGGGGCACCGTCCTGATGGAGTGTCCCGCG
                       SmaI                                    SalI
16381   TCGCTGGTGGCGAAGTGGGCCCCGGGAGTGGCGAGTTTCGAGGCGGTCGACGACAGGGTCACCCG
             BamHI
16446   GATCCAGATGGGCGCGTGGTCGTGGTCGGCGCTCATCGGCTTCCTGATCACCTTCAGTTGCCGCT

16511   TCACCGTCGAGGGTCCGCCCGAACTCGTCGCCGCGGCGCGGAGGGTGATGGGCCTCATCGACGTC

16576   GGGATTCCGTCGCACGACCCCCTCGCGGAGCCGTCGAGCCGCACACCCGGCCCCTCGGCCGGCCG
               ***                                       ***
16641   GTGACGCCGTGGCCGCGGCACCCCCGCACCGCGGGGAACCGCCGGGTCAGCGGACCGCCTGTCCC
                                                              KpnI
16706   AGCTCGGCGCGCTGCCGCAGCGGTTCCCACCAGTCCCGGTTCTCCCGGTACCAGGAGACGGTCTC

16771   CGCGAGGCCGGTGGCGAAATCCTTGCGGGGCTCGTAGCCCAGCTCCAGGGTGATCTTGGCGCAGT

16836   CCACCGAGTAGCGCCTGTCGTGTCCCTTGCGGTCGGCGACGTACTCCACCGACTCCCAGCCGGCC
                                                        SacI
16901   CCGCACGCCTCCAGGAGCAGTGACACCAGTTCCCTGTTGGTGAGCTCGGTGCCGCCGCCGATGTT

16966   GTAGACCTCGCCGGGTCTGCCCTTCGTGCGGACCAGTTCGATGCCCTGGACGTGGTCGTCGATGT
                                                             XhoI
17031   GCAGCCAGTCGCGGACGTTGAGCCCGTCCCCGTACAGCGGGACGGTGCGGCCCTCGAGGAGGCGC

17096   GTGATGAACAGCGGGATCAGCTTCTCGGGGAAGTGGTGATGGCCGTAGTTGTTGGAGCAGCGGGT

17161   CACCCGGACGTCGAGGCCGTGGGTGCGGTGGTGGGCGAGGGCGACGAGGTCGGCGGCGGCCTTCG

17226   AGGCCGCGTAGGGCGAACTGGGTGACAGCGGGTGCGTCTCCGGCCACGAACCGTAGGGGATCGAG
                                                      NotI
17291   CCGTACACCTCGTCCGTGGAGACCTGGACGAAGACGCCGCGGCCGCGTCCGTGGTGGCGCAGCGC

17356   CGCGTCGAGCAGGACCTGCGTTCCGCCCACGTTCGTGCGGACGAACTCGGCGCCCCCAGGATCG

17421   ACCGGTCCACGTGCGACTCCGCGGCGAAGTGCACGATCTGGTCGTGCTCGGCGACCAGCCGGTCC
                                                            SmaI
17486   ACGACCGCGGCGTCGCAGACATCGCCCTGGACGAGGCGGAACCCGGGGTGGGCACGGACCGGGTC

17551   GAGGTTGGCCGGGTTGCCGGCATAGGTCAGTTTGTCGAGCACGGTGATGCGGACCCCGGCGGGCC

17616   CGTGCGGGCCGAGCAGGGTGCGGACGTAGTGGGAGCCGATGAAGCCGGCACCACCGGTGACGAGG
                        <- gilE
          BamHI        ***
17681   ATCCTCGTGGCGGTCATGACGAGATACGCACCTCGCTGTGGTCCCGAGGACCAGCCGGTGGGCC

17746   GCCGGCACACCGGCGGCGGGGGTCACCTCGACGTTCCGCCCGATCAGGGAACTCTCCACGCGGCG

17811   GACCCCCTGGACCGTGGCCCCGGCGAGGACGATGGAGAACTCGATCTCGCTGGACTCGATCCGGC

17876   AGTCCGCCGCTATCGACGTGGACGGGCCGACGTAGGAGCCGGTGATCCGCGTGTTGGCGCCGATC

17941   ACGGCCGGCCCCACGATCCGCGATCCGCGGATCTCGGCGCCCGCCTCGATCGTGACCTGGCCGAT
                    SalI           SalI
18006   GACCTCGCTGTCCGCGTCGACATAGCCGTCGACCCGGCCCTTGGCGCCCTCCAGCACGGCCCGGT

18071   TGACCTCCAGCATGTCGATGACGTTCCCGGTGTCCTTCCAGTAACCGGAAATGGTGGTGGAGCGG
```

Figure 9. cont.

```
                                                    PstI
18136   ACGTCGTACCCGTGGTCGATGAGCCACTGCAGGGCGTCGGTGATCTCCAGCTCGCCGCGTGCGGA

18201   CGGCTCGATCCCCGGACGGCCTCGTGCACCACGGAGGTGAACAGGAAGACGCCGACCAGGGCCA

18266   GGTCGCTGCGCGGAGCGGCCGGCTTCTCCTCCAGCGCCACCGCCTTCCCGTCGTCGTCGAGTTCG

18331   ACGACACCGAAGGCGCTGGGGTCGGCCACCTTGGTCAGGAGGATGTGCGTGTCGGGCCGGCTCTC

18396   GCGGAACCCGGCCACGAGATCCGCGATACCGCCCACGATGAAGTTGTCTCCGAGGTACATGACGA
                           SmaI
18461   AGTCGTCGTCGCCGAGGAACTCCCGGGCGATCAGGACGGCATGGGCGAGACCGAGCGGCGCCGCC

18526   TGCCGTATGTAGGTGACGTCCAGACCGAAGGCGGAGCCGTCGCCGACCGCCTGCTGGATCTCGGC

18591   GGCCGTGTCCCCGACGACGATGCCGACCTCGGTGATGCCTGCCTCCGCGATCGCCTCCAACCCGT

18656   AGAAGAGCACGGGCTTGTTGGCTACGGGGACGAGCTGCTTGGCGTAGGAATGGGTGATGGGCCTC
                                                  <- gilD
18721   AGGCGGGTTCCGGCCCCGCCGGACAGTACGAGAGCCTTCATGGCGGCGCAGTCTAGGCGGGCGGG 18786   GAAACATCTCAATCGGCCCGGCAGCGCACGGATGTCTGGAAACAACGGTCGGTAGAGGTCAGGAA
                                                                SacI
18851   CTGACCTCTACCGCTCATAATCTGGCCGCTCCCCTCTCCCCGGAGATCAGCTTCGAGAGCTCGGT
              gilH ->
18916   CCCTACCGAAGGAGCGAAACAGATGATCAGGATCGCCGTCATCCTCGGAAGCACGCGTCCCGGCC 18981   GCCGCGGGGCCGTGGTGGCCCAATGGGTCGCCGAGGTCGCCGCGCGGCATCCCGCGGCGGTGATG
                      SalI
19046   GGCGAGGCGGAGTTCGAGCTGGTCGACCTGGCGGAGTACGGCCTCCCGTTGCTCGACGAGCCCGT

19111   GCCGGCGATGTTCGGCCAGTACCAGAAGGAGGAGACCCGGCGGTGGGCCGCCGCCATCGGCTCGT

19176   TCGACGGATTCGTCTTCGTCACGCCGGAGTACAACCACTCGGTGCCCGCCGCGCTGAAGAACGCC

19241   ATCGACCACCTCTTCGCCGAGTGGACCGACAAGGCGGCCGGGTTCGTCAGCTACGGCGTGCACGG

19306   GGGAACCCGTGCCGTCGAGCACCTGCGGCTGGCCCTGGCCGAGGTGAAGGTGGCCGGGGTGCGCA

19371   GCCAGGTCGTCCTGTCGGTGTTCAACGACTTCGACTACACGGGATGCGACATGACGGACCCGACG

19436   GCCATGGGCCGGTTCACGCCGGGACCGCAGCAGGAGCAGACGGTGAACACGATGCTGGACGAGGT
              SalI
19501   CGTCGCCTGGTCGACGGCGCTCAAGCCGCTGCGTACTGCTGCGACCGCTGAGGCGGACGGCCGGG
                    ***
19566   CCGTGTCGGTGTGACGCACCGGTCCGCCCGCCGGACCCCCTGGTGAACGTGCTGGTCACGGCCCC

19631   TCGTGCGTACGCTACGAGGGCCGTGACCAGCACGTTCGCCTGTACGGGCGAGCGTGGCCGCCACG
                                                                 SmaI
19696   CCGCGGGTGGGCGGCGGCAGCACGCCGGCCGGACCGATCGCCGAGTGGCTTGTTACGTGCCCGGG

19761   GCGACGGCGCCGGAGGGGACGCGCCGAAAAAAACCGGTCAGTCGAGTTCCCCTTCGATAACACG
        EcoRV
19826   GATATCCCCCCGTCCTCACTTCGGGTGACCTACTTCGGCCGTGCGACTCCGAGCATCGTGAGCGG
        gilOI ->
19891   CATGACGTTGCACGCCGCAGAAGCCATACCGTCACACGTACCGGTTCTCGTCGTGGGAGCCGGCC
```

Figure 9. cont.

```
19956  CGACAGGTCTCATGCTCGGCGCCGAGCTGGCGCTCCACGGCAGCCGGCCGCTGGTGATCGACGCG
                                          SmaI
20021  CTGCCGAGCCCGAGCGGACAGTCCCGGGCCCTGGGCTTCACGGTGAGGACGCTGGAGATCTTCAA
20086  GCAGCGCGGCATCCTGGGCCGTTTCCAGGGACTCGCCCCGGTGCCCGGAGTCCATTTCGCCGGCC
20151  TCAGCATCAAGGGCGATCACCTCTCCAGCTCGATGCGCCCGGCCAACCAGTACCCGCAGTCCAAG
20216  ACCGAACAGGTCCTCGCCGCCTGGGCCGAGGAGCTGGGAGTACCGGTGCGGCGCCCGTGGACGCT
                                            KpnI
20281  GACGTCCATGGAGCCCACTGGCACCGGGTACCGCTGCGTGCTCAGCGGCCCGGCCGGGCAGCAGA
             SalI
20346  CCGTCGACGCCGACTACGTGGTCGGCTGCGACGGAGCGGGGAGCTTCGTCCGCGAGGCGATCGGC
       SphI
20411  ATGCCGACCAAGCGCACTCCCCCATCCGTACAGATGCTCCTCGGTGATCTGCGCGGATGCGGTCT
20476  GCCCGACGAACCCTTCGGGGTCAAGCACGAAAAGGGCATGGTCATGTCCGCACCGCTGGGCGACG
                                                           NotI
20541  GGACGGAACGCGTCATCGTCTGTGACTTCACCCAGCCGATGCGGCCGCAGGGCACTCCCGTCACG
20606  CACGACGAGATCAAGGCCGCCTACGAGCAGGTCGTCGGCAGCCCCCTGGCGGACGGCAATGTCT
            SacI
20671  CTGGGCGAGCTCGTTCTCGGACGCGTCCTCCCTCGTGGAGTCCTACCGGTCCGGTCGTGCGCTGC
20736  TCGTCGGCGACACGGCGCACACCCATCTCCCCGCCGGCGGGCAGGGCATGAACGTCTCGATACAG
20801  GACGCGGTGAACGTCGGCTGGAAGCTCGCGCTGGTGAGCCAGGGCCGCGCGCCGGACACCCTGCT
                                             KpnI
20866  GGACACCTACCACGCCGAGCGGTACCCGGTCGGCAGGGAACTGCTGCTCAACACCGCCGCCCAGG
20931  GCCAGGTCTTCCTGCGCGGCCCGGAAGTGGACCCGCTGCGCGAGGTCCTGCGGCGACTGCTGAAC
20996  ATCCGGGAGGTGTCCGTCCTGCTGGCCGACGGAGTCAGCGGACTGGACATCCGCTACGACATGGG
21061  CCTCCCGGAAGCACCGCCACCCACGGGTGAACGGCTGCCGCCGGACGTGTTCCACGTCGTCGGGA
21126  CCGGCGGCGACGCCGTCGAGGAGTTGCGGCACGGCGCCGCTCTGCTGATCGTCCCGTCCCCCGAC
21191  AGCCCGGCGTCCTCGCTGGTCGCTCCGTGGCGGGACCAGGTGCGCGTCGTGCACGCGCGCCCCAC
21256  GGACCCGGACTGGGGCGGGGAGCCGGCCGCGTCGTCGCACTGGTTCGTACGACCGGACGGACACA
                                  EcoRI
21321  TCGCGTGGGCGGGCACCGAATTCAGCGAGTTGAGCGCCTCACTGAGCCGCTGGCTCGGTCAGCCC
              ***                          gilG ->
21386  GCCGCGTAACCAGAGGAGGAAGAACCCTTGTTCAGCTCTCTCATCGTCGCCCGGATGGACACCGG
21451  CCACGCCGAAGCGGTGGCCGACGTCTTCGCCGGCTTCGACGCCACCGACATGCCCGCGCGGATGG
21516  GCACGCGGCGCCGCGAACTCTTCCGCTACCGCGGCCTCTACTTCCACCTCCAGGACTTCGAGACC
21581  CCCGACGGGACCGAAGCGGTCGAGGCGGCCAAGTCCGACCCGCGGTTCATCCGGGTGAGCAACGA
21646  CCTCAGGCCCTACATCGAGGCCTACGCCCCGGACTGGCAATCACCGAAGGACGCCATGGCAGAGC
                                  gilA ->
                                   ***
21711  GCTTCTATCACTGGAGTTCGAAACGATGAGCCGCAGGGTCTTCATCACCGGGGTCGGTGTCGTCG
```

Figure 9. cont.

| | |
|---|---|
| 21776 | CGCCGGGAGCCGTCGGACGTGACCCCTTCTGGGAGCTGCTGACCCAAGGGCGCACGGCCACCCGC |
| 21841 | CGGCTCAGCCTCTGCGACCCGGAGCCCTTCCGGTCCCAGGTGGCCGCGGAGGCCGACTTCGACGC |
| 21906 | CGAGGCGGCGGGGCTGTCGGAGCGGCAGTCCGCGGAACTGGACCGGGCGGCGCAGTTCGCCCTGG |
| 21971 | TCGCCGCCCGTGAAGCGGTCGAGGACGCGGCATGGTCCGAGACATGTCCTCCCGAACGCGCCGGA |
| |                                            XhoI |
| 22036 | GTGATCGTGGGTTCGGCCGTCGGAGCCACGACCAAG<u>CTCGAG</u>GAGGTCTACCGGCAGCTCAGCCG |
| 22101 | TGACGGCTCCCTCTGGGACGTGGCCCCCGACTCCCCCGCCGAGCTGTACTCGTACTTCGTGCCCA |
| |                                                                        SalI |
| 22166 | GCTCGTTCGCCTCCGGCATCGCACACGACCTCGGCGTCACGGGGCAGAGCGGCGTCGT<u>GTCGACC</u> |
| 22231 | GGGTGCACCTCCGGGATCGACTCCGTCGGCAACGCCTGGGAACTGATCCAGAGCGGCATCCTGGA |
| 22296 | CTCCGCCGTCTGCGGTGCCACCGACGCCCCCATCTCGCCCATCACCGTCGCCTGCTTCGACACGA |
| 22361 | TCAAGGCGACATCGACGTACAACGACACCCCGGAGAGCGCCTCACGGCCGTTCGACGCCACACGG |
| 22426 | GGCGGCTTCGTCCTCGGCGAGGGCAGCGCGATGTTCGTCCTCGAATCGGAGGAATCCGTCCACCG |
| 22491 | TCGCGGCGCACGCGTCTACGGCGAGATCCGCGGCTACGCGAGCCGCTGCAACGCCTACCACATGA |
| 22556 | CCGGTCTCAAGGCCGACGGACGCGAGCTGGCGGAGGCCGTCGTCTCCGCTCTCGGCCAGGCAGGC |
| |     SmaI |
| 22621 | GTGGA<u>CCCGGG</u>CCGGCTCGACTACGTCAACGCCCACGGCAGCGGCACGAAGCAGAACGACCGCCA |
| 22686 | CGAGACCGCCGCGCTGAAGTCGTCCCTCGGACCCGCCGCCCACGACGTGCCGATCAGTTCGATCA |
| 22751 | AGTCGATGATCGGCCATTCGCTGGGCGCCATCGGGTCGTTGGAGATCGCCGCCTGCGCCCTGGCG |
| |                                                               BamHI |
| 22816 | CTGCGGGACGACGTGATCCCGCCGACGGCCAATCTCACCCGGCC<u>GGATCC</u>GGAACTCGATCTGGA |
| 22881 | CTACGTGCCGGTCCACGCGCGCAAGCAGCCGACCAACAGCGTGCTCACGACCGGAAGCGGCTTCG |
| |                                                                gilB -><br>                                                               *** |
| 22946 | GTGGGTTTCAGAGCGCCATGGTTCTCACGGACCCGGAGCATCACTATGACCGCACACATCACCG |
| 23011 | GCATCGACATCGTCTCCCCGCTGGGCCTGTCCCGCGAGGAACACTGGAAGGCCCTCCTCGACGGA |
| 23076 | TGCAGCGGTCTGAGGGCGACGCAGTCGTTCGACTCCAGCAGGTACGACAACCCCATCAGCGGGGA |
| 23141 | GGTGCCCCACTTCGCCCCGGAGGGCCTGCCCAAGCGGCTGCTGCCGGCCACCGACCGGATGACCC |
| |                                                  SalI                  SalI |
| 23206 | AGATGTCGCTGGTCGCCGCGGCGGGGGCGTTCGACGACAGCGGT<u>GTCGAC</u>ACGAGCCGG<u>GTCGAC</u> |
| 23271 | CCCCTCGGAGTCGGTGTCATGACGGCGTCCACCGCGGGGGGTTACGCGTTCGGGCAGAAGGAGCT |
| | <u>PstI</u> |
| 23336 | <u>GCAG</u>AACCTGTGGTCCAAGGGGCCCAGGTACGTCAGCACCCATCAGTCCTACGCCTGGTTCTACG |
| 23401 | CGGTCAACACCGGTCAGATCTCCATCCGGCACGGCTGCCAGGGCCACAGCGGAGTGATCGTCGCG |
| 23466 | GACGACGCCGGCGGGCTCGACGCGATCTCCTTCGCCGCCCGCCGTCTGGCGCGCGGCAACCGCGT |
| 23531 | CATGCTCACCGGGTCGGTGGACAGCACGATGTGTCCCTGGGGGCGGGTCGCGCACACCTCGACCG |

Figure 9. cont.

```
                SphI
23596   GCATGCTCTCGGCATCCACCGACGCGCGGGCCGCGTACCTTCCGTTCGACGCACGAGCCAACGGG
                                                        PstI
23661   TGGGTCAACGGCGAAGGCGGCGCGCACCTCGTGCTGCAGACCCACAGTGACGGCCGCTACGCGGC
                                                  SmaI
23726   GGTGCTCGGTCACGGTGCGACCATGGACGATCCCCGCGCCGCCCCGGGCACGGGCCTCGTCCGGG

23791   CGATCCACCTCGCGCTCGGCGCGGCGCGGCTGCGCCCCGGCGACATCAGTGTGGTGTTCGCCGAC
                  SmaI
23856   GCGGCCGGCACCCGGGAGGCGGACACCGCCGAGGCCGCCGCCCTCGCCGAGGTCTTCGGGCCGGA

23921   TTCCGTCCCCGTCACCGCGCCCAAGGCGGCGACCGGCCGGATGGGCTGCGGGACGGCCGCACTCG

23986   ACGTCGCGACGGCGGTGCTCGCCCTCCGCGACCAGACGATTCCCCCCACCGTCAACGTCCAGGCC

24051   GACGCGTCCCTGGGGGTCAACCTGTGCAGCGTCGCCACACACCACCCCCTCACCAACGTCCTGGT
              SmaI                                        ***
24116   CCTGGCCCGGGGCGTCGGTGGGTTCAACTCGGCCCTGATCGTCGGGAAATGAGAGAAGGAGCAAG
        gilC ->                                 XhoI            SalI
24181   GAATGTCCGCACGCGTCACCATGGACGATCTCAGGCGAGCCCTCGAGGAGGGCTCCGGTGTCGAC 24246   GAGGGCGTCGATCTTGACACCGACCTCGAAACCATGGCGTTCTCCGAGCTGGGGTACGACTCCCT
                                                        SacI
24311   GGCGGTGCTGGAGACCGGCCTGCGCCTCGGCCGCGAGAACGACATCGAGCTCGACGACTCGGTGT 24376   TCGCCGACCTCGACACGCCTCAGCAGATGCTGGACGCGGTCAACGATGCCCTCGCGCGTCAGGCG
                   gilF ->
                   ***
24441   GCGGCATCGTGACCTCTCCCCGTCATGCCCTGGTCACCGGCGGTTCCAGCGGCATAGGAAAGTCC

24506   GTCGCACGGCGCCTGGCCTCGGCCGGCCACACCGTCACGATCTGCGGTCGTGACTCCGAAAGGCT

24571   CCAGCAGGCCGCCAAGGAACTGTCGGAGCAGGGTGCACCCGTCACCTCGCTGATCGCCGACGTCA
                                                                 BamHI
24636   GCAAGCCCCGCCAGGTGGGCGATCTGGTCCGCGAGGCCGTGGAGACGAACGGTCCCCTCGGGATC

24701   CTCGTCAACAACGCGGGCAGGAACGGAGGCGGCCGGACCGCGGAGCTGAGCGACGAGCTGTGGCG

24766   GGAGGTACTGAGCACCAACCTCGACAGCGTTTTCTACGTCACGCGGGAGGTGCTGGCCCGTGGCG

24831   GCATCGGCGAGGTGGACCACGCCCGGATCATCAACATCGCCTCCACCGCGGGGAAGCAGGGAGTT

24896   CTGCTGGCCGCCCCGTACTCCGCCTCCAAGCACGGTGTCGTCGGCTTCACCAAGGCGGTGGGCAA
                                                     SmaI
24961   GGAGCTGGCCCCTCAGGGGATCACCGTGAACGCCGTCTGCCCGGGCTACGTGGAGACCCCGATGG

25026   CCTCACGGGTCCGGCAGGCCTACGCAGACGCCTGGGAGACCACGGAGGCCGAGGTGCTGTCCGCC

25091   TTCGAGGCGAAGATCCCGCTCGGCCGGTACAGCACGCCCGACGAGGTCGCCTCGCTGGTCGAGTA

25156   CCTCACGACCGAAGGAGCCGCCTCGATCACGGCTCAGGCGTTCAACGTGTGCGGCGGCCTCGGCA
              ***              gilK ->
25221   ACTTCTAGGAGATGATTCACATGGCCGATCCGGCTCGCACAGACCTGCACTCCGCCACGATCACC

25286   GGCAGCGCCGACGCGGTGTACCGCCGTCTGGAGGACGTCGGGCAGTGGTCCCAGATGTTCGAACC
```

Figure 9. cont.

```
                      SmaI
25351   GACCATCCACGGCGCGGAACTGGCCCGGGACGGGAACAGGCAGACGATCCAGCTGTGGGCCACCG
                                  SacI
25416   CCAACGGAGAACCCAAGGCCTGGGTCTCCGAGCGTGAGCTCGACCCCGTCGCGCGCACCATCCGC

25481   TTCGCGCAGACCGTCACCTCCTCGCCCGTCGCCGAGATGTCCGGCGCGTGGCAGGTGCTGCCCCT

25546   GTCCGAGGACACCTGCCGGGTCGAACTCACGCACACCTACCGTGCGGAGAACGACTCGGCGGAGT
                                                            SacI
25611   CGCTCACATGGATCGCCCGAGCCGTGGAGACCAACAGCACGAAGGAGCTCTCGGCGCTCAAGTTC

25676   GCCTGCGAACGGGACGCCGACAGCGAGGCCAGTCCCTTCACCTTCACCGATGCGGTGGACACCAC
             SalI
25741   GGTCGACCCCGTCCTGCTGTTCTCGTTCCTGGACCGCGGTGAGCTGTGGGCGGGACGCCTGGAGC
                                          PstI
25806   ACGTCGCCGAGGCCGAGATGAGGGAGTTCTCCGACGGCCTGCAGTTCCTCCGGATGCGGACGCGC

25871   ACCCCGGACGGTGACACGCACGTCACCGAGTCCTACCGGGTGTCGCAGAGCCCGGCCCGGCTGCT

25936   GTACAAGCAGGTGACGCTGCCCGCGCTGCTGTCGCTGCACACCGGCGAGTGGACCATCACCCCGG

26001   CCGGGGAGAGCTGGCGGGTCACGTCGAAGCACACCGTGGCGATCGATCCCGACGCGGTGCACAAG

26066   GTCCTCGGTGCCGACGCGACGGTCTCGGACGCCAAGCGGCTCGCCCGGCGCAACCTGGGCAACAA
                                                                    ***
26131   CAGCCTGCGGACCCTCGAAGCAGCGGTCCGGTGGGCCGGCACCGCCGTGTCGCAGAGGTGAGTGG
             gilOIV ->
26196   GGACATGACGGAGCCCGAGACCTCGGACGTTCTCGTCGTCGGCGCCGGGCCCAGCGGACTGCTCC
             BamHI
26261   TGGCCGGGATCCTCGCCGGGGCGGGTGCGCGGGTCACGGTGCTGGAGGCGCGGGACGCGCCCAGC 26326   CCGCAGACCCGCGCCTCCACCTTGCACGCCCGTGCCAGGGAGATCCTCGACCACCACGGAGTGGA
                                                                    SmaI
26391   GTTCTCCCCGGAGCTGCCCTGGAGTGCCCACGGACACTACGGCGGCCTGCGCGTGGACCTCTCCC
        SmaISalI
26456   GGGTCGACTCCGGGCGGGCCGGTGTCTGGAAGTGCCCCCAGCCGGAACTGGTACGGACGCTGACC 26521   GGCTGGGCCCGCGGGCACGGCGCGCGGCTGCTCCACGGGGAGCACGTGGAGTCCGTCCGCGAGCA
                    SmaI
26586   GGGCGGGCGCTGTCTGGTGCGTACCCGGGCCGGCACCACGTTCAGCGGGACCCTGCTGGTCGCGG

26651   CGGACGGCCGGCGGAGCACGGTGCGGTCGCTGCTGGGCATCGGGTGCGGGGGTGCGCCGGCCACG

26716   CGCGTACTGGTGCAGGCCGATGTCCACGGCGACGGGCTGGCGGGGCGGCGCTTCGAGCGACACGG
                                  SmaI         SmaI
26781   GCGGTACACCGTGACCGCCGCACCGATCAGCCCCGGGATCACCCGGGTGATGCTGCACGATCCGC

26846   GCTGGCCCGCGGGCGAGGAACGCACGCTGGAGGACCTCCGTAGAGCCTGGAAGGAGTCCACCGGC

26911   GAGACCCTGCCGGCCGAGCCGTCGTGGTCACGGACCTTCAGCGACGACACGACAGTGGCACACCC

26976   GCTGGTCAAGGGCCGTGTCGTGCTGTGCGGCGACGCCGCCCACCCCTTCGTCCCCATCGGCGGCC

27041   AGGCGCTGAACACGTCGTTGATGGACGCCGAGGCGCTGGGCTGGCGGGTCCTGGGGTATCTGGAC

27106   GACGGGGACCGGCAAGGCCTCCTCGACTACCAGGACGAGCGGTTCTCGTGGCTGACCGTTCTCGC
```

Figure 9. cont.

```
27171   GGGGAGACTGCGCGCCCAGGCACGTCTGCTGTTCGACACCGACGCGGCGGCCACGGAACGCAAGG

27236   CGCTGGTCGCCGCGAGACTGGCCGGGGACGCGGACTACCGGCGCAGGATCGCCGACGCCCTGGCC
                SalI
27301   GGTGTCGACGTGTGCTACCTGACGCCCGGCGGCGCGGTCCGCCGGCGTCTGTCCCCGGCCCGGCT

27366   CCGGGAGACCGGAGTGAACCCCGGCGCCCGCCGCGTGCAGCGGGCGCTCGTCCCCGACGACGGAA
                     BamHI               KpnI
27431   CGCGCACGGACGCCTGGATCCGTCCCGATCACCACTGGTACCCGGTGGCCCGCGACGGGGCCCGG
                                                              gilP ->
                                                              ***
27496   CAGGACTGGGACGACGCGGTGCGCCTCCACGACGACTTGGAACCCGAGGTGACGCGGTGAGAGCG
                                                                KpnI
27561   TTCCTGTTCCCCGGTCAGGGGACCCAGAAGATCGGCATGGGCACCTACCTGCGAGAACGGTACCC

27626   CCACCTGATCGCGCCGTTGTGGCGGGAGGCGGACGACGTCCTGGGTTTCCCCCTCACCCGCCTCT

27691   GCGAGGAAGGCCCCGGCGAGAAGCTCCGCCACATGCCGGTCACCCAGCCCGCCGTCTTCCTGTGC

27756   AGTTACGCCGCGCTCGTCGCCGCGCAGGCGAACGGCGCGGAGCCGGACGTCATCGCGGGCCACAG

27821   TCTGGGCGAGTACTCGGCGCTGGCGGCGGCCGGCGTCCTCACCTGGCAGGAGGTCCTTCAGCTCG

27886   TCCACCGCCGCGGTCAGCTCATGGCGGAGGTGCAGCACAAGGTGGACGGGAAGATGGCGGCCGTC

27951   ATCGGTCTCGCCATCGGGCAGGTCGAGGAGATCTGCGAGCAGGTGCGGTCCGAGACCGGTGAGGT

28016   GGTCGAGGTGGCCAACCACAACGAGCCCCTCCAGGTCGTCGTCTCCGGCCAGTGCGCTGCCATAG

28081   ACCTCCTGGTCCAGCGCGTCGCGACGGCGACCGACGTCCGCACGTCCGTCCTGAGGATCGGTGGC

28146   CCGGCCCACTCCAGTCTCATGGGCAGCGTCGCGGGGGACTTCGTGGAGTACCTCCGGCGCTTCGA
                                 SalI
28211   CTTCTGCACGCCCAAGACGATGCTGATCTCCGGGTCGACCGCCGAGCCCTACGCGAGTGCGGAGG

28276   AGATCAGGCACCAGCTCGGCAGGCAGCTGGTGCACCGGGTGCGGTGGGTGGACGTGATGGCGCAG
            XhoI
28341   CTCGAGAGGCTGGGGGTCGCACAGACCTGGGAGCTGGGGCCGGGCAAGGTCCTCTCGGGATTCGT

28406   ACAGCGGTCGCTGCCTCAGGTGCGGACGTACCGCGCGAATGATCTGCCGTCCTTCCTGGCCGGCG
                        ***                 gilQ ->
28471   TGACGGGCTGGTGAGCCGGTGAAGCACGCAGTGCCGCATCAGGCAACCGGCGCCGCTCCCGACGG

28536   AGGGGGGTCCGCGCCCCGGTCCCTCGTGCTGATGCTCCCCGGCCAGGGGTCGCAGTTCGCTGCCA

28601   TGGGAGTCCCGCTCTACGAGTCCGACGCCCGGTTCAGGAAGGCGCTCGACGACTTCTTCGACGCG

28666   TTCGGCACCGGTGCCGAGCGGCTCCGGCGCGAGTGGCTGCACGGTTCGGCCCAGGGCATCGAACG

28731   TGGGTCCTTCGCGCAGCCGATGCTGTTCGGCCTCGACTACGCGGCGGGCGCGGTGTGGCTGGAGG
            SacI         SalI
28796   AGCTCAAGGGTGTCGACGTGACGCTGGTCGGTCACAGCGTGGGCGAGCTGGCGGCGGCCACCCTC
                                      XhoI
28861   GCGGGGGCCTTCGACCTCGAGCTGGCGGGGGCACTCCTGGCCGAGCGGGCCCGGCTCCTCGACGC
                SmaI
28926   CGCCCCCCGGGGAGGGATGATCGCGTGCCGCGCGACGGAGGAGTCGCTGCGGGAGCATCTCGACG
```

Figure 9. cont.

```
28991   CCCTGGGCGGACGCGCCGTCATCGCGGCGGAGAACGCGGACAACCAGTGCGTCGTGAGCTGTGCC
                                     KpnI
29056   GAGGAAGACCTCCCGGACACGATGCGGTACCTCGGCTCGCACGGTGTGACGTGCCTGCGCGTCGC
29121   CTCGACCGAACCGTTCCACTCCCCCCTCCTCGCCCCCGCCGCCGCCCGGTTCGAGGAGTTCCTGG
29186   CCCGGCGCGGTCATCGTCTGTCCACGACGGAACTGCCCATGGTCTCGGCCTACTCGGCGCGGAGG
29251   ATCAGCGGCCGGGAGATCATGCCCGCCTCGTTCTGGACGCGTCAGATGGCTGAGAAGGTGCGTTT
29316   CTGGGAGGCGCTCCGCCACAACTTCGACTCCGGTCCCCGCACGTTCGTGGAAATCGGCCCAGGGA
29381   CCGTCCTCTCCCTGGCCGCACGTCGGCTGCCGTCCGTACGGGCCCGGCGTTCCACGGTGATCTCC
29446   ACGATGCCGCGTCATCGGCCCCACCCGGAGCACTGGGAATCGGCCATACATGAGGTCGCCGAGGA
        EcoRI   ***                                                    SmaI
29511   ATTCTGTTGACCATTGCACTACGTGCAACGCGCAAGGCCGGCCATGGGTGTCCCCCGAGTTCCCG
                                                                      XhoI
29576   GGAGGCACCCATGGCCTTGTCGGTGAAATGTTCAACCAAATGAACCACCTCTCGAGGGCGCCCG
29641   GATCAAAGATGTTCACCGATTTGCATAGTCGAAAAAATACGGACAGCAACGGAAGCGGAGTGTTA
29706   TCCTGCAATCTGCACGCAACGGGGGAAACGGGGGAGGATTCCAAGTGCAGGACCCGGTGGACCGG
29771   ACCTCGGGGAACTCCAGAGGCGCAAGCACCGTCGGACCCGAGCAGTCCCGCAAAGACGCGGGGCA
                                    KpnI
29836   CTCCTGTCGCCGAAGAGGGCCCGGTACCGTCACGCAGCAGTTTTCGCCGACCCTCCACCATTTCT
29901   TCACCGTCACGAGATCTCTTCGGGCCGACGGGGACCACACGGGCAGAGACTGAAGGACCGGCGCT
29966   CGACCTCGCCGGCTCCCGCCCCTCCACCCCTTCCCCGCGTTGCCCCTGACCGCATGGGCGGCATC
30031   TCGGTGCCGCGTTTCTTCCGCGCCTGGCGCGAGGGGAGATCTCCCATCAAGGGGGCCTTTCAAG
                XhoI
30096   GCCCTCTCGCCTCGAGGGCACCGCACGCCGAAGACCGATCACAAAAGTATCCGAACGGCTCCGAC
                                                                gilt ->
30161   CGAGGTCATATCTGAGACTGATCGAATATCCAACGGGGAGATGTGATGGGTTTCATCCGGTTTGA
30226   CGTTCTGGGCCCGCTCAGGGTCCGGTGCGACGACACCCTGCTTCAATTGACCGGGCGCAAGTACC
30291   GCACCGTGGTTTCGTATCTCGCTCTTCAACCCGAGTATTCGGTGGCGATAGAGGACCTCGTCCGA
30356   GCCGCTTGGAGCGACAAGCGCCCGTCCAGCGCGCACCACCAGGTCCGTAAGATGGTCTCCGCACT
30421   CCGGACCAGCCTGGACCAGGACTGGGACCTGGTGGCGACGTCCCAGGACGGCTACATGCTGAAGT
                                                     EcoRI
30486   TGCCGCCCAAGCAGTCCGACGTATCCGAATTCTGCCGCCTCTTCGACCAGGTGATGTCGGGTCCC
30551   CTGACGAGCGACGACGACCTGTCGGCCGCGTATTCGGCGCTGGCGCTCTGGCGCGGACGCCCTTG
30616   CGAAGGGTCCGAGCCCCATGGGCAGGAGCGCCGGATCTCTCAATTGGTGGAACAGCACCGCGTCC
30681   TCTTGAACAAGACCGTTCAGGGATTCGGCGACAGGGGCAGGTCCGATGAACTCGCCTCGATACTG
30746   CACGTCGCATCGAAGATTCACGGACAGCCGGTCACCGCTCGCTCCGGTGTCGCCGTTCCCGCGCC
```

Figure 9. cont.

```
                                                             SaII
30811    CGCTGTTTCGTACGCGGGCACGACACAAGTCCCCGAACCTTCGGGGTCGACCACCCCTCCCCCAC
                                       PstI            NotI
30876    GCCCCGGCTCCCCCGTCGGTCCGCGCTGCCTGCCACGGGATCTGCAGGACTTCGGCGGCCGCGAA
              PstI
30941    CGCGAAATCAATGAGCTGCAGAAACTGTTGACCGCGGAAGGACCCCACCCACAGTTGGTGGCGAC

31006    CGTTCACGGAATGAGCGGCGTGGGTAAAACCGCCGTCGCCGTCCGCCTGGCGCACAGACTAGCCC

31071    ATCACTATCCGGACGGCCAGCTCTTTGTATCCCTGGACGGCTTTTCTTCGGCCTCCACCGCCACC

31136    GTGTCGAATGCGCTGGGAATACTCCTCAGACAGAAAGGCCTGGCGGACGAGGACATTTCACCTTC

31201    GGAAGACGGCCGCCTCGCACAATGGCGGACCATCACCGCCGGACAGAAGCTGCTCGTCGTGCTCG
                                                         XhoI
31266    ACGACGTGTGCGACATCGAGCAAGTAGAACCCCTCATCCCGCCCTCGAGCGAAAGCGCCTGCATC

31331    ATCACGTCGCGCATCATCCTCAATGGCATCGACGGCGCTCATCACATCTCACTCGAAGTACCGGA

31396    CGAGGACGAATGTCTGGAGATACTCAGTTGCATGATCGGCAGACGCTTCGACGACGAGGAGACGA

31461    AGGACGCCCGCGCGCTGATCCAGCAGTGCGCCAATCTGCCGCTGGCACTCCGTCTCGCCGCCGCC
              EcoRV
31526    CGGATATCGACGCGCGACTTCCTGAACCTCCGGGAACTCAGTGAGCAACTGTCGTCCTCGGCTTC

31591    CATCTTCAGTGAACTGGAAGTTCCCGGCCGTAGTCTGGTCGGCCGGCTCATGACGTCCTTCACGT
                                        KpnI
31656    GCCTGGAGGACTTCGATCACGACCGGTACCTCCGATTATCGCTGCTCCCCTGCCCCGAGATCGAT
                                                                    PstI
31721    GAAACGTCGGTCGCGGCCGTGCTGGGCGTATCCACCGACTGGGCACGGCGTGCCTGCAGGCGCTT
                                                                    PstI
31786    CGCAGACCGCGCGTTGCTGCAACGCACACGATGCGGTACGTACCGGATGCACCCGCTGCTGCTGC

31851    AGGCGGCACAGCTGGAAGCGCAGAAGACCATCCCGTTCGAGGAGCAACGCCGGCTCGTCCGCGCC
                                                                 SmaI
31916    GCTTTCCTCCATTACAAGGCGTCGAACGGCCTCGTGGGAGCCAGCCGCATCAGCCCTTCCCGGGT

31981    TCCTGACGGACACGTGGTACTGAGGACCCTCACGCAGTCCGCGAAGCTGGCCGCGCGGCTCGGCC

32046    TCCAGGAGGAGTTGGCCGATCTGTACACCGCCTGGAAGGAACTGCTCCCCCTCGTGCTGGACCGC

32111    CGGCAGCAGGAGGCGGTCGGGCGACGCGTACTCGCCGTTTCACAGCACCTGGACCGGCCCGCGTG
                                                                        *
32176    CGAGGGAGCACCCCACCGGAGGCGTCCGCGGCAGGCACGGGACATGCTGCCCGAGGGGCAGCGGT
                **
32241    GAACGAGGGCCGGCCGGAGGAAGGCAGTCGGACGATGACGACCGTTTGTCCGTACATCGGGAGAC
                                                                   SmaI
32306    CGGGGTGCCACGTGAAACATGTGACCCGGTCACCGGATGTCCGATCGCAGCCGCACCCGGGGGCG
                  gilU ->
32371    AACTGACCATGGACCGCGTTCTTCCGTATGCAGCCGGCAGTGAGGCACTCCTGTCGTCGAGAGAG

32436    CACGGCCCCACGGTGAGCGAGAGAACCGTCTCGGCGCAGGAGATCGTCGTGGGCGGCGGGGGTCT

32501    GCTGGGGAGACACATCCTCGGCGTGCTGGGCAATCGGCTCAGCCGGCGGGTACGCATCCCGTGGG

32566    ACGACCACGGCCGCGCCTGTGAGCAGCTCTACGCGCTGGGCAGGGACCTGGCTCAGCAGCCGGCG
```

Figure 9. cont.

```
32631  CGCTGGAACCTGTACTGGTGCGCGGGACTGGCCGTCTTCCACACCCCCGCCGAGCAGGTGGAGCG
32696  AGAACGCCTCCAGGTCAGCCTCCTCCTGGCGGGCATCAACGACGGGCTCGAACGCTCGGGGGGCC
32761  CCACCGGCGGCGCGTTGTTCCTGGCCTCCTCAGCCGGCGGCGCGTTCGCGGGCTCGGAACACCCG
32826  CCGTTCACCGAGTTCTCCCCGCCCGTGCCCACGAACCCGTACGGCGCGTCCAAACTCGCCGTCGA
32891  GGAGGAGGCCGAGGTTCTGGCGCGCCGTTGGCGACTGCCCACGGTGTCGGGTCGGATCACGAACC
32956  TGTACGGCCCCGGCCAGAACCTCGACAAGAACCAGGGCCTGGTCAGTGCCCTCGTCAAAGCGCAG
33021  CTGACCGGTGAACCCCTGCGGCTGCGGGCCGCCCTGGAGACCACGCGCGACTACATCTACGCACG
33086  GGACTGCGCCCGGATGGTCGTCTCGGCGATGGAGACCGTACGGTCCCGCACCCGCGGCACGGACC
33151  CCCATGTCCGCAAGATATTCAGCAGCGGACGCCGTCTGCGGATCGACGAACTGCTCCGGATCGCC
                                                          KpnI
33216  GAGCGCCTCTTCGACCGGCCGGTACCCGTCGTCCACGAGCCGGTGGCGGGAGGGGCGAACGTCAA
              SmaI
33281  CCTCTCGGTCGAGTCCCGGGTATGGGCGGACCTCGAATCGTCCCCCTTCCTCAGCATCGAGGAAG
                                                     KpnI           ***
33346  GGATGCGCGCCGTCCGCTCCGACCTCAGGTACCGACTCGGGCACGGGTGAGCGACACGAACGACA
33411  AAAGACCCAGGCCGCACATCAGCGCGGCCTGGGTCCGATGAGCCGCCTTCGGGATTCGAACCCGA
33476  GACCTACGCATTACGAGTGCGTTGCTCTGGCCATCTGAGCTAAGGCGGCGTGCTGGGTGCACCCA
33541  TGGTGCGATCAGCGACGTCGGTAAGTCTACACAGTTTCGAGGGGTGGTTCGTACCGGCCCCGGAG
                                 ***
33606  CGGGCCGGGGCTGCCTCCGGTGGGCGGGGCGGCTACGAGCAGCGTGTGCCGTCGGCGGGCGGGGT
                                             SalI
33671  GCCGTCGAGGAGGTAGGTGTTGATGGCGGAGTCGACGCAGGCGCTGCCGCGGCCGTACGGGGTGT
33736  GGCCGTCGCCGTCGTAGGTGAGGAGGCGGGCCGTGGCGAGCTGGCCGGCCAGACCCTCGGCCCAG
              <- proteinase  SmaI
33801  CGGTACGGGGTGGCCGGGTCCCGGG
```

GILVOCARCIN GENE CLUSTER, RECOMBINANT PRODUCTION AND USE THEREOF

This application claims the benefit of U.S. Provisional Application No. 60/477,957, filed on Jun. 13, 2003, which is incorporated herein by reference.

FIELD OF INVENTION

The present invention relates generally to polyketides and polyketide biosynthesis. In particular, the invention pertains to the nucleic acids encoding gilvocarcin polyketide synthase and the tailoring enzymes of the gilvocarcin biosynthesis, and to recombinant vectors and host cells containing such genes, and to the recombinant production of gilvocarcins and uses thereof.

BACKGROUND OF INVENTION

Polyketides represent a large family of diverse compounds synthesized from 2-carbon units through a series of condensations and subsequent modifications. Avermectin, candicidin, epothilone, erythromycin, FK-506, FK-520, narbomycin, oleandomycin, picromycin, rapamycin, spincoyn, tetracycline, and tylosin are examples of such compounds. Polyketides occur in many types of organisms, including fungi and mycelial bacteria, in particular, the actinomycetes. Polyketides can be divided into macrocyclic/polyether-type compounds, biosynthetically encoded by type-1 polyketide synthases (PKSs), and into multicyclic, aromatic compounds, whose core structures are encoded by type-2 PKSs. Type-1 PKSs are "complex" or "modular" PKSs which include assemblies of several large multifunctional proteins carrying, between them, a set of separate active sites for each step of carbon chain assembly and modification. As such, structural diversity occurs in this class from variations in the number and type of active sites in the PKSs. This class of PKSs displays a one-to-one correlation between the number and clustering of active sites in the primary sequence of the PKS and the structure of the polyketide backbone. The second class of PKSs, called Type-2 PKSs, is represented by the synthases for aromatic compounds. Type-2 PKSs have a single set of iteratively used active sites.

Angucycline group antibiotics, which are arranged by a type-2 PKS are structurally characterized by their angular, polyketide-derived benz[a]anthracene-derived backbone (angucyclinone), which is often further decorated with sugar moieties (angucyclines). Angucyclines/angucyclinones form the largest and structurally most diverse sub-group of the multicyclic, aromatic polyketides. Knobler, R. M., Radlwimmer, F. B. and Lane, M. J. *Nucleic Acid Res.* 20:4553-4557 (1992); Matsumoto, A. and Hanawalt, P. C. *Cancer Res.* 60:3921-3926 (2000). Yamashita, N., Shin-Ya, K., Furihata, K., Hayakawa, Y. and Seto, H. *J. Antibiot.* 51: 1105-1108 (1998); Nakashima, T. et al. U.S. Pat. No. 6,030,951. A very interesting set of natural products with respect to their biosyntheses as well as their biological activities derive from this angucycline/angucyclinone group. However, they are not easily recognizable as such, since their polyketide-derived skeleton is rearranged in a series of steps, initiated by oxidative biosynthetic processes. The gilvocarcin-type anticancer antibiotics (Morimoto, M., Okubo, S., Tomita, F. and Marumo, H. *J. Antibiot.* 34:701-707 (1981); Breiding-Mack, S. and Zeeck, A. *J. Antibiot.* 40:953-960 (1987); Yamashita, Y. and Nakano, H. *Nucleic Acids Res. Symp. Ser.* 20:65-67 (1988); Elespuru, R. K. and Gonda, S. K. *Science.* 223:69-71 (1984)) and the jadomycins (Oyola, R., Arce, R., Alegria, A. E. and Garcia, C. *Photophysical properties of gilvocarcins v and m and their binding constant to calf thymus DNA. Photochem. Photobiol.* 65:802-810 (1997)) are examples of such 'rearranged angucyclines'. Both of them, and the kinamycins (Takahashi, K. and Tomita, F. *J. Antibiot.* 36:1531-1535 (1983)), have in common biosynthetic rearrangement cascades that begin with an oxidative cleavage of the 5,6-bond of an angucyclinone intermediate (FIG. 1).

Given the difficulty in producing polyketide compounds by traditional chemical methodology, and the typically low expression of polyketides in wild-type cells that produce them naturally, there has been considerable interest in finding improved or alternate means to produce polyketide compounds. This interest has resulted in the cloning, analysis, and manipulation by recombinant DNA technology of genes that encode PKS enzymes.

Gilvocarcin-Type Natural Aryl-C-Glycoside Antibiotics

The benzo[d]naphtho[1,2-b]pyran-6-one C-glycoside antibiotics, often referred to as gilvocarcin-type aryl-C-glycosides, were discovered in Japan in the early 1980s. Studies have shown that these molecules are decaketides, and that they originate either from one acetate starter and nine malonate extender units or from one propionate starter and nine malonate extender units, depending on the 8-side chain. The incorporation pattern suggests the key intermediate to be an angucyclinone, such as 2 in FIG. 2., which then rearranges to form the coumarin frame. Krohn, K. and Rohr, J. Angucyclines: *Total Syntheses, New Structures, and Biosynthetic Studies of an Emerging New Class of Antibiotics. Topics Curr. Chem.* 188, 127-195 (1997); Takahashi, K. & Tomita, F. *Gilvocarcins, New Antitumor Antibiotics. 4. Mode of action" J.Antibiot.* 35: 1038-1041 (1982); Carter, G. T., Fantini, A. A., James, J. C., Borders, D. B. & White, R. J. *Biosynthesis of Ravidomycin.* Use of 13C-13C Double Quantum NMR to Follow Precursor Incorporation. *Tetrahedron Lett.* 25, 255-258 (1984); Carter, G. T., Fantini, A. A., James, J. C., Borders, D. B. & White, R. J. *Biosynthesis of Chrysomycins A and B. Origin of the Chromophore. J. Antibiot.* 38, 242-248 (1985). Gilvocarcins are biosynthesized by a type-II polyketide synthase (PKS) and the necessary post-PKS tailoring enzymes. Among these, the key enzyme responsible for the tremendous structural change from the suppossed angucyclinone intermediate (e.g., 2 in FIG. 2.) to the unique tetracyclic lactone structure of the gilvocarcins is proposed to be a C—C-bond cleaving oxygenase. Other key post-PKS tailoring steps with respect to important structural features of gilvocarcin V are the oxygenation/dehydration reactions necessary for the formation of the vinyl side chain, and the C-glycosyltransfer step, through which the 6-deoxy-D-fuco-hexofuranose moiety is attached.

This distinct family of antitumor antibiotics shows excellent antitumor activity and remarkably low toxicity, and therefore has remained to be attractive for synthetic organic chemistry as well as for biological activity studies since their discovery. The group consists of the gilvocarcins (syn. toromycins, anandimycins), ravidomycins, the ravidomycin analogues FE35A and B, the chrysomycins (syn. virenomycin, albacarcins; including recent derivatives possessing branched ketofuranose and ketopyranose sugar moieties), and BE-12406 A and B (FIG. 3.). Hirayama, N., Takahashi, K.; Shirahata, K., Ohashi, Y., Sasada, Y. Bull. *Chem. Soc. Jap.* 54:1338-1342 (1981); Krohn, K. et al. *J. Topics Curr. Chem.* 188:127-195 (1997); Hosoya, T., Takashiro, E., Matsumoto, T., Suzuki, K. *J. Am. Chem. Soc.* 116:1004-1015 (1994); Knobler, R. M. et al. *Nucleic Acid Res.* 20:4553-4557 (1992);

Matsumoto, A. et al. *Cancer Res.* 60:3921-3926 (2000); Yamashita, N. et al. *Antibiot.* 51:1105-1108 (1998); Nakashima, T. et al. U.S. Pat. No. 6,030,951; Morimoto, M. et al. *Antibiot.* 34:701-707 (1981).

Gilvocarcin V (GV) (FIG. 4.), the principal product of *Streptomyces griseoflavus* Gö 3592 and of various other *Streptomyces* strains, is the most important member of the gilvocarcin-type aryl-C-glycosides, because of its potent bactericidal, virucidal, cytotoxic and antitumor activities. GV is one of the strongest antitumor compounds among these drugs, requiring only low concentrations and maintaining a low in vivo toxicity. The exact molecular mechanisms responsible for the in vivo mode of action of GV are still widely unknown. However, it was found that GV exhibits a strong tendency to intercalate with DNA. Both equilibrium DNA binding and UV light-induced DNA adduct formation was found, causing also topoisomerase II inhibition. Knobler, R. M. et al. *Nucleic Acid Res.* 20:4553-4557 (1992). The vinyl group is essential for the antitumor activity, since the minor congeners gilvocarcins M and E, in which the vinyl group is replaced by a methyl group and an ethyl group, respectively, are significantly less effective. Yamashita, Y. et al. *Nucleic Acids Res. Symp. Ser.* 20: 65-67 (1988); Elespuru, R. K. et al. *Science.* 223:69-71 (1984); Oyola, R. et al. *Photochem. Photobiol.* 65:802-810 (1997). Photobiological studies showed that the vinyl group undergoes a [2+2] cycloaddition with DNA thymine residues under photoirradiation. Moreover, it was shown recently that Givocarcin V promotes protein-DNA cross-linking when photo-activated by near-UV light, and histone H3, which plays an important role in DNA replication and transcription, was identified as one of the selectively cross-linked proteins (FIG. 5.). This cross-linking with histone H3, believed to be part of the unique molecular mechanisms of the potent antitumor activity of gilvocarcin V, might contribute to the better and more specific activity of GV compared to other intercalating antitumor drugs. Matsumoto, A. et al. *Cancer Res.,* 60:3921-3926 (2000).[3b]

The molecular architecture of gilvocarcin V in conjunction with its biological activity makes GV an excellent target for the study of its biosynthesis and the development of novel, improved anticancer, immunosuppressant, antibiotic, antiviral and neuroprotective drugs through combinatorial biosynthesis.

SUMMARY OF INVENTION

In one aspect, the present invention provides isolated nucleic acid compounds comprising a sequence identical or complementary to all or part of a coding sequence for the gilvocarcin V biosynthetic gene cluster from *Streptomyces griseoflavus* (SEQ ID NO:1). Preferably, a part of said coding sequence is one or more open reading frame (ORF) selected from the group consisting of ORF1, ORF2, ORF3, ORF4, ORF5, ORF6, ORF7, ORF8, ORF9, ORF10, ORF11, ORF12, ORF13, ORF14, ORF15, ORF16, ORF17, ORF18, ORF19, ORF20, ORF21, ORF22, ORF23, ORF24, ORF25 and ORF26.

In one embodiment, the present invention provides an isolated nucleic acid strand that encodes a gilvocarcin gene cluster or subunit thereof comprising a nucleotide sequence identical or complementary to, or an amino acid sequence encoded by a nucleotide sequence identical or complementary to, all or part of a coding sequence for gilvocarcin V biosynthetic gene cluster from *Streptomyces griseoflavus* (SEQ ID NO:1). Preferably, the gene cluster encodes a functional PKS or a functional arrangement of the PKS and selected post-PKS tailoring enzymes. The gene cluster may be derived from a single species or may be hybrid in nature. In certain embodiments, the gene cluster is a replacement gene cluster. The replacement gene cluster may be a hybrid, mutant, analog or derivative thereof.

In another embodiment, the invention provides an isolated nucleic acid that encodes three or more open reading frames (ORFs) comprising a sequence identical or complementary to all or part of a coding sequence for enzymes performing the biosynthesis of gilvocarcin V from *Streptomyces griseoflavus* (SEQ ID NO:1). Preferably, the ORFs encode a functional PKS or a functional arrangement of the PKS and selected post-PKS tailoring enzymes. In certain embodiments, an ORF may be derived from a single species or may be hybrid in nature. In certain embodiments at least one of the ORFs is derived from the gilvocarcin V gene cluster. In other embodiments, at least one ORF is derived from a non-gilvocarcin V producing *Streptomyces* strain, or is hybrid in nature. In yet other embodiments, at least one ORF is a mutant, analog or derivative of the native coding sequence.

In still another embodiment, the present invention provides isolated nucleic acid compounds comprising three or more genes of the coding sequence for the biosynthesis of gilvocarcin from *Streptomyces griseoflavus*. Preferably, the mixture of genes encode a functional PKS or a functional arrangement of the PKS and selected post-PKS tailoring enzymes. In certain embodiments, a gene may be derived from a single species or may be hybrid in nature. In certain embodiments at least one gene is derived from the gilvocarcin V biosynthetic gene cluster. In other embodiments, at least one gene is derived from a non-gilvocarcin V producing *Streptomyces* strain, or is hybrid in nature. Non-limiting exemplary non-gilvocarcin V biosynthetic genes are preferably subunits of the gilvocarcin M, gilvocarcin E, defucosyl-gilvocarcin V, ravidomycin, deacetyl-ravidomycin, FE35A, FE35B, chrysomycin A, chrysomycin B, BE-12406 A, or BE-12406 B gene cluster. In yet other embodiments, at least one gene may be a mutant, analog or derivative of the native coding sequence. It is also preferred that the encoded activity of the gene is, for example and without limitation, a ketosynthase activity, a chain lengthening activity, an acyltransferase activity, an acyl carrier protein activity, an oxygenase activity, a reductase activity, an oxidoreductase activity, a cyclase activity, a glycosyltransferase activity, a methyltransferase activity, an activity encoded by any gene belonging to the biosynthesis or modification of a sugar moiety, a regulatory activity, a repressor activity, or a transporter activity.

In another aspect, the present invention provides recombinant expression vectors encoding a gilvocarcin gene cluster, hybrids, mutants, analogs or derivatives thereof. In certain embodiments, vectors encode one or more subunit of gilvocarcin gene cluster, hybrids, mutants, analogs or derivatives thereof.

In another aspect, the present invention provides a host cell transformed with a recombinant expression vector described herein.

In still another aspect, the invention provides a method of preparing gilvocarcin V, said method comprising transforming a host cell with a recombinant DNA vector that encodes a gilvocarcin V gene cluster or subunit thereof, and culturing said host cell under conditions such that gilvocarcin is produced and/or gilvocarcin analogs are produced. In one embodiment, the method is practiced with an *E. coli* host cell. In certain other embodiments, the method is practiced with a *Streptomyces* host cell. The gene cluster may be a replacement gene cluster and preferably a functional gene cluster. In certain embodiments, the invention provides methods for preparing new polketide-type compounds, preferably, gilvocarcin V-type polyketides. The gilvocarcin V-type polyketide produced may be gilvocarcin V or gilvocarcin hybrids, mutants, analogs or derivatives thereof. Such polyketides are useful as antibiotics, antitumor agents, and immunosuppressants, and for a wide variety of other pharmacological purposes.

These and other embodiments and aspects of the invention will be more fully understood after consideration of the attached Drawings and their brief description below, together with the detailed description, example, and claims that follow.

BRIEF DESCRIPTION OF THE DRAWINGS

FIG. 3. provides the structure of gilvocarcin-type anticancer drugs.

FIG. 6. A shows the gilvocarcin gene cluster.

FIG. 6. B shows a simplified gilvocarcin gene cluster, in which the polyketide synthase and associated genes are depicted in black, the genes encoding the tailoring enzymes are in pink (i.e. gray, if printed in black/white), and the regulatory, resistance and so far unknown genes are shown in white. Shown are two alternative pathways towards gilvocarcin V.

FIG. 9. is the nucleotide sequence of the Gilvocarcin V gene cluster which sets out ORF1-26 (SEQ ID NO:1).

DETAILED DESCRIPTION

Figure 1:
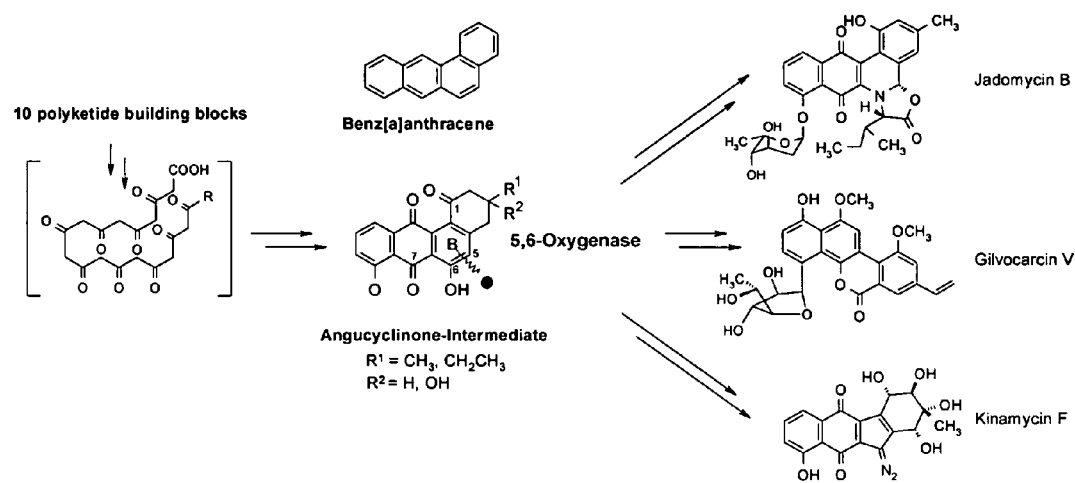
FIG. 1. schematically illustrates formation of jadomycins, gilvocarcins and kinamycins.
Figure 2:
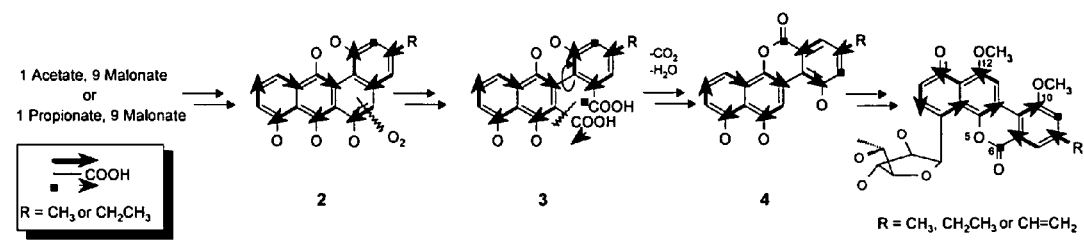
FIG. 2. schematically illustrates intermediates in biosynthesis of gilvocarcin.
Figure 4:
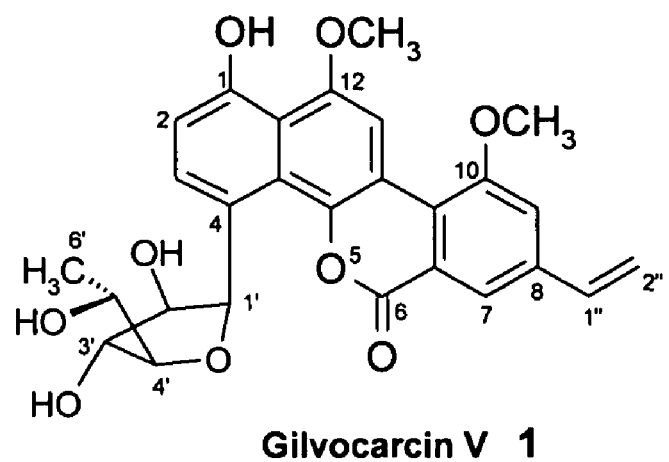
FIG. 4. provides the structure of gilvocarcin V.
Figure 5:
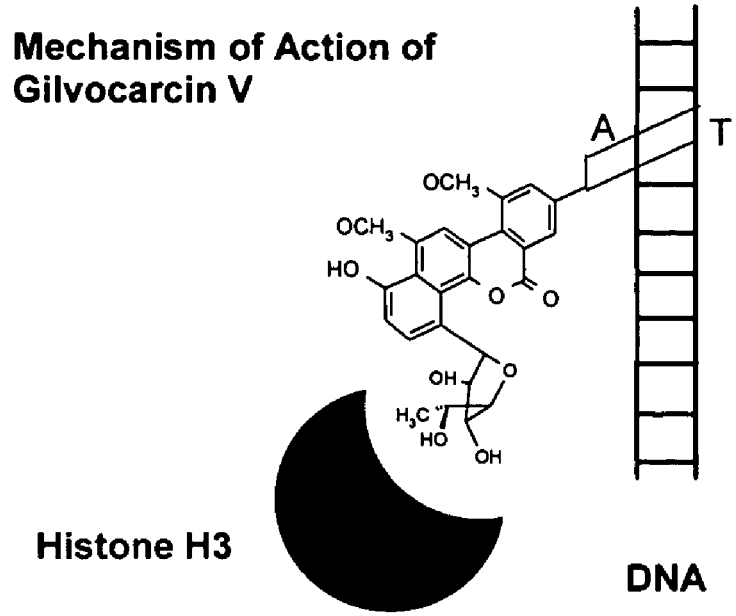
FIG. 5. illustrates the hypothesized mechanism of action of gilvocarcin V.

Given the valuable pharmaceutical properties of gilvocarcin-type aryl-C-glycosides, there is a need for methods and reagents for producing large quantities of gilvocarcin-type aryl-C-glycosides, for producing gilvocarcin-type aryl-C-glycosides in host cells that do not produce gilvocarcin-type aryl-C-glycosides naturally, and for producing novel gilvocarcin-type aryl-C-glycosides compounds not found in nature. The present invention provides the protein encoding nucleic acids, methods and reagents that produce gilvocarcins, with particular application to methods and reagents for producing the gilvocarcin-type aryl-C-glycosides known as gilvocarcin V ("GV") and its analogs and derivatives and novel compounds related through structure or genetics to gilvocarcin V.

The practice of the present invention will employ, unless otherwise indicated, conventional methods of chemistry, microbiology, molecular biology and recombinant DNA techniques within the skill of the art. Such techniques are explained fully in the literature. See, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition), and Practical Streptomyces Genetics (T. Kieser, M. J. Bibb, M. J. Buttner, K. F. Chater, D. A. Hopwood, Norwich, UK: The John Innes Foundation; current edition).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, reference to "a polyketide" includes mixtures of polyketides, reference to "a polyketide synthase" includes mixtures of polyketide synthases, and the like.

Definitions

As used herein the term "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eucaryotic mRNA, genomic DNA sequences from procaryotic or eucaryotic DNA, and even synthetic DNA sequences. A transcription termination sequence will usually be located 3' to the coding sequence.

As used herein the term DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

As used herein the term "functional PKS" refers to a set of genes (e.g., three or more) or subunits of a biosynthesis gene cluster, which catalyzes the synthesis of a polyketide, including without limitation a "minimal PKS".

As used herein the term "gene" refers to a segment of DNA or its complement that is involved in producing a polypeptide chain, including regions preceding (leader) and following (trailer) the coding sequence as well as intervening sequences (introns) between individual coding sequence (exons). A "gilvocarcin V gene" refers to any of the ORFs of SEQ ID NO:1.

As used herein the term "gene cluster" refers to a set of (e.g., three or more) closely related genes that code for the same or similar proteins and which are usually grouped together on the same chromosome. A "gilvocarcin V gene cluster" refers to the set of genes encoded by SEQ ID NO:1.

As used herein the term "genetically engineered host cell" is meant a host cell where the native gene cluster or subunits thereof has/have been deleted using recombinant DNA techniques. Thus, the term would not encompass mutational events occurring in nature. A "host cell" is a cell derived from a procaryotic microorganism or a eucaryotic cell line cultured as a unicellular entity, which can be, or has been, used as a recipient for recombinant vectors bearing the PKS gene clusters of the invention. The term includes the progeny of the original cell which has been transfected. It is understood that the progeny of a single parental cell may not necessarily be completely identical in morphology or in genomic or total DNA complement to the original parent, due to accidental or deliberate mutation. Progeny of the parental cell, which are sufficiently similar to the parent to be characterized by the relevant property, such as the presence of a nucleotide sequence encoding desired biosynthetic enzymes, are included in the definition, and are covered by the above terms.

As used herein the term "gilvocarcin V analog" refers to a compound or molecule that resembles gilvocarcin V and that contains one or more structural differences relative to gilvocarcin V. Preferably, the gilvocarcin analog has gilvocarcin-type activity although a gilvocarcin analog may have enhanced or the same activity as products of the gilvocarcin V gene cluster. For example, the degree of saturation of at least one bond in the gilvocarcin structure can be changed (e.g., a single bond can be changed to a double or triple bond, or the converse), a bond can be removed, one or more carbon, oxygen or hydrogen atoms can be replaced with a different atom or a chemical moiety (e.g., a halogen, oxygen, nitrogen, sulfur, hydroxy, methoxy, alkyl, aryl, cycloalkyl, heterocycle, amine, amide, ketone, aldehyde, etc.) and the like. In addition, the C-glycosidically-linked sugar moiety can be changed, modified or replaced by other sugar moieties including deoxysugars, amino sugars, keto sugars, halogenated sugars etc., which may be connected as C-, O-, N- or S-glycosides at any possible position of the gilvocarcin molecule. Also other peripheral groups, such as OH groups, methyl groups, O-methyl groups, halogene atoms etc. can be added, modified or removed. Other types of derivatives of gilvocarcin that would be encompassed by the term "gilvocarcin analog" are known in the art.

As used herein the term "gilvocarcin V derivative" refers to a polyketide compound or molecule, that may be produced from gilvocarcin in one or more steps or with few chemical or moiety modifications.

As used herein the term "gilvocarcin V-type polyketide" refers to a compound or molecule that is encoded by at least one native gilvocarcin V gene or a hybrid, mutant, analog or derivative thereof.

As used herein the term "minimal PKS" refers to those minimum number of PKS genes or subunits of a biosynthesis polyketide gene cluster required for biosynthesis of a polyketide, such as gilvocarcin. For example, in *Streptomyces griseoflavus* the required genes to encode the minimal PKS are ketosynthase I (KSI) and ketosynthase II (KSII, also known as chain length factor CLF) and an acyl carrier protein (ACP). Thus, these three genes, without the other components of the native clusters, can be included in one or more recombinant vectors, to constitute a "minimal" replacement PKS gene cluster.

As used herein the term "mutant" refers to a nucleic acid compound, protein, molecule, vector or cell resulting from mutation of the native wild type coding sequence or subunits thereof.

As used herein the term "mutation" refers to any change that alters a native coding sequence either by displacement, addition, deletion, insertion, cross-linking, or other destruction or substitution of one or more nucleotides of the native coding sequence. Techniques for modifying nucleotide sequences, such as site-directed mutagenesis, are also known to those skilled in the art.

As used herein the term "nucleic acid" sequence can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA such as, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. A transcription termination sequence will usually be located 3' to the coding sequence.

As used here the term "open reading frame" or "ORF" refers to a region of a nucleic acid molecule that contains a series of triplet bases coding for amino acids without any termination codons. An "open reading frame" does include any start codons.

As used herein, the term "polyketide-type compound" refers to a compound or molecule that is encoded by at least one native polyketide subunit, or hybrid, mutant, analog, or derivative thereof, including for example, without limitation, gilvocarcin V-type polyketides.

As used herein, the term "post-PKS enzyme" or "post-PKS modifying enzyme" or "post-PKS tailoring enzyme" refers to a protein or enzyme that is involved in modifications of a polyketide after a polyketide is synthesized by polyketide synthase. Exemplary, post-PKS enzymes involved in gilvocarcin synthesis include, without limitation, a C—C-bond cleaving oxygenase involved in forming the tetraxyclic lactone structure, oxygenase/dehydratase involved in forming the vinyl side chain, and C-glycosyltransferase involved in attaching the 6-deoxy-D-fuco-hexofuranose moiety.

As used herein, the term "post-PKS modifying step" or "post-PKS tailoring step" refers to an action or actions taken by a protein or enzyme to modify a polyketide after it has been synthesized by polyketide synthase. Exemplary post-PKS tailoring steps involved in gilvocarcin synthesis include, without limitation, the formation of the tetracyclic lactone structure by a C—C-bond cleaving oxygenase, oxygenation/dehydration reactions for the formation of the vinyl side chain, and a C-glycosyltransfer step involved in attaching a 6-deoxy-D-fuco-hexofuranose moiety.

As used herein the term "replacement gene cluster" means any set of genes and/or genes encoding tailoring steps capable of producing a "functional PKS" when under the direction of one or more compatible control elements, as defined above, in a host cell transformed therewith. The term "replacement gene cluster" encompasses three or more genes encoding the various proteins necessary to catalyze the production of a polyketide. A "replacement gene cluster" need not include all of the genes found in the corresponding cluster in nature. Rather, the gene cluster need only encode the necessary components to catalyze the production of an active polyketide. Thus, if the gene cluster includes, for example, eight genes in its native state and only three of these genes are necessary to provide an active polyketide, only these three genes need be present. Furthermore, a replacement gene cluster can include genes derived from a single species, or may be hybrid in nature with, e.g., a gene derived from a cluster for the synthesis of a particular polyketide replaced with a corresponding gene from a cluster for the synthesis of another polyketide. Hybrid clusters can include genes derived from both Type I and Type II PKSs. As explained above, Type I PKSs include several large multifunctional proteins carrying, between them, a set of separate active sites for each step of carbon chain assembly and modification. Type II PKSs, on the other hand, have a single set of iteratively used active sites.[43] The genes included in the replacement gene cluster need not be the native genes, but can be mutants or analogs thereof. Mutants or analogs may be prepared by the deletion, insertion or substitution of one or more nucleotides of the coding sequence. Techniques for modifying nucleotide sequences, such as site-directed mutagenesis, are described in the literature. See e.g., Sambrook, et al. Molecular Cloning: A Laboratory Manual (Current Edition); DNA Cloning: A Practical Approach, Vol. I & II (D. Glover, ed.) and Nucleic Acid Hybridization (B. Hames & S. Higgins, eds., Current Edition).

The term, "replacement gene cluster" may also contain genes coding for modifications to the core polyketide catalyzed by a PKS, including, for example, genes encoding hydroxylases, methylases or other alkylases, oxidases, reductases, glycotransferases, lyases, ester or amide synthases, and various hydrolases such as esterases and amidases. The genes included in the replacement gene cluster need not be on the same plasmid or if present on the same plasmid, can be controlled by the same or different control sequences.

As used herein, the term "subunit" refers to a part of a complete gene cluster including, for example, a module, domain, gene, or open reading frame, and parts thereof. A "subunit" may comprise for example, a gene or genes derived from a single species or may be hybrid in nature (e.g., a gene derived from a cluster for the synthesis of a particular polyketide replaced with a corresponding gene from a cluster for the synthesis of another polyketide.). A "subunit" may comprise mutants, analogs or derivatives of the native gene(s). Mutants, analogs or derivatives thereof may be prepared by techniques known to those of skill in the art, including, without limitation, the displacement, addition, deletion, insertion, cross-linking, or other destruction or substitution of one or more nucleotides of the coding sequence. Techniques for modifying nucleotide sequences, such as site-directed mutagenesis, are also known in to those skilled in the art.

Cloning and Identification of the Gilvocarcin Biosynthetic Gene Cluster

Central to the present invention is the identification and cloning of the gilvocarcin ("gil") gene cluster (SEQ ID NO:1). Identification of the gilvocarcin gene cluster was achieved by generating a *S. griseoflavus* genomic cosmid library using the *Streptomyces-E. coli* shuttle vector pOJ446. For the generation of a genomic cosmid library, isolation and subsequent random fragmentation of high molecular weight genomic DNA was performed, followed by ligation of these fragments to vector arms containing cos sequences, packaging into λ particles and transduction into a suitable *E. coli* host strain. DNA fragments of the NDP-glucose-4,6-dehydratase (an enzyme catalyzing a key step in 6-deoxysugar biosynthesis) (See Decker, H.; Gaisser, S.; Pelzer, S.; Schneider, P.; Westrich, L.; Wohlleben, W.; Bechthold, A. *FEMS Microbiol. Lett.* 141:195-201 (1996)) and also the actI PKS (See Hopwood, D. A. *Chem. Rev.* 97:2465-2497 (1997)) genes, highly conserved among *Streptomyces*, were used to probe the cosmid library. Cosmid DNA isolated from clones hybridizing with both probes was analyzed by restriction mapping and Southern blot experiments. Hybridization using both probes with one of the cosmids increased the likelihood that the cosmid would contain the entire gilvocarcin cluster. One of the cosmids, cos-G9B3, was transformed into *S. lividans* TK24, where it stimulated the production of gilvocarcins V and M in the same quantities as the wild-type strain (20-30mg/L of (1) in FIG. 6.B), proving that it most likely contains the entire gene cluster of gilvocarcin biosynthesis.

Subcloning of cos-G9B3-DNA fragments into pUC19 or pBluescript II SK(+) followed by sequencing revealed the entire gilvocarcin gene cluster (FIG. 6.A). The cluster spans a 32.9 kB region and consists of 26 ORFs identified as follows. ORF1 is gilS, encoded on the complement to SEQ ID NO:1, and represented on SEQ ID NO:1 as nucleotides (nt) 802-4068 read in the 3' to 5' direction. ORF2 is gilN, encoded on the complement to SEQ ID NO:1 and represented on SEQ ID NO:1 as nt 4308-5198 read in the 3' to 5' direction. ORF3 is gilL, encoded on the complement to SEQ ID NO:1 and represented on SEQ ID NO:1 as nt 5417-6052 read in the 3' to 5' direction. ORF4 is gilOIII, encoded by the complement to SEQ ID NO:1 and represented on SEQ ID NO:1 as nt 6576-7769 read in the 3' to 5' direction. ORF5 is gilGT, encoded by the complement to SEQ ID NO:1 and represented on SEQ ID NO:1 as nt 7777-9261 read in the 3' to 5' direction. ORF6 is gilM, encoded by the complement to SEQ ID NO:1 and represented on SEQ ID NO:1 as nt 9261-10001 read in the 3' to 5' direction. ORF7 is gilR, encoded by the complement to SEQ ID NO:1 and represented on SEQ ID NO:1 as nt 10020-11513 read in the 3' to 5' direction. ORF8 is gilOII, encoded by the complement to SEQ ID NO:1 and represented on SEQ ID NO:1 as nt 11513-12196 read in the 3' to 5' direction. ORF9 is gilMT, encoded by the complement to SEQ ID NO:1 and represented on SEQ ID NO:1 as nt 12354-13424 read in the 3' to 5' direction. ORF10 is gilJ, encoded by the complement to SEQ ID NO:1 and represented on SEQ ID NO:1 as nt 13814-15466 read in the 3' to 5' direction. ORF11 is gilI, nt 15619-16641 of SEQ ID NO:1 read in the 5' to 3' direction. SEQ ID NO:2 is the amino acid sequence of ORF11. ORF12 is gilE, encoded by the complement to SEQ ID NO:1 and represented on SEQ ID NO:1 as nt 16690-17697 read in the 3' to 5'direction. ORF13 is gilD, encoded by the complement to SEQ ID NO:1 and represented on SEQ ID NO:1 as nt 17697-18761 read in the 3' to 5' direction. ORF14 is gilH, nt 18938-19576 of SEQ ID NO:1 read in the 5' to 3' direction. SEQ ID NO:3 is the amino acid sequence of ORF14. ORF15 is gilOI, nt 19892-21391 of SEQ ID NO:1 read in the 5' to 3' direction. SEQ ID NO:4 is the amino acid sequence of ORF15. ORF16 is gilG, nt 21413-21736 of SEQ ID NO:1 read in the 5' to 3' direction. SEQ ID NO:13 is the amino acid sequence of ORF16. ORF17 is gilA, nt 21736-22992 of SEQ ID NO:1 read in the 5' to 3' direction. SEQ ID NO:5 is the amino acid sequence of ORF17. ORF18 is gilB, nt 22992-24164 of SEQ ID NO:1 read in the 5' to 3' direction. SEQ ID NO:14 is the amino acid sequence of ORF18. ORF19 is gilC, nt 24183-24449 of SEQ ID NO:1 read in the 5' to 3' direction. SEQ ID NO:6 is the amino acid sequence of ORF19. ORF20 is gilF, nt 24449-25225 of SEQ ID NO:1 read in the 5' to 3' direction. SEQ ID NO:15 is the amino acid sequence of ORF20. ORF21 is gilK, nt 25241-26188 of SEQ ID NO:1 read in the 5' to 3' direction. SEQ ID NO:7 is the amino acid sequence of ORF21. ORF22 is gilOIV, nt 26200-27552 of SEQ ID NO:1 read in the 5' to 3' direction. SEQ ID NO:8 is the amino acid sequence of ORF22. ORF23 is gilP, nt 27552-28481 of SEQ ID NO:1 read in the 5' to 3' direction. SEQ ID NO:16 is the amino acid of ORF23. ORF24 is gilQ, nt 28501-29517 of SEQ ID NO:1 read in the 5' to 3' direction. SEQ ID NO:9 is the amino acid sequence of ORF24. ORF25 is gilT, nt 30206-32239 of SEQ ID NO:1 read in the 5' to 3' direction. SEQ ID NO:10 is the amino acid sequence of ORF25. ORF26 is gilU, nt 32379-33392 of SEQ ID NO:1 read in the 5' to 3' direction. SEQ ID NO:11 is the amino acid sequence of ORF26.

The database analysis yielded genes encoding the type II PKS and associated enzymes (gil G, A, B, C, F, K, P and Q), several genes encoding proteins involved in post-PKS tailoring steps (gil OIII, GT, R, OII, MT, E, D, H, OI, OIV, and U), and genes of regulation and self resistance enzymes (gil S, J, I and T), this group also includes three genes coding for proteins of unknown function (gil L, M and N).

Methods

Cosmid Library Generation

A cosmid library of the gilvocarcin V producer *Streptomyces griseoflavus* Gö3592 using pOJ446 as a host was constructed using standard methods. Transduction into *E. coli* XL 1-Blue MRF' yielded several thousand colonies, which were pooled and used as a master culture. An initial library evaluation of cosmid DNA from several randomly chosen transductants by restriction enzyme analysis revealed whether these clones have inserts and if so, the size of the inserts. It was expected that the inserts should ideally have the size of 30 to 40 kb, since from comparison with known, related molecules, this was the expected size of the entire gene cluster of the gilvocarcin pathway. As such, we were able to generate a cosmid containing the complete gilvocarcin gene cluster.

The high molecular weight donor DNA was isolated according to the following standard methods. CRM medium supplemented with 0.5% (w/v) glycine was inoculated with *S. griseoflavus* Gö3592 spores and incubated for 24 hours or until the culture reached nearly stationary phase. Cells were harvested by centrifugation and resuspended in lysis buffer containing 1 mg/mL lysozyme. After incubation for 15-60 min at 37° C., a 10% SDS solution and proteinase K (0.5 mg/mL) was added to lyse the cells and the lysed cells were incubated at 55° C. for two hours. The resulting viscous solution was extracted with 5 M NaCl solution and phenol/chloroform 1:1 and centrifuged. The aqueous phase was transferred to a fresh tube and again extracted with chloroform, then the DNA in the water phase was precipitated by adding 0.6 vol. of isopropanol and spooled onto a sealed Pasteur pipette. After rinsing with 70% ethanol, air drying and dissolving in TE-buffer, the concentration and purity of the DNA was estimated by measuring the optical density of the solution at 260 and 280 nm. DNA size was checked on a 0.3% agarose gel by conventional electrophoresis. For cosmid cloning, the DNA should be ≧150 kB.

The partial digestion and dephosphorylation of the donor DNA was performed as follows by standard methods. The restriction enzyme Sau3AI was used for the partial digestion, since it recognizes a 4-base-pair-sequence thus ensuring random fragmentation and generation of cohesive ends that can be ligated into the BamHI site of vector pOJ446. Bierman, M. et al. *Plasmid cloning vectors for the conjugal transfer of DNA from Escherichia coli to Streptomyces spp. Gene* 116: 43-49 (1992). The amount of enzyme and incubation time to digest the DNA to the point where its average size is approximately in the size range of 30-40 kB was determined empirically by an enzyme dilution series and then scaled up to digest 200-300 µg of chromosomal DNA. A subsequent dephosphorylation step with calf intestinal phosphatase (CIP) prevented segments of different regions of chromosomal DNA from ligating to one another and forming a recombinant vector containing noncontiguous segments of the genome. The extent of dephosphorylation was determined using a small batch of dephosphorylated DNA in a ligase reaction and subsequent gel electrophoresis of the ligated and unligated DNA samples. The complete dephosphorylation showed no differences between ligated and unligated DNA.

Cosmid pOJ446 is a low copy shuttle vector containing three cos sequences and an apramycin resistance gene. It also carries the origin of replication from *E. coli* and *Streptomyces* allowing an easy transfer between these two species. To prepare the two cos arms necessary for the in vitro packaging reaction, cosmid pOJ446 was cut at the unique HpaI site situated between two cos sites. Afterwards, the resulting ends were dephosphorylated to prevent re-ligation. The linearized vector was cut with BamHI to yield two vector arms each containing a cos site and a ligatable end. Finally, phenol/chloroform extraction and ethanol precipitation was used to purify the DNA.

Ligation and packaging was performed according to the following standard methods. Different ratios of donor to vector DNA were ligated with T4 DNA ligase for 16 hours at 16° C. To favor the formation of cosmid-insert concatemers and not circular DNA the ligation was carried out at DNA concentrations of about 1 µg/µL or greater. The ligation was monitored by agarose gel electrophoresis of ligation mixture, using unligated DNA samples as a control. Successful ligation showed a significant shift of the chromosomal smear to a higher molecular weight and the disappearance of the vector bands. The in vitro packaging reaction was done using Gigapack III XL packaging extracts (Stratagene), a kit which contains all required enzymes necessary to pack concatemeric DNA into preformed λ phage particles. The packaging was carried out as described in the Stratagene manual.

Transduction into *E. coli* XL 1-Blue MRF' was performed by the following standard methods. LB medium supplemented with 10 mM $MgSO_4$ and 0.2% (w/v) maltose was inoculated with a single colony of *E. coli* XL 1-Blue MRF' and grown at 37° C. for 4-6 hours. After cell harvesting by centrifugation, the cells were diluted to an $OD_{600}$ of 0.5 with sterile 10 mM $MgSO_4$ solution. Two hundred µL of cell solution was then infected with in vitro packaged phage and incubated for 30 min at room temperature. Additional LB broth was added and after incubation for 1 hour, 100 µL aliquots were plated on LB plates containing 100 µg/mL apramycin and incubated at 37° C. overnight. To evaluate the quality of the constructed library, randomly picked colonies were proliferated in LB medium supplemented with 100 µg/mL apramycin. Cosmid DNA was then isolated according to standard isolation procedures and used for restriction enzyme digests.

Labeling, Synthesis of Hybridization Probes and Colony Hybridization

Gene probes were labeled by PCR using the digoxigenin (DIG) system (Roche). The 4,6-dehydratase gene was amplified by PCR from genomic *S. griseoflavus* DNA using a method developed by Bechthold et al. Decker, H. et al. *A general approach for cloning and characterizing dndp-glucose dehydratase genes from actinomycetes. FEMS Microbiology Letters* 141:195-201 (1996) The PKS probe was prepared from plasmid pIJ2345, which contains parts of the actinorhodin minimal PKS (actI) of *S. coelicolor*. Malpartida, F. and Hopwood, D. *Physical and genetic characterisation of the gene cluster for the antibiotic actinorhodin in Streptomyces coelicolo A*3(2). *Mol. Gen. Genet* 205:66-73 (1986). Labeled DNA probes were purified by gel electrophoresis and labeling efficiency was estimated in a spot test with a DIG-labeled control.

Colony hybridization was carried out as described in the DIG user manual (Roche, online) for membrane hybridization. Roche, Molecular &. Biochemicals. http://biochem.roche.com/prodinfo_fst.htm?/prod_inf/manuals/dig_man/dig._joc.htm. Briefly, colonies were grown overnight on LB agar containing 100 µg/mL apramycin. Nylon membranes (Roche) were placed on the agar plates and punched to mark the orientation. After a short incubation time, the membranes were removed and successively blotted for 15 minutes on Whatmann 3MM paper soaked in denaturation, neutralization and 2×SSC solutions. UV-light was used to cross-link the transferred DNA to the membrane. Membranes were then pre-hybridized for 2 hours at 42° C. in DIG Easy Hyb hybridization solution. Probes were denatured by boiling to produce single-stranded DNA and added to start the hybridization process. Probe concentration, hybridization time and temperature, and the stringency of subsequent washing steps with SSC solution were determined empirically for each probe (e.g., 2× at 45° C. with 2 mol SSC solution for 15 min., then 2× at 68° C. with 0.1 mol SSC solution for 30 min). To reduce nonspecific binding of the anti-digoxigenin-AP conjugate, the membrane was treated with blocking buffer for 30-60 min before the antibody solution was added. After removal of unbound antibodies, nitroblue tetrazolium salt (NBT) and 5-bromo-4-chloro-3-indolyl phosphate toluidinum salt (BCIP), the colorimetric substrates for AP, were added to initiate the color reaction.

Cosmid DNA isolated from clones hybridizing with both probes were analyzed by restriction mapping and Southern blot experiments. In order to confirm that the cosmid DNA indeed contained genes of the gilvocarcin gene cluster, the corresponding cosmids were introduced into *S. lividans* TK24 or *S. albus* by protoplast fusion. Hopwood, D. A. *Genetic contributions to understanding polyketide synthases. Chem. Rev.* 97:2465-2497 (1997); Hopwood, D. A. et al. *Genetic Manipulation of Streptomyces. A Laboratory Manual* (The John Innes Foundation, Norwich, UK) (1985); Kieser, T., Bibb, M. J., Buttner, M. J., Chater, K. F. and Hopwood, D. A. *Practical Streptomyces Genetics* (The John Innes Foundation, Norwich, UK) (2000). The resulting recombinant strains were then screened for gilvocarcin resistance and the production of new metabolites. Resistance against gilvocarcin V and/or a production of gilvocarcins or biosynthetic intermediates with the gilvocarcin chromophore, were easily detected on TLC with use of the unique yellow fluorescence (UV light, 366 nm), which proved the presence of genes of the gilvocarcin pathway.

Nucleotide Sequence Analysis

The nucleotide sequence of isolated clones was determined using conventional methodology. Automated thermocycle sequencing of pUC19 or pBluescript II SK(+)-based subclones using taq DNA polymerase and fluorescent dye-labeled terminators was carried out at the UK biotechnology resource service laboratory on an ABI 377 and 310 DNA sequencers. Both, standard (M13 forward and reverse, T7, or T3) and custom made primers (18-21 nucleotides) were used.

Functional Assignment of the Gilvocarcin Biosynthetic Gene Cluster

The genes encoding the PKS and associated enzymes are in a type II PKS arrangement, in which the minimal PKS gene cluster, encoded by gilABC (consisting of ketosynthase (KS) α, KSβ, and the acyl carrier protein (ACP)), is flanked by the PKS-associated ketoreductase (KR, encoded by gilF) and two cyclases (encoded by gilG and gilK). Unexpectedly, the genes gilP and gilQ, which encode a malonyl CoA:ACP transacylase (MAT) and an acyl transferase (AT), respectively, were found to be located further downstream of gilABC. Although essential for polyketide biosynthesis, MATs are usually not found in type-II PKS gene clusters, and are often 'recruited' from the fatty acid synthase. Summers, R. G., Ali, A., Shen, B., Wessel, W. A. and Hutchinson, C. R. *Biochemistry* 34:9389-9402 (1995). The gilvocarcin gene cluster disclosed herein is the third example in which such a gene was located, but the first one where the cluster is associated with a known structure. Novakova, R.; Bistakova, J.; Homerova, D.; Rezuchova, B.; Kormanec, J. *Gene* 297:197-208 (2002). GilQ resembles AT proteins found in producers of aromatic polyketides with starter units other than acetate, such as doxorubicin, enterocin, etc. Hutchinson, C. R. *Chem. Rev.* 97:2525-2536 (1997); Moore, B. S. and Hertweck, C. *Nat. Prod. Rep*). 19:70-99 (2002); Marti, T., Hu, Z., Pohl, N. L., Shah, A. N. and Khosla, C. *J. Biol. Chem.* 275:33443-33448 (2000). Therefore, gilQ might play a role in the choice of the starter unit (propionate vs. acetate for the production of gilvocarcin V and gilvocarcin M, respectively).

The following genes are suspected to be responsible for the post-PKS tailoring steps including the above mentioned biosynthetic steps towards the key structural features of GV. Four oxygenase-encoding genes were found (gilOI, gilOII, gilOIII and gilOIV). Genes gilOI and gilOIV encode FAD-dependent oxygenases assumed to catalyze the oxidative rearrangement of a putative angucyclinone-precursor to the unique coumarin-based aromatic core of the gilvocarcins. The corresponding enzymes gilOI and gilOIV are closely related to jadF and jadH (gilOI: 37% aa-identity to jadF and 41% aa-identity to jadH; gilOIV: 37% aa-identity to jadF and 29% aa-identity to jadH), which probably catalyze a similar rearrangement in the jadomycin pathway.

The other two oxygenases, gilOII and gilOIII, are most likely responsible for the anthrone oxidation leading to the angucyclinone intermediate X (gilOII), and for the generation of the 8-vinyl group. For the latter, we assume a hydroxylation in 1"-position through gilOIII followed by dehydration, since gilOIII is a P-450 hydroxylase predestined for such a reaction. Other oxidoreductase encoding genes are gilH (encoding a KR presumably involved in the hydroquinone generation) and gilR (encoding an oxidoreductase of unclear function).

Figure 7:
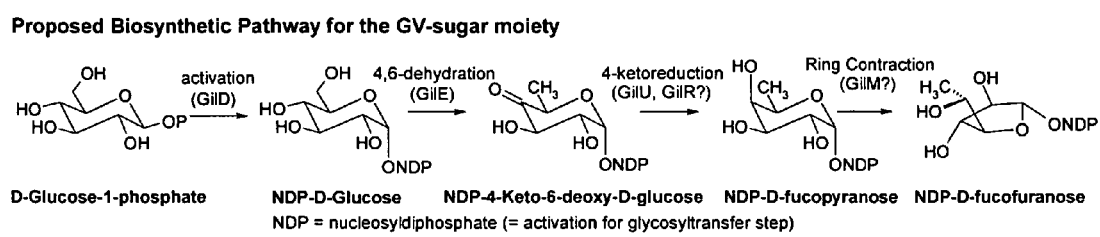
FIG. 7. illustrates proposed biosynthetic pathway for gilvocarcin V sugar moiety.

The C-glycosidically linked D-fucofuranose is a unique deoxysugar not found in any other polyketide, and whose biosynthesis requires only a few enzymes (FIG. 7). Hosoya T. et al. *J. Am. Chem. Soc.* 116:1004-1015 (1994). This is confirmed by the presence of only a few typical deoxysugar biosynthesis genes in the gil cluster. Two of these crucial genes, gilD and gilE, encode NDP-glucose synthase and 4,6-dehydratase, respectively. A third gene possibly involved in the D-fucose biosynthesis is gilU located at the end of the gil cluster. GilU, apparently an epimerase/dehydratase, or oxidoreductase gilR, might function as 4-KR, while it is unclear how the contraction from the pyranose to the furanose is catalyzed. Without intending to be bound by theory, gilM is a possible candidate to encode the enzyme responsible for shrinking the pyranose to furanose.

GilGT encodes the glycosyl transferase (GT) responsible for the unusual p-OH activated C-glycosylation. Synthetic model studies suggest that the favored mechanism for C-glycosyltransfer is an initial O-glycosylation followed by a Fries-like rearrangement. See e.g., Hosoya, T. et al. *J. Am. Chem. Soc.* 116:1004-1015 (1994); Palmacci, E. R. and Seeberger, P. H. *Org. Lett.* 3:1547-1550 (2001). Although principally possible, it is difficult to imagine in an enzymatic environment that such a rearrangement to the p-position occurs. GilGT resembles mostly lanGT2 and urdGT2 both of which transfer D-olivoses to angucyclinone acceptor molecules, the latter being also a C-GT. Künzel, E., Faust, B., Oelkers, C., Weissbach, U., Bearden D. W., Weitnauer, G., Westrich, L., Bechthold, A. and Rohr, J. *Inactivation of the urdGT2 Gene, Which Encodes a Glycosyltransferase Responsible for the C-Glycosyltransfer of Activated D-Olivose, Leads to Formation of the Novel Urdamycins* 1, J, and K J. Am. Chem. Soc. 121:11058-11062 (1999). However, in contrast to gilGT, urdGT2 places its sugar moiety ortho to a phenolic OH-group. An interesting novelty of gilGT is its unusual size, due to its N-terminal part being approximately 120 amino acids longer than any other polyketide GT found so far. The BLAST analysis of the deduced aa-sequence of gilGT (495 aa, MW 53846 g/Mol) revealed 38% aa-identity with lanGT2 from the landomycin producer *S. cyanogenus*, 31% identity with urdGT2 from *S. fradiae* Tü2717, and 25% identity with jadS, the O-GT of the jadomycin pathway from *S. venezuelae*. Without intending to be bound by theory, the similarity of gilGT with lanGT2, urdGT and jadS may point to an angucyclinone-shaped acceptor substrate for gilGT, since lanGT2, urdGT2 and jadS transfer their sugar substrates to an angucyclinone-type aglycon. Künzel, E. et al. *J. Am. Chem. Soc.* 121:11058-11062 (1999); Bechthold, A. and Rohr, J. *Bioorganic Chemistry* (eds. Diederichsen, U., Lindhorst, T. K., Westermann, B. & Wessjohann, L. A.) 313-321 (Wiley-VCH, Weinheim, 1999); Kirschning, A., Bechthold, A. and Rohr, J. *Chemical and Biochemical Aspects of Deoxysugars and Deoxysugar Oligosaccharides. Topics Curr. Chem.* 188:1-84 (1997); Wohlert, S.-E., Bechthold, A., Beninga, C., Henkel, T., Holzenkämpfer, M., Kirschning, A., Oelkers, C., Ries, M., Weber, S., Weissbach, U., Westrich, L. & Rohr, J. *Bioorganic Chemistry* (eds. Diederichsen, U., Lindhorst, T. K., Westermann, B. & Wessjohann, L. A.) 305-312 (Wiley-VCH, Weinheim, N.Y., Chichester, Brisbane, Singapore, Toronto, 1999); Hoffmeister, D., Ichinose, K., Domann, S., Faust, B., Trefzer, A., Dräger, G., Kirschning, A., Fischer, C., Künzel, E., Bearden, D. W., Rohr, J. and Bechthold, A. *The NDP-Sugar Co-Substrate Concentration and the Enzyme Expression Level Influence the Substrate Specificity of Glycosyltransferases: Cloning and Characterization of Deoxysugar Biosynthetic Genes of the Urdamycin Biosynthetic Gene Cluster. Chem. Biol.* 7:821-831 (2000); Trefzer, A., Hoffmeister, D., Künzel, E., Stockert, S., Weitnauer, G., Westrich, L., Rix, U., Fuchser, J., Bindseil, K. U., Rohr, J. and Bechthold, A. *Function of Glycosyltransferase Genes Involved in Urdamycin a Biosynthesis. Chem. Biol.* 7:133-142 (2000); Trefzer, A., Fischer, C., Stockert, S., Westrich, L., Künzel, E., Girreser, U., Rohr, J. and Bechthold, A. *Elucidation of the Function of Two Glycosyltransferase Genes (aanGT1 and lanGT4) Involved in Landomycin Biosynthesis and Generation of New Oligosaccharide Antibiotics. Chem. Biol.* 8:1239-1252 (2001); Krohn, K. et al, *Topics Curr. Chem.* 188:127-195 (1997); Westrich, L., Domann, S., Faust, B., Bedford, D., Hopwood, D. A. and Bechthold, A. *Cloning and Characterization of a Gene Cluster from Streptomyces cyanogenus S136 Probably Involved in Landomycin Biosynthesis. FEMS Microbiol. Lett.* 170:381-387 (1999).

Methods

ORF assignments were accomplished using the GCG software package (University of Wisconsin) and the NCBI database. When applying the GCG software on *Streptomyces*, assignment priority will be given to ORFs with consistently high G/C %. Preliminary gene assignments were then derived from the translated amino acid sequence similarity of translated genes of known function using the BLAST (Basic Local Alignment Search Tool) program, and standard protein sequence data bases (Genbank, EMBO, Swiss Prot). Altschul, S. F., Gish, W., Miller, W., Myers, E. W. and Lipman, D. J. *Basic Local Alignment Research Tool. J. Mol. Biol.* 215:403-410 (1990); Altschul, S. F. and Lipman, D. J. *Protein Data Base Searches for Multiple Alignments. Proc. Natl. Acad. Sci. USA* 87: 5509-5513 (1990); Altschul, S. F. et al. *Gapped BLAST and Psi-BLAST—A New Generation of Protein Database Search Programs. Nucl. Acid Res.* 25:3389-3402 (1997).

Host-Vector System

Identification and cloning of the gilvocarcin V gene cluster led to the discovery of a host-vector system for the efficient recombinant production of both novel and known polyketides. The coding sequences which collectively encode a gilvocarcin V gene cluster or hybrids, mutants, analogs or derivatives thereof, can be inserted into one or more expression vectors, using methods known to those of skill in the art. The replacement gene cluster need not correspond to the complete native gilvocarcin gene cluster but need only encode a minimal PKS gene cluster to catalyze the production of a polyketide.

The recombinant vector(s) of the present invention includes replacement gene clusters derived from a single gene cluster, or may comprise hybrid replacement gene clusters with, e.g., a gene of one cluster replaced by the corresponding gene from another gene cluster. For example, acyl carrier proteins (ACPs) or certain deoxysugar genes are readily interchangeable among different synthases without an effect on the product structure. Furthermore, a given ketosynthase (KS) or ketoreductase (KR) may recognize or reduce polyketide chains of different chain lengths. Accordingly, these genes may be freely interchangeable in the constructs described herein. Thus, the replacement clusters of the present invention can be derived from any combination of PKS gene sets, which ultimately function to produce an identifiable polyketide.

Expression vectors also include control sequences operably linked to the desired PKS coding sequence. Suitable expression systems for use with the present invention include systems, which function in eucaryotic and procaryotic host cells. However, procaryotic systems are preferred, and in particular, systems compatible with Streptomyces species are of particular interest. Control elements for use in such systems include promoters, optionally containing operator sequences, and ribosome binding sites. Particularly useful promoters include control sequences derived from PKS gene clusters, such as one or more act promoters. However, other bacterial promoters, such as those derived from sugar metabolizing enzymes, such as galactose, lactose (lac) and maltose, will also find use in the present constructs. Additional examples include promoter sequences derived from biosynthetic enzymes such as tryptophan (trp), the beta-lactamase (bla) promoter system, bacteriophage lambda PL, and T5. In addition, synthetic promoters, such as the tac promoter, which do not occur in nature also function in bacterial host cells.

Other regulatory sequences may also be desirable which allow for regulation of expression of the replacement PKS gene cluster relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored and this characteristic provides a built-in marker for selecting cells successfully transformed by the present constructs.

The various subunits of gene clusters of interest can be cloned into one or more recombinant vectors as individual cassettes, with separate control elements, or under the control of, e.g., a single promoter. These subunits can include flanking restriction sites to allow for the easy deletion and insertion of other subunits so that hybrid gene clusters can be generated. The design of such unique restriction sites is known to those of skill in the art and can be accomplished using the techniques described above, such as site-directed mutagenesis and PCR.

Further, the vectors, which collectively encode a replacement gene cluster can be inserted in to one or more host cell, using methods known to those of skill in the art. As such, the present invention also provides host cells which have their naturally occurring gene substantially deleted, transformed with vectors encoding a replacement gene cluster or parts thereof, for the production of active polyketides. The invention provides for the production of significant quantities of product at an appropriate stage of the growth cycle. The polyketides so produced can be used as therapeutic agents, to treat a number of disorders, depending on the type of polyketide, like immunosuppressants, anti-tumor agents, as well as for the treatment of viral, bacterial and parasitic infections. The ability to recombinantly produce polyketides also provides a powerful tool for characterizing biosynthetic enzymes and the mechanism of their actions.

More particularly, host cells for the recombinant production of the subject polyketides can be derived from any organism with the capability of harboring a recombinant PKS gene cluster. Thus, the genetically engineered host cells of the present invention can be derived from either procaryotic or eucaryotic organisms. Preferably, the host may be *E. coli*. However, more preferred host cells are those constructed from the actinomycetes (act), a class of mycelial bacteria which are abundant producers of a number of polyketides. A particularly preferred genus for use with the present system is *Streptomyces*. Thus, for example, *S. ambofaciens, S. argillaceus, S. avermitilis, S. azureus, S. cinnamonensis, S. coelicolor, S. curacoi, S. cyanogenus, S. erythraeus, S. fradiae, S. galilaeus, S. glaucescens, S. globisporus, S. griseus, S. hygroscopicus, S. lividans, S. parvulus, S. peucetius, S. rimosus, S. roseofulvus, S. thermotolerans, S. venezuelae, S. violaceoruber*, among others, will provide convenient host cells for the subject invention. See e.g., Hopwood, D. A. and Sherman, D. H. Ann. Rev. *Genet.* 24:37-66 (1990); O'Hagan, D. *The Polyketide Metabolites* (Ellis Horwood Limited, 1991).

The above-described host cells are genetically engineered by deleting the naturally occurring PKS genes or genes encoding post-PKS tailoring enzymes therefrom, using standard techniques, such as by homologous or heterologous recombination. See e.g., Khosla, C. et al. *Molec. Microbiol.* 6:3237 (1992) One or more recombinant vector, collectively encoding a replacement gene cluster of the present invention, is then introduced into a host cell. The vector(s) can include native or hybrid combinations of gilvocarcin gene cluster subunits, or mutants, analogs, or derivatives thereof. Methods for introducing the recombinant vectors of the present invention into suitable host cells are known to those of skill in the art and typically include the use of $CaCl_2$ or other agents, such as divalent cations and DMSO. DNA can also be introduced into bacterial cells by electroporation. Once the genes or gene clusters are expressed, the polyketide producing colonies can be identified and isolated using known techniques. The produced polyketides can then be further characterized, e.g. by NMR and mass spectroscopy.

Generation of New Gilvocarcin-Type Compound Producing Hybrids, Mutants, Analogs and Derivatives of *Streptomyces griseoflavus*

The generation of new gilvocarcin-type drugs, and gilvocarcin analogs and derivatives thereof can be produced by known methods in the art. Native gene sequences or parts thereof can be used alone or in combination with non-native gene sequences or parts thereof to produce analogs or hybrids of *Streptomyces griseoflavus*. For example, the replacement gene or gene cluster or subunits thereof of interest can be obtained from an organism that expresses the same, using recombinant methods, such as by screening cDNA or genomic libraries, derived from cells expressing the gene of interest, or by deriving the gene from a vector known to include the same. The gene can then be isolated and combined with other desired genes, using standard techniques. If the gene in question is already present in a suitable expression vector, it can be combined in situ, with, e.g., other PKS subunits or genes encoding tailoring enzymes such as deoxysugar genes, as desired. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. Edge. *Nature* 292:756 (1981); Nambair et al. *Science* 223:1299 (1984); Jay et al. *J. Biol. Chem.* 259:6311 (1984).

The replacement gene clusters of the present invention are derived from a single gene cluster, or may comprise hybrid replacement gene clusters with, e.g., a gene for one cluster replaced by the corresponding gene from another gene cluster. Non-limiting exemplary non-gilvocarcin V biosynthetic genes may be subunits of the gilvocarcin M, gilvocarcin E, defucosyl-gilvocarcin V, ravidomycin, deacetyl-ravidomycin, FE35A, FE35B, chrysomycin A, chrysomycin B, BE-12406 A, or BE-12406 B gene cluster. For example, deoxysugar pathways have common enzymes, which start the pathway, and which then can be complemented with various genes known from various sugar pathways in order to create novel or altered sugar moieties. Accordingly, these genes are freely interchangeable in the constructs described herein. Thus, the replacement clusters of the present invention can be derived from any combination of gene sets, which ultimately function to produce an identifiable new polyketide-type compound.

Examples of hybrid replacement gilvocarcin gene clusters include clusters with genes derived from two or more of the act gene clusters, such as granaticin (gra), gilvocarcin (gil), urdamycin (urd), landomycin (lan), mithramycin (mtm), tetracenomycin (tcm), oxytetracycline (otc), tetracycline (tet), erythromycin (ery), oleandomycin (ole), griseusin, nanaomycin, medermycin, daunorubicin, tylosin, carbomycin, spiramycin, avermectin, monensin, nonactin, curamycin, rifamycin and candicidin synthase gene clusters, among others.

Mutations can be made to the native gene sequences and such mutants used in place of the native sequence, so long as the mutants are able to function with other genes to collectively catalyze the synthesis of an identifiable polyketide. Such mutations can be made to the native sequences using conventional techniques such as by preparing synthetic oligonucleotides including the mutations and inserting the mutated sequence into the gene encoding a PKS subunit using restriction endonuclease digestion. See e.g., Kunkel, T. A. *Proc. Natl. Acad. Sci. USA* 82:448(1985); Geisselsoder et al. *BioTechniques* 5:786 1987). Alternatively, the mutations can be effected using a mismatched primer (generally 10-20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods Enzyvnol.* 100:468 (1983). Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See e.g., Dalbie-McFarland et al. *Proc. Natl. Acad. Sci USA* 79:6409 (1982).

In summary, this mixing and matching on biosynthetic genes, also called combinatorial biosynthesis is a new method of drug derivatization and SAR (structure-activity-relationship) assessment, which not only generates new drug analogs and derivatives but also the bacterial mutant strains for the biotechnological production of the new drugs.

Gene recombination is a well-known method in the art used for generating new gilvocarcin-type drug analogs and derivatives and new bacterial mutants. For example, gene recombination involves transforming a host cell, including the GV producer *Streptomyces griseoflavus* Gö 3592 or the newly generated GV-producer *S. lividans* TK24 (cos-G9B3) or other strains, with a recombinant vector encoding specific foreign genes. For the plasmid constructions, *Streptomyces-E. coli* shuttle vectors containing the strong constitutive ermE* promoter, which allows an overexpression of the inserted genes can be used. The recombinant vectors may be transferred into a host cell by either protoplast transformation or conjugal plasmid transfer. Non-limiting exemplary suitable genes and plasmids known in the art include the oxygenase genes jadF,G,H, and the GT-encoding genes jadS, urdGT2, lanGT2 and various other plasmids with deoxysugar biosynthesis genes.

Gene disruption, a method of generating a knockout or minus-mutants, can also be used to generate mutations for inclusion in a replacement PKS gene cluster. Knockouts are made by standard methods well established in the art, namely, insertional inactivation and in-frame gene deletion. See, e.g., Künzel, E.; Faust, B.; Oelkers, C.; Weissbach, U.; Bearden D. W.; Weitnauer, G.; Westrich, L., Bechthold, A. and Rohr, J. *J. Am. Chem. Soc.* 121:11058-11062 (1999); Westrich, L.; Domann, S.; Faust, B.; Bedford, D.; Hopwood, D. A. and Bechthold, A. *FEMS Microbiol. Lett.* 170, 381-387 (1999); Remsing, L. L., Garcia-Bernardo, J., Gonzalez, A., Kunzel, E., Rix, U., Brana, A. F., Bearden, D. W., Mendez, C., Salas, J. A. and Rohr, J. *Ketopremithramycins and Ketomithramycins, Four New Aureolic Acid-Type Compounds Obtained Upon Inactivation of Two Genes Involved in the Biosynthesis of the Deoxysugar Moieties of the Antitumor Drug Mithramycin by Streptomyces argillaceus, Reveal Novel Insights into Post-Pks Tailoring Steps of the Mithramycin Biosynthetic Pathway. J. Am. Chem. Soc.* 124:1606-1614 (2002).

Generally, insertional inactivation is obtained by subcloning a gene fragment from a strain containing the gene of interest into a suitable plasmid (e.g. pBSKT, pBluescript or pUC18-derivatives etc.), inserting an apramycin or other resistance cassette into the plasmid and transformation of this plasmid construct into the same strain from which the gene of interest came. Selection for both thiostreptone resistance (in the plasmid) and for apramycin or other suitable antibiotic resistance then indicates the knockout of the target gene. A stable double-crossover mutant is achieved by replacing the wild-type region by the in vitro-altered one. Remsing, L. et al. *J. Am. Chem. Soc.* 124:1606-1614 (2002).

Another method to inactivate genes is the Donnenberg method. See e.g., Donnenberg, M. S. and Kaper, J. B. *Construction of an Eae Deletion Mutant of Enteropathogenic Escherichia Coli by Using a Positive-Selection Suicide Vector. Infect. Immun.* 59: 4310-4317 (1991); Donnenberg, M. S. and Kaper, J. B. *Enteropathogenic Escherichia coli. Infect. Immun.* 60:3953-3961 (1992); Donnenberg-laboratory webpage: http://medschool.umaryland.edu/infemsd/resources.htm. In this method, suitable fragments for gene inactivation are cloned into pCVD442 and introduced into *E. coli* SM10-λ. The *E. coli* SM10-λ strain supplies the tra genes for conjugation of the pCVD442 inactivation construct into *E. coli* RR1 cells containing cos-G9B3. Cells growing under selection for apramycin, ampicillin and streptomycin (for streptomycin sensitive *E. coli* SM10-λ donor cells) should have the pCVD442 derivative integrated into cos-G9B3 via a single cross over event. Growing the cells without the addition of ampicillin and plating them out on agar plates containing 5% (w/v) sucrose should give colonies containing either the original cos-G9B3 or a mutated version of cos-G9B3 with the desired deletion. Restriction enzyme analysis is used to differentiate between these two colonies.

Also, the recently developed REDIRECT© technology can be used, which allows a fast insertion of an antibiotic resistance marker into the gene of interest through PCR. See e.g., Gust, B., Kieser, T. and Chater, K. F. *Redirect Technology: PCR Targeting System in Streptomyces coelicolor.* The John Innes Center; www.plantbioscience.com (2002).

As an alternative method for generating knockouts, in-frame gene deletion can be used to inactivate unwanted biosynthetic genes. Kulowski, K. et al. *Functional characterization of the jadI gene as a cyclase forming angucyclinones. Journal of the American Chemical Society* 121:1786-1794 (1999). Such methods are known to those skilled in the art.

EXAMPLES

The generation of the specific gene minus mutants such as, inter alia, gilGT, gilOI, gilOIV and gilMT are useful for determining the biosynthetic steps of gilvocarcin V and lead to the creation of gilvocarcin-type drug mutants and the discovery of new gilvocarcin-type drug analogs and derivatives thereof.

Inactivation of GilGT

Figure 8:
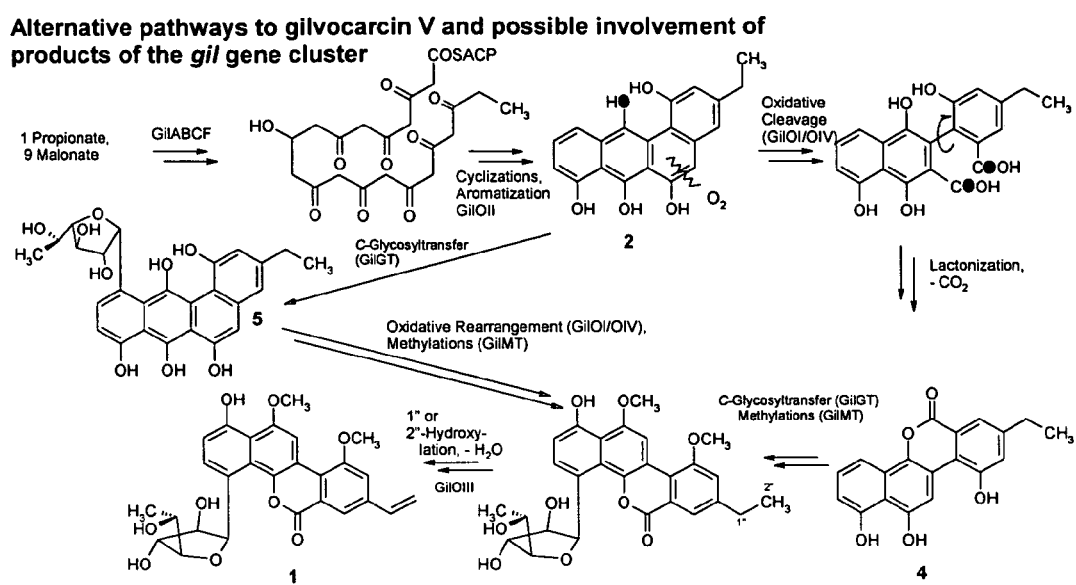
FIG. 8. illustrates the hypothesized alternative pathways to gilvocarcin V and possible involvement of products of the gilvocarcin gene cluster.

For generation of a gilGT-minus-mutant, an in-frame deletion of a 267 base-pair (bp) segment flanked by two XhoI restriction sites within the gilGT gene is anticipated. For this, a SphI fragment of cos-G9B3 carrying gilGT is cloned into the same site of pUC19. Digestion with XhoI and religation of the vector removes the 267 bp-fragment. The resulting shorter gene fragment is then rescued as an EcoRI-HindIII fragment and cloned into a suitable *Streptomyces* suicide plasmid (e.g. pBSKT or pHZ1358; both carrying the tsr thiostrepton resistance gene). The resulting plasmid is then introduced into the *S. griseoflavus* Gö3592 wild type strain either by protoplast transformation or by conjugal transfer from *E. coli* ET12567 (pUB307). Selection for thiostrepton resistance should yield *S. griseoflavus* mutant strains with the entire vector integrated into the chromosome by a single crossover event. These mutants are used to generate a stable double crossover mutant by allowing them to grow without selective pressure and subsequent screening for thiostrepton sensitive mutants. A successful second crossover event, yielding the gilGT-minus mutant strain, is verified by southern hybridization experiments. Without intending to be bound by theory, it is expected that the gilGT-minus mutant will accumulate the acceptor substrate of gilGT, namely either angucyclinone 2 or defucogilvocarvin E 4 (Scheme 1 of FIG. 8).

To confirm that the resulting product(s) of the inactivation gilGT-mutants are really only an effect of the respective gene inactivation, the gilGT-mutants will be complemented with gilGT. For these experiments, gene fragments containing the gilGT gene will be ligated into an expression vector containing an antibiotic resistance marker, such as pEM4, pWHM3 or pUWL201-1 (all thiostreptone), and the minus-mutants will be transformed with the resulting plasmid. Growth in a medium containing thiostreptone will yield the complementation strain, whose product spectrum will be analyzed and compared to the wild-type strain. We expect an essentially identical product spectrum as from the wild-type strain. It is hypothesized that the inactivation of gilGT will help to clarify the sequence of events of the gilvocarcin biosynthesis, and will provide insights regarding the gilGT acceptor substrate, which is important for the generation of new gilvocarcin-type analogs.

Inactivation of GilOI

Without intending to be bound by theory, it is hypothesized that that gilOI/gilOIV encode the enzymes catalyzing a C—C-bond cleaving step for gilvocarcin biosynthesis. As with gilGT, in-frame deletion is possible for gilOI, due to the two suitable KpnI sites found in gilOI, which should allow the deletion of a 578-bp fragment. Inactivation of gilOI follows the general experimental procedure outlined above for the gilGT inactivation and confirmation complementation. Without intending to be bound by theory, we expect due to the inactivation of gilOI/gilOIV an accumulation of either angucyclinone (2) or a glycosylated intermediate, such as (5) as set out in Scheme 1 of FIG. 8.

Mutation of GilGT.

The sequence comparison of gilGT with other glycosyltransferase encoding genes, in particular with urdGT2, showed that gilGT is about 300 base pairs longer at the beginning of the ORF, i.e. gilGT translates into a protein, which contains roughly 100 extra amino acids at its N-terminal end. The mutation, in which this extra portion of gilGT is removed, will be achieved by overexpression of a 300-bp shorter version of gilGT gene into the gilGT-mutant.

It is hypothesized that if the unique portion of gilGT is responsible for forcing the activated D-fucose from the pyranose into the furanose configuration, then the mutation experiment might yield a gilvocarcin bearing a fucopyranose moiety instead of the fucofuranose moiety, presuming that the remaining portion of the GT remains functional.

Synthetic studies suggest that such C-glycosides arise from O-glycoside intermediates via Fries-like rearrangement. Therefore, the glycosylation sequence probably leads first to the O-glycoside, and then the sugar moiety migrates to the neighbor carbon atom. For most C-glycosides, like the C-glycosidic D-olivose in urdamycin A, this is an ortho-shift. However, gilvocarcin V does not possess an oxygen atom in ortho-position, and since the Fries-rearrangement allows both, an o- and p-shift the C-glycosylation must proceed via the p-OH group. We hypothesize that the unique extra segment of gilGT might encode larger binding sites enabling this more complicated p-Fries rearrangement (e.g. through suiting two donor and two acceptor substrates). Therefore, the anticipated mutation gilGT might yield a molecule bearing an O-glycosidically linked sugar at 1-position instead of the usual C-glycosidically linked sugar at 4-position.

Complementation of the GilGT-Minus Mutant with Foreign GT-genes (UrdGT2, LanGT2 or JadS)

If the acceptor substrate of gilGT is angucyclinone (2) then the gilGT-minus-mutant (see above) is likely to be successfully complemented with urdGT2, which is a gene encoding the C-glycosyltransferase of the urdamycin pathway, for which a similar acceptor substrate is discussed. As the result of this complementation experiment, we expect an ortho-C-glycosylated product. This can be either an angucycline, or a novel gilvocarcin-type molecule depending on the substrate flexibility of the downstream enzymes of gilvocarcin biosynthesis. To accomplish this complementation experiment, the urdGT2 genes are inserted into plasmid pEM4, a pHWM3-derived overexpression vector. UrdGT2 is known to possess very broad substrate specificity to both the acceptor as well as the NDP (nucleosyldiphosphate)-activated sugar donor substrate. In case it should be unable to handle activated D-fucose (or one of its biosynthetic intermediates) provided by *S. griseoflavus* Gö3592, the resulting mutant strain *S. griseoflavus* gilGT-minus (urdGT2) can be complemented with designed plasmids (pLN2 derivatives) (See e.g., Rodriguez, L., Aguirrezabalaga, I., Allende, N., Brana, A. F., Mendez, C. & Salas, J. A. *Engineering Deoxysugar Biosynthetic Pathways from Antibiotic-Producing Microorganisms: A Tool to Produce Novel Glycosylated Bioactive Compounds. Chem. Biol.* 9:721-729 (2002)) providing NDP (nucleosyldiphosphate)-D-olivose, NDP-D-mycarose or NDP-D-rhodinose, which are known sugar donor substrates of urdGT2. These plasmids (e.g., pLNR for NDP-D-olivose) are available from our collaboration with J. A. Salas et al., or can be designed. For example, to achieve D-rhodinose, urdR in pLNR (Generates D-Olivose) has to be replaced by mtmU (Generating an Axial 4-OH) and complemented with urdQ; for D-mycarose, pLNR needs to be complemented with mtmC.

Complementation experiments using lanGT2 and jadS can be carried out following the same procedure. Here, O-glycosidically bound sugars are expected, since lanGT2 and jadS yield O-glycosides.

Complementation of the Gil Gene Cluster with Other Suitable Deoxysugar Biosynthesis Genes As illustrated in Scheme 2 of FIG. 7, there are only a few genes necessary to encode the biosynthesis of the deoxysugar moiety of gilvocarcin V. These genes can be complemented with other known genes of sugar pathways to generate various new gilvocarcin-type drugs with alternated sugar moieties. Basically, the gil gene cluster contains all elements to achieve activation (necessary for the glycosyltransfer) and 6-deoxygenation (a common step of all deoxysugar pathways, catalyzed by a 4,6-dehydratase). The gil cluster does not contain genes of branching elements (such as C-methyltransferases), amination elements (transaminases) and further deoxygenating enzymes. Only a few genes are needed to alter the D-fucofuranose moiety of GV sugar into an amino sugar (with or without methyl groups), into a branched sugar, or into a more deoxygenated sugar. Many of these genes, e.g. those encoding the 3-deoxygantion or 2-deoxygenation, are known from many pathways. Without intending to be bound by theory, both, pyranose or furanose GV moieties are expected.

Inactivation Experiments to Generate Increased Hydrophilicity.

Gene inactivation experiments can be used to generate less lipophilic gilvocarcin-type drugs: (i) inactivation of gilMT (presumably the methyltransferase responsible for the introduction of both O-methyl groups in 10- and 12-position), (ii) inactivation of gilE (the 4,6-dehydratase catalyzing the first deoxygenation step in deoxysugar biosynthesis), and (iii) inactivation of gilU (or gilR, one of which is probably the ketoreductase of the sugar pathway). The experimental procedure will be analogous to the above-described examples. Without intending to be bound by theory, we expect that the first experiment should yield unmethylated GV, the second might yield a D-glucose analog of GV, and the third might yield a GV-analog with a keto sugar, which often is found as the hydrate form. All anticipated derivatives should be significantly more hydrophilic than the parent drug. Also, combinations of these mutations, e.g. a gilMT/gilE-double mutant can be envisaged, if the previous experiments are successful.

Determining Gilvocarcin Therapeutic Indications

The gilvocarcins, its analogs and derivatives thereof, of the present invention are useful as antibiotics, antitumor agents, immunosuppressants, antivirals and neuroprotective agents. Considering the fact that gilvocarcins are quite lipophilic compounds making them good candidates to pass the blood-brain barrier (BBB), brain tumors may be treatable by targeted submission of light (e.g., through fiber optics) after gilvocarcin chemotherapy. This would cause only few systemic side effects due to the absence of light elsewhere. This is attractive, since brain tumor surgery is often impossible. Targeted submission of light through fiber optics after gilvocarcin chemotherapy may be also an attractive treatment of prostate cancer. A more selective systemic treatment of leukemia might be possible with photoactivatable drugs like gilvocarcin V, since blood can be channeled outside the human body, where it is light exposed, while no major side effects will occur inside the body due to the exclusion of light. Also treatment of proliferative eye diseases, such as glaucoma, may be another future application of gilvocarcin-type anticancer drugs.

To determine anticancer therapeutic uses of gilvocarcin, its analogs and derivatives thereof, a compound derived from the host-vector recombinant production system is assayed as drugs against selected cancers or diseases in vitro and in vivo. Initially gilvocarcin and gilvocarcin analogs and derivatives are screened against selected human skin, brain, leukemia and prostate cancer cell lines, e.g., UACC-62, MALME-3M, SK-MEL-5 (melanoma), SF-268, SNB-75, U251 (brain tumors), CCRF-CEM, K-562, MOLT-4 (leukemia), and PC-3, DU-145 (prostate). To gain initial toxicity data on non-cancerous cells, similar experiments can be performed using normal epithelial and fibroblast cell cultures, purchased from ATCC or Clonetics.

The MTT assay, which measures the reduction of 3-(4,5-dimethylthiazol-2-yl)-2,5-diphenyl-2H tetrazolium bromide (MTT) by mitochondrial succinate dehydrogenase to an insoluble, colored, formazan product, is performed according to described standard procedures.

The SRB assay is a rapid and sensitive method to measure drug-induced cytotoxicity. It measures the uptake of sulforhodamin B (SRB), which is dependent on the cellular protein quantities, and is performed in 96-well microtiter plates according to the protocol published by Boyd et al. (NCI). See also, Skehan, P. et al. *New colorimetric cytotoxicity assay for anticancer-drug screening. Journal of the National Cancer Institute.* 82:1107-12 (1990).

Although illustrative embodiments of the present invention have been described in detail, it is to be understood that the present invention is not limited to those precise embodiments, and that various changes and modifications can be effected therein by one skilled in the art without departing from the scope and spirit of the invention as defined by the appended claims.

What is claimed:

1. An isolated nucleic acid molecule comprising a polynucleotide sequence selected from the group consisting of:
   a) a gilOI polynucleotide sequence that remains hybridized to the entirety of the full length complement of bases 19892 to 21391 of SEQ ID NO: 1 under stringent conditions of washing twice with 2 molar SSC buffer at a temperature of 45° C. and then twice with 0.1 molar SSC buffer at a temperature of 68° C., and encodes a polypeptide having FAD-dependent oxygenase activity;
   b) a gilOII polynucleotide sequence that remains hybridized to the entirety of the full length complement of bases 11513 to 12196 of SEQ ID NO: 1 under stringent conditions of washing twice with 2 molar SSC buffer at a temperature of 45° C. and then twice with 0.1 molar SSC buffer at a temperature of 68° C., and encodes a post-poly-ketide synthase (post-PKS) tailoring polypeptide having oxygenase activity;
   c) a gilOIII polynucleotide sequence that remains hybridized to the entirety of the full length complement of bases 6576 to 7769 of SEQ ID NO: 1 under stringent conditions of washing twice with 2 molar SSC buffer at a temperature of 45° C. and then twice with 0.1 molar SSC buffer at a temperature of 68° C., and encodes a post-PKS tailoring polypeptide having oxygenase activity; and
   d) a gilOIV polynucleotide sequence that remains hybridized to the entirety of the full length complement of bases 26200 to 27552 of SEQ ID NO: 1 under stringent conditions of washing twice with 2 molar SSC buffer at a temperature of 45° C. and then twice with 0.1 molar SSC buffer at a temperature of 68° C., and encodes a polypeptide having FAD-dependent oxygenase activity.

2. An isolated nucleic acid molecule comprising at least one polynucleotide sequence selected from the group consisting of:
   a) a full length gilOI polynucleotide sequence that encodes the GilOI polypeptide encoded by bases 19892 to 21391 of SEQ ID NO: 1; wherein the polypeptide has FAD-dependent oxygenase activity;
   b) a full length gilOII polynucleotide sequence that encodes the GilII polypeptide encoded by the reverse complement of bases 11513 to 12196 of SEQ ID NO: 1; wherein the polypeptide has oxygenase activity;
   c) a full length gilOIII polynucleotide sequence that encodes the GilOIII polypeptide encoded by the reverse complement of bases 6576 to 7769 of SEQ ID NO: 1; wherein the polypeptide has oxygenase activity; and
   d) a full length giOIV polynucleotide sequence that encodes the GilIV polypeptide encoded by bases 26200 to 27552 of SEQ ID NO: 1; wherein the polypeptide has FAD-dependent oxygenase activity.

3. The nucleic acid molecule of either claim 1 or claim 2 wherein the nucleic acid molecule encodes the gilOI, gilOII, gilOIII and gilOIV oxygenases.

4. The nucleic acid molecule of either claim 1 or claim 2 wherein the nucleic acid molecule encodes the gilOI and gilOIV.

5. A recombinant DNA expression vector comprising the nucleic acid molecule of either claim 1 or claim 2, wherein the nucleic acid is operably linked to expression control sequences.

6. A host cell comprising a recombinant DNA expression vector comprising the nucleic acid molecule of either claim 1 or claim 2, wherein the nucleic acid is operably linked to expression control sequences.

7. A bacterial host cell comprising a recombinant DNA expression vector comprising the nucleic acid molecule of either claim 1 or claim 2, wherein the nucleic acid is operably linked to expression control sequences.

* * * * *

SEQUENCE LISTING

```
<160> NUMBER OF SEQ ID NOS: 16

<210> SEQ ID NO 1
<211> LENGTH: 33825
<212> TYPE: DNA
<213> ORGANISM: Streptomyces griseoflavus
<220> FEATURE:
<221> NAME/KEY: misc_feature
<222> LOCATION: (802)..(4068)
<223> OTHER INFORMATION: ORF1 encoded on the complement of SEQ ID NO:1
<220> FEATURE:
<221> NAME/KEY: misc_feature
<222> LOCATION: (4308)..(5198)
<223> OTHER INFORMATION: ORF2 encoded on the complement of SEQ ID NO:1
<220> FEATURE:
<221> NAME/KEY: misc_feature
<222> LOCATION: (5417)..(6052)
<223> OTHER INFORMATION: ORF3 encoded on the complement of SEQ ID NO:1
<220> FEATURE:
<221> NAME/KEY: misc_feature
<222> LOCATION: (6576)..(7769)
<223> OTHER INFORMATION: ORF4 encoded on the complement of SEQ ID NO:1
<220> FEATURE:
<221> NAME/KEY: misc_feature
<222> LOCATION: (7777)..(9261)
<223> OTHER INFORMATION: ORF5 encoded on the complement of SEQ ID NO:1
<220> FEATURE:
<221> NAME/KEY: misc_feature
<222> LOCATION: (9261)..(10001)
<223> OTHER INFORMATION: ORF6 encoded on the complement of SEQ ID NO:1
<220> FEATURE:
<221> NAME/KEY: misc_feature
<222> LOCATION: (10020)..(11513)
<223> OTHER INFORMATION: ORF7 encoded on the complement of SEQ ID NO:1
```

```
<220> FEATURE:
<221> NAME/KEY: misc_feature
<222> LOCATION: (11513)..(12196)
<223> OTHER INFORMATION: ORF8 encoded on the complement of SEQ ID NO:1
<220> FEATURE:
<221> NAME/KEY: misc_feature
<222> LOCATION: (12354)..(13424)
<223> OTHER INFORMATION: ORF9 encoded by the complement of SEQ ID NO:1
<220> FEATURE:
<221> NAME/KEY: misc_feature
<222> LOCATION: (13814)..(15466)
<223> OTHER INFORMATION: ORF10 encoded by the complement of SEQ ID NO:1
<220> FEATURE:
<221> NAME/KEY: CDS
<222> LOCATION: (15619)..(16641)
<223> OTHER INFORMATION: ORF11
<220> FEATURE:
<221> NAME/KEY: misc_feature
<222> LOCATION: (16690)..(17697)
<223> OTHER INFORMATION: ORF12 encoded by the complement of SEQ ID NO:1
<220> FEATURE:
<221> NAME/KEY: misc_feature
<222> LOCATION: (17697)..(18761)
<223> OTHER INFORMATION: ORF13 encoded by the complement of SEQ ID NO:1
<220> FEATURE:
<221> NAME/KEY: CDS
<222> LOCATION: (18938)..(19576)
<223> OTHER INFORMATION: ORF14
<220> FEATURE:
<221> NAME/KEY: CDS
<222> LOCATION: (19892)..(21391)
<223> OTHER INFORMATION: ORF15
<220> FEATURE:
<221> NAME/KEY: CDS
<222> LOCATION: (21736)..(22992)
<223> OTHER INFORMATION: ORF17
<220> FEATURE:
<221> NAME/KEY: CDS
<222> LOCATION: (24183)..(24449)
<223> OTHER INFORMATION: ORF19
<220> FEATURE:
<221> NAME/KEY: CDS
<222> LOCATION: (25241)..(26188)
<223> OTHER INFORMATION: ORF21
<220> FEATURE:
<221> NAME/KEY: CDS
<222> LOCATION: (26200)..(27552)
<223> OTHER INFORMATION: ORF22
<220> FEATURE:
<221> NAME/KEY: CDS
<222> LOCATION: (28501)..(29517)
<223> OTHER INFORMATION: ORF24
<220> FEATURE:
<221> NAME/KEY: CDS
<222> LOCATION: (30206)..(32239)
<223> OTHER INFORMATION: ORF25
<220> FEATURE:
<221> NAME/KEY: CDS
<222> LOCATION: (32379)..(33392)
<223> OTHER INFORMATION: ORF26

<400> SEQUENCE: 1
ctgcagatcc caaggtcat  ccgccgcgcc gccgtcgccg accccggctg gcgcctcgtc      60
gtcgccgacg ccgaccagat ggaaccgagg gtgctggcgg ccatctcccg cgaccccggc     120
ctgatggagg tggccggccg ggagggcgac ctctaccagt cggtgtccga ccgcgccttc     180
tccggcgacc gcgcccaggc caagctcgcc gtcctcggcg ccgtctacgg ccagacctcc     240
ggcgacggcc tgaagaacct cgccgcgctc aggcgccgct tccccaaggc ggtggcctac     300
gtcgacgagg ccgcccgcgc cggcgaggag ggccgtctcg tacggacctg gctgggccgc     360 acctgccccgc ccgccgtccg cccgacggac gacgcggcgg aggaggccgg catcccgccc     420
gcccaggagg agccgggccc agcggcccga ccgtgggccc cggaggccga ggcccgcccg     480
```

-continued

| | |
|---|---|
| tgggtcccgg gctacgcctc gaccgacgcc cgcgcccggg gccgcttcgc ccgcaacttc | 540 |
| gtggtccagg gcagcgccgc cgactgggcc ctgctgctgc tcgcggcgct gcggaggacg | 600 |
| ctgagcggca tggcggccga actggtcttc ttccagcacg acgaggtgat cgtgcactgc | 660 |
| cccgaggagg aggcggcgac ggtggcggag gcgatccggc agtccgccga cctcgccggc | 720 |
| cggctgacgt tcggaccgac ccccgtgcgc ttcccgttca cgacggcggt cgtggagtgc | 780 |
| tacgccgacg ccaagtgatc agctcgccgg ccgggcaccg ccacgagtc cgcgcaactc | 840 |
| ctccaccacg gcccgctcgt ccgtgccgtc cagcgcggcg agcgccgacc gccactgctc | 900 |
| gcgcgcctcg cccaccccgcc cccgctcgcg cagcagcaga ccgtactggt ggcgggccag | 960 |
| accaccggtg tagcggtcgg ctcgggcgtc cgcgcggcgc agcagttcgg cgcactcggc | 1020 |
| gtcggcccgg ccggcgtgcc ccagcagccg cagggcgcgc accaggccga gccgggtctg | 1080 |
| ggactctccg tgccagtcgc cgtgcccggc gaggatgcgc aggctctcct cgaagtgcgg | 1140 |
| cagggcggcg gccggttcac ccagccggag gtgggcgtag ccgatgttgc agtgggcgga | 1200 |
| gtgccgcacg atcaccgctc cgatgcggtc cccgatcacg agcgagcgcc ggtgctggtc | 1260 |
| gatcgccgcg cgcggatcgg tgtgctcgta caggttgccg aggtggctga gggtgacggc | 1320 |
| ctcgccgtag gggtcggcca actgccgcga gtgggtgagg ctctgccgca gtgcccgctc | 1380 |
| cgactccgcg taccggccga gcccttcgag cagcagcccc cggtggttga gggcgcgccg | 1440 |
| gatccaggag acggctccga gccgccgcca gatctccagc gcgcggtcgg tgagggcgag | 1500 |
| ggcctcgccg gtgcgaccgg tcaggaagtg cagccccgcc agatcgccca gcgcgcacgc | 1560 |
| ctcggcggcc tcgtccccga gccgccgcgc cacccgcagg gccgcccgcc cgagcacctc | 1620 |
| cagctcgggg acccggccgc cgcgcaggag gtaggggtgg agcaggcgga ggagtacggc | 1680 |
| gatgtggacg tcgtgacggc cccggtcacc gcccccgccg gtgccctcac cggcgtaccg | 1740 |
| cccgacgagg gtgacgatgt tctccagctc ccggtcgccc caggcgaagg ccgcccccgc | 1800 |
| gtcgtcgaac gggggtacgg acgcgacgtg agcggtgtgc ccggcggct gggacggggt | 1860 |
| cgggcggcgg cggtcgtcct ggtcggggcc gggttcgacg atcgcggtga gggcgcgttc | 1920 |
| ggcgacggcg gcgtaccagc gcagggcggt ctcgcgggg tgctcgcgcg tgccggtccg | 1980 |
| agggccggcg tcctcgcggg gtgcggcgtc ctcgcggggt gcggcatcct cgcggagtac | 2040 |
| ggcctcctcg cggggtgcgg cgccctcgcg gggtgcggcg ccctcgcgga gtacggcgcc | 2100 |
| ctcgcggagt acggcgccct cgcggagtac ggcgccctcg cggagtacgg catcctcgcg | 2160 |
| gagtacggca tcctcgcgga gtacggcgtc ctcgcggagt gcggcgtcct cgcggggcgc | 2220 |
| ggtctgcgga cccgccgccg ctcgggctcg ttcgcgggcg aagtcacgga ccaggtcgtg | 2280 |
| ggggacgtag cggccgtacg cggtctcctc cacgagggcc acgtcgacga gccggtccag | 2340 |
| cgcggcctcc gcccggcgtt cgccggtgcc ggtgagccgg gcgagcagcg gcgcgccgta | 2400 |
| ggcgggcagg tcgagcgcgc cgatgcggca cagggcgagg gcggcgtcgc ggtccgtctc | 2460 |
| acggtcggag acggtgagcg cgtcgtgcgc gacggccagc gagcggcgca cgctgaggtc | 2520 |
| gtcgtactcc aggtgcggca accggctgtc ggtggcggag agctgaccgg cgaggtcgtc | 2580 |
| gggcgtgagg gcccggcgcg cggcgagccg ggccgcgacc acccgcaggg ccagcggaag | 2640 |
| ccggccggta gcgcgacga gcgggtgccc ggcgccgaga ccgtcccggc cggagaccgc | 2700 |
| ccgcagcagg gcggcactgt cctcgtcgga cagcgggccg agcgggacac ggacggcacc | 2760 |
| gtcgagcgtg gtgagcggcg aacgctggt gacgatcacc gcacagcggg gtccgcccgg | 2820 |
| cagcagcggc cgcacctgcg cggcgtccgc ggcgtcgtcc agcaccagga gggtgcgggt | 2880 |

```
gggcgcgagc agcgagcgca gcagggcggc ggccgcgtcc ggccgttcgg ggacggcgca    2940
gggctcggtg cccaggtcgc gcaggagagc gctgagggcc tgggcggggg tgaggggggt    3000
catgccgggg gtcgtgccgt gcaggttgac gtagagctga ccgtcgacga aacgttccgc    3060
cagtgtgtgt gcgacctgga cggcgagcgc gctcttcccc acaccagcgg taccgctgac    3120
gacgacggca gggggcccgg cggcgggccg ggggcacgg gtgagcacac ggatcagctc     3180
gtcccgcacc gcgtcccgcc cggtgaagtg agcaggcgcg ggcggcagtt gcgccggcct    3240
gggcggcaca ccgcccccctc ctgcggcctc cgcgcaccga ccgtgctcct gccgctcccc    3300
ctgccccgc agcacctcca cgtgggcctc gcgcaccccc ggccccggtt cgacgccgag     3360
ttcgtccgcc aggcgggccc gcagatcccg gtggaccacc agcgcctccg cctgacggcc    3420
ggtgcggtgc agcgcgagca tcagctgacg gtggtacgac tcccgcagcg gatgttcggc    3480
ggccagtgcc gccagttcgg gcacgagatc ggccaggcgc tcgccgccca gggccagttc    3540
ggcgtcgtac cgccactcca ggagcagcag ccgcgcctcg cgcagccgcc gcaccagggc    3600
gtagccgccc acttccgggg gcatcccggc cagcgggttc cccgccaca gcgcgagcgc     3660
ggcggcgcac tcgcgcgcca cccgctccca gtcccgggcg gtgtgcgcgg cgcgggcggc    3720
tgcggtgtgc gcgtcgaaga cctggacgtc cacctcgccc tctcccaccc gcagcagata    3780
tccggtgggc acggtgagca gccggcccgg gtcgtcgagc agccgccgca accgggcgac    3840
gtgattgtgc agcgagggca gcgcggagac gggcggcgca ccgccccaca gggcgtcctt    3900
cagcgcctcg acggacacga cccgcccggc gtcgagcagc aacgcgacga acagcgcacg    3960
gagtttggga cttccggtca cctggacgga cccgggggcg tcgggcccct cgccgtcgta    4020
cagcaccggt gttcccagca gtccgaaccg cagtccgcgc cgtgtcacgc cgcaccactg    4080
ccttccgggt gaccgaacgg acaaccaatg gccttatgtt agcgatccgt tggcaaagtc    4140
tgatgtgatc actacatcgg atccggcccg ggggtgcgcg cgtagaacgc gcagctcggg    4200
ggagtgtcgc cgccgcggcc cggtccgcac acgagggttc ccggtcggac agaggtgaac    4260
ggccgggccc tcgttctctt ctgccgccgc gttcgccctt cgggtcagat gacgggcggc    4320
cgtccgagcc gggtgagccg ccacaccgtc cgccagcgca tggcccgccg ctccccggcc    4380
ggctcccgca gcccctccgc gaaaccgccg aaccaggcgc gcagcccctg gaccgaccga    4440
gtccgcagca gggtgagcag gacccacacc ccgaggtgca cggggatcag cgcgagcggc    4500
agccgccgcc gggccagcca gacccggttg cgggcgttca cccggaagta gatcgcgtgc    4560
cgggccggcg aggtcttggg gtgctggagc agcaggtcgg gcgcgtagag gatgcgccac    4620
cccgcgtcgg cggcacgcca ggcgaggtcg gtctcctcgt gcgcgaagaa gaacgcgccg    4680
ggccagtcgc cgatctcgtc gagcatcgac atccgcagcg cgtgcccgcc cccgaggaac    4740
ccggtgacgt accgcccctt catcgggtcc gcctttccga gccggggcac gtgccgctgc    4800
tgcgtctccc ccagctcgtc ggcgatccgg aagccgacga cgccgagccg gtcgtccgcc    4860
gcgtacaact ccccacccg gcgcagcaca tcggcgtcca ccagcagacc gtcgtcgtcc     4920
agttcgacga cgacgtccac gtccccgaac tcccgcagcc gctcgatccc cacgttccgc    4980
ccgcccgggc agccgaggtt ctccgccagc tcgacggtgg tgacctcacc gggcagggac    5040
agccgccggg cgaactcggg cagcggacag ccgttcccca cgatcacgat ccgcgcgggc    5100
gccacgtcct gcttcgccac ggactccagc agcgcgtcca cctcggccgg ccggttcccc    5160
atggtcacga cggcgacggc gatcctcggc gtccccatgc cctcaccca ctccacccgg     5220
ctgctccgct gacgggcgat gctaaccgtt cacggtgagg acgcatgcat gacacccacc    5280
```

-continued

```
accgcggcgt actccgcccc cgccccacac gaacaggaca cacgtgtccc tggtgctcgc    5340
ccggggacga ccggaggggc cccgtgcggc agccgcggcc ggctgccgca cggggccgg     5400
gagcggtcgc cggtcagcgg gtggtgacga aggggctctg gtgcgtgtgc ggggtggtga    5460
gttcgtcgag catggcgatc gcgaggtcgc ggcgcgtcgt ccatgcccgt ccgccgggaa    5520
ggtcggcggt gacccgcagc tcgtcgcccg ggcgtgcctc gtcgctgagc cgggcgggac    5580
gcatgaccgt ccactccagg tcgcgggctc cggtgaggat gtcctccatg cggcgcatgt    5640
ccgcgtacag ggtccgcccg gggccgttgc gcaggatgcc gtagaccggc cgctgccatc    5700
gcaccccgcc ccgggtgacc ggatgtgtca ggccggcgct cacgacgacc aggcgcctga    5760
cgtccgccgc gcgcatcccg tccacgacgg cccgggcgga cgccgagtag accgtgaccg    5820
gcctccagga gtacgcgct cccaggcagg acaggacggc gtcggcgccc ttgaacacgg     5880
acgtcatgtc cgcgacgtcc gtgacgtccg ccgtttccac ggtcagcctc tcccccggag    5940
tgaccgaacc cggacgccgg acgacggcga cgacgtcatg gccggccgca caggccaggg    6000
ccgtcacctg ccgtccggtc gggccgcttg caccgagcac tgctactttc atgccgtctc    6060
cagacgatgc gcggacgatg tacgacgca tgccggacgat gtgcgtcgtg cggtggtcga    6120
gaaggtgccc cggtcggcgc ccttcccgaa cgacgcccca tcgtaggagt cgcggcgccc    6180
ggccccgggt ccgaggccgt gggcaccgtc gagaacaggc cgcccgggcg gggccgttgc    6240
ggcgggcgcc acggagcggg agcgcgggcg gcacgccgcc ggctcccgcc cgcgttcccg    6300
ggcggcacgc cgccacccct caggaggagc cctgccgcgc cgtccgcgcg gacgttgcgg    6360
gggccgtcct ggccagttcg agggcgccca tcggacagga ccggatcaac cgctccacct    6420
gccggacatc gccgaacccg tcggccgccc ccgctgagac ggtgatctgc tgctcggggc    6480
tgcggaagac ggccctggac aacccctcgc actgttcgtg caactcgcac cgccggccgt    6540
cgatcctgac caccgtcacg tcctcgacgg gctcaggcag ttcgtccatg gaacgtcaca    6600
tccatcctct cgatcccgcg gatggtgttg tgcagcctcc aggtcggctc ccccacctcg    6660
atcctgtcga cgtgacggac cagcgcctcc aggaggctct gcccctccag gcgggacagg    6720
gcctgaccga cgcaggcgtg gataccgtgc ccgaaaccga cgtgctgggc cgcgccctgc    6780
cgggcgacgt cgaaggactc cgggtccttc cagaaccgct cgtcacggtt ggccgaaccg    6840
aagaggagga ggacgcgcga tccgcggggc agcgcggctc cgcccagctc cgtgtcctcg    6900
gcgacgtagc gggtgaaccc gcgcagcggc gattccagcc ggatgatctc gttgaaggcc    6960
gacgagacca gggagggtc ctcccgcaga cggcgccact ggtcctggtg cgtgccgagc    7020
agccacagca tgctggagag cgcgctgacg gacgtgtcca tggacggggc gaggaagtca    7080
ccgagcagtc cgggcagcag cttgtcctcg atcttgccct cgcgggcctc cgagacgagt    7140
tcggcacccc agctccccgg acgcagattg ccgggctgtg acatccggtg gaggaactcg    7200
cccatctcgc cgagcagcgg caggccggcc gcgtccggt cgttcagggg accgaaggcg     7260
ttgaatccgg cgctggccca ctccaggagc ctttccttcc cctcgccctc ggccatccc    7320
agcagatcgg gcaccacggc cagcgggaag gcgaccgcga agtcctggac ggcgtcgaac    7380
gacttccggg cgacgaggtc ccggacaaga cggtccgccc aggacgtgac gtacccgttg    7440
atgtcggcca tcgcgcgggg cttcaggtgg cgggccacga gccccgcac gtaggcgtgg     7500
tacggcgggt cgctggtgaa gctactgccc ttctgcgcct tgttcagggt gtcggtcaga    7560
ccgacgccct cgccgacac gaacgtccg tggcggtgca gggccgcgta cacctcgtcg      7620
tagcgggcgg cgcagtgcac ctggtgcgcc gtcaggtaca ccaccggtgc cgcgtcgcgc    7680
```

```
agcgcaccgt acaggggta cgggtcggtt atcgacgcgt ccgtgtacgg atcgagatcg    7740
aggtggggga tcgtcgatgt ggagatcacc gcttcatcct ttccgcgcga ggaggtcttc    7800
gatcagcggc accatgccca cggccgtcgg cgcggtcgcg ccctgctccg ccagtctccg    7860
ggccctggag gagtaggacg gatccccgag catctccttg accacctgcg tgatcgcctc    7920
cggggtgccc tcctcgcggt agagcgtccg cgcgcacccg tagtccgtga ggtgcttcag    7980
cctcgggacg aaggcctcga aggggttgag gatcagctgc ggagtcgccg tgttgatggc    8040
gttgatggcc gtcagtccgc ccgccggatg gatgatcacc tcacaggtcg ggaggatggc    8100
ctccagcggg atccagccgg cgcgcacccg ggggtacttc tcctgcagcc gctgcccctc    8160
cgcctcgccg atggccacga cgacctcgac ctcgagctcc agcagcccgt cgacgatggc    8220
cgagatgcgt ccatcgcgc cggggaaggc gtaccggaag cttcccatcg tcaggcacac    8280
gcgcccggcg tccggagccg tcagcatcca cggctcgatc gcccgctgca tgttgtgcgg    8340
ggtccagcgc atgaaggtgc cggtcgcccc gaccaggccg ggcgggcaga tgtcgatctt    8400
cagtgagggg tcgggcagtg cgtccgagcc gatcctggcc agctcgtccg ccatctcctc    8460
gaggaggtac tcctcgtagc cgccgacgtc gaacaggtcc caggactgcc ggacgaaggg    8520
gatgccgagg aaccgggcgg cgatctcggc accgtgtccc tggctccccg cgatcaggac    8580
gtcggcgccc cacgtccggg cgacgtccac caggtcgtcg aagacgtggc ttccctgacg    8640
cccgaaccag tggcccaggt agggcatctc ctgttcgggc cggtgggggt actcgatcgc    8700
cggcttgccg ccgcggccg ccttgatgct ctcggtcgtg tgcccccggg ccaccggag    8760 ggacggcaga ccgatgccgg tgacggcgcc ggacatctcc tcgaaggacg ccaccaggac    8820
gtcgtgcccg gacaaccgga gtgccgaggc gaggggtccg atggcgaacg cgctggccgg    8880
gctcgtgccc gcggcgtaga agagggcctt cacgcggcgc cctcccgtga ccggtccctt    8940
gtcgcgttcc gcgaagtagg cctccttcag gcccacggtc tcgaagtcga tgacggcgag    9000
gcccgaggtc agcagacgac tcgaacgcag ctcccggacc aggtccaggt agttgtccat    9060
ctcgtcgaag cccaggatga agaaactctc cgcctcacgg ccgtacttga tggcgcgcac    9120
cggtgttatc tccccgcccc gcttcacgaa ggcgccgatg ctggggaaga cgtgctcgtg    9180
ttcgaccgtg atgcgctcgt cgagggacaa ctcgtaccac ggggtgaggt agttgacgac    9240
aaggacggcg gcgaacttca tgccgggctc tccgatcggg ttgcctgcgg acgcagtacg    9300
gcatgcatgt gccagatgtg ggagacgacg ttccggcctt cgtccaccat ctgggcggcg    9360
aggttgtcgg tggggcgtt cacctcgaag gtccgcgggt cgaccatctg cgcgacggcc    9420
tccggcggca gcgagctgtg gtaccgcgtc gcctcgatca ccttgatgtc ccagtcggcg    9480
ccgaacgcct cccgcaactc cggttcgag atgcggcgcg acccgggta gtcggggtc    9540 agctccttcg agaaggtgaa caggtgcagc tcggccccct ccttgcacag ggtccgcagg    9600
agctccgtgt agcgcggcac ctcctcctgc ggcagcgtgt ggaagaaggc gctgtccagg    9660
acggcgtcgt accggacacc ggactccgcg aggcggaagg cgtcggtcac ctggaagtcg    9720
acgctcacgc cgtggtcccg ggccttgtcg cgcccgcact ggacggcgac ctccgagatg    9780
tcgaccgcgg agaccgcag cccccgggaa gccaggtaga gcgcgttgtc tccgagcccg    9840
cagcccagat cgagcacgtg cccgcggaag ccgccgcgat cacagatcgc gcgtacggcc    9900
ggctgcgggc cgccgatgtt ccacggcatg agggggcctg acttctcccc gtcctggtag    9960
agcttctcga aggggatctt ctccgtgctg ccgttggca tcgagcgcca ctcctctcag   10020
agtcctatgg acatgctgtg atggaaggtg ttcaaggggt cccacgcgcg cttcgccgac   10080
```

-continued

| | |
|---|---|
| cgcagacggg cgtagttgtc cttgtagtac aggtggtgcc agggctcccc ggagcggttg | 10140 |
| cgggccgggt ccaggagatc cgcgtcgggt tagttgatgt agcagccgtc cgtgcggccg | 10200 |
| ccggtgacgg gcacccctcc cgtgccggcg aagaactcct cgtagagccc gcgcagccag | 10260 |
| ccgaggtgca gctcgtccag ctccgcgtcc tgccaggccg agaaccagga cgacttcacg | 10320 |
| acggagtccc gctgggggac ggcggcgtcc gacggccccc gccggttgat ctctccccg | 10380 |
| tagctgttga acatgacgta cgaggcctgg ccggggtggt cggcgtgcag gtgccggtgg | 10440 |
| agcaccgaga gctgctcgtc ggtgggtgcc gcgcggtggt aggcggactt ggaggcggag | 10500 |
| cgggcgccca tgacgtcacc gcagtcggcc tgactcatgt agcgggttcc ggtgagccag | 10560 |
| ctcatgacac ccctcgggg gatgcccacc acgccggtgc cctcggtcag ggacgcgacg | 10620 |
| aaccgcgcga ggatctcgcc ctcggggtcc acgtcggcgt cctgctggac catcagctgc | 10680 |
| aggacgcccg agctgacgtg gttcacgaag aaggtggcga acagcgagga ctccggcgac | 10740 |
| cccggctcga gtggcgttc atgccactcg aagaaacgtc tcatcacagt gacgaaggac | 10800 |
| gtctcgtcga tcatggccca ggggaacacc accttctgga cgtgcagtcg gccggcggcg | 10860 |
| cggggcaggc cgacgggttc cgtggcgagg tgctccgggc tgcggaactc gtacgccgtg | 10920 |
| accacgccga agttgccgcc gccaccgccg gtgtgtgccc agaagagctc accgagatcg | 10980 |
| ccggtgtcgt cggccctcgc cgtcacgagg cgaacggtgc gggactcgtc gacgacggcg | 11040 |
| acctccaccg cgtgcaggtg gtcgaccacc agccccagct ggcgcgacag cggcccgtaa | 11100 |
| ccacctccgg cgaccaggcc gcccatgccg accgcggagc aggccccgag cggcagggcc | 11160 |
| gcgttccacc ggcggaacag ggccttctgg acctggtcga ccgtcgcacc ggaaccgacg | 11220 |
| cgcaccccgg cgccgtccgc ggccgggccg atggcatgga ggttgtgcag gtccaggacg | 11280 |
| aggtcccggc gcggcgtgcc gacgaagtcc tggccgcagt gaccgccgga ccggcaggcg | 11340 |
| acccccccgcc cttccgtgac ggccttctgc agggaggcga cgacgtcgtc cggcgtggcg | 11400 |
| gggaggaaga actcctcggg ctcgacgacg aaccggtggt tgtccgagtg cgacagttcg | 11460 |
| atgtaccgcg gtcctcgcg gcccaccgtg aacggcggta cggaagcggt cacgacgcgt | 11520 |
| accccctcgac cgactgggtg aacacggtct cgtaggtgtt ggactcccgc gaggtcagca | 11580 |
| gcgccttgcc gcgtgcgcgc atctcccggt cgtgcgccgg gcgttcctcc tcgggcatgg | 11640 |
| cgtggaacgc ctcgtaggag gccgcgtcgt cccactgggc gtagttgatg accatgtcgc | 11700 |
| cgtcgagcgc cctgaggatg ctgtgggacc ggtacccggg cacctgccgc atccagtcgt | 11760 |
| ccggcttctc cagcagggac acgagctcgc cctggtcctt ggggtcgcac cccatcagga | 11820 |
| cgatgacggt caggtccccc cggtccgggc cgatctccgt gcgggcggca ccgtccttcg | 11880 |
| tctggacgga caccacctcg gtcttcagca ggtgcaccga cgtggtgagt cggtgaagt | 11940 |
| aggggaccgt gttgtgcttg aagttctccc cctcgtaccg ctccctcagg tcgttgatcg | 12000 |
| accgccactg tatgtagttg gccgcacagg gcctcgccac ccccgcgtgc agggtcgacg | 12060 |
| accgccatcc cgggtagttc gcgttcgcga tgatgccgcg catggcgtcc aggagggtcg | 12120 |
| cctgcttctc cgagtcggtg gtgttgaaca ggttgaacac ggtcagggag ccgttctcgg | 12180 |
| gctcgatgat cggcatgagg ccttccatga ggtgtcggac ggccccggag ggccggctgt | 12240 |
| ggctgatggg ttctgacctc ggtgacgacg aggacgcggg cggccggctc tccgggccgc | 12300 |
| ccggaccgcc tgtcgggatg cccgccgcac accggcccg gcgccggcg tcaccggctg | 12360 |
| cggggagagc ccggtgtacc ggtctccccc gagaccttcc ttccttcgac gacggactgg | 12420 |
| agtccggcgc ggctgacccc gaccagctcg atcccgacct cggccatcag gagccggaac | 12480 |

```
tcctccacgg tgcgctgttt gccttcgcac aggaggagca tgtccatgtc catgagggag    12540
atcgccttgt ccgccgtgtc gtccaggccc gccacagcct ccacgacggc gatgtgcgcc    12600
ccctcgtgca tggcctccgc gatgttcctg aggatgagac gggaacggcc gtcgtcccag    12660
tcgtgcagca cgttggagat catgaacagg tcgctgcccg acggaacgcc gtcgaagaag    12720
gagccggact tcaccgtgac gcggtgggcc accgccgcgt ccgacagctc cggcagggac    12780
cgcgacacga cgtccggctg gtcgaagagg cgccggtca tctcggggtg cttgcggagc     12840
acggcggcca gcagcgcccc cctcccccg cccacgtcgg tgacactgct gaaccgggag     12900
aagtcgaacg cctcgatcac gggctggatg acgcgcttgg acagttcggt catggccgag    12960
ttgaagacgg ccgcggtgtc gggatccgac tccatgaact cccacacgcc cgaaccgtgc    13020
atcgcggcga agggagagcg gccggtgcgc accgcggtgg ccaggtgggc ccaggtcgcg    13080
cgttcggccg tcgaccccgt ccaccgcgcg aagttgcgca tggagccgtc gtcggaggcc    13140
agggcccggc ccagctccgt cagctccagc gtgtcgtgct cgcccctccg cagcagcccc    13200
acggaggcgc cggcgcggaa gaagcgctcc gcggtgtcgt gctccaaccc cagccggacc    13260
gccagttgtg cgggcgtcag cccgccggcg ccaggccgt cggccacgcc cagttccgcg    13320
aacgtgctga cgacaccggc gcgccagcct cccatcagga ggtcgaggat ctgcacagcg    13380
acgggtgccg acggggcag cgatcccgat gcagtaatgg tcatgatgtc ccttcgactg     13440
gtggacatgc ggggaggtga ggcaccgctg caagggcagt tcgctctcga acacactttg    13500
ttcgtgatgc ctcaccggcg ctaggtatcc tcatgggatg gtcccgggaa gcagcgcctg    13560
aactgcgcag agtgctgccg gacgggagcg gatcgcccgc ccgcactctg cggctggtgg    13620 aacgacgac cgtgcggagc cgggccggca cggtccggtg gaagggcggc cctgcggtga    13680
tccgggcggc ccgcccccgt gctcccggcg tcccacgctc cgtaggcgcg ggacgccgga    13740
cacctcatga tcccgacgac ggccctgtgg ggtccggccg cgacggggc gctcctcgag     13800 gagcgcggtg ctacttcgcg tccacgtcgg cttcctcggc cccgcgggga gcgttctccc    13860
ctccccactg ctgggcgtcc cccttgggcc gcgggatgag gaaggtcgcc agcatcccga    13920
gcgccagcag cgcggcgcag gtgtagccgt tgatctggat cgcgtacgac atggcgtcgc    13980
gggcggcgtc ggcggcggcc gccgtgtccg ggttctcact cagtccggag atcatcgcgc    14040
cggcgctgtc ggagaccgcc gacgacagct cgttcgcctc cggcgcgggc gtccctggt     14100 cgacgagccg gtcggacagg tcggagtcca gtgccgtgaa gaaggtcgac gtcagaatcg    14160
cgatgccgag cgcggaaccg agctggcgtg cggcgctctg gatgccggat ccctggccgg    14220
cgtgccgcgg cggcacgtcc gccaggacga cgttggtgac ctgcgccgta gcgaacccga    14280
ctcccatgcc gtacaggaag agggcgatgc cgatgaccca ccactgcgag tcgctgctgg    14340
ccagcagacc gaacatcagc agaccgacgg cctcgaggac gaggccgatg cgcaccagcc    14400 cgatgggcc gacgttctcg gccatgccga agctcgcacc gctcgcgaag aagctgccga    14460
ccgcgacgac gaagacgatc agtccggtct ggagcaccga gtaccccagc gtgtactgga    14520
gccacagggg gagaacggcg agcatgccga actccgccag cgccgatgatc agcgtcgcga    14580 tgttgcccgt gctgaaggac ttgatgccga acagcgaggt gtccatcagc ggcgccgtgc    14640
cgtccacccg ggtgagccgg acctggcgct gcaggaacag cccaggcac accacgaga    14700 cgaccagggc gaccgggatg accgacagct ccaccgggtc gccgaaggga ccgaagctct    14760
tgcgcgggtc ccaccagccg tagttgcggc cctcgatcag cgcgaaggcg agaagtccga    14820
ggcccagcac cgacagcacg ccgccgacgg cgtcgacctt gcccggctgc gcgggggact    14880
```

```
ggtccaggaa cttcatgacg cccgcgatga tcagcaccac gacgaagatg ttgatgccga   14940
acgcccaccg ccaggagaac tcggcgagcc agccgcccag gagcgggccg accgcggcg    15000 ccgcaccgat cgtggacccc cagatggcga aggccttgcc ccggtcggct ccccggaagg   15060
acatgttgag cagggcgagc gaggtcggca tgatgatcgc gccgccgacg ccctgggcga   15120
accggctggc gatcaggagt tccccggagg gcgccagggc ggcggcgatg ctcgccagcc   15180
cgaacaccac ggtgccgatg aggaacagcc ggcgtgctcc caccacgtcc gacagacgcc   15240
ccatcaccag cagcagagcg gccaggatga tcgcgtagga ctcctggatc cactgggcgc   15300
cgaaggccga gatctcgagg tcgtcgatga tcggcggcat caccacgttg acgatggtga   15360
agtccacgac caccagcgac acaccgagag aaatggcgag caagcccagc caggggtccc   15420
ggttggccgt tgaggaccga gttggattgt cagacactgc gttcatccgt cctatgtgac   15480
acacatggcc cagttgggtc gccggggggcg agacaagggg gtagggcggg ggagcctccc   15540 gccccggcg caatggcact atgacaggag aagaggacgg attctgacct ctactgacac   15600
cgatccggag ggcaattc ttg atc gcc aac cgc acg ttg gaa ctc ctc agc    15651
                   Leu Ile Ala Asn Arg Thr Leu Glu Leu Leu Ser
                     1               5                  10 ctg tta cag acc cag agg gag tgg acc ggt gac ggg ctg gcc gag cgg   15699
Leu Leu Gln Thr Gln Arg Glu Trp Thr Gly Asp Gly Leu Ala Glu Arg
            15                  20                  25 ctg ggt gtg tcc ccg cgg acc gtc cgg cgc gac atc aac cga ctc cgc   15747
Leu Gly Val Ser Pro Arg Thr Val Arg Arg Asp Ile Asn Arg Leu Arg
        30                  35                  40 gag ctg ggc tac ccc gtc acg gcg acg aaa ggc ccc tcc ggc tcc tac   15795
Glu Leu Gly Tyr Pro Val Thr Ala Thr Lys Gly Pro Ser Gly Ser Tyr
    45                  50                  55 cgg ctg tcc cgc gga gcg cgt ctt cct ccc ctg ata gtc gac gac gag   15843
Arg Leu Ser Arg Gly Ala Arg Leu Pro Pro Leu Ile Val Asp Asp Glu
60                  65                  70                  75 cag gcc ctc gcc atc gcc ctg tcc ctg cag acc gcg ccg gcc tcg gtg   15891
Gln Ala Leu Ala Ile Ala Leu Ser Leu Gln Thr Ala Pro Ala Ser Val
                80                  85                  90 acc ggc atg gga gac gcc acc aaa cgt gcg ctg aac tcc atc cag gaa   15939
Thr Gly Met Gly Asp Ala Thr Lys Arg Ala Leu Asn Ser Ile Gln Glu
            95                  100                 105 ctg ttg cca cct cat ctg gcc cac cgg ctc gcc acc ttc tcc gtc gaa   15987
Leu Leu Pro Pro His Leu Ala His Arg Leu Ala Thr Phe Ser Val Glu
        110                 115                 120 cag atc gag aac gcg tgg gaa ctc gct ccg ccg cag gtc gac ccc tcc   16035
Gln Ile Glu Asn Ala Trp Glu Leu Ala Pro Pro Gln Val Asp Pro Ser
    125                 130                 135 ctg ctc gca cag ctc agc agc gcc gcc cag cag cgt gac ctc gtg agg   16083
Leu Leu Ala Gln Leu Ser Ser Ala Ala Gln Gln Arg Asp Leu Val Arg
140                 145                 150                 155 ttc tcc tac cgc tcc atc cac cac gac tcg atg cag gac ggg gag gtc   16131
Phe Ser Tyr Arg Ser Ile His His Asp Ser Met Gln Asp Gly Glu Val
                160                 165                 170 ctg gcc gaa ccc cac cgg ctc gtc gtc tgg tcg gga cgc tgg tac ctg   16179
Leu Ala Glu Pro His Arg Leu Val Val Trp Ser Gly Arg Trp Tyr Leu
            175                 180                 185 gtg gcc tac gac cag cag cgg agc tca tgg cac gcc tac cgg gtc gac   16227
Val Ala Tyr Asp Gln Gln Arg Ser Ser Trp His Ala Tyr Arg Val Asp
        190                 195                 200 cgc atc aag gat ctg gcg ccc acc gcc tgg cgc ttc ggc gag cgg gag   16275
Arg Ile Lys Asp Leu Ala Pro Thr Ala Trp Arg Phe Gly Glu Arg Glu
    205                 210                 215
```

```
ggt ccc gac gag gac atc acc cgc ttc gta cag aac cag ccc gat cgc     16323
Gly Pro Asp Glu Asp Ile Thr Arg Phe Val Gln Asn Gln Pro Asp Arg
220                 225                 230                 235 ggt gac acc ccg gac acc tgg ccc tgc tgg ggc acc gtc ctg atg gag     16371
Gly Asp Thr Pro Asp Thr Trp Pro Cys Trp Gly Thr Val Leu Met Glu
                240                 245                 250 tgt ccc gcg tcg ctg gtg gcg aag tgg gcc ccg gga gtg gcg agt ttc     16419
Cys Pro Ala Ser Leu Val Ala Lys Trp Ala Pro Gly Val Ala Ser Phe
        255                 260                 265 gag gcg gtc gac gac agg gtc acc cgg atc cag atg ggc gcg tgg tcg     16467
Glu Ala Val Asp Asp Arg Val Thr Arg Ile Gln Met Gly Ala Trp Ser
    270                 275                 280 tgg tcg gcg ctc atc ggc ttc ctg atc acc ttc agt tgc cgc ttc acc     16515
Trp Ser Ala Leu Ile Gly Phe Leu Ile Thr Phe Ser Cys Arg Phe Thr
285                 290                 295 gtc gag ggt ccg ccc gaa ctc gtc gcc gcg gcg cgg agg gtg atg ggc     16563
Val Glu Gly Pro Pro Glu Leu Val Ala Ala Ala Arg Arg Val Met Gly
300                 305                 310                 315 ctc atc gac gtc ggg att ccg tcg cac gac ccc ctc gcg gag ccg tcg     16611
Leu Ile Asp Val Gly Ile Pro Ser His Asp Pro Leu Ala Glu Pro Ser
                320                 325                 330 agc cgc aca ccc ggc ccc tcg gcc ggc cgg tgacgccgtg gccgcggcac       16661
Ser Arg Thr Pro Gly Pro Ser Ala Gly Arg
            335                 340 ccccgcaccg cggggaaccg ccgggtcagc ggaccgcctg tcccagctcg gcgcgctgcc   16721
gcagcggttc ccaccagtcc cggttctccc ggtaccagga cggtctccc gcgaggccgg    16781 tggcgaaatc cttgcggggc tcgtagccca gctccagggt gatcttggcg cagtccaccg   16841
agtagcgcct gtcgtgtccc ttgcggtcgg cgacgtactc caccgactcc cagccggccc   16901
cgcacgcctc caggagcagt gacaccagtt ccctgttggt gagctcggtg ccgccgccga   16961
tgttgtagac ctcgccgggt ctgcccttcg tgcggaccag ttcgatgccc tggacgtggt   17021
cgtcgatgtg cagccagtcg cggacgttga gcccgtcccc gtacagcggg acggtgcggc   17081
cctcgaggag gcgcgtgatg aacagcggga tcagcttctc ggggaagtgg tgatggccgt   17141
agttgttgga gcagcgggtc acccggacgt cgaggccgtg ggtgcggtgg tgggcgaggg   17201
cgacgaggtc ggcggcggcc ttcgaggccg cgtagggcga actgggtgac agcgggtgcg   17261
tctccggcca cgaaccgtag gggatcgagc cgtacacctc gtccgtggag acctggacga   17321
agacgccgcg gccgcgtccg tggtggcgca gcgccgcgtc gagcaggacc tgcgttccgc   17381
ccacgttcgt gcggacgaac tcggcgcccc ccaggatcga ccggtccacg tgcgactccg   17441
cggcgaagtg cacgatctgg tcgtgctcgg cgaccagccg gtccacgacc gcggcgtcgc   17501
agacatcgcc ctggacgagg cggaacccgg ggtgggcacg gaccgggtcg aggttggccg   17561
ggttgccggc ataggtcagt ttgtcgagca cggtgatgcg gaccccggcg ggcccgtgcg   17621
ggccgagcag ggtgcggacg tagtgggagc cgatgaagcc ggcaccaccg gtgacgagga   17681
tcctcgtggc ggtcatgacg agatacgcac ctcgctgtgg tccccgagga ccagccggtg   17741
ggccgccggc acaccggcgg cggggtcac ctcgacgttc cgcccgatca gggaactctc    17801
cacgcggcgg accccctgga ccgtggcccc ggcgaggacg atggagaact cgatctcgct   17861
ggactcgatc cggcagtccg ccgctatcga cgtggacggg ccgacgtagg agccggtgat   17921
ccgcgtgttg gcgccgatca cggccggccc cacgatccgc gatccgcgga tctcggcgcc   17981
cgcctcgatc gtgacctggc cgatgacctc gctgtccgcg tcgacatagc cgtcgacccg   18041
gcccttggcg ccctccagca cggcccggtt gacctccagc atgtcgatga cgttcccggt   18101
```

```
                                                -continued gtccttccag taaccggaaa tggtggtgga gcggacgtcg tacccgtggt cgatgagcca   18161
ctgcagggcg tcggtgatct ccagctcgcc gcgtgcggac ggctcgatcc cccggacggc   18221
ctcgtgcacc acggaggtga acaggaagac gccgaccagg gccaggtcgc tgcgcggagc   18281
ggccggcttc tcctccagcg ccaccgcctt cccgtcgtcg tcgagttcga cgacaccgaa   18341
ggcgctgggg tcggccacct tggtcaggag gatgtgcgtg tcgggccggc tctcgcggaa   18401
cccggccacg agatccgcga taccgcccac gatgaagttg tctccgaggt acatgacgaa   18461
gtcgtcgtcg ccgaggaact cccgggcgat caggacggca tgggcgagac cgagcggcgc   18521
cgcctgccgt atgtaggtga cgtccagacc gaaggcggag ccgtcgccga ccgcctgctg   18581
gatctcggcg gccgtgtccc cgacgacgat gccgacctcg gtgatgcctg cctccgcgat   18641
cgcctccaac ccgtagaaga gcacgggctt gttggctacg gggacgagct gcttggcgta   18701
ggaatgggtg atgggcctca ggcgggttcc ggccccgccg acagtacga gagccttcat   18761 ggcggcgcag tctaggcggg cggggaaaca tctcaatcgg cccggcagcg cacggatgtc   18821
tggaaacaac ggtcggtaga ggtcaggaac tgacctctac cgctcataat ctggccgctc   18881
ccctctcccc ggagatcagc ttcgagagct cggtccctac cgaaggagcg aaacag atg   18940
                                                                    Met
```

| | | | | | | | | | | | | | | | | |
|---|---|---|---|---|---|---|---|---|---|---|---|---|---|---|---|---|
| atc | agg | atc | gcc | gtc | atc | ctc | gga | agc | acg | cgt | ccc | ggc | cgc | cgc | ggg | 18988 |
| Ile | Arg | Ile | Ala | Val | Ile | Leu | Gly | Ser | Thr | Arg | Pro | Gly | Arg | Arg | Gly | |
| | | | 345 | | | | 350 | | | | 355 | | | | | |
| gcc | gtg | gtg | gcc | caa | tgg | gtc | gcc | gag | gtc | gcc | gcg | cgg | cat | ccc | gcg | 19036 |
| Ala | Val | Val | Ala | Gln | Trp | Val | Ala | Glu | Val | Ala | Ala | Arg | His | Pro | Ala | |
| | | | 360 | | | | 365 | | | | 370 | | | | | |
| gcg | gtg | atg | ggc | gag | gcg | gag | ttc | gag | ctg | gtc | gac | ctg | gcg | gag | tac | 19084 |
| Ala | Val | Met | Gly | Glu | Ala | Glu | Phe | Glu | Leu | Val | Asp | Leu | Ala | Glu | Tyr | |
| 375 | | | | 380 | | | | 385 | | | | | | | 390 | |
| ggc | ctc | ccg | ttg | ctc | gac | gag | ccc | gtg | ccg | gcg | atg | ttc | ggc | cag | tac | 19132 |
| Gly | Leu | Pro | Leu | Leu | Asp | Glu | Pro | Val | Pro | Ala | Met | Phe | Gly | Gln | Tyr | |
| | | | 395 | | | | 400 | | | | 405 | | | | | |
| cag | aag | gag | gag | acc | cgg | cgg | tgg | gcc | gcc | gcc | atc | ggc | tcg | ttc | gac | 19180 |
| Gln | Lys | Glu | Glu | Thr | Arg | Arg | Trp | Ala | Ala | Ala | Ile | Gly | Ser | Phe | Asp | |
| | | | 410 | | | | 415 | | | | 420 | | | | | |
| gga | ttc | gtc | ttc | gtc | acg | ccg | gag | tac | aac | cac | tcg | gtg | ccc | gcc | gcg | 19228 |
| Gly | Phe | Val | Phe | Val | Thr | Pro | Glu | Tyr | Asn | His | Ser | Val | Pro | Ala | Ala | |
| | | | 425 | | | | 430 | | | | 435 | | | | | |
| ctg | aag | aac | gcc | atc | gac | cac | ctc | ttc | gcc | gag | tgg | acc | gac | aag | gcg | 19276 |
| Leu | Lys | Asn | Ala | Ile | Asp | His | Leu | Phe | Ala | Glu | Trp | Thr | Asp | Lys | Ala | |
| | | | 440 | | | | 445 | | | | 450 | | | | | |
| gcc | ggg | ttc | gtc | agc | tac | ggc | gtg | cac | ggg | gga | acc | cgt | gcc | gtc | gag | 19324 |
| Ala | Gly | Phe | Val | Ser | Tyr | Gly | Val | His | Gly | Gly | Thr | Arg | Ala | Val | Glu | |
| 455 | | | | 460 | | | | 465 | | | | | | | 470 | |
| cac | ctg | cgg | ctg | gcc | ctg | gcc | gag | gtg | aag | gtg | gcc | ggg | gtg | cgc | agc | 19372 |
| His | Leu | Arg | Leu | Ala | Leu | Ala | Glu | Val | Lys | Val | Ala | Gly | Val | Arg | Ser | |
| | | | 475 | | | | 480 | | | | 485 | | | | | |
| cag | gtc | gtc | ctg | tcg | gtg | ttc | aac | gac | ttc | gac | tac | acg | gga | tgc | gac | 19420 |
| Gln | Val | Val | Leu | Ser | Val | Phe | Asn | Asp | Phe | Asp | Tyr | Thr | Gly | Cys | Asp | |
| | | | 490 | | | | 495 | | | | 500 | | | | | |
| atg | acg | gac | ccg | acg | gcc | atg | ggc | cgg | ttc | acg | ccg | gga | ccg | cag | cag | 19468 |
| Met | Thr | Asp | Pro | Thr | Ala | Met | Gly | Arg | Phe | Thr | Pro | Gly | Pro | Gln | Gln | |
| | | | 505 | | | | 510 | | | | 515 | | | | | |
| gag | cag | acg | gtg | aac | acg | atg | ctg | gac | gag | gtc | gtc | gcc | tgg | tcg | acg | 19516 |
| Glu | Gln | Thr | Val | Asn | Thr | Met | Leu | Asp | Glu | Val | Val | Ala | Trp | Ser | Thr | |
| 520 | | | | 525 | | | | 530 | | | | | | | | |

```
gcg ctc aag ccg ctg cgt act gct gcg acc gct gag gcg gac ggc cgg      19564
Ala Leu Lys Pro Leu Arg Thr Ala Ala Thr Ala Glu Ala Asp Gly Arg
535                 540                 545                 550 gcc gtg tcg gtg tgacgcaccg gtccgcccgc cggaccccct ggtgaacgtg          19616
Ala Val Ser Val ctggtcacgg cccctcgtgc gtacgctacg agggccgtga ccagcacgtt cgcctgtacg    19676
ggcgagcgtg gccgccacgc cgcgggtggg cggcggcagc acgccggccg gaccgatcgc    19736
cgagtggctt gttacgtgcc cggggcgacg gcgccggagg gggacgcgcc gaaaaaaacc    19796
ggtcagtcga gttccccttc gataacacgg atatcccccc gtcctcactt cgggtgacct    19856
acttcggccg tgcgactccg agcatcgtga gcggc atg acg ttg cac gcc gca       19909
                                      Met Thr Leu His Ala Ala
                                      555                 560 gaa gcc ata ccg tca cac gta ccg gtt ctc gtc gtg gga gcc ggc ccg      19957
Glu Ala Ile Pro Ser His Val Pro Val Leu Val Val Gly Ala Gly Pro
                565                 570                 575 aca ggt ctc atg ctc ggc gcc gag ctg gcg ctc cac ggc agc cgg ccg      20005
Thr Gly Leu Met Leu Gly Ala Glu Leu Ala Leu His Gly Ser Arg Pro
            580                 585                 590 ctg gtg atc gac gcg ctg ccg agc ccg agc gga cag tcc cgg gcc ctg      20053
Leu Val Ile Asp Ala Leu Pro Ser Pro Ser Gly Gln Ser Arg Ala Leu
        595                 600                 605 ggc ttc acg gtg agg acg ctg gag atc ttc aag cag cgc ggc atc ctg      20101
Gly Phe Thr Val Arg Thr Leu Glu Ile Phe Lys Gln Arg Gly Ile Leu
    610                 615                 620 ggc cgt ttc cag gga ctc gcc ccg gtg ccc gga gtc cat ttc gcc ggc      20149
Gly Arg Phe Gln Gly Leu Ala Pro Val Pro Gly Val His Phe Ala Gly
625                 630                 635                 640 ctc agc atc aag ggc gat cac ctc tcc agc tcg atg cgc ccg gcc aac      20197
Leu Ser Ile Lys Gly Asp His Leu Ser Ser Ser Met Arg Pro Ala Asn
                645                 650                 655 cag tac ccg cag tcc aag acc gaa cag gtc ctc gcc gcc tgg gcc gag      20245
Gln Tyr Pro Gln Ser Lys Thr Glu Gln Val Leu Ala Ala Trp Ala Glu
                660                 665                 670 gag ctg gga gta ccg gtg cgg cgc ccg tgg acg ctg acg tcc atg gag      20293
Glu Leu Gly Val Pro Val Arg Arg Pro Trp Thr Leu Thr Ser Met Glu
            675                 680                 685 ccc act ggc acc ggg tac cgc tgc gtg ctc agc ggc ccg gcc ggg cag      20341
Pro Thr Gly Thr Gly Tyr Arg Cys Val Leu Ser Gly Pro Ala Gly Gln
        690                 695                 700 cag acc gtc gac gcc gac tac gtg gtc ggc tgc gac gga gcg ggg agc      20389
Gln Thr Val Asp Ala Asp Tyr Val Val Gly Cys Asp Gly Ala Gly Ser
705                 710                 715                 720 ttc gtc cgc gag gcg atc ggc atg ccg acc aag cgc act ccc cca tcc      20437
Phe Val Arg Glu Ala Ile Gly Met Pro Thr Lys Arg Thr Pro Pro Ser
                725                 730                 735 gta cag atg ctc ctc ggt gat ctg cgc gga tgc ggt ctg ccc gac gaa      20485
Val Gln Met Leu Leu Gly Asp Leu Arg Gly Cys Gly Leu Pro Asp Glu
                740                 745                 750 ccc ttc ggg gtc aag cac gaa aag ggc atg gtc atg tcc gca ccg ctg      20533
Pro Phe Gly Val Lys His Glu Lys Gly Met Val Met Ser Ala Pro Leu
            755                 760                 765 ggc gac ggg acg gaa cgc gtc atc gtc tgt gac ttc acc cag ccg atg      20581
Gly Asp Gly Thr Glu Arg Val Ile Val Cys Asp Phe Thr Gln Pro Met
        770                 775                 780 cgg ccg cag ggc act ccc gtc acg cac gac gag atc aag gcc gcc tac      20629
Arg Pro Gln Gly Thr Pro Val Thr His Asp Glu Ile Lys Ala Ala Tyr
785                 790                 795                 800
```

-continued

| | |
|---|---|
| gag cag gtc gtc ggc agc ccc ctg gcg gac ggc gaa tgt ctc tgg gcg<br>Glu Gln Val Val Gly Ser Pro Leu Ala Asp Gly Glu Cys Leu Trp Ala<br>              805                    810                  815 | 20677 |
| agc tcg ttc tcg gac gcg tcc tcc ctc gtg gag tcc tac cgg tcc ggt<br>Ser Ser Phe Ser Asp Ala Ser Ser Leu Val Glu Ser Tyr Arg Ser Gly<br>820                    825                    830 | 20725 |
| cgt gcg ctg ctc gtc ggc gac acg gcg cac acc cat ctc ccc gcc ggc<br>Arg Ala Leu Leu Val Gly Asp Thr Ala His Thr His Leu Pro Ala Gly<br>    835                    840                    845 | 20773 |
| ggg cag ggc atg aac gtc tcg ata cag gac gcg gtg aac gtc ggc tgg<br>Gly Gln Gly Met Asn Val Ser Ile Gln Asp Ala Val Asn Val Gly Trp<br>850                    855                    860 | 20821 |
| aag ctc gcg ctg gtg agc cag ggc cgc gcg ccg gac acc ctg ctg gac<br>Lys Leu Ala Leu Val Ser Gln Gly Arg Ala Pro Asp Thr Leu Leu Asp<br>865                  870                  875                  880 | 20869 |
| acc tac cac gcc gag cgg tac ccg gtc ggc agg gaa ctg ctc ctc aac<br>Thr Tyr His Ala Glu Arg Tyr Pro Val Gly Arg Glu Leu Leu Leu Asn<br>                885                    890                    895 | 20917 |
| acc gcc gcc cag ggc cag gtc ttc ctg cgc ggc ccg gaa gtg gac ccg<br>Thr Ala Ala Gln Gly Gln Val Phe Leu Arg Gly Pro Glu Val Asp Pro<br>                    900                    905                    910 | 20965 |
| ctg cgc gag gtc ctg cgg cga ctg ctg aac atc cgg gag gtg tcc gtc<br>Leu Arg Glu Val Leu Arg Arg Leu Leu Asn Ile Arg Glu Val Ser Val<br>                915                    920                    925 | 21013 |
| ctg ctg gcc gac gga gtc agc gga ctg gac atc cgc tac gac atg ggc<br>Leu Leu Ala Asp Gly Val Ser Gly Leu Asp Ile Arg Tyr Asp Met Gly<br>930                    935                    940 | 21061 |
| ctc ccg gaa gca ccg cca ccc acg ggt gaa cgg ctg ccg ccg gac gtg<br>Leu Pro Glu Ala Pro Pro Pro Thr Gly Glu Arg Leu Pro Pro Asp Val<br>945                  950                  955                  960 | 21109 |
| ttc cac gtc gtc ggg acc ggc ggc gac gcc gtc gag gag ttg cgg cac<br>Phe His Val Val Gly Thr Gly Gly Asp Ala Val Glu Glu Leu Arg His<br>                    965                    970                    975 | 21157 |
| ggc gcc gct ctg ctg atc gtc ccg tcc ccc gac agc ccg gcg tcc tcg<br>Gly Ala Ala Leu Leu Ile Val Pro Ser Pro Asp Ser Pro Ala Ser Ser<br>                    980                    985                    990 | 21205 |
| ctg gtc gct ccg tgg cgg gac cag gtg cgc gtc gtg cac gcg cgc ccc<br>Leu Val Ala Pro Trp Arg Asp Gln Val Arg Val Val His Ala Arg Pro<br>995                    1000                 1005 | 21253 |
| acg gac ccg gac tgg ggc ggg gag ccg gcc gcg tcg tcg cac tgg<br>Thr Asp Pro Asp Trp Gly Gly Glu Pro Ala Ala Ser Ser His Trp<br>1010                 1015               1020 | 21298 |
| ttc gta cga ccg gac gga cac atc gcg tgg gcg ggc acc gaa ttc<br>Phe Val Arg Pro Asp Gly His Ile Ala Trp Ala Gly Thr Glu Phe<br>1025               1030               1035 | 21343 |
| agc gag ttg agc gcc tca ctg agc cgc tgg ctc ggt cag ccc gcc<br>Ser Glu Leu Ser Ala Ser Leu Ser Arg Trp Leu Gly Gln Pro Ala<br>1040               1045               1050 | 21388 |
| gcg  taaccagagg aggaagaacc cttgttcagc tctctcatcg tcgcccggat<br>Ala | 21441 |
| ggacaccggc cacgccgaag cggtggccga cgtcttcgcc ggcttcgacg ccaccgacat | 21501 |
| gcccgcgcgg atgggcacgc ggcgccgcga actcttccgc taccgcggcc tctacttcca | 21561 |
| cctccaggac ttcgagaccc ccgacgggac cgaagcggtc gaggcggcca agtccgaccc | 21621 |
| gcggttcatc cgggtgagca acgacctcag gccctacatc gaggcctacg ccccggactg | 21681 |
| gcaatcaccg aaggacgcca tggcagagcg cttctatcac tggagttcga aacg atg<br>                                                                                                          Met<br>                                                                                                           1055 | 21738 |

```
                                                           -continued
agc cgc agg gtc ttc atc acc ggg gtc ggt gtc gtc gcg ccg gga          21783
Ser Arg Arg Val Phe Ile Thr Gly Val Gly Val Val Ala Pro Gly
            1060                1065                1070 gcc gtc gga cgt gac ccc ttc tgg gag ctg ctg acc caa ggg cgc          21828
Ala Val Gly Arg Asp Pro Phe Trp Glu Leu Leu Thr Gln Gly Arg
            1075                1080                1085 acg gcc acc cgc cgg ctc agc ctc tgc gac ccg gag ccc ttc cgg          21873
Thr Ala Thr Arg Arg Leu Ser Leu Cys Asp Pro Glu Pro Phe Arg
            1090                1095                1100 tcc cag gtg gcc gcg gag gcc gac ttc gac gcc gag gcg gcg ggg          21918
Ser Gln Val Ala Ala Glu Ala Asp Phe Asp Ala Glu Ala Ala Gly
            1105                1110                1115 ctg tcg gag cgg cag tcc gcg gaa ctg gac cgg gcg gcg cag ttc          21963
Leu Ser Glu Arg Gln Ser Ala Glu Leu Asp Arg Ala Ala Gln Phe
            1120                1125                1130 gcc ctg gtc gcc gcc cgt gaa gcg gtc gag gac gcg gca tgg tcc          22008
Ala Leu Val Ala Ala Arg Glu Ala Val Glu Asp Ala Ala Trp Ser
            1135                1140                1145 gag aca tgt cct ccc gaa cgc gcc gga gtg atc gtg ggt tcg gcc          22053
Glu Thr Cys Pro Pro Glu Arg Ala Gly Val Ile Val Gly Ser Ala
            1150                1155                1160 gtc gga gcc acg acc aag ctc gag gag gtc tac cgg cag ctc agc          22098
Val Gly Ala Thr Thr Lys Leu Glu Glu Val Tyr Arg Gln Leu Ser
            1165                1170                1175 cgt gac ggc tcc ctc tgg gac gtg gcc ccc gac tcc ccc gcc gag          22143
Arg Asp Gly Ser Leu Trp Asp Val Ala Pro Asp Ser Pro Ala Glu
            1180                1185                1190 ctg tac tcg tac ttc gtg ccc agc tcg ttc gcc tcc ggc atc gca          22188
Leu Tyr Ser Tyr Phe Val Pro Ser Ser Phe Ala Ser Gly Ile Ala
            1195                1200                1205 cac gac ctc ggc gtc acg ggg cag agc ggc gtc gtg tcg acc ggg          22233
His Asp Leu Gly Val Thr Gly Gln Ser Gly Val Val Ser Thr Gly
            1210                1215                1220 tgc acc tcc ggg atc gac tcc gtc ggc aac gcc tgg gaa ctg atc          22278
Cys Thr Ser Gly Ile Asp Ser Val Gly Asn Ala Trp Glu Leu Ile
            1225                1230                1235 cag agc ggc atc ctg gac tcc gcc gtc tgc ggt gcc acc gac gcc          22323
Gln Ser Gly Ile Leu Asp Ser Ala Val Cys Gly Ala Thr Asp Ala
            1240                1245                1250 ccc atc tcg ccc atc acc gtc gcc tgc ttc gac acg atc aag gcg          22368
Pro Ile Ser Pro Ile Thr Val Ala Cys Phe Asp Thr Ile Lys Ala
            1255                1260                1265 aca tcg acg tac aac gac acc ccg gag agc gcc tca cgg ccg ttc          22413
Thr Ser Thr Tyr Asn Asp Thr Pro Glu Ser Ala Ser Arg Pro Phe
            1270                1275                1280 gac gcc aca cgg ggc ggc ttc gtc ctc ggc gag ggc agc gcg atg          22458
Asp Ala Thr Arg Gly Gly Phe Val Leu Gly Glu Gly Ser Ala Met
            1285                1290                1295 ttc gtc ctc gaa tcg gag gaa tcc gtc cac cgt cgc ggc gca cgc          22503
Phe Val Leu Glu Ser Glu Glu Ser Val His Arg Arg Gly Ala Arg
            1300                1305                1310 gtc tac ggc gag atc cgc ggc tac gcg agc cgc tgc aac gcc tac          22548
Val Tyr Gly Glu Ile Arg Gly Tyr Ala Ser Arg Cys Asn Ala Tyr
            1315                1320                1325 cac atg acc ggt ctc aag gcc gac gga cgc gag ctg gcg gag gcc          22593
His Met Thr Gly Leu Lys Ala Asp Gly Arg Glu Leu Ala Glu Ala
            1330                1335                1340 gtc gtc tcc gct ctc ggc cag gca ggc gtg gac ccg ggc cgg ctc          22638
Val Val Ser Ala Leu Gly Gln Ala Gly Val Asp Pro Gly Arg Leu
            1345                1350                1355
```

```
                                      -continued
gac tac gtc aac gcc cac ggc agc ggc acg  aag cag aac gac cgc     22683
Asp Tyr Val Asn Ala His Gly Ser Gly Thr  Lys Gln Asn Asp Arg
                1360                1365                1370 cac gag acc gcc gcg ctg aag tcg tcc ctc  gga ccc gcc gcc cac     22728
His Glu Thr Ala Ala Leu Lys Ser Ser Leu  Gly Pro Ala Ala His
                1375                1380                1385 gac gtg ccg atc agt tcg atc aag tcg atg  atc ggc cat tcg ctg     22773
Asp Val Pro Ile Ser Ser Ile Lys Ser Met  Ile Gly His Ser Leu
                1390                1395                1400 ggc gcc atc ggg tcg ttg gag atc gcc gcc  tgc gcc ctg gcg ctg     22818
Gly Ala Ile Gly Ser Leu Glu Ile Ala Ala  Cys Ala Leu Ala Leu
                1405                1410                1415 cgg gac gac gtg atc ccg ccg acg gcc aat  ctc acc cgg ccg gat     22863
Arg Asp Asp Val Ile Pro Pro Thr Ala Asn  Leu Thr Arg Pro Asp
                1420                1425                1430 ccg gaa ctc gat ctg gac tac gtg ccg gtc  cac gcg cgc aag cag     22908
Pro Glu Leu Asp Leu Asp Tyr Val Pro Val  His Ala Arg Lys Gln
                1435                1440                1445 ccg acc aac agc gtg ctc acg acc gga agc  ggc ttc ggt ggg ttt     22953
Pro Thr Asn Ser Val Leu Thr Thr Gly Ser  Gly Phe Gly Gly Phe
                1450                1455                1460 cag agc gcc atg gtt ctc acg gac ccg gag  cat cac tca tgaccgcaca  23002
Gln Ser Ala Met Val Leu Thr Asp Pro Glu  His His Ser
                1465                1470 catcaccggc atcgacatcg tctccccgct gggcctgtcc cgcgaggaac actggaaggc 23062 cctcctcgac ggatgcagcg gtctgagggc gacgcagtcg ttcgactcca gcaggtacga 23122 caaccccatc agcggggagg tgccccactt cgccccggag ggcctgccca gcggctgct  23182 gccggccacc gaccggatga cccagatgtc gctggtcgcc gcggcggggg cgttcgacga 23242 cagcggtgtc gacacgagcc gggtcgaccc cctcggagtc ggtgtcatga cggcgtccac 23302 cgcgggggt tacgcgttcg gcagaaagga gctgcagaac ctgtggtcca aggggcccag  23362
gtacgtcagc acccatcagt cctacgcctg gttctacgcg gtcaacaccg gtcagatctc 23422 catccggcac ggctgccagg ccacagcgg agtgatcgtc gcggacgacg ccggcgggct  23482
cgacgcgatc tccttcgccg cccgccgtct ggcgcgcggc aaccgcgtca tgctcaccgg 23542 gtcggtggac agcacgatgt gtccctgggg gcgggtcgcg cacacctcga ccggcatgct 23602 ctcggcatcc accgacgcgc gggccgcgta ccttccgttc gacgcacgag ccaacgggtg 23662 ggtcaacggc gaaggcggcg cgcacctcgt gctgcagacc cacagtgacg gccgctacgc 23722 ggcggtgctc ggtcacggtg cgaccatgga cgatccccgc gccgcccgg gcacgggcct   23782 cgtccgggcg atccacctcg cgctcggcgc ggcgcggctg cgccccggcg acatcagtgt 23842 ggtgttcgcc gacgcggccg gcacccggga ggcggacacc gccgaggccg ccgccctcgc 23902 cgaggtcttc gggccggatt ccgtcccccgt caccgcgccc aaggcggcga ccggccggat 23962 gggctgcggg acgccgcac tcgacgtcgc gacggcggtg ctcgccctcc gcgaccagac  24022 gattccccc accgtcaacg tccaggccga cgcgtccctg ggggtcaacc tgtgcagcgt  24082
cgccacacac cacccctca ccaacgtcct ggtcctggcc cggggcgtcg gtgggttcaa   24142
ctcggccctg atcgtcggga aatgagagaa ggagcaagga atg tcc  gca cgc gtc  24197
                                          Met Ser  Ala Arg Val
                                               1475 acc atg  gac gat ctc agg cga  gcc ctc gag gag ggc  tcc ggt gtc    24242
Thr Met  Asp Asp Leu Arg Arg  Ala Leu Glu Glu Gly  Ser Gly Val
    1480                1485                       1490
```

```
gac gag ggc gtc gat ctt gac acc gac ctc gaa acc atg gcg ttc      24287
Asp Glu Gly Val Asp Leu Asp Thr Asp Leu Glu Thr Met Ala Phe
    1495                1500                1505 tcc gag ctg ggg tac gac tcc ctg gcg gtg ctg gag acc ggc ctg      24332
Ser Glu Leu Gly Tyr Asp Ser Leu Ala Val Leu Glu Thr Gly Leu
1510                1515                1520 cgc ctc ggc cgc gag aac gac atc gag ctc gac gac tcg gtg ttc      24377
Arg Leu Gly Arg Glu Asn Asp Ile Glu Leu Asp Asp Ser Val Phe
    1525                1530                1535 gcc gac ctc gac acg cct cag cag atg ctg gac gcg gtc aac gat      24422
Ala Asp Leu Asp Thr Pro Gln Gln Met Leu Asp Ala Val Asn Asp
1540                1545                1550 gcc ctc gcg cgt cag gcg gcg gca tcg tgacctctcc ccgtcatgcc        24469
Ala Leu Ala Arg Gln Ala Ala Ala Ser
    1555                1560 ctggtcaccg gcggttccag cggcatagga aagtccgtcg cacggcgcct ggcctcggcc   24529
ggccacaccg tcacgatctg cggtcgtgac tccgaaaggc tccagcaggc cgccaaggaa   24589
ctgtcggagc agggtgcacc cgtcacctcg ctgatcgccg acgtcagcaa gccccgccag   24649
gtgggcgatc tggtccgcga ggccgtggag acgaacggtc ccctcgggat cctcgtcaac   24709
aacgcgggca ggaacggagg cggccggacc gcggagctga gcgacgagct gtggcgggag   24769
gtactgagca ccaacctcga cagcgttttc tacgtcacgc gggaggtgct ggcccgtggc   24829
ggcatcggcg aggtggacca cgcccggatc atcaacatcg cctccaccgc ggggaagcag   24889
ggagttctgc tggccgcccc gtactccgcc tccaagcacg tgtcgtcgg cttcaccaag   24949 gcggtgggca aggagctggc ccctcagggg atcaccgtga acgccgtctg cccgggctac   25009
gtggagaccc cgatggcctc acgggtccgg caggcctacg cagacgcctg ggagaccacg   25069
gaggccgagg tgctgtccgc cttcgaggcg aagatcccgc tcggccggta cagcacgccc   25129
gacgaggtcg cctcgctggt cgagtacctc acgaccgaag gagccgcctc gatcacggct   25189
caggcgttca acgtgtgcgg cggcctcggc aacttctagg agatgattca c atg gcc   25246
                                                        Met Ala gat ccg gct cgc aca gac ctg cac tcc gcc acg atc acc ggc agc        25291
Asp Pro Ala Arg Thr Asp Leu His Ser Ala Thr Ile Thr Gly Ser
1565                1570                1575 gcc gac gcg gtg tac cgc cgt ctg gag gac gtc ggg cag tgg tcc       25336
Ala Asp Ala Val Tyr Arg Arg Leu Glu Asp Val Gly Gln Trp Ser
1580                1585                1590 cag atg ttc gaa ccg acc atc cac ggc gcg gaa ctg gcc cgg gac      25381
Gln Met Phe Glu Pro Thr Ile His Gly Ala Glu Leu Ala Arg Asp
1595                1600                1605 ggg aac agg cag acg atc cag ctg tgg gcc acc gcc aac gga gaa      25426
Gly Asn Arg Gln Thr Ile Gln Leu Trp Ala Thr Ala Asn Gly Glu
1610                1615                1620 ccc aag gcc tgg gtc tcc gag cgt gag ctc gac ccc gtc gcg cgc      25471
Pro Lys Ala Trp Val Ser Glu Arg Glu Leu Asp Pro Val Ala Arg
1625                1630                1635 acc atc cgc ttc gcg cag acc gtc acc tcc tcg ccc gtc gcc gag      25516
Thr Ile Arg Phe Ala Gln Thr Val Thr Ser Ser Pro Val Ala Glu
1640                1645                1650 atg tcc ggc gcg tgg cag gtg ctg ccc ctg tcc gag gac acc tgc      25561
Met Ser Gly Ala Trp Gln Val Leu Pro Leu Ser Glu Asp Thr Cys
1655                1660                1665 cgg gtc gaa ctc acg cac acc tac cgt gcg gag aac gac tcg gcg      25606
Arg Val Glu Leu Thr His Thr Tyr Arg Ala Glu Asn Asp Ser Ala
1670                1675                1680
```

```
gag tcg ctc aca tgg atc gcc cga gcc gtg gag  acc aac agc acg      25651
Glu Ser Leu Thr Trp Ile Ala Arg Ala Val Glu  Thr Asn Ser Thr
1685                1690                1695 aag gag ctc tcg gcg ctc aag ttc gcc tgc gaa  cgg gac gcc gac      25696
Lys Glu Leu Ser Ala Leu Lys Phe Ala Cys Glu  Arg Asp Ala Asp
1700                1705                1710 agc gag gcc agt ccc ttc acc ttc acc gat gcg  gtg gac acc acg      25741
Ser Glu Ala Ser Pro Phe Thr Phe Thr Asp Ala  Val Asp Thr Thr
1715                1720                1725 gtc gac ccc gtc ctg ctg ttc tcg ttc ctg gac  cgc ggt gag ctg      25786
Val Asp Pro Val Leu Leu Phe Ser Phe Leu Asp  Arg Gly Glu Leu
1730                1735                1740 tgg gcg gga cgc ctg gag cac gtc gcc gag gcc  gag atg agg gag      25831
Trp Ala Gly Arg Leu Glu His Val Ala Glu Ala  Glu Met Arg Glu
1745                1750                1755 ttc tcc gac ggc ctg cag ttc ctc cgg atg cgg  acg cgc acc ccg      25876
Phe Ser Asp Gly Leu Gln Phe Leu Arg Met Arg  Thr Arg Thr Pro
1760                1765                1770 gac ggt gac acg cac gtc acc gag tcc tac cgg  gtg tcg cag agc      25921
Asp Gly Asp Thr His Val Thr Glu Ser Tyr Arg  Val Ser Gln Ser
1775                1780                1785 ccg gcc cgg ctg ctg tac aag cag gtg acg ctg  ccc gcg ctg ctg      25966
Pro Ala Arg Leu Leu Tyr Lys Gln Val Thr Leu  Pro Ala Leu Leu
1790                1795                1800 tcg ctg cac acc ggc gag tgg acc atc acc ccg  gcc ggg gag agc      26011
Ser Leu His Thr Gly Glu Trp Thr Ile Thr Pro  Ala Gly Glu Ser
1805                1810                1815 tgg cgg gtc acg tcg aag cac acc gtg gcg atc  gat ccc gac gcg      26056
Trp Arg Val Thr Ser Lys His Thr Val Ala Ile  Asp Pro Asp Ala
1820                1825                1830 gtg cac aag gtc ctc ggt gcc gac gcg acg gtc  tcg gac gcc aag      26101
Val His Lys Val Leu Gly Ala Asp Ala Thr Val  Ser Asp Ala Lys
1835                1840                1845 cgg ctc gcc cgg cgc aac ctg ggc aac aac agc  ctg cgg acc ctc      26146
Arg Leu Ala Arg Arg Asn Leu Gly Asn Asn Ser  Leu Arg Thr Leu
1850                1855                1860 gaa gca gcg gtc cgg tgg gcc ggc acc gcc gtg  tcg cag agg          26188
Glu Ala Ala Val Arg Trp Ala Gly Thr Ala Val  Ser Gln Arg
1865                1870                1875 tgagtgggga c atg acg  gag ccc gag acc tcg  gac gtt ctc gtc gtc   26235
            Met Thr  Glu Pro Glu Thr Ser  Asp Val Leu Val Val
            1880                1885                     1890 ggc gcc ggg ccc agc  gga ctg ctc ctg gcc  ggg atc ctc gcc ggg    26280
Gly Ala Gly Pro Ser  Gly Leu Leu Leu Ala  Gly Ile Leu Ala Gly
1895                 1900                 1905 gcg ggt gcg cgg gtc  acg gtg ctg gag gcg  cgg gac gcg ccc agc    26325
Ala Gly Ala Arg Val  Thr Val Leu Glu Ala  Arg Asp Ala Pro Ser
                1910                1915                1920 ccg cag acc cgc gcc  tcc acc ttg cac gcc  cgt gcc agg gag atc    26370
Pro Gln Thr Arg Ala  Ser Thr Leu His Ala  Arg Ala Arg Glu Ile
                1925                1930                1935 ctc gac cac cac gga  gtg gag ttc tcc ccg  gag ctg ccc tgg agt    26415
Leu Asp His His Gly  Val Glu Phe Ser Pro  Glu Leu Pro Trp Ser
                1940                1945                1950 gcc cac gga cac tac  ggc ggc ctg cgc gtg  gac ctc tcc cgg gtc    26460
Ala His Gly His Tyr  Gly Gly Leu Arg Val  Asp Leu Ser Arg Val
                1955                1960                1965
```

-continued

| | | |
|---|---|---|
| gac tcc ggg cgg gcc ggt gtc tgg aag tgc ccc cag ccg gaa ctg<br>Asp Ser Gly Arg Ala Gly Val Trp Lys Cys Pro Gln Pro Glu Leu<br>1970                        1975                  1980 | 26505 |
| gta cgg acg ctg acc ggc tgg gcc cgc ggg cac ggc gcg cgg ctg<br>Val Arg Thr Leu Thr Gly Trp Ala Arg Gly His Gly Ala Arg Leu<br>1985                        1990                  1995 | 26550 |
| ctc cac ggg gag cac gtg gag tcc gtc cgc gag cag ggc ggg cgc<br>Leu His Gly Glu His Val Glu Ser Val Arg Glu Gln Gly Gly Arg<br>2000                        2005                  2010 | 26595 |
| tgt ctg gtg cgt acc cgg gcc ggc acg ttc agc ggg acc ctg<br>Cys Leu Val Arg Thr Arg Ala Gly Thr Thr Phe Ser Gly Thr Leu<br>2015                        2020                  2025 | 26640 |
| ctg gtc gcg gcg gac ggc cgg cgg agc acg gtg cgg tcg ctg ctg<br>Leu Val Ala Ala Asp Gly Arg Arg Ser Thr Val Arg Ser Leu Leu<br>2030                        2035                  2040 | 26685 |
| ggc atc ggg tgc ggg ggt gcg ccg gcc acg cgc gta ctg gtg cag<br>Gly Ile Gly Cys Gly Gly Ala Pro Ala Thr Arg Val Leu Val Gln<br>2045                        2050                  2055 | 26730 |
| gcc gat gtc cac ggc gac ggg ctg gcg ggg cgg cgc ttc gag cga<br>Ala Asp Val His Gly Asp Gly Leu Ala Gly Arg Arg Phe Glu Arg<br>2060                        2065                  2070 | 26775 |
| cac ggg cgg tac acc gtg acc gcc gca ccg atc agc ccc ggg atc<br>His Gly Arg Tyr Thr Val Thr Ala Ala Pro Ile Ser Pro Gly Ile<br>2075                        2080                  2085 | 26820 |
| acc cgg gtg atg ctg cac gat ccg cgc tgg ccc gcg ggc gag gaa<br>Thr Arg Val Met Leu His Asp Pro Arg Trp Pro Ala Gly Glu Glu<br>2090                        2095                  2100 | 26865 |
| cgc acg ctg gag gac ctc cgt aga gcc tgg aag gag tcc acc ggc<br>Arg Thr Leu Glu Asp Leu Arg Arg Ala Trp Lys Glu Ser Thr Gly<br>2105                        2110                  2115 | 26910 |
| gag acc ctg ccg gcc gag ccg tcg tgg tca cgg acc ttc agc gac<br>Glu Thr Leu Pro Ala Glu Pro Ser Trp Ser Arg Thr Phe Ser Asp<br>2120                        2125                  2130 | 26955 |
| gac acg aca gtg gca cac ccg ctg gtc aag ggc cgt gtc gtg ctg<br>Asp Thr Thr Val Ala His Pro Leu Val Lys Gly Arg Val Val Leu<br>2135                        2140                  2145 | 27000 |
| tgc ggc gac gcc gcc cac ccc ttc gtc ccc atc ggc ggc cag gcg<br>Cys Gly Asp Ala Ala His Pro Phe Val Pro Ile Gly Gly Gln Ala<br>2150                        2155                  2160 | 27045 |
| ctg aac acg tcg ttg atg gac gcc gag gcg ctg ggc tgg cgg gtc<br>Leu Asn Thr Ser Leu Met Asp Ala Glu Ala Leu Gly Trp Arg Val<br>2165                        2170                  2175 | 27090 |
| ctg ggg tat ctg gac gac ggg gac cgg caa ggc ctc ctc gac tac<br>Leu Gly Tyr Leu Asp Asp Gly Asp Arg Gln Gly Leu Leu Asp Tyr<br>2180                        2185                  2190 | 27135 |
| cag gac gag cgg ttc tcg tgg ctg acc gtt ctc gcg ggg aga ctg<br>Gln Asp Glu Arg Phe Ser Trp Leu Thr Val Leu Ala Gly Arg Leu<br>2195                        2200                  2205 | 27180 |
| cgc gcc cag gca cgt ctg ctg ttc gac acc gac gcg gcg gcc acg<br>Arg Ala Gln Ala Arg Leu Leu Phe Asp Thr Asp Ala Ala Ala Thr<br>2210                        2215                  2220 | 27225 |
| gaa cgc aag gcg ctg gtc gcc gcg aga ctg gcc ggg gac gcg gac<br>Glu Arg Lys Ala Leu Val Ala Ala Arg Leu Ala Gly Asp Ala Asp<br>2225                        2230                  2235 | 27270 |
| tac cgg cgc agg atc gcc gac gcc ctg gcc ggt gtc gac gtg tgc<br>Tyr Arg Arg Arg Ile Ala Asp Ala Leu Ala Gly Val Asp Val Cys<br>2240                        2245                  2250 | 27315 |
| tac ctg acg ccc ggc ggc gcg gtc cgc cgg cgt ctg tcc ccg gcc<br>Tyr Leu Thr Pro Gly Gly Ala Val Arg Arg Arg Leu Ser Pro Ala<br>2255                        2260                  2265 | 27360 |

```
cgg ctc cgg gag acc gga gtg aac ccc ggc gcc cgc cgc gtg cag      27405
Arg Leu Arg Glu Thr Gly Val Asn Pro Gly Ala Arg Arg Val Gln
            2270                2275                2280 cgg gcg ctc gtc ccc gac gac gga acg cgc acg gac gcc tgg atc      27450
Arg Ala Leu Val Pro Asp Asp Gly Thr Arg Thr Asp Ala Trp Ile
            2285                2290                2295 cgt ccc gat cac cac tgg tac ccg gtg gcc cgc gac ggg gcc cgg      27495
Arg Pro Asp His His Trp Tyr Pro Val Ala Arg Asp Gly Ala Arg
            2300                2305                2310 cag gac tgg gac gac gcg gtg cgc ctc cac gac gac ttg gaa ccc      27540
Gln Asp Trp Asp Asp Ala Val Arg Leu His Asp Asp Leu Glu Pro
            2315                2320                2325 gag gtg acg cgg tgagagcgtt cctgttcccc ggtcagggga cccagaagat      27592
Glu Val Thr Arg
cggcatgggc acctacctgc gagaacggta cccccacctg atcgcgccgt gtgggcggga      27652
ggcggacgac gtcctgggtt tccccctcac ccgcctctgc gaggaaggcc ccggcgagaa      27712
gctccgccac atgccggtca cccagcccgc cgtcttcctg tgcagttacg ccgcgctcgt      27772
cgccgcgcag gcgaacggcg cggagccgga cgtcatcgcg gccacagtc tgggcgagta      27832
ctcggcgctg gcggcggccg gcgtcctcac ctggcaggag gtccttcagc tcgtccaccg      27892
ccgcggtcag ctcatggcgg aggtgcagca caaggtggac gggaagatgg cggccgtcat      27952
cggtctcgcc atcgggcagg tcgaggagat ctgcgagcag gtgcggtccg agaccggtga      28012
ggtggtcgag gtggccaacc acaacgagcc cctccaggtc gtcgtctccg ccagtgcgc       28072
tgccatagac ctcctggtcc agcgcgtcgc gacggcgacc gacgtccgca cgtccgtcct      28132
gaggatcggt ggcccggccc actccagtct catgggcagc gtcgcggggg acttcgtgga      28192
gtacctccgg cgcttcgact tctgcacgcc caagacgatg ctgatctccg ggtcgaccgc      28252
cgagccctac gcgagtgcgg aggagatcag gcaccagctc ggcaggcagc tggtgcaccg      28312
ggtgcggtgg gtggacgtga tggcgcagct cgagaggctg ggggtcgcac agacctggga      28372
gctggggccg ggcaaggtcc tctcgggatt cgtacagcgg tcgctgcctc aggtgcggac      28432
gtaccgcgcg aatgatctgc cgtccttcct ggccggcgtg acgggctggt gagccggtga      28492
agcacgca gtg ccg cat cag gca acc ggc gcc gct ccc gac gga ggg        28539
         Val Pro His Gln Ala Thr Gly Ala Ala Pro Asp Gly Gly
             2330                2335                2340 ggg tcc gcg ccc cgg tcc ctg gtg ctg atg ctc ccc ggc cag ggg        28584
Gly Ser Ala Pro Arg Ser Leu Val Leu Met Leu Pro Gly Gln Gly
            2345                2350                2355 tcg cag ttc gct gcc atg gga gtc ccg ctc tac gag tcc gac gcc        28629
Ser Gln Phe Ala Ala Met Gly Val Pro Leu Tyr Glu Ser Asp Ala
            2360                2365                2370 cgg ttc agg aag gcg ctc gac gac ttc ttc gac gcg ttc ggc acc        28674
Arg Phe Arg Lys Ala Leu Asp Asp Phe Phe Asp Ala Phe Gly Thr
            2375                2380                2385 ggt gcc gag cgg ctc cgg cgc gag tgg ctg cac ggt tcg gcc cag        28719
Gly Ala Glu Arg Leu Arg Arg Glu Trp Leu His Gly Ser Ala Gln
            2390                2395                2400 ggc atc gaa cgt ggg tcc ttc gcg cag ccg atg ctg ttc ggc ctc        28764
Gly Ile Glu Arg Gly Ser Phe Ala Gln Pro Met Leu Phe Gly Leu
            2405                2410                2415 gac tac gcg gcg ggc gcg gtg tgg ctg gag gag ctc aag ggt gtc        28809
Asp Tyr Ala Ala Gly Ala Val Trp Leu Glu Glu Leu Lys Gly Val
            2420                2425                2430 gac gtg acg ctg gtc ggt cac agc gtg ggc gag ctg gcg gcg gcc        28854
Asp Val Thr Leu Val Gly His Ser Val Gly Glu Leu Ala Ala Ala
            2435                2440                2445
```

| | | | | | | | | | | | | |
|---|---|---|---|---|---|---|---|---|---|---|---|---|
| acc | ctc | gcg | ggg | gcc | ttc | gac | ctc | gag | ctg | gcg | ggg | gca | ctc | ctg | 28899 |
| Thr | Leu | Ala | Gly | Ala | Phe | Asp | Leu | Glu | Leu | Ala | Gly | Ala | Leu | Leu | |
| | | 2450 | | | | 2455 | | | | 2460 | | | | | | acc ctc gcg ggg gcc ttc gac ctc gag ctg gcg ggg gca ctc ctg 28899
Thr Leu Ala Gly Ala Phe Asp Leu Glu Leu Ala Gly Ala Leu Leu
        2450              2455              2460 gcc gag cgg gcc cgg ctc ctc gac gcc gcc ccc cgg gga ggg atg 28944
Ala Glu Arg Ala Arg Leu Leu Asp Ala Ala Pro Arg Gly Gly Met
        2465              2470              2475 atc gcg tgc cgc gcg acg gag gag tcg ctg cgg gag cat ctc gac 28989
Ile Ala Cys Arg Ala Thr Glu Glu Ser Leu Arg Glu His Leu Asp
        2480              2485              2490 gcc ctg ggc gga cgc gcc gtc atc gcg gcg gag aac gcg gac aac 29034
Ala Leu Gly Gly Arg Ala Val Ile Ala Ala Glu Asn Ala Asp Asn
        2495              2500              2505 cag tgc gtc gtg agc tgt gcc gag gaa gac ctc ccg gac acg atg 29079
Gln Cys Val Val Ser Cys Ala Glu Glu Asp Leu Pro Asp Thr Met
        2510              2515              2520 cgg tac ctc ggc tcg cac ggt gtg acg tgc ctg cgc gtc gcc tcg 29124
Arg Tyr Leu Gly Ser His Gly Val Thr Cys Leu Arg Val Ala Ser
        2525              2530              2535 acc gaa ccg ttc cac tcc ccc ctc ctc gcc ccc gcc gcc gcc cgg 29169
Thr Glu Pro Phe His Ser Pro Leu Leu Ala Pro Ala Ala Ala Arg
        2540              2545              2550 ttc gag gag ttc ctg gcc cgg cgc ggt cat cgt ctg tcc acg acg 29214
Phe Glu Glu Phe Leu Ala Arg Arg Gly His Arg Leu Ser Thr Thr
        2555              2560              2565 gaa ctg ccc atg gtc tcg gcc tac tcg gcg cgg agg atc agc ggc 29259
Glu Leu Pro Met Val Ser Ala Tyr Ser Ala Arg Arg Ile Ser Gly
        2570              2575              2580 cgg gag atc atg ccc gcc tcg ttc tgg acg cgt cag atg gct gag 29304
Arg Glu Ile Met Pro Ala Ser Phe Trp Thr Arg Gln Met Ala Glu
        2585              2590              2595 aag gtg cgt ttc tgg gag gcg ctc cgc cac aac ttc gac tcc ggt 29349
Lys Val Arg Phe Trp Glu Ala Leu Arg His Asn Phe Asp Ser Gly
        2600              2605              2610 ccc cgc acg ttc gtg gaa atc ggc cca ggg acc gtc ctc tcc ctg 29394
Pro Arg Thr Phe Val Glu Ile Gly Pro Gly Thr Val Leu Ser Leu
        2615              2620              2625 gcc gca cgt cgg ctg ccg tcc gta cgg gcc cgg cgt tcc acg gtg 29439
Ala Ala Arg Arg Leu Pro Ser Val Arg Ala Arg Arg Ser Thr Val
        2630              2635              2640 atc tcc acg atg ccg cgt cat cgg ccc cac ccg gag cac tgg gaa 29484
Ile Ser Thr Met Pro Arg His Arg Pro His Pro Glu His Trp Glu
        2645              2650              2655 tcg gcc ata cat gag gtc gcc gag gaa ttc tgt tgaccattgc 29527
Ser Ala Ile His Glu Val Ala Glu Glu Phe Cys
        2660              2665 actacgtgca acgcgcaagg ccggccatgg gtgtccccg agttcccggg aggcacccat 29587 ggccttgtcg gtgaaatgtt caaccaaatg aaccacctct cgagggcgcc ccggatcaaa 29647 gatgttcacc gatttgcata gtcgaaaaaa tacggacagc aacggaagcg gagtgttatc 29707 ctgcaatctg cacgcaacgg gggaaacggg ggaggattcc aagtgcagga cccggtggac 29767 cggacctcgg ggaactccag aggcgcaagc accgtcggac ccgagcagtc ccgcaaagac 29827 gcggggcact cctgtcgccg aagagggccc ggtaccgtca cgcagcagtt ttcgccgacc 29887 ctccaccatt tcttcaccgt cacgagatct cttcgggccg acggggacca cacgggcaga 29947 gactgaagga ccggcgctcg acctcgccgg ctcccgcccc tccacccctt ccccgcgttg 30007 cccctgaccg catgggcggc atctcggtgc gcgtttcttc ccgcgcctgg cgcgagggga 30067

```
gatctcccat caaggggggc ctttcaaggc cctctcgcct cgagggcacc gcacgccgaa    30127
gaccgatcac aaaagtatcc gaacggctcc gaccgaggtc atatctgaga ctgatcgaat    30187
atccaacggg gagatgtg atg ggt ttc atc cgg ttt gac gtt ctg ggc ccg     30238
                    Met Gly Phe Ile Arg Phe Asp Val Leu Gly Pro
                    2670                2675 ctc agg gtc cgg tgc gac gac acc ctg ctt caa ttg acc ggg cgc         30283
Leu Arg Val Arg Cys Asp Asp Thr Leu Leu Gln Leu Thr Gly Arg
2680            2685                2690 aag tac cgc acc gtg gtt tcg tat ctc gct ctt caa ccc gag tat         30328
Lys Tyr Arg Thr Val Val Ser Tyr Leu Ala Leu Gln Pro Glu Tyr
2695            2700                2705 tcg gtg gcg ata gag gac ctc gtc cga gcc gct tgg agc gac aag         30373
Ser Val Ala Ile Glu Asp Leu Val Arg Ala Ala Trp Ser Asp Lys
2710            2715                2720 cgc ccg tcc agc gcg cac cac cag gtc cgt aag atg gtc tcc gca         30418
Arg Pro Ser Ser Ala His His Gln Val Arg Lys Met Val Ser Ala
2725            2730                2735 ctc cgg acc agc ctg gac cag gac tgg gac ctg gtg gcg acg tcc         30463
Leu Arg Thr Ser Leu Asp Gln Asp Trp Asp Leu Val Ala Thr Ser
2740            2745                2750 cag gac ggc tac atg ctg aag ttg ccg ccc aag cag tcc gac gta         30508
Gln Asp Gly Tyr Met Leu Lys Leu Pro Pro Lys Gln Ser Asp Val
2755            2760                2765 tcc gaa ttc tgc cgc ctc ttc gac cag gtg atg tcg ggt ccc ctg         30553
Ser Glu Phe Cys Arg Leu Phe Asp Gln Val Met Ser Gly Pro Leu
2770            2775                2780 acg agc gac gac gac ctg tcg gcc gcg tat tcg gcg ctg gcg ctc         30598
Thr Ser Asp Asp Asp Leu Ser Ala Ala Tyr Ser Ala Leu Ala Leu
2785            2790                2795 tgg cgc gga cgc cct tgc gaa ggg tcc gag ccc cat ggg cag gag         30643
Trp Arg Gly Arg Pro Cys Glu Gly Ser Glu Pro His Gly Gln Glu
2800            2805                2810 cgc cgg atc tct caa ttg gtg gaa cag cac cgc gtc ctc ttg aac         30688
Arg Arg Ile Ser Gln Leu Val Glu Gln His Arg Val Leu Leu Asn
2815            2820                2825 aag acc gtt cag gga ttc ggc gac agg ggc agg tcc gat gaa ctc         30733
Lys Thr Val Gln Gly Phe Gly Asp Arg Gly Arg Ser Asp Glu Leu
2830            2835                2840 gcc tcg ata ctg cac gtc gca tcg aag att cac gga cag ccg gtc         30778
Ala Ser Ile Leu His Val Ala Ser Lys Ile His Gly Gln Pro Val
2845            2850                2855 acc gct cgc tcc ggt gtc gcc gtt ccc gcg ccc gct gtt tcg tac         30823
Thr Ala Arg Ser Gly Val Ala Val Pro Ala Pro Ala Val Ser Tyr
2860            2865                2870 gcg ggc acg aca caa gtc ccc gaa cct tcg ggg tcg acc acc cct         30868
Ala Gly Thr Thr Gln Val Pro Glu Pro Ser Gly Ser Thr Thr Pro
2875            2880                2885 ccc cca cgc ccc ggc tcc ccc gtc ggt ccg cgc tgc ctg cca cgg         30913
Pro Pro Arg Pro Gly Ser Pro Val Gly Pro Arg Cys Leu Pro Arg
2890            2895                2900 gat ctg cag gac ttc ggc ggc cgc gaa cgc gaa atc aat gag ctg         30958
Asp Leu Gln Asp Phe Gly Gly Arg Glu Arg Glu Ile Asn Glu Leu
2905            2910                2915 cag aaa ctg ttg acc gcg gaa gga ccc cac cca cag ttg gtg gcg         31003
Gln Lys Leu Leu Thr Ala Glu Gly Pro His Pro Gln Leu Val Ala
2920            2925                2930 acc gtt cac gga atg agc ggc gtg ggt aaa acc gcc gtc gcc gtc         31048
Thr Val His Gly Met Ser Gly Val Gly Lys Thr Ala Val Ala Val
2935            2940                2945
```

| | | |
|---|---|---|
| cgc ctg gcg cac aga cta gcc cat cac tat ccg gac ggc cag ctc<br>Arg Leu Ala His Arg Leu Ala His His Tyr Pro Asp Gly Gln Leu<br>2950     2955     2960 | | 31093 |
| ttt gta tcc ctg gac ggc ttt tct tcg gcc tcc acc gcc acc gtg<br>Phe Val Ser Leu Asp Gly Phe Ser Ser Ala Ser Thr Ala Thr Val<br>2965     2970     2975 | | 31138 |
| tcg aat gcg ctg gga ata ctc ctc aga cag aaa ggc ctg gcg gac<br>Ser Asn Ala Leu Gly Ile Leu Leu Arg Gln Lys Gly Leu Ala Asp<br>2980     2985     2990 | | 31183 |
| gag gac att tca cct tcg gaa gac ggc cgc ctc gca caa tgg cgg<br>Glu Asp Ile Ser Pro Ser Glu Asp Gly Arg Leu Ala Gln Trp Arg<br>2995     3000     3005 | | 31228 |
| acc atc acc gcc gga cag aag ctg ctc gtc gtg ctc gac gac gtg<br>Thr Ile Thr Ala Gly Gln Lys Leu Leu Val Val Leu Asp Asp Val<br>3010     3015     3020 | | 31273 |
| tgc gac atc gag caa gta gaa ccc ctc atc ccg ccc tcg agc gaa<br>Cys Asp Ile Glu Gln Val Glu Pro Leu Ile Pro Pro Ser Ser Glu<br>3025     3030     3035 | | 31318 |
| agc gcc tgc atc atc acg tcg cgc atc atc ctc aat ggc atc gac<br>Ser Ala Cys Ile Ile Thr Ser Arg Ile Ile Leu Asn Gly Ile Asp<br>3040     3045     3050 | | 31363 |
| ggc gct cat cac atc tca ctc gaa gta ccg gac gag gac gaa tgt<br>Gly Ala His His Ile Ser Leu Glu Val Pro Asp Glu Asp Glu Cys<br>3055     3060     3065 | | 31408 |
| ctg gag ata ctc agt tgc atg atc ggc aga cgc ttc gac gac gag<br>Leu Glu Ile Leu Ser Cys Met Ile Gly Arg Arg Phe Asp Asp Glu<br>3070     3075     3080 | | 31453 |
| gag acg aag gac gcc cgc gcg ctg atc cag cag tgc gcc aat ctg<br>Glu Thr Lys Asp Ala Arg Ala Leu Ile Gln Gln Cys Ala Asn Leu<br>3085     3090     3095 | | 31498 |
| ccg ctg gca ctc cgt ctc gcc gcc gcc cgg ata tcg acg cgc gac<br>Pro Leu Ala Leu Arg Leu Ala Ala Ala Arg Ile Ser Thr Arg Asp<br>3100     3105     3110 | | 31543 |
| ttc ctg aac ctc cgg gaa ctc agt gag caa ctg tcg tcc tcg gct<br>Phe Leu Asn Leu Arg Glu Leu Ser Glu Gln Leu Ser Ser Ser Ala<br>3115     3120     3125 | | 31588 |
| tcc atc ttc agt gaa ctg gaa gtt ccc ggc cgt agt ctg gtc ggc<br>Ser Ile Phe Ser Glu Leu Glu Val Pro Gly Arg Ser Leu Val Gly<br>3130     3135     3140 | | 31633 |
| cgg ctc atg acg tcc ttc acg tgc ctg gag gac ttc gat cac gac<br>Arg Leu Met Thr Ser Phe Thr Cys Leu Glu Asp Phe Asp His Asp<br>3145     3150     3155 | | 31678 |
| cgg tac ctc cga tta tcg ctc ctc ccc tgc ccc gag atc gat gaa<br>Arg Tyr Leu Arg Leu Ser Leu Leu Pro Cys Pro Glu Ile Asp Glu<br>3160     3165     3170 | | 31723 |
| acg tcg gtc gcg gcc gtg ctg ggc gta tcc acc gac tgg gca cgg<br>Thr Ser Val Ala Ala Val Leu Gly Val Ser Thr Asp Trp Ala Arg<br>3175     3180     3185 | | 31768 |
| cgt gcc tgc agg cgc ttc gca gac cgc gcg ttg ctg caa cgc aca<br>Arg Ala Cys Arg Arg Phe Ala Asp Arg Ala Leu Leu Gln Arg Thr<br>3190     3195     3200 | | 31813 |
| cga tgc ggt acg tac cgg atg cac ccg ctg ctg ctg cag gcg gca<br>Arg Cys Gly Thr Tyr Arg Met His Pro Leu Leu Leu Gln Ala Ala<br>3205     3210     3215 | | 31858 |
| cag ctg gaa gcg cag aag acc atc ccg ttc gag gag caa cgc cgg<br>Gln Leu Glu Ala Gln Lys Thr Ile Pro Phe Glu Glu Gln Arg Arg<br>3220     3225     3230 | | 31903 |
| ctc gtc cgc gcc gct ttc ctc cat tac aag gcg tcg aac ggc ctc<br>Leu Val Arg Ala Ala Phe Leu His Tyr Lys Ala Ser Asn Gly Leu<br>3235     3240     3245 | | 31948 |

```
gtg gga gcc agc cgc atc agc cct tcc cgg gtt cct gac gga cac      31993
Val Gly Ala Ser Arg Ile Ser Pro Ser Arg Val Pro Asp Gly His
3250                3255                3260 gtg gta ctg agg acc ctc acg cag tcc gcg aag ctg gcc gcg cgg      32038
Val Val Leu Arg Thr Leu Thr Gln Ser Ala Lys Leu Ala Ala Arg
3265                3270                3275 ctc ggc ctc cag gag gag ttg gcc gat ctg tac acc gcc tgg aag      32083
Leu Gly Leu Gln Glu Glu Leu Ala Asp Leu Tyr Thr Ala Trp Lys
3280                3285                3290 gaa ctg ctc ccc ctc gtg ctg gac cgc gg cag cag gag gcg gtc       32128
Glu Leu Leu Pro Leu Val Leu Asp Arg Arg Gln Gln Glu Ala Val
3295                3300                3305 ggg cga cgc gta ctc gcc gtt tca cag cac ctg gac cgg ccc gcg      32173
Gly Arg Arg Val Leu Ala Val Ser Gln His Leu Asp Arg Pro Ala
3310                3315                3320 tgc gag gga gca ccc cac cgg agg cgt ccg cgg cag gca cgg gac      32218
Cys Glu Gly Ala Pro His Arg Arg Arg Pro Arg Gln Ala Arg Asp
3325                3330                3335 atg ctg ccc gag ggg cag cgg tgaacgaggg ccggccggag aaggcagtc      32269
Met Leu Pro Glu Gly Gln Arg
3340                3345 ggacgatgac gaccgtttgt ccgtacatcg ggagaccggg gtgccacgtg aaacatgtga 32329 cccggtcacc ggatgtccga tcgcagccgc acccgggggc gaactgacc atg gac cgc 32387
                                                      Met Asp Arg gtt ctt ccg tat gca gcc ggc agt gag gca ctc ctg tcg tcg aga      32432
Val Leu Pro Tyr Ala Ala Gly Ser Glu Ala Leu Leu Ser Ser Arg
3350                3355                3360 gag cac ggc ccc acg gtg agc gag aga acc gtc tcg gcg cag gag      32477
Glu His Gly Pro Thr Val Ser Glu Arg Thr Val Ser Ala Gln Glu
3365                3370                3375 atc gtc gtg ggc ggc ggg ggt ctg ctg ggg aga cac atc ctc ggc      32522
Ile Val Val Gly Gly Gly Gly Leu Leu Gly Arg His Ile Leu Gly
3380                3385                3390 gtg ctg ggc aat cgg ctc agc cgg cgg gta cgc atc ccg tgg gac      32567
Val Leu Gly Asn Arg Leu Ser Arg Arg Val Arg Ile Pro Trp Asp
3395                3400                3405 gac cac ggc cgc gcc tgt gag cag ctc tac gcg ctg ggc agg gac      32612
Asp His Gly Arg Ala Cys Glu Gln Leu Tyr Ala Leu Gly Arg Asp
3410                3415                3420 ctg gct cag cag ccg gcg cgc tgg aac ctg tac tgg tgc gcg gga      32657
Leu Ala Gln Gln Pro Ala Arg Trp Asn Leu Tyr Trp Cys Ala Gly
3425                3430                3435 ctg gcc gtc ttc cac acc ccc gcc gag cag gtg gag cga gaa cgc      32702
Leu Ala Val Phe His Thr Pro Ala Glu Gln Val Glu Arg Glu Arg
3440                3445                3450 ctc cag gtc agc ctc ctc ctg gcg ggc atc aac gac ggg ctc gaa      32747
Leu Gln Val Ser Leu Leu Leu Ala Gly Ile Asn Asp Gly Leu Glu
3455                3460                3465 cgc tcg ggg ggc ccc acc ggc ggc gcg ttg ttc ctg gcc tcc tca      32792
Arg Ser Gly Gly Pro Thr Gly Gly Ala Leu Phe Leu Ala Ser Ser
3470                3475                3480 gcc ggc ggc gcg ttc gcg ggc tcg gaa cac ccg ccg ttc acc gag      32837
Ala Gly Gly Ala Phe Ala Gly Ser Glu His Pro Pro Phe Thr Glu
3485                3490                3495 ttc tcc ccg ccc gtg ccc acg aac ccg tac ggc gcg tcc aaa ctc      32882
Phe Ser Pro Pro Val Pro Thr Asn Pro Tyr Gly Ala Ser Lys Leu
3500                3505                3510
```

-continued

| | | |
|---|---|---|
| gcc gtc gag gag gag gcc gag gtt ctg gcg cgc cgt tgg cga ctg<br>Ala Val Glu Glu Glu Ala Glu Val Leu Ala Arg Arg Trp Arg Leu<br>3515                    3520                        3525 | 32927 |
| ccc acg gtg tcg ggt cgg atc acg aac ctg tac ggc ccc ggc cag<br>Pro Thr Val Ser Gly Arg Ile Thr Asn Leu Tyr Gly Pro Gly Gln<br>3530                    3535                        3540 | 32972 |
| aac ctc gac aag aac cag ggc ctg gtc agt gcc ctc gtc aaa gcg<br>Asn Leu Asp Lys Asn Gln Gly Leu Val Ser Ala Leu Val Lys Ala<br>3545                    3550                        3555 | 33017 |
| cag ctg acc ggt gaa ccc ctg cgg ctg cgg gcc gcc ctg gag acc<br>Gln Leu Thr Gly Glu Pro Leu Arg Leu Arg Ala Ala Leu Glu Thr<br>3560                    3565                        3570 | 33062 |
| acg cgc gac tac atc tac gca cgg gac tgc gcc cgg atg gtc gtc<br>Thr Arg Asp Tyr Ile Tyr Ala Arg Asp Cys Ala Arg Met Val Val<br>3575                    3580                        3585 | 33107 |
| tcg gcg atg gag acc gta cgg tcc cgc acc cgc ggc acg gac ccc<br>Ser Ala Met Glu Thr Val Arg Ser Arg Thr Arg Gly Thr Asp Pro<br>3590                    3595                        3600 | 33152 |
| cat gtc cgc aag ata ttc agc agc gga cgc cgt ctg cgg atc gac<br>His Val Arg Lys Ile Phe Ser Ser Gly Arg Arg Leu Arg Ile Asp<br>3605                    3610                        3615 | 33197 |
| gaa ctg ctc cgg atc gcc gag cgc ctc ttc gac cgg ccg gta ccc<br>Glu Leu Leu Arg Ile Ala Glu Arg Leu Phe Asp Arg Pro Val Pro<br>3620                    3625                        3630 | 33242 |
| gtc gtc cac gag ccg gtg gcg gga ggg gcg aac gtc aac ctc tcg<br>Val Val His Glu Pro Val Ala Gly Gly Ala Asn Val Asn Leu Ser<br>3635                    3640                        3645 | 33287 |
| gtc gag tcc cgg gta tgg gcg gac ctc gaa tcg tcc ccc ttc ctc<br>Val Glu Ser Arg Val Trp Ala Asp Leu Glu Ser Ser Pro Phe Leu<br>3650                    3655                        3660 | 33332 |
| agc atc gag gaa ggg atg cgc gcc gtc cgc tcc gac ctc agg tac<br>Ser Ile Glu Glu Gly Met Arg Ala Val Arg Ser Asp Leu Arg Tyr<br>3665                    3670                        3675 | 33377 |
| cga ctc ggg cac ggg tgagcgacac gaacgacaaa agacccaggc cgcacatcag<br>Arg Leu Gly His Gly<br>3680 | 33432 |
| cgcggcctgg gtccgatgag ccgccttcgg gattcgaacc cgagacctac gcattacgag | 33492 |
| tgcgttgctc tggccatctg agctaaggcg gcgtgctggg tgcacccatg gtgcgatcag | 33552 |
| cgacgtcggt aagtctacac agtttcgagg ggtggttcgt accggccccg gagcgggccg | 33612 |
| gggctgcctc cggtgggcgg ggcggctacg agcagcgtgt gccgtcggcg ggcggggtgc | 33672 |
| cgtcgaggag gtaggtgttg atggcggagt cgacgcaggc gctgccgcgg ccgtacgggg | 33732 |
| tgtggccgtc gccgtcgtag gtgaggaggc gggccgtggc gagctggccg gccagaccct | 33792 |
| cggcccagcg gtacggggtg gccgggtccc ggg | 33825 |

<210> SEQ ID NO 2
<211> LENGTH: 341
<212> TYPE: PRT
<213> ORGANISM: Streptomyces griseoflavus

<400> SEQUENCE: 2

Leu Ile Ala Asn Arg Thr Leu Glu Leu Leu Ser Leu Leu Gln Thr Gln
1               5                   10                15

Arg Glu Trp Thr Gly Asp Gly Leu Ala Glu Arg Leu Gly Val Ser Pro
                   20                   25                 30

Arg Thr Val Arg Arg Asp Ile Asn Arg Leu Arg Glu Leu Gly Tyr Pro
             35                   40                 45

```
Val Thr Ala Thr Lys Gly Pro Ser Gly Ser Tyr Arg Leu Ser Arg Gly
 50                  55                  60

Ala Arg Leu Pro Pro Leu Ile Val Asp Asp Glu Gln Ala Leu Ala Ile
 65                  70                  75                  80

Ala Leu Ser Leu Gln Thr Ala Pro Ala Ser Val Thr Gly Met Gly Asp
                 85                  90                  95

Ala Thr Lys Arg Ala Leu Asn Ser Ile Gln Glu Leu Leu Pro Pro His
                100                 105                 110

Leu Ala His Arg Leu Ala Thr Phe Ser Val Glu Gln Ile Glu Asn Ala
            115                 120                 125

Trp Glu Leu Ala Pro Pro Gln Val Asp Pro Ser Leu Leu Ala Gln Leu
    130                 135                 140

Ser Ser Ala Ala Gln Gln Arg Asp Leu Val Arg Phe Ser Tyr Arg Ser
145                 150                 155                 160

Ile His His Asp Ser Met Gln Asp Gly Glu Val Leu Ala Glu Pro His
                165                 170                 175

Arg Leu Val Val Trp Ser Gly Arg Trp Tyr Leu Val Ala Tyr Asp Gln
            180                 185                 190

Gln Arg Ser Ser Trp His Ala Tyr Arg Val Asp Arg Ile Lys Asp Leu
    195                 200                 205

Ala Pro Thr Ala Trp Arg Phe Gly Glu Arg Glu Gly Pro Asp Glu Asp
210                 215                 220

Ile Thr Arg Phe Val Gln Asn Gln Pro Asp Arg Gly Asp Thr Pro Asp
225                 230                 235                 240

Thr Trp Pro Cys Trp Gly Thr Val Leu Met Glu Cys Pro Ala Ser Leu
                245                 250                 255

Val Ala Lys Trp Ala Pro Gly Val Ala Ser Phe Glu Ala Val Asp Asp
            260                 265                 270

Arg Val Thr Arg Ile Gln Met Gly Ala Trp Ser Trp Ser Ala Leu Ile
    275                 280                 285

Gly Phe Leu Ile Thr Phe Ser Cys Arg Phe Thr Val Glu Gly Pro Pro
290                 295                 300

Glu Leu Val Ala Ala Ala Arg Arg Val Met Gly Leu Ile Asp Val Gly
305                 310                 315                 320

Ile Pro Ser His Asp Pro Leu Ala Glu Pro Ser Ser Arg Thr Pro Gly
                325                 330                 335

Pro Ser Ala Gly Arg
            340

<210> SEQ ID NO 3
<211> LENGTH: 213
<212> TYPE: PRT
<213> ORGANISM: Streptomyces griseoflavus

<400> SEQUENCE: 3

Met Ile Arg Ile Ala Val Ile Leu Gly Ser Thr Arg Pro Gly Arg Arg
 1               5                  10                  15

Gly Ala Val Val Ala Gln Trp Val Ala Glu Val Ala Ala Arg His Pro
                 20                  25                  30

Ala Ala Val Met Gly Glu Ala Glu Phe Glu Leu Val Asp Leu Ala Glu
             35                  40                  45

Tyr Gly Leu Pro Leu Leu Asp Glu Pro Val Pro Ala Met Phe Gly Gln
     50                  55                  60

Tyr Gln Lys Glu Glu Thr Arg Arg Trp Ala Ala Ala Ile Gly Ser Phe
 65                  70                  75                  80
```

```
Asp Gly Phe Val Phe Val Thr Pro Glu Tyr Asn His Ser Val Pro Ala
                85                  90                  95

Ala Leu Lys Asn Ala Ile Asp His Leu Phe Ala Glu Trp Thr Asp Lys
            100                 105                 110

Ala Ala Gly Phe Val Ser Tyr Gly Val His Gly Gly Thr Arg Ala Val
        115                 120                 125

Glu His Leu Arg Leu Ala Leu Ala Glu Val Lys Val Ala Gly Val Arg
    130                 135                 140

Ser Gln Val Val Leu Ser Val Phe Asn Asp Phe Asp Tyr Thr Gly Cys
145                 150                 155                 160

Asp Met Thr Asp Pro Thr Ala Met Gly Arg Phe Thr Pro Gly Pro Gln
                165                 170                 175

Gln Glu Gln Thr Val Asn Thr Met Leu Asp Glu Val Val Ala Trp Ser
            180                 185                 190

Thr Ala Leu Lys Pro Leu Arg Thr Ala Ala Thr Ala Glu Ala Asp Gly
        195                 200                 205

Arg Ala Val Ser Val
    210

<210> SEQ ID NO 4
<211> LENGTH: 500
<212> TYPE: PRT
<213> ORGANISM: Streptomyces griseoflavus

<400> SEQUENCE: 4

Met Thr Leu His Ala Ala Glu Ala Ile Pro Ser His Val Pro Val Leu
1               5                   10                  15

Val Val Gly Ala Gly Pro Thr Gly Leu Met Leu Gly Ala Glu Leu Ala
            20                  25                  30

Leu His Gly Ser Arg Pro Leu Val Ile Asp Ala Leu Pro Ser Pro Ser
        35                  40                  45

Gly Gln Ser Arg Ala Leu Gly Phe Thr Val Arg Thr Leu Glu Ile Phe
    50                  55                  60

Lys Gln Arg Gly Ile Leu Gly Arg Phe Gln Gly Leu Ala Pro Val Pro
65                  70                  75                  80

Gly Val His Phe Ala Gly Leu Ser Ile Lys Gly Asp His Leu Ser Ser
                85                  90                  95

Ser Met Arg Pro Ala Asn Gln Tyr Pro Gln Ser Lys Thr Glu Gln Val
            100                 105                 110

Leu Ala Ala Trp Ala Glu Glu Leu Gly Val Pro Val Arg Arg Pro Trp
        115                 120                 125

Thr Leu Thr Ser Met Glu Pro Thr Gly Thr Gly Tyr Arg Cys Val Leu
    130                 135                 140

Ser Gly Pro Ala Gly Gln Gln Thr Val Asp Ala Asp Tyr Val Val Gly
145                 150                 155                 160

Cys Asp Gly Ala Gly Ser Phe Val Arg Glu Ala Ile Gly Met Pro Thr
                165                 170                 175

Lys Arg Thr Pro Pro Ser Val Gln Met Leu Leu Gly Asp Leu Arg Gly
            180                 185                 190

Cys Gly Leu Pro Asp Glu Pro Phe Gly Val Lys His Glu Lys Gly Met
        195                 200                 205

Val Met Ser Ala Pro Leu Gly Asp Gly Thr Glu Arg Val Ile Val Cys
    210                 215                 220

Asp Phe Thr Gln Pro Met Arg Pro Gln Gly Thr Pro Val Thr His Asp
225                 230                 235                 240
```

```
Glu Ile Lys Ala Ala Tyr Glu Gln Val Val Gly Ser Pro Leu Ala Asp
                245                 250                 255

Gly Glu Cys Leu Trp Ala Ser Ser Phe Ser Asp Ala Ser Ser Leu Val
            260                 265                 270

Glu Ser Tyr Arg Ser Gly Arg Ala Leu Leu Val Gly Asp Thr Ala His
        275                 280                 285

Thr His Leu Pro Ala Gly Gly Gln Gly Met Asn Val Ser Ile Gln Asp
    290                 295                 300

Ala Val Asn Val Gly Trp Lys Leu Ala Leu Val Ser Gln Gly Arg Ala
305                 310                 315                 320

Pro Asp Thr Leu Leu Asp Thr Tyr His Ala Glu Arg Tyr Pro Val Gly
                325                 330                 335

Arg Glu Leu Leu Leu Asn Thr Ala Ala Gln Gly Gln Val Phe Leu Arg
            340                 345                 350

Gly Pro Glu Val Asp Pro Leu Arg Glu Val Leu Arg Arg Leu Leu Asn
        355                 360                 365

Ile Arg Glu Val Ser Val Leu Leu Ala Asp Gly Val Ser Gly Leu Asp
    370                 375                 380

Ile Arg Tyr Asp Met Gly Leu Pro Glu Ala Pro Pro Thr Gly Glu
385                 390                 395                 400

Arg Leu Pro Pro Asp Val Phe His Val Val Gly Thr Gly Gly Asp Ala
                405                 410                 415

Val Glu Glu Leu Arg His Gly Ala Ala Leu Leu Ile Val Pro Ser Pro
            420                 425                 430

Asp Ser Pro Ala Ser Ser Leu Val Ala Pro Trp Arg Asp Gln Val Arg
        435                 440                 445

Val Val His Ala Arg Pro Thr Asp Pro Asp Trp Gly Gly Glu Pro Ala
    450                 455                 460

Ala Ser Ser His Trp Phe Val Arg Pro Asp Gly His Ile Ala Trp Ala
465                 470                 475                 480

Gly Thr Glu Phe Ser Glu Leu Ser Ala Ser Leu Ser Arg Trp Leu Gly
                485                 490                 495

Gln Pro Ala Ala
            500

<210> SEQ ID NO 5
<211> LENGTH: 419
<212> TYPE: PRT
<213> ORGANISM: Streptomyces griseoflavus

<400> SEQUENCE: 5

Met Ser Arg Arg Val Phe Ile Thr Gly Val Gly Val Val Ala Pro Gly
1               5                   10                  15

Ala Val Gly Arg Asp Pro Phe Trp Glu Leu Leu Thr Gln Gly Arg Thr
            20                  25                  30

Ala Thr Arg Arg Leu Ser Leu Cys Asp Pro Glu Pro Phe Arg Ser Gln
        35                  40                  45

Val Ala Ala Glu Ala Asp Phe Asp Ala Glu Ala Ala Gly Leu Ser Glu
    50                  55                  60

Arg Gln Ser Ala Glu Leu Asp Arg Ala Ala Gln Phe Ala Leu Val Ala
65                  70                  75                  80

Ala Arg Glu Ala Val Glu Asp Ala Ala Trp Ser Glu Thr Cys Pro Pro
                85                  90                  95

Glu Arg Ala Gly Val Ile Val Gly Ser Ala Val Gly Ala Thr Thr Lys
            100                 105                 110
```

Leu Glu Glu Val Tyr Arg Gln Leu Ser Arg Asp Gly Ser Leu Trp Asp
            115                 120                 125

Val Ala Pro Asp Ser Pro Ala Glu Leu Tyr Ser Tyr Phe Val Pro Ser
        130                 135                 140

Ser Phe Ala Ser Gly Ile Ala His Asp Leu Gly Val Thr Gly Gln Ser
145                 150                 155                 160

Gly Val Val Ser Thr Gly Cys Thr Ser Gly Ile Asp Ser Val Gly Asn
                165                 170                 175

Ala Trp Glu Leu Ile Gln Ser Gly Ile Leu Asp Ser Ala Val Cys Gly
            180                 185                 190

Ala Thr Asp Ala Pro Ile Ser Pro Ile Thr Val Ala Cys Phe Asp Thr
        195                 200                 205

Ile Lys Ala Thr Ser Thr Tyr Asn Asp Thr Pro Glu Ser Ala Ser Arg
210                 215                 220

Pro Phe Asp Ala Thr Arg Gly Gly Phe Val Leu Gly Glu Gly Ser Ala
225                 230                 235                 240

Met Phe Val Leu Glu Ser Glu Ser Val His Arg Arg Gly Ala Arg
            245                 250                 255

Val Tyr Gly Glu Ile Arg Gly Tyr Ala Ser Arg Cys Asn Ala Tyr His
        260                 265                 270

Met Thr Gly Leu Lys Ala Asp Gly Arg Glu Leu Ala Glu Ala Val Val
            275                 280                 285

Ser Ala Leu Gly Gln Ala Gly Val Asp Pro Gly Arg Leu Asp Tyr Val
        290                 295                 300

Asn Ala His Gly Ser Gly Thr Lys Gln Asn Asp Arg His Glu Thr Ala
305                 310                 315                 320

Ala Leu Lys Ser Ser Leu Gly Pro Ala Ala His Asp Val Pro Ile Ser
            325                 330                 335

Ser Ile Lys Ser Met Ile Gly His Ser Leu Gly Ala Ile Gly Ser Leu
            340                 345                 350

Glu Ile Ala Ala Cys Ala Leu Ala Leu Arg Asp Asp Val Ile Pro Pro
            355                 360                 365

Thr Ala Asn Leu Thr Arg Pro Asp Pro Glu Leu Asp Leu Asp Tyr Val
        370                 375                 380

Pro Val His Ala Arg Lys Gln Pro Thr Asn Ser Val Leu Thr Thr Gly
385                 390                 395                 400

Ser Gly Phe Gly Gly Phe Gln Ser Ala Met Val Leu Thr Asp Pro Glu
                405                 410                 415

His His Ser

<210> SEQ ID NO 6
<211> LENGTH: 89
<212> TYPE: PRT
<213> ORGANISM: Streptomyces griseoflavus

<400> SEQUENCE: 6

Met Ser Ala Arg Val Thr Met Asp Asp Leu Arg Arg Ala Leu Glu Glu
1               5                   10                  15

Gly Ser Gly Val Asp Glu Gly Val Asp Leu Asp Thr Asp Leu Glu Thr
            20                  25                  30

Met Ala Phe Ser Glu Leu Gly Tyr Asp Ser Leu Ala Val Leu Glu Thr
        35                  40                  45

Gly Leu Arg Leu Gly Arg Glu Asn Asp Ile Glu Leu Asp Asp Ser Val
    50                  55                  60

Phe Ala Asp Leu Asp Thr Pro Gln Gln Met Leu Asp Ala Val Asn Asp
65                  70                  75                  80

Ala Leu Ala Arg Gln Ala Ala Ala Ser
                85

<210> SEQ ID NO 7
<211> LENGTH: 316
<212> TYPE: PRT
<213> ORGANISM: Streptomyces griseoflavus

<400> SEQUENCE: 7

Met Ala Asp Pro Ala Arg Thr Asp Leu His Ser Ala Thr Ile Thr Gly
1               5                   10                  15

Ser Ala Asp Ala Val Tyr Arg Arg Leu Glu Asp Val Gly Gln Trp Ser
                20                  25                  30

Gln Met Phe Glu Pro Thr Ile His Gly Ala Glu Leu Ala Arg Asp Gly
            35                  40                  45

Asn Arg Gln Thr Ile Gln Leu Trp Ala Thr Ala Asn Gly Glu Pro Lys
        50                  55                  60

Ala Trp Val Ser Glu Arg Glu Leu Asp Pro Val Ala Arg Thr Ile Arg
65                  70                  75                  80

Phe Ala Gln Thr Val Thr Ser Ser Pro Val Ala Glu Met Ser Gly Ala
                85                  90                  95

Trp Gln Val Leu Pro Leu Ser Glu Asp Thr Cys Arg Val Glu Leu Thr
            100                 105                 110

His Thr Tyr Arg Ala Glu Asn Asp Ser Ala Glu Ser Leu Thr Trp Ile
        115                 120                 125

Ala Arg Ala Val Glu Thr Asn Ser Thr Lys Glu Leu Ser Ala Leu Lys
130                 135                 140

Phe Ala Cys Glu Arg Asp Ala Asp Ser Glu Ala Ser Pro Phe Thr Phe
145                 150                 155                 160

Thr Asp Ala Val Asp Thr Thr Val Asp Pro Val Leu Leu Phe Ser Phe
                165                 170                 175

Leu Asp Arg Gly Glu Leu Trp Ala Gly Arg Leu Glu His Val Ala Glu
            180                 185                 190

Ala Glu Met Arg Glu Phe Ser Asp Gly Leu Gln Phe Leu Arg Met Arg
        195                 200                 205

Thr Arg Thr Pro Asp Gly Asp Thr His Val Thr Glu Ser Tyr Arg Val
210                 215                 220

Ser Gln Ser Pro Ala Arg Leu Leu Tyr Lys Gln Val Thr Leu Pro Ala
225                 230                 235                 240

Leu Leu Ser Leu His Thr Gly Glu Trp Thr Ile Thr Pro Ala Gly Glu
                245                 250                 255

Ser Trp Arg Val Thr Ser Lys His Thr Val Ala Ile Asp Pro Asp Ala
            260                 265                 270

Val His Lys Val Leu Gly Ala Asp Ala Thr Val Ser Asp Ala Lys Arg
        275                 280                 285

Leu Ala Arg Arg Asn Leu Gly Asn Asn Ser Leu Arg Thr Leu Glu Ala
290                 295                 300

Ala Val Arg Trp Ala Gly Thr Ala Val Ser Gln Arg
305                 310                 315

<210> SEQ ID NO 8
<211> LENGTH: 451
<212> TYPE: PRT
<213> ORGANISM: Streptomyces griseoflavus

<400> SEQUENCE: 8

```
Met Thr Glu Pro Glu Thr Ser Asp Val Leu Val Gly Ala Gly Pro
1               5                   10                  15

Ser Gly Leu Leu Leu Ala Gly Ile Leu Ala Gly Ala Gly Ala Arg Val
            20                  25                  30

Thr Val Leu Glu Ala Arg Asp Ala Pro Ser Pro Gln Thr Arg Ala Ser
        35                  40                  45

Thr Leu His Ala Arg Ala Arg Glu Ile Leu Asp His His Gly Val Glu
    50                  55                  60

Phe Ser Pro Glu Leu Pro Trp Ser Ala Gly His Tyr Gly Gly Leu
65              70                  75                  80

Arg Val Asp Leu Ser Arg Val Asp Ser Gly Arg Ala Gly Val Trp Lys
                85                  90                  95

Cys Pro Gln Pro Glu Leu Val Arg Thr Leu Thr Gly Trp Ala Arg Gly
            100                 105                 110

His Gly Ala Arg Leu Leu His Gly Glu His Val Glu Ser Val Arg Glu
        115                 120                 125

Gln Gly Gly Arg Cys Leu Val Arg Thr Arg Ala Gly Thr Thr Phe Ser
    130                 135                 140

Gly Thr Leu Leu Val Ala Ala Asp Gly Arg Arg Ser Thr Val Arg Ser
145                 150                 155                 160

Leu Leu Gly Ile Gly Cys Gly Gly Ala Pro Ala Thr Arg Val Leu Val
                165                 170                 175

Gln Ala Asp Val His Gly Asp Gly Leu Ala Gly Arg Arg Phe Glu Arg
            180                 185                 190

His Gly Arg Tyr Thr Val Thr Ala Ala Pro Ile Ser Pro Gly Ile Thr
        195                 200                 205

Arg Val Met Leu His Asp Pro Arg Trp Pro Ala Gly Glu Glu Arg Thr
    210                 215                 220

Leu Glu Asp Leu Arg Arg Ala Trp Lys Glu Ser Thr Gly Glu Thr Leu
225                 230                 235                 240

Pro Ala Glu Pro Ser Trp Ser Arg Thr Phe Ser Asp Asp Thr Thr Val
                245                 250                 255

Ala His Pro Leu Val Lys Gly Arg Val Val Leu Cys Gly Asp Ala Ala
            260                 265                 270

His Pro Phe Val Pro Ile Gly Gly Gln Ala Leu Asn Thr Ser Leu Met
        275                 280                 285

Asp Ala Glu Ala Leu Gly Trp Arg Val Leu Gly Tyr Leu Asp Asp Gly
    290                 295                 300

Asp Arg Gln Gly Leu Leu Asp Tyr Gln Asp Glu Arg Phe Ser Trp Leu
305                 310                 315                 320

Thr Val Leu Ala Gly Arg Leu Arg Ala Gln Ala Arg Leu Leu Phe Asp
                325                 330                 335

Thr Asp Ala Ala Ala Thr Glu Arg Lys Ala Leu Val Ala Ala Arg Leu
            340                 345                 350

Ala Gly Asp Ala Asp Tyr Arg Arg Ile Ala Asp Ala Leu Ala Gly
        355                 360                 365

Val Asp Val Cys Tyr Leu Thr Pro Gly Gly Ala Val Arg Arg Arg Leu
    370                 375                 380

Ser Pro Ala Arg Leu Arg Glu Thr Gly Val Asn Pro Gly Ala Arg Arg
385                 390                 395                 400

Val Gln Arg Ala Leu Val Pro Asp Gly Thr Arg Thr Asp Ala Trp
                405                 410                 415
```

```
Ile Arg Pro Asp His His Trp Tyr Pro Val Ala Arg Asp Gly Ala Arg
            420                 425                 430

Gln Asp Trp Asp Asp Ala Val Arg Leu His Asp Asp Leu Glu Pro Glu
            435                 440                 445

Val Thr Arg
    450

<210> SEQ ID NO 9
<211> LENGTH: 339
<212> TYPE: PRT
<213> ORGANISM: Streptomyces griseoflavus

<400> SEQUENCE: 9

Val Pro His Gln Ala Thr Gly Ala Ala Pro Asp Gly Gly Ser Ala
1               5                   10                  15

Pro Arg Ser Leu Val Leu Met Leu Pro Gly Gln Gly Ser Gln Phe Ala
            20                  25                  30

Ala Met Gly Val Pro Leu Tyr Glu Ser Asp Ala Arg Phe Arg Lys Ala
            35                  40                  45

Leu Asp Asp Phe Phe Asp Ala Phe Gly Thr Gly Ala Glu Arg Leu Arg
    50                  55                  60

Arg Glu Trp Leu His Gly Ser Ala Gln Gly Ile Glu Arg Gly Ser Phe
65              70                  75                  80

Ala Gln Pro Met Leu Phe Gly Leu Asp Tyr Ala Ala Gly Ala Val Trp
                85                  90                  95

Leu Glu Glu Leu Lys Gly Val Asp Val Thr Leu Val Gly His Ser Val
            100                 105                 110

Gly Glu Leu Ala Ala Ala Thr Leu Ala Gly Ala Phe Asp Leu Glu Leu
            115                 120                 125

Ala Gly Ala Leu Leu Ala Glu Arg Ala Arg Leu Leu Asp Ala Ala Pro
    130                 135                 140

Arg Gly Gly Met Ile Ala Cys Arg Ala Thr Glu Glu Ser Leu Arg Glu
145                 150                 155                 160

His Leu Asp Ala Leu Gly Gly Arg Ala Val Ile Ala Ala Glu Asn Ala
                165                 170                 175

Asp Asn Gln Cys Val Val Ser Cys Ala Glu Glu Asp Leu Pro Asp Thr
            180                 185                 190

Met Arg Tyr Leu Gly Ser His Gly Val Thr Cys Leu Arg Val Ala Ser
            195                 200                 205

Thr Glu Pro Phe His Ser Pro Leu Leu Ala Pro Ala Ala Ala Arg Phe
    210                 215                 220

Glu Glu Phe Leu Ala Arg Arg Gly His Arg Leu Ser Thr Thr Glu Leu
225                 230                 235                 240

Pro Met Val Ser Ala Tyr Ser Ala Arg Arg Ile Ser Gly Arg Glu Ile
                245                 250                 255

Met Pro Ala Ser Phe Trp Thr Arg Gln Met Ala Glu Lys Val Arg Phe
            260                 265                 270

Trp Glu Ala Leu Arg His Asn Phe Asp Ser Gly Pro Arg Thr Phe Val
            275                 280                 285

Glu Ile Gly Pro Gly Thr Val Leu Ser Leu Ala Ala Arg Arg Leu Pro
    290                 295                 300

Ser Val Arg Ala Arg Arg Ser Thr Val Ile Ser Thr Met Pro Arg His
305                 310                 315                 320
```

Arg Pro His Pro Glu His Trp Glu Ser Ala Ile His Glu Val Ala Glu
                325                 330                 335

Glu Phe Cys

<210> SEQ ID NO 10
<211> LENGTH: 678
<212> TYPE: PRT
<213> ORGANISM: Streptomyces griseoflavus

<400> SEQUENCE: 10

Met Gly Phe Ile Arg Phe Asp Val Leu Gly Pro Leu Arg Val Arg Cys
1               5                   10                  15

Asp Asp Thr Leu Leu Gln Leu Thr Gly Arg Lys Tyr Arg Thr Val Val
            20                  25                  30

Ser Tyr Leu Ala Leu Gln Pro Glu Tyr Ser Val Ala Ile Glu Asp Leu
        35                  40                  45

Val Arg Ala Ala Trp Ser Asp Lys Arg Pro Ser Ser Ala His His Gln
    50                  55                  60

Val Arg Lys Met Val Ser Ala Leu Arg Thr Ser Leu Asp Gln Asp Trp
65                  70                  75                  80

Asp Leu Val Ala Thr Ser Gln Asp Gly Tyr Met Leu Lys Leu Pro Pro
                85                  90                  95

Lys Gln Ser Asp Val Ser Glu Phe Cys Arg Leu Phe Asp Gln Val Met
            100                 105                 110

Ser Gly Pro Leu Thr Ser Asp Asp Leu Ser Ala Ala Tyr Ser Ala
        115                 120                 125

Leu Ala Leu Trp Arg Gly Arg Pro Cys Glu Gly Ser Glu Pro His Gly
    130                 135                 140

Gln Glu Arg Arg Ile Ser Gln Leu Val Glu Gln His Arg Val Leu Leu
145                 150                 155                 160

Asn Lys Thr Val Gln Gly Phe Gly Asp Arg Gly Arg Ser Asp Glu Leu
                165                 170                 175

Ala Ser Ile Leu His Val Ala Ser Lys Ile His Gly Gln Pro Val Thr
            180                 185                 190

Ala Arg Ser Gly Val Ala Val Pro Ala Pro Ala Val Ser Tyr Ala Gly
        195                 200                 205

Thr Thr Gln Val Pro Glu Pro Ser Gly Ser Thr Thr Pro Pro Pro Arg
    210                 215                 220

Pro Gly Ser Pro Val Gly Pro Arg Cys Leu Pro Arg Asp Leu Gln Asp
225                 230                 235                 240

Phe Gly Gly Arg Glu Arg Glu Ile Asn Glu Leu Gln Lys Leu Leu Thr
                245                 250                 255

Ala Glu Gly Pro His Pro Gln Leu Val Ala Thr Val His Gly Met Ser
            260                 265                 270

Gly Val Gly Lys Thr Ala Val Ala Val Arg Leu Ala His Arg Leu Ala
        275                 280                 285

His His Tyr Pro Asp Gly Gln Leu Phe Val Ser Leu Asp Gly Phe Ser
    290                 295                 300

Ser Ala Ser Thr Ala Thr Val Ser Asn Ala Leu Gly Ile Leu Leu Arg
305                 310                 315                 320

Gln Lys Gly Leu Ala Asp Glu Asp Ile Ser Pro Ser Glu Asp Gly Arg
                325                 330                 335

Leu Ala Gln Trp Arg Thr Ile Thr Ala Gly Gln Lys Leu Leu Val Val
            340                 345                 350

```
Leu Asp Asp Val Cys Asp Ile Glu Gln Val Glu Pro Leu Ile Pro Pro
        355                 360                 365

Ser Ser Glu Ser Ala Cys Ile Ile Thr Ser Arg Ile Ile Leu Asn Gly
        370                 375                 380

Ile Asp Gly Ala His His Ile Ser Leu Glu Val Pro Asp Glu Asp Glu
385                 390                 395                 400

Cys Leu Glu Ile Leu Ser Cys Met Ile Gly Arg Arg Phe Asp Asp Glu
                405                 410                 415

Glu Thr Lys Asp Ala Arg Ala Leu Ile Gln Gln Cys Ala Asn Leu Pro
            420                 425                 430

Leu Ala Leu Arg Leu Ala Ala Arg Ile Ser Thr Arg Asp Phe Leu
        435                 440                 445

Asn Leu Arg Glu Leu Ser Glu Gln Leu Ser Ser Ala Ser Ile Phe
        450                 455                 460

Ser Glu Leu Glu Val Pro Gly Arg Ser Leu Val Gly Arg Leu Met Thr
465                 470                 475                 480

Ser Phe Thr Cys Leu Glu Asp Phe Asp His Asp Arg Tyr Leu Arg Leu
                485                 490                 495

Ser Leu Leu Pro Cys Pro Glu Ile Asp Glu Thr Ser Val Ala Ala Val
                500                 505                 510

Leu Gly Val Ser Thr Asp Trp Ala Arg Arg Ala Cys Arg Arg Phe Ala
        515                 520                 525

Asp Arg Ala Leu Leu Gln Arg Thr Arg Cys Gly Thr Tyr Arg Met His
        530                 535                 540

Pro Leu Leu Leu Gln Ala Ala Gln Leu Glu Ala Gln Lys Thr Ile Pro
545                 550                 555                 560

Phe Glu Glu Gln Arg Arg Leu Val Arg Ala Ala Phe Leu His Tyr Lys
                565                 570                 575

Ala Ser Asn Gly Leu Val Gly Ala Ser Arg Ile Ser Pro Ser Arg Val
            580                 585                 590

Pro Asp Gly His Val Val Leu Arg Thr Leu Thr Gln Ser Ala Lys Leu
        595                 600                 605

Ala Ala Arg Leu Gly Leu Gln Glu Glu Leu Ala Asp Leu Tyr Thr Ala
        610                 615                 620

Trp Lys Glu Leu Leu Pro Leu Val Leu Asp Arg Arg Gln Gln Glu Ala
625                 630                 635                 640

Val Gly Arg Arg Val Leu Ala Val Ser Gln His Leu Asp Arg Pro Ala
                645                 650                 655

Cys Glu Gly Ala Pro His Arg Arg Pro Arg Gln Ala Arg Asp Met
                660                 665                 670

Leu Pro Glu Gly Gln Arg
        675

<210> SEQ ID NO 11
<211> LENGTH: 338
<212> TYPE: PRT
<213> ORGANISM: Streptomyces griseoflavus

<400> SEQUENCE: 11

Met Asp Arg Val Leu Pro Tyr Ala Ala Gly Ser Glu Ala Leu Leu Ser
1               5                   10                  15

Ser Arg Glu His Gly Pro Thr Val Ser Glu Arg Thr Val Ser Ala Gln
            20                  25                  30

Glu Ile Val Val Gly Gly Gly Leu Leu Gly Arg His Ile Leu Gly
        35                  40                  45
```

```
Val Leu Gly Asn Arg Leu Ser Arg Arg Val Arg Ile Pro Trp Asp Asp
 50                  55                  60

His Gly Arg Ala Cys Glu Gln Leu Tyr Ala Leu Gly Arg Asp Leu Ala
 65                  70                  75                  80

Gln Gln Pro Ala Arg Trp Asn Leu Tyr Trp Cys Ala Gly Leu Ala Val
                 85                  90                  95

Phe His Thr Pro Ala Glu Gln Val Glu Arg Glu Arg Leu Gln Val Ser
                100                 105                 110

Leu Leu Leu Ala Gly Ile Asn Asp Gly Leu Glu Arg Ser Gly Gly Pro
            115                 120                 125

Thr Gly Gly Ala Leu Phe Leu Ala Ser Ala Gly Ala Phe Ala
130                 135                 140

Gly Ser Glu His Pro Pro Phe Thr Glu Phe Ser Pro Val Pro Thr
145                 150                 155                 160

Asn Pro Tyr Gly Ala Ser Lys Leu Ala Val Glu Glu Ala Glu Val
                165                 170                 175

Leu Ala Arg Arg Trp Arg Leu Pro Thr Val Ser Gly Arg Ile Thr Asn
            180                 185                 190

Leu Tyr Gly Pro Gly Gln Asn Leu Asp Lys Asn Gln Gly Leu Val Ser
            195                 200                 205

Ala Leu Val Lys Ala Gln Leu Thr Gly Glu Pro Leu Arg Leu Arg Ala
210                 215                 220

Ala Leu Glu Thr Thr Arg Asp Tyr Ile Tyr Ala Arg Asp Cys Ala Arg
225                 230                 235                 240

Met Val Val Ser Ala Met Glu Thr Val Arg Ser Arg Thr Arg Gly Thr
                245                 250                 255

Asp Pro His Val Arg Lys Ile Phe Ser Ser Gly Arg Arg Leu Arg Ile
                260                 265                 270

Asp Glu Leu Leu Arg Ile Ala Glu Arg Leu Phe Asp Arg Pro Val Pro
            275                 280                 285

Val Val His Glu Pro Val Ala Gly Gly Ala Asn Val Asn Leu Ser Val
            290                 295                 300

Glu Ser Arg Val Trp Ala Asp Leu Glu Ser Ser Pro Phe Leu Ser Ile
305                 310                 315                 320

Glu Glu Gly Met Arg Ala Val Arg Ser Asp Leu Arg Tyr Arg Leu Gly
                325                 330                 335

His Gly

<210> SEQ ID NO 12
<211> LENGTH: 33825
<212> TYPE: DNA
<213> ORGANISM: Streptomyces griseoflavus
<220> FEATURE:
<221> NAME/KEY: CDS
<222> LOCATION: (21413)..(21736)
<223> OTHER INFORMATION: ORF16 shown on this duplicate of SEQ ID NO:1
      due to sequence overlap with ORF17
<220> FEATURE:
<221> NAME/KEY: CDS
<222> LOCATION: (22992)..(24164)
<223> OTHER INFORMATION: ORF18 shown on this duplicate of SEQ ID NO:1
      due to sequence overlap with ORF17
<220> FEATURE:
<221> NAME/KEY: CDS
<222> LOCATION: (24449)..(25225)
<223> OTHER INFORMATION: ORF20 shown on this duplicate of SEQ ID NO:1
      due to sequence overlap with ORF19
```

```
<220> FEATURE:
<221> NAME/KEY: CDS
<222> LOCATION: (27552)..(28481)
<223> OTHER INFORMATION: ORF23 shown on this duplicate of SEQ ID NO:1
      due to sequence overlap with ORF22

<400> SEQUENCE: 12
ctgcagatcc caaggtcat ccgccgcgcc gccgtcgccg accccggctg gcgcctcgtc      60
gtcgccgacg ccgaccagat ggaaccgagg gtgctggcgg ccatctcccg cgaccccggc     120
ctgatggagg tggccggccg ggagggcgac ctctaccagt cggtgtccga ccgcgccttc     180
tccggcgacc gcgcccaggc caagctcgcc gtcctcggcg ccgtctacgg ccagacctcc     240
ggcgacggcc tgaagaacct cgccgcgctc aggcgccgct tccccaaggc ggtggcctac     300
gtcgacgagg ccgcccgcgc cggcgaggag gccgtctcg tacggacctg gctgggccgc      360
acctgcccgc ccgccgtccg cccgacggac gacgcggcgg aggaggccgg catcccgccc     420
gcccaggagg agccgggccc agcggcccga ccgtgggccc cggaggccga ggcccgcccg     480
tgggtcccgg gctacgcctc gaccgacgcc ccgcccgggg ccgcttcgc ccgcaacttc      540
gtggtccagg gcagcgccgc cgactgggcc ctgctgctgc tcgcggcgct gcggaggacg     600
ctgagcggca tggcggccga actggtcttc ttccagcacg acgaggtgat cgtgcactgc     660
cccgaggagg aggcggcgac ggtggcggag gcgatccggc agtccgccga cctcgccggc     720
cggctgacgt tcggaccgac ccccgtgcgc ttcccgttca cgacggcggt cgtggagtgc     780
tacgccgacg ccaagtgatc agctcgccgg ccgggcaccg gccacgagtc cgcgcaactc     840
ctccaccacg gcccgctcgt ccgtgccgtc cagcgcggcg agcgccgacc gccactgctc     900
gcgcgcctcg cccaccccgcc cccgctcgcg cagcagcaga ccgtactggt ggcgggccag     960
accaccggtg tagcggtcgg ctcgggcgtc ccgcgcggcgc agcagttcgg cgcactcggc    1020
gtcgcccgg ccggcgtgcc ccagcagccg cagggcgcgc accaggccga gccgggtctg     1080
ggactctccg tgccagtcgc cgtgcccggc gaggatgcgc aggctctcct cgaagtgcgg    1140
cagggcggcg gccggttcac ccagccggag gtgggcgtag ccgatgttgc agtgggcgga    1200
gtgccgcacg atcaccgctc cgatgcggtc cccgatcacg agcgagcgcc ggtgctggtc    1260
gatcgccgcg cgcggatcgg tgtgctcgta caggttgccg aggtggctga gggtgacggc    1320
ctcgccgtag gggtcggcca actgccgcga gtgggtgagg ctctgccgca gtgcccgctc    1380
cgactccgcg taccgccga gcccttcgag cagcagcccc cggtggttga gggcgcgccg     1440
gatccaggag acggctccga gccgccgcca gatctccagc gcgcggtcgg tgagggcgag    1500
ggcctcgccg gtgcgaccgg tcaggaagtg cagccccgcc agatcgccca gcgcgcacgc    1560
ctcggcggcc tcgtccccga gccgccgcgc caccgcagg gccgcccgcc cgagcacctc     1620
cagctcgggg accgccgc cgcgcaggag gtaggggtgg agcaggcgga ggagtacggc      1680
gatgtgggacg tcgtgacggc cccggtcacc gcccccgccg gtgccctcac cggcgtaccg    1740
cccgacgagg gtgacgatgt tctccagctc ccggtcgccc caggcgaagg ccgccccgc     1800
gtcgtcgaac gggggtacgg acgcgacgtg agcggtgtgc ccgggcggct gggacggggt    1860
cgggcggcgg cggtcgtcct ggtcggggcc gggttcgacg atcgcggtga gggcgcgttc    1920
ggcgacggcg gcgtaccagc gcagggcggt ctcggcgggg tgctcgcgcg tgccggtccg    1980
agggccggcg tcctcgcggg gtgcggcgtc ctcgcgggt gcggcatcct cgcggagtac     2040
ggcctcctcg cggggtgcgg cgccctcgcg gggtgcggcg ccctcgcgga gtacggcgcc    2100
ctcgcggagt acggcgccct cgcggagtac ggcgccctcg cggagtacgg catcctcgcg    2160
```

-continued

```
gagtacggca tcctcgcgga gtacggcgtc ctcgcggagt gcggcgtcct cgcggggcgc    2220
ggtctgcgga cccgccgccg ctcgggctcg ttcgcgggcg aagtcacgga ccaggtcgtg    2280
ggggacgtag cggccgtacg cggtctcctc cacgagggcc acgtcgacga gccggtccag    2340
cgcggcctcc gcccggcgtt cgccggtgcc ggtgagccgg gcgagcagcg gcgcgccgta    2400
ggcgggcagg tcgagcgcgc cgatgcggca cagggcgagg gcggcgtcgc ggtccgtctc    2460
acggtcggag acggtgagcg cgtcgtgcgc gacggccagc gagcggcgca cgctgaggtc    2520
gtcgtactcc aggtgcggca accggctgtc ggtggcggag agctgaccgg cgaggtcgtc    2580
gggcgtgagg gcccggcgcg cggcgagccg ggccgcgacc acccgcaggg ccagcggaag    2640
ccggccggtg agcgcgacga gcgggtgccc ggcgccgaga ccgtcccggc cggagaccgc    2700
ccgcagcagg gcggcactgt cctcgtcgga cagcgggccg agcgggacac ggacggcacc    2760
gtcgagcgtg gtgagcggcg aacggctggt gacgatcacc gcacagccgg gtccgcccgg    2820
cagcagcggc cgcaccctgc gcggcgtccgc ggcgtcgtcc agcaccagga gggtgcgggt    2880
gggcgcgagc agcgagcgca gcagggcggc ggccgcgtcc ggccgttcgg ggacggcgca    2940
gggctcggtg cccaggtcgc gcaggagagc gctgagggcc tgggcggggg tgaggggggt    3000
catgccgggg gtcgtgccgt gcaggttgac gtagagctga ccgtcgacga aacgttccgc    3060
cagtgtgtgt gcgacctgga cggcgagcgc gctcttcccc acaccagcgg taccgctgac    3120
gacgacggca gggggcccgg cggcgggccg gggggcacgg gtgagcacac ggatcagctc    3180
gtcccgcacc gcgtcccgcc cggtgaagtg agcaggcgcg ggcggcagtt gcgccggcct    3240
gggcggcaca ccgcccctc ctgcggcctc cgcgcaccga ccgtgctcct gccgctcccc    3300 ctgccccgc agcacctcca cgtgggcctc gcgcacccc ggccccggtt cgacgccgag    3360
ttcgtccgcc aggcgggccc gcagatcccg gtggaccacc agcgcctccg cctgacggcc    3420
ggtgcggtgc agcgcgagca tcagctgacg gtggtacgac tcccgcagcg gatgttcggc    3480
ggccagtgcc gccagttcgg gcacgagatc ggccaggcgc tcgccgccca gggccagttc    3540
ggcgtcgtac cgccactcca ggagcagcag ccgcgcctcg cgcagccgcc gcaccagggc    3600
gtagccgccc acttccgggg gcatcccggc cagcgggttc cccgccaca gcgcgagcgc    3660 ggcggcgcac tcgcgcgcca cccgctccca gtcccgggcg gtgtgcgcgg cgcgggcggc    3720
tgcggtgtgc gcgtcgaaga cctggacgtc cacctcgccc tctcccaccc gcagcagata    3780
tccggtgggc acggtgagca gccggcccgg gtcgtcgagc agccgccgca accgggcgac    3840
gtgattgtgc agcgagggca gcgcggagac gggcggcgca ccgccccaca gggcgtcctt    3900
cagcgcctcg acggacacga cccgcccggc gtcgagcagc aacgcgacga acagcgcacg    3960
gagtttggga cttccggtca cctggacgga cccgggggcc tcgggcccct cgccgtcgta    4020
cagcaccggt gttcccagca gtccgaaccg cagtccgcgc cgtgtcacgc cgcaccactg    4080
ccttccgggt gaccgaacgg acaaccaatg gccttatgtt agcgatccgt tggcaaagtc    4140
tgatgtgatc actacatcgg atccggcccg ggggtgcgcg cgtagaacgc gcagctcggg    4200
ggagtgtcgc cgccgcggcc cggtccgcac acgagggttc ccggtcggac agaggtgaac    4260
ggccgggccc tcgttctctt ctgccgccgc gttcgcccct cgggtcagat gacgggcggc    4320
cgtccgagcc gggtgagccg ccacaccgtc cgccagcgca tggcccgccg ctccccggcc    4380
ggctcccgca gcccctccgc gaaaccgccg aaccaggcgc gcagcccctg gaccgaccga    4440
gtccgcagca gggtgagcag gacccacacc ccgaggtgca cggggatcag cgcgagcggc    4500
agccgccgcc gggccagcca gacccggttg cgggcgttca cccggaagta gatcgcgtgc    4560
```

```
cggggccggcg aggtcttggg gtgctggagc agcaggtcgg gcgcgtagag gatgcgccac   4620
cccgcgtcgg cggcacgcca ggcgaggtcg gtctcctcgt gcgcgaagaa gaacgcgccg   4680
ggccagtcgc cgatctcgtc gagcatcgac atccgcagcg cgtgcccgcc cccgaggaac   4740
ccggtgacgt acccgcccTT catcgggtcc gcctttccga gccggggcac gtgccgctgc   4800
tgcgtctccc ccagctcgtc ggcgatccgg aagccgacga cgccgagccg gtcgtccgcc   4860
gcgtacaact cccccacccg gcgcagcaca tcggcgtcca ccagcagacc gtcgtcgtcc   4920
agttcgacga cgacgtccac gtccccgaac tcccgcagcc gctcgatccc cacgttccgc   4980
ccgcccgggc agccgaggtt ctccgccagc tcgacggtgg tgacctcacc gggcagggac   5040
agccgccggg cgaactcggg cagcggacag ccgttcccca cgatcacgat ccgcgcgggc   5100
gccacgtcct gcttcgccac ggactccagc agcgcgtcca cctcggccgg ccggttcccc   5160
atggtcacga cggcgacggc gatcctcggc gtccccatgc cctcaccccA ctccacccgg   5220
ctgctccgct gacgggcgat gctaaccgtt cacggtgagg acgcatgcat gacacccacc   5280
accgcggcgt actccgcccc cgccccacac gaacaggaca cacgtgtccc tggtgctcgc   5340
ccggggacga ccggagggc cccgtgcgg agccgcggcc ggctgccgca cggggccgg     5400
gagcggtcgc cggtcagcgg gtggtgacga aggggctctg gtgcgtgtgc ggggtggtga   5460
gttcgtcgag catggcgatc gcgaggtcgc ggcgcgtcgt ccatgcccgt ccgccgggaa   5520
ggtcggcggt gacccgcagc tcgtcgcccg ggcgtgcctc gtcgctgagc cgggcgggac   5580
gcatgaccgt ccactccagg tcgcgggctc cggtgaggat gtcctccatg cggcgcatgt   5640
ccgcgtacag ggtccgcccg gggccgttgc gcaggatgcc gtagaccggc cgctgccatc   5700
gcaccccgcc ccgggtgacc ggatgtgtca ggcggcgct cacgacgacc aggcgcctga    5760
cgtccgccgc gcgcatcccg tccacgacgg cccgggcgga cgccgagtag accgtgaccg   5820
gcctccagga gtacgcgct cccaggcagg acaggacggc gtcggcgccc ttgaacacgg    5880
acgtcatgtc cgcgacgtcc gtgacgtccg ccgtttccac ggtcagcctc tccccccggag  5940
tgaccgaacc cggacgccgg acgacggcga cgacgtcatg gccggccgca caggccaggg   6000
ccgtcacctg ccgtccggtc gggccgcttg caccgagcac tgctactttc atgccgtctc   6060
cagacgatgc gcggacgatg tacgacgca tgcggacgat gtgcgtcgtg cggtggtcga    6120
gaaggtgccc cggtcggcgc ccttcccgaa cgacgcccca tcgtaggagt cgcggcgccc   6180
ggcccccggt ccgaggccgt gggcaccgtc gagaacaggc cgcccgggcg gggccgttgc   6240
ggcggccgc acggagcggg agcgcgggcg gcacgccgcc ggctcccgcc cgcgttcccg    6300
ggcggcacgc cgccaccect caggaggagc cctgccgcgc cgtccgcgcg gacgttgcgg   6360
gggccgtcct ggccagttcg agggcgccca tcggacagga ccggatcaac cgctccacct   6420
gccggacatc gccgaacccg tcggccgccc ccgctgagac ggtgatctgc tgctcggggc   6480
tgcggaagac ggccctggac aaccctcgc actgttcgtg caactcgcac cgccggccgt    6540
cgatcctgac caccgtcacg tcctcgacgg gctcaggcag ttcgtccatg aacgtcaca    6600
tccatcctct cgatcccgcg gatggtgttg tgcagcctcc aggtcggctc ccccacctcg   6660
atcctgtcga cgtgacggac cagcgcctcc aggaggctct gcccctccag gcgggacagg   6720
gcctgaccga cgcaggcgtg gataccgtgc ccgaaccga cgtgctgggc gcgcgccctgc   6780
cgggcgacgt cgaaggactc cgggtccttc cagaaccgct cgtcacggtt ggccgaaccg    6840
aagaggagga ggacgcgcga tccgcgggggc agcgcggctc cgcccagctc cgtgtcctcg   6900
gcgacgtagc gggtgaaccc gcgcagcggc gattccagcc ggatgatctc gttgaaggcc   6960
```

```
gacgagacca gggaggggtc ctcccgcaga cggcgccact ggtcctggtg cgtgccgagc    7020
agccacagca tgctggagag cgcgctgacg gacgtgtcca tggacggggc gaggaagtca    7080
ccgagcagtc cgggcagcag cttgtcctcg atcttgccct cgcgggcctc cgagacgagt    7140
tcggcacccc agctccccgg acgcagattg ccgggctgtg acatccggtg gaggaactcg    7200
cccatctcgc cgagcagcgg caggccggcc cgcgtccggt cgttcagggg accgaaggcg    7260
ttgaatccgg cgctggccca ctccaggagc ctttccttcc cctcgccctc cggccatccc    7320
agcagatcgg gcaccacggc cagcgggaag gcgaccgcga agtcctggac ggcgtcgaac    7380
gacttccggg cgacgaggtc ccggacaaga cggtccgccc aggacgtgac gtacccgttg    7440
atgtcggcca tcgcgcgggg cttcaggtgg cgggccacga gccccgcac gtaggcgtgg     7500 tacggcgggt cgctggtgaa gctactgccc ttctgcgcct tgttcagggt gtcggtcaga    7560
ccgacgccct cgccggacac gaacgtgccg tggcggtgca gggccgcgta cactcgtcg     7620 tagcgggcgg cgcagtgcac ctggtgcgcc gtcaggtaca ccaccggtgc cgcgtcgcgc    7680
agcgcaccgt acaggggta cgggtcggtt atcgacgcgt ccgtgtacgg atcgagatcg     7740
aggtggggga tcgtcgatgt ggagatcacc gcttcatcct ttccgcgcga ggaggtcttc    7800
gatcagcggc accatgccca cggccgtcgg cgcggtcgcg ccctgctccg ccagtctccg    7860
ggccctggag gagtaggacg gatccccgag catctccttg accacctgcg tgatcgcctc    7920
cggggtgccc tcctcgcggt agagcgtccg cgcgcacccg tagtccgtga ggtgcttcag    7980
cctcgggacg aaggcctcga aggggttgag gatcagctgc ggagtcgccg tgttgatggc    8040
gttgatggcc gtcagtccgc ccgccggatg gatgatcacc tcacaggtcg ggaggatggc    8100
ctccagcggg atccagccgg cgcgcacccg ggggtacttc tcctgcagcc gctgcccctc    8160
cgcctcgccg atggccacga cgacctcgac ctcgagctcc agcagccctt cgacgatggc    8220
cgagatgcgc tccatcgcgc cggggaaggc gtaccggaag cttcccatcg tcaggcacac    8280
gcgcccggcg tccggagccg tcagcatcca cggctcgatc gcccgctgca tgttgtgcgg    8340
ggtccagcgc atgaaggtgc cggtcgcccc gaccaggccg ggcgggcaga tgtcgatctt    8400
cagtgagggg tcgggcagtg cgtccgagcc gatcctggcc agctcgtccg ccatctcctc    8460
gaggaggtac tcctcgtagc cgccgacgtc gaacaggtcc caggactgcc ggacgaaggg    8520
gatgccgagg aaccgggcgg cgatctcggc accgtgtccc tggctccccg cgatcaggac    8580
gtcggcgccc cacgtccggg cgacgtccac caggtcgtcg aagacgtggc ttccctgacg    8640
cccgaaccag tggcccaggt agggcatctc ctgttcgggc cggtgggggt actcgatcgc    8700
cggcttgccg ccggcggccg ccttgatgct ctcggtcgtg tgcccccggg ccaccgggag    8760
ggacggcaga ccgatgccgg tgacggcgcc ggacatctcc tcgaaggacg ccaccaggac    8820
gtcgtgcccg acaaccgga gtgccgaggc gaggggtccg atggcgaacg cgctggccgg    8880
gctcgtgccc gcgcgtaga agagggcctt cacgcggcgc cctcccgtga ccggtccctt    8940
gtcgcgttcc gcgaagtagg cctccttcag gcccacggtc tcgaagtcga tgacggcgag    9000
gcccgaggtc agcagacgac tcgaacgcag ctcccgacc aggtccaggt agttgtccat     9060
ctcgtcgaag cccaggatga agaaactctc cgcctcacgg ccgtacttga tggcgcgcac    9120
cggtgttatc tccccgcccc gcttcacgaa ggcgccgatg ctgggggaga cgtgctcgtg   9180
ttcgaccgtg atgcgctcgt cgagggacaa ctcgtaccac ggggtgaggt agttgacgac    9240
aaggacggcg gcgaacttca tgccgggctc tccgatcggg ttgcctgcgg acgcagtacg    9300
gcatgcatgt gccagatgtg ggagacgacg ttcccggctt cgtccaccat ctgggcggcg    9360
```

```
aggttgtcgg tgggggcgtt cacctcgaag gtccgcgggt cgaccatctg cgcgacggcc   9420
tccggcggca gcgagctgtg gtaccgcgtc gcctcgatca ccttgatgtc ccagtcggcg   9480
ccgaacgcct cccgcaactc cggttcggag atgcggcgcg gacccgggta gtcgggggtc   9540
agctccttcg agaaggtgaa caggtgcagc tcggccccct ccttgcacag ggtccgcagg   9600
agctccgtgt agcgcggcac ctcctcctgc ggcagcgtgt ggaagaaggc gctgtccagg   9660
acggcgtcgt accggacacc ggactccgcg aggcggaagg cgtcggtcac ctggaagtcg   9720
acgctcacgc cgtggtcccg ggccttgtcg cgcccgcact ggacggcgac ctccgagatg   9780
tcgaccgcg agaccgcag ccccgggaa gccaggtaga gcgcgttgtc tccgagcccg   9840
cagcccagat cgagcacgtg cccgcggaag ccgccgcgat cacagatcgc gcgtacggcc   9900
ggctgcgggc cgccgatgtt ccacggcatg aggggcctg acttctcccc gtcctggtag   9960
agcttctcga aggggatctt ctccgtgctg cccgttggca tcgagcgcca ctcctctcag  10020
agtcctatgg acatgctgtg atggaagtg ttcaaggggt cccacgcgcg cttcgccgac  10080
cgcagacggg cgtagttgtc cttgtagtac aggtggtgcc agggctcccc ggagcggttg  10140
cgggccgggt ccaggagatc cgcgtcgggg tagttgatgt agcagccgtc cgtgcggccg  10200
ccggtgacgg gcaccctcc cgtgccggcg aagaactcct cgtagagccc gcgcagccag  10260
ccgaggtgca gctcgtccag ctccgcgtcc tgccaggccg agaaccagga cgacttcacg  10320
acggagtccc gctggggac ggcggcgtcc gacggccccc gccggttgat ctctcccccg  10380
tagctgttga acatgacgta cgaggcctgg ccggggtggt cggcgtgcag gtgccggtgg  10440
agcaccgaga gctgctcgtc ggtgggtgcc gcgcggtggt aggcggactt ggaggcggag  10500
cgggcgccca tgacgtcacc gcagtcggcc tgactcatgt agcgggttcc ggtgagccag  10560
ctcatgacac ccctcgggg gatgcccacc acgccggtgc cctcggtcag ggacgcgacg  10620
aaccgcgcga ggatctcgcc ctcggggtcc acgtcggcgt cctgctggac catcagctgc  10680
aggacgcccg agctgacgtg gttcacgaag aaggtggcga acagcgagga ctccggcgac  10740
cccggctcgg agtggcgttc atgccactcg aagaaacgtc tcatcacagt gacgaaggac  10800
gtctcgtcga tcatggccca ggggaacacc accttctgga cgtgcagtcg gccggcggcg  10860
cggggcaggc cgacgggttc cgtggcgagg tgctccgggc tgcggaactc gtacgccgtg  10920
accacgccga agttgccgcc gccaccgccg gtgtgtgccc agaagagctc accgagatcg  10980
ccggtgtcgt cggccctcgc cgtcacgagg cgaacggtgc gggactcgtc gacgacggcg  11040
acctccaccg cgtgcaggtg gtcgaccacc agccccagct ggcgcgacag cggcccgtaa  11100
ccacctccgg cgaccaggcc gcccatgccg accgcggagc aggccccgag cggcagggcc  11160
gcgttccacc ggcggaacag ggccttctgg acctggtcga ccgtcgcacc ggaaccgacg  11220
cgcaccccgg cgccgtccgc ggccgggccg atggcatgga ggttgtgcag gtccaggacg  11280
aggtcccggc gcggcgtgcc gacgaagtcc tggccgcagt gaccgccgga ccggcaggcg  11340
accccccgcc cttccgtgac ggccttctgc agggaggcga cgacgtcgtc ggcgtggcg  11400
gggaggaaga actcctcggg ctcgacgacg aaccggtggt tgtccgagtg cgacagttcg  11460
atgtaccgcg ggtcctcgcg gcccaccgtg aacggcggta cggaagcggt cacgacgcgt  11520
accctcgac cgactgggtg aacacggtct cgtaggtgtt ggactccgc gaggtcagca  11580
gcgccttgcc gcgtgcgcgc atctcccggt cgtgcgccgg gcgttcctcc tcgggcatgg  11640
cgtggaacgc ctcgtaggag gccgcgtcgt cccactgggc gtagttgatg accatgtcgc  11700
cgtcgagcgc cctgaggatg ctgtgggacc ggtacccggg cacctgccgc atccagtcgt  11760
```

```
ccggcttctc cagcagggac acgagctcgc cctggtcctt ggggtcgcac cccatcagga    11820
cgatgacggt caggtccccc cggtccgggc cgatctccgt gcgggcggca ccgtccttcg    11880
tctggacgga caccacctcg gtcttcagca ggtgcaccga cgtggtgagt tcggtgaagt    11940
aggggaccgt gttgtgcttg aagttctccc cctcgtaccg ctccctcagg tcgttgatcg    12000
accgccactg tatgtagttg gccgcacagg gcctcgccac cccgcgtgc agggtcgacg    12060 accgccatcc cgggtagttc gcgttcgcga tgatgccgcg catggcgtcc aggagggtcg    12120
cctgcttctc cgagtcggtg gtgttgaaca ggttgaacac ggtcagggag ccgttctcgg    12180
gctcgatgat cggcatgagg ccttccatga ggtgtcggac ggccccggag ggccggctgt    12240
ggctgatggg ttctgacctc ggtgacgacg aggacgcggg cggccggctc ccgggccgc    12300 ccggaccgcc tgtcgggatg cccgccgcac acccggcccg gcggcggcg tcaccggctg    12360 cggggagagc ccggtgtacc ggtctccccc gagaccttcc ttccttcgac gacggactgg    12420
agtccggcgc ggctgacccc gaccagctcg atcccgacct cggccatcag gagccggaac    12480
tcctccacgg tgcgctgttt gccttcgcac aggaggagca tgtccatgtc catgagggag    12540
atcgccttgt ccgccgtgtc gtccaggccc gccacagcct ccacgacggc gatgtgcgcc    12600
ccctcgtgca tggcctccgc gatgttcctg aggatgagac gggaacggcc gtcgtcccag    12660
tcgtgcagca cgttggagat catgaacagg tcgctgcccg acggaacgcc gtcgaagaag    12720
gagccggact tcaccgtgac gcggtgggcc accgccgcgt ccgacagctc cggcagggac    12780
cgcgacacga cgtccggctg gtcgaagagg acgccggtca tctcggggtg cttgcggagc    12840
acggcggcca gcagcgcccc cctccccccg cccacgtcgg tgacactgct gaaccgggag    12900
aagtcgaacg cctcgatcac gggctggatg acgcgcttgg acagttcggt catggccgag    12960
ttgaagacgg ccgcggtgtc gggatccgac tccatgaact cccacacgcc cgaaccgtgc    13020
atcgcggcga agggagagcg gccggtgcgc accgcggtgg ccaggtgggc ccaggtcgcg    13080
cgttcggccg tcgaccccgt ccaccgcgcg aagttgcgca tggagccgtc gtcggaggcc    13140
agggcccggc ccagctccgt cagctccagc gtgtcgtgct cgcccctccg cagcagcccc    13200
acggaggcgc cggcgcggaa gaagcgctcc gcggtgtcgt gctccaaccc cagccggacc    13260
gccagttgtg cgggcgtcag cccgccggcg gccaggccgt cggccacgcc cagttccgcg    13320
aacgtgctga cgacaccggc gcgccagcct cccatcagga ggtcgaggat ctgcacagcg    13380
acgggtgccg acgggggcag cgatcccgat gcagtaatgg tcatgatgtc ccttcgactg    13440
gtggacatgc ggggaggtga ggcaccgctg caagggcagt tcgctctcga acacactttg    13500
ttcgtgatgc ctcaccggcg ctaggtatcc tcatgggatg gtcccgggaa gcagcgcctg    13560
aactgcgcag agtgctgccg gacgggagcg gatcgcccgc ccgcactctg cggctggtgg    13620
aacggacgac cgtgcggagc cgggccggca cggtccggtg aaagggcggc cctgcggtga    13680
tccgggcggc ccgcccccgt gctcccggcg tcccacgctc cgtaggcgcg ggacgccgga    13740
cacctcatga tcccgacgac ggccctgtgg ggtccggccg cgacggggc gctcctcgag    13800 gagcgcggtg ctacttcgcg tccacgtcgg cttcctcggc cccgcgggga gcgttctccc    13860
ctccccactg ctgggcgtcc cccttgggcc gcgggatgag gaaggtcgcc agcatcccga    13920
gcgccagcag cgcggcgcag gtgtagccgt tgatctggat cgcgtacgac atggcgtcgc    13980
gggcggcgtc ggcggcggcc gccgtgtccg ggttctcact cagtccggag atcatcgcgc    14040
cggcgctgtc ggagaccgcc gacgacagct cgttcgcctc cggcgcgggc gtcccctggt    14100
cgacgagccg gtcggacagg tcggagtcca gtgccgtgaa gaaggtcgac gtcagaatcg    14160
```

```
cgatgccgag cgcggaaccg agctggcgtg cggcgctctg gatgccggat ccctggccgg    14220
cgtgccgcgg cggcacgtcc gccaggacga cgttggtgac ctgcgccgta gcgaacccga    14280
ctcccatgcc gtacaggaag agggcgatgc cgatgaccca ccactgcgag tcgctgctgg    14340
ccagcagacc gaacatcagc agaccgacgg cctcgaggac gaggccgatg cgcaccagcc    14400
cgatggggcc gacgttctcg gccatgccga agctcgcacc gctcgcgaag aagctgccga    14460
ccgcgacgac gaagacgatc agtccggtct ggagcaccga gtaccccagc gtgtactgga    14520
gccacagggg gagaacggcg agcatgccga actccgccag cgcgatgatc agcgtcgcga    14580
tgttgcccgt gctgaaggac ttgatgccga acagcgaggt gtccatcagc ggcgccgtgc    14640
cgtccacccg ggtgagccgg acctggcgct gcaggaacag ccccaggcac accacggaga    14700
cgaccagggc gaccgggatg accgacagct ccaccgggtc gccgaaggga ccgaagctct    14760
tgcgcgggtc ccaccagccg tagttgcggc cctcgatcag cgcgaaggcg agaagtccga    14820
ggcccagcac cgacagcacg ccgccgacgg cgtcgacctt gcccggctgc gcgggggact    14880
ggtccaggaa cttcatgacg cccgcgatga tcagcaccac gacgaagatg ttgatgccga    14940
acgcccaccg ccaggagaac tcggcgagcc agccgcccag gagcgggccg accgcggcgg    15000
ccgcaccgat cgtggacccc cagatggcga aggccttgcc ccggtcggct ccccggaagg    15060
acatgttgag cagggcgagc gaggtcggca tgatgatcgc gccgccgacg ccctgggcga    15120
accggctggc gatcaggagt tccccggagg gcgccagggc ggcggcgatg ctcgccagcc    15180
cgaacaccac ggtgccgatg aggaacagcc ggcgtgctcc caccacgtcc gacagacgcc    15240
ccatcaccag cagcagagcg gccaggatga tcgcgtagga ctcctggatc cactgggcgc    15300
cgaaggccga gatctcgagg tcgtcgatga tcggcggcat caccacgttg acgatggtga    15360
agtccacgac caccagcgac acaccgagag aaatggcgag caagcccagc cagggggtccc    15420
ggttggccgt tgaggaccga gttggattgt cagacactgc gttcatccgt cctatgtgac    15480
acacatggcc cagttgggtc gccgggggcg agacaagggg gtagggcggg ggagcctccc    15540
gcccccggcg caatggcact atgacaggag aagaggacgg attctgacct ctactgacac    15600
cgatccggag ggcaattctt gatcgccaac cgcacgttgg aactcctcag cctgttacag    15660
acccagaggg agtggaccgg tgacgggctg gccgagcggc tgggtgtgtc cccgcggacc    15720
gtccggcgcg acatcaaccg actccgcgag ctgggctacc ccgtcacggc gacgaaaggc    15780
ccctccggct cctaccggct gtcccgcgga gcgcgtcttc ctcccctgat agtcgacgac    15840
gagcaggccc tcgccatcgc cctgtccctg cagaccgcgc cggcctcggt gaccggcatg    15900
ggagacgcca ccaaacgtgc gctgaactcc atccaggaac tgttgccacc tcatctggcc    15960
caccggctcg ccaccttctc cgtcgaacag atcgagaacg cgtgggaact cgctccgccg    16020
caggtcgacc cctccctgct cgcacagctc agcagcgccg cccagcagcg tgacctcgtg    16080
aggttctcct accgctccat ccaccacgac tcgatgcagg acgggaggt cctggccgaa    16140
ccccaccggc tcgtcgtctg gtcgggacgc tggtacctgg tggcctacga ccagcagcgg    16200
agctcatggc acgcctaccg ggtcgaccgc atcaaggatc tggcgcccac cgcctggcgc    16260
ttcggcgagc gggagggtcc cgacgaggac atcacccgct tcgtacagaa ccagcccgat    16320
cgcggtgaca ccccggacac ctggccctgc tgggcaccg tcctgatgga gtgtcccgcg    16380
tcgctggtgg cgaagtgggc cccgggagtg gcgagtttcg aggcggtcga cgacagggtc    16440
acccggatcc agatgggcgc gtggtcgtgg tcggcgctca tcggcttcct gatcaccttc    16500
agttgccgct tcaccgtcga gggtccgccc gaactcgtcg ccgcgcgcg gagggtgatg    16560
```

```
ggcctcatcg acgtcgggat tccgtcgcac gaccccctcg cggagccgtc gagccgcaca   16620
cccggcccct cggccggccg gtgacgccgt ggccgcggca ccccgcacc gcggggaacc    16680
gccgggtcag cggaccgcct gtcccagctc ggcgcgctgc cgcagcggtt cccaccagtc   16740
ccggttctcc cggtaccagg agacggtctc cgcgaggccg gtggcgaaat ccttgcgggg   16800
ctcgtagccc agctccaggg tgatcttggc gcagtccacc gagtagcgcc tgtcgtgtcc   16860
cttgcggtcg gcgacgtact ccaccgactc ccagccggcc ccgcacgcct ccaggagcag   16920
tgacaccagt tccctgttgg tgagctcggt gccgccgccg atgttgtaga cctcgccggg   16980
tctgcccttc gtgcggacca gttcgatgcc ctggacgtgg tcgtcgatgt gcagccagtc   17040
gcggacgttg agcccgtccc cgtacagcgg gacggtgcgg ccctcgagga ggcgcgtgat   17100
gaacagcggg atcagcttct cggggaagtg gtgatggccg tagttgttgg agcagcgggt   17160
cacccggacg tcgaggccgt gggtgcggtg gtgggcgagg gcgacgaggt cggcggcggc   17220
cttcgaggcc gcgtagggcg aactgggtga cagcgggtgc gtctccggcc acgaaccgta   17280
ggggatcgag ccgtacacct cgtccgtgga gacctggacg aagacgccgc ggccgcgtcc   17340
gtggtggcgc agccgccgcgt cgagcaggac ctgcgttccg cccacgttcg tgcggacgaa   17400
ctcggcgccc cccaggatcg accggtccac gtgcgactcc gcggcgaagt gcacgatctg   17460
gtcgtgctcg gcgaccagcc ggtccacgac gcgggcgtcg cagacatcgc cctgacgag   17520
gcggaacccg gggtgggcac ggaccgggtc gaggttggcc gggttgccgg cataggtcag   17580
tttgtcgagc acggtgatgc ggaccccggc ggggcccgtgc gggccgagca gggtgcggac   17640
gtagtgggag ccgatgaagc cggcaccacc ggtgacgagg atcctcgtgg cggtcatgac   17700
gagatacgca cctcgctgtg gtccccgagg accagccggt gggccgccgg cacaccggcg   17760
gcggggtca cctcgacgtt ccgcccgatc agggaactct ccacgcggcg gacccctgg    17820
accgtggccc cggcgaggac gatggagaac tcgatctcgc tggactcgat ccggcagtcc   17880
gccgctatcg acgtggacgg gccgacgtag gagccggtga tccgcgtgtt ggcgccgatc   17940
acggccggcc ccacgatccg cgatccgcgc atctcggcgc ccgcctcgat cgtgacctgg   18000
ccgatgacct cgctgtccgc gtcgacatag ccgtcgaccc ggcccttggc gccctccagc   18060
acggcccggt tgacctccag catgtcgatg acgttcccgg tgtccttcca gtaaccggaa   18120
atggtggtgg agcggacgtc gtaccgtggg tcgatgagcc actgcagggc gtcggtgatc   18180
tccagctcgc cgcgtgcgga cggctcgatc ccccggacgg cctcgtgcac cacgagtg    18240
aacaggaaga cgccgaccag ggccaggtcg ctgcgcggag cggccggctt ctcctccagc   18300
gccaccgcct tcccgtcgtc gtcgagttcg acgacaccga aggcgctggg gtcggccacc   18360
ttggtcagga ggatgtgcgt gtcgggccgg ctctcgcgga accggccac gagatccgcg    18420
ataccgccca cgatgaagtt gtctccgagg tacatgacga agtcgtcgtc gccgaggaac   18480
tcccgggcga tcaggacggc atgggcgaga ccgagcggcg ccgcctgccg tatgtaggtg   18540
acgtccagac cgaaggcgga gccgtcgccg accgcctgct ggatctcggc ggccgtgtcc   18600
ccgacgacga tgccgacctc ggtgatgcct gcctccgcga tcgcctccaa cccgtagaag   18660
agcacgggct tgttggctac ggggacgagc tgcttggcgt aggaatgggt gatgggcctc   18720
aggcgggttc cggccccgcc ggacagtacg agagccttca tggcggcgca gtctaggcgg   18780
gcggggaaac atctcaatcg gcccggcagc gcacggatgt ctggaaacaa cggtcggtag   18840
aggtcaggaa ctgacctcta ccgctcataa tctggccgct cccctctccc cggagatcag   18900
cttcgagagc tcggtcccta ccgaaggagc gaaacagatg atcaggatcg ccgtcatcct   18960
```

```
cggaagcacg cgtcccggcc gccgcggggc cgtggtggcc caatgggtcg ccgaggtcgc    19020
cgcgcggcat cccgcggcgg tgatgggcga ggcggagttc gagctggtcg acctggcgga    19080
gtacggcctc ccgttgctcg acgagcccgt gccggcgatg ttcggccagt accagaagga    19140
ggagacccgg cggtgggccg ccgccatcgg ctcgttcgac ggattcgtct tcgtcacgcc    19200
ggagtacaac cactcggtgc ccgccgcgct gaagaacgcc atcgaccacc tcttcgccga    19260
gtggaccgac aaggcggccg ggttcgtcag ctacggcgtg cacggggaa cccgtgccgt     19320 cgagcacctg cggctggccc tggccgaggt gaaggtggcc ggggtgcgca gccaggtcgt    19380
cctgtcggtg ttcaacgact tcgactacac gggatgcgca atgacggacc cgacggccat    19440
gggccggttc acgccgggac cgcagcagga gcagacggtg aacacgatgc tggacgaggt    19500
cgtcgcctgg tcgacggcgc tcaagccgct gcgtactgct gcgaccgctg aggcggacgg    19560
ccgggccgtg tcggtgtgac gcaccggtcc gcccgccgga cccctggtg aacgtgctgg     19620 tcacggcccc tcgtgcgtac gctacgaggg ccgtgaccag cacgttcgcc tgtacgggcg    19680
agcgtggccg ccacgccgcg ggtgggcggc ggcagcacgc cggccggacc gatcgccgag    19740
tggcttgtta cgtgcccggg gcgacggcgc cggagggggga cgcgccgaaa aaaaccggtc    19800
agtcgagttc cccttcgata acacggatat ccccccgtcc tcacttcggg tgacctactt    19860
cggccgtgcg actccgagca tcgtgagcgg catgacgttg cacgccgcag aagccatacc    19920
gtcacacgta ccggttctcg tcgtgggagc cggcccgaca ggtctcatgc tcggcgccga    19980
gctggcgctc cacggcagcc ggccgctggt gatcgacgcg ctgccgagcc cgagcggaca    20040
gtcccgggcc ctgggcttca cggtgaggac gctggagatc ttcaagcagc gcggcatcct    20100
gggccgtttc cagggactcg ccccggtgcc cggagtccat ttcgccggcc tcagcatcaa    20160
gggcgatcac ctctccagct cgatgcgccc ggccaaccag tacccgcagt ccaagaccga    20220
acaggtcctc gccgcctggg ccgaggagct gggagtaccg gtgcggcgcc cgtggacgct    20280
gacgtccatg gagcccactg gcaccgggta ccgctgcgtg ctcagcggcc cggccgggca    20340
gcagaccgtc gacgccgact acgtggtcgg ctgcgacgga gcggggagct tcgtccgcga    20400
ggcgatcggc atgccgacca agcgcactcc cccatccgta cagatgctcc tcggtgatct    20460
gcgcggatgc ggtctgcccg acgaacccct tcggggtcaag cacgaaaagg gcatggtcat    20520
gtccgcaccg ctgggcgacg ggacggaacg cgtcatcgtc tgtgacttca cccagccgat    20580
gcggccgcag ggcactcccg tcacgcacga cgagatcaag gccgcctacg agcaggtcgt    20640
cggcagcccc ctggcggacg gcgaatgtct ctgggcgagc tcgttctcgg acgcgtcctc    20700
cctcgtggag tcctaccggt ccggtcgtgc gctgctcgtc ggcgacacgg cgcacaccca    20760
tctccccgcc ggcgggcagg gcatgaacgt ctcgatacag gacgcggtga acgtcggctg    20820
gaagctcgcg ctggtgagcc agggccgcgc gccggacacc ctgctggaca cctaccacgc    20880
cgagcggtac ccggtcggca gggaactgct gctcaacacc gccgcccagg ccaggtctt     20940 cctgcgcggc ccggaagtgg acccgctgcg cgaggtcctg cggcgactgc tgaacatccg    21000
ggaggtgtcc gtcctgctgg ccgacggagt cagcggactg gacatccgct acgacatggg    21060
cctcccggaa gcaccgccac ccacgggtga acggctgccg ccggacgtgt tccacgtcgt    21120
cgggaccggg ggcgacgccg tcgaggagtt gcggcacggc gccgctctgc tgatcgtccc    21180
gtcccccgac agcccggcgt cctcgctggt cgctccgtgg cgggaccagg tgcgcgtcgt    21240
gcacgcgcgc cccacggacc cggactgggg cggggagccg gccgcgtcgt cgcactggtt    21300
```

```
cgtacgaccg dacggacaca tcgcgtgggc gggcaccgaa ttcagcgagt tgagcgcctc    21360
actgagccgc tggctcggtc agcccgccgc gtaaccagag gaggaagaac cc ttg ttc    21418
                                                          Leu Phe
                                                            1 agc tct ctc atc gtc gcc cgg atg gac acc ggc cac gcc gaa gcg gtg     21466
Ser Ser Leu Ile Val Ala Arg Met Asp Thr Gly His Ala Glu Ala Val
        5                   10                  15 gcc gac gtc ttc gcc ggc ttc gac gcc acc gac atg ccc gcg cgg atg     21514
Ala Asp Val Phe Ala Gly Phe Asp Ala Thr Asp Met Pro Ala Arg Met
    20                  25                  30 ggc acg cgg cgc cgc gaa ctc ttc cgc tac cgc ggc ctc tac ttc cac     21562
Gly Thr Arg Arg Arg Glu Leu Phe Arg Tyr Arg Gly Leu Tyr Phe His
 35                  40                  45                  50 ctc cag gac ttc gag acc ccc gac ggg acc gaa gcg gtc gag gcg gcc     21610
Leu Gln Asp Phe Glu Thr Pro Asp Gly Thr Glu Ala Val Glu Ala Ala
                55                  60                  65 aag tcc gac ccg cgg ttc atc cgg gtg agc aac gac ctc agg ccc tac     21658
Lys Ser Asp Pro Arg Phe Ile Arg Val Ser Asn Asp Leu Arg Pro Tyr
            70                  75                  80 atc gag gcc tac gcc ccg gac tgg caa tca ccg aag gac gcc atg gca     21706
Ile Glu Ala Tyr Ala Pro Asp Trp Gln Ser Pro Lys Asp Ala Met Ala
        85                  90                  95 gag cgc ttc tat cac tgg agt tcg aaa cga tgagccgcag ggtcttcatc       21756
Glu Arg Phe Tyr His Trp Ser Ser Lys Arg
    100                 105 accggggtcg gtgtcgtcgc gccgggagcc gtcggacgtg accccttctg ggagctgctg    21816
acccaagggc gcacggccac ccgccggctc agcctctgcg acccggagcc cttccggtcc    21876
caggtggccg cggaggccga cttcgacgcc gaggcggcgg ggctgtcgga gcggcagtcc    21936
gcggaactgg accgggcggc gcagttcgcc ctggtcgccg cccgtgaagc ggtcgaggac    21996
gcggcatggt ccgagacatg tcctcccgaa cgcgccggag tgatcgtggg ttcggccgtc    22056
ggagccacga ccaagctcga ggaggtctac cggcagctca gccgtgacgg ctccctctgg    22116
gacgtggccc ccgactcccc cgccgagctg tactcgtact cgtgcccag ctcgttcgcc     22176 tccggcatcg cacacgacct cggcgtcacg gggcagagcg cgtcgtgtc gacgggtgc      22236 acctccggga tcgactccgt cggcaacgcc tgggaactga tccagagcgg catcctggac    22296
tccgccgtct gcggtgccac cgacgccccc atctcgccca tcaccgtcgc ctgcttcgac    22356
acgatcaagg cgacatcgac gtacaacgac accccggaga gcgcctcacg gccgttcgac    22416
gccacacggg gcggcttcgt cctcggcgag ggcagcgcga tgttcgtcct cgaatcggag    22476
gaatccgtcc accgtcgcgg cgcacgcgtc tacggcgaga tccgcggcta cgcgagccgc    22536
tgcaacgcct accacatgac cggtctcaag gccgacggac gcgagctggc ggaggccgtc    22596
gtctccgctc tcggccaggc aggcgtggac ccgggccggc tcgactacgt caacgcccac    22656
ggcagcggca cgaagcagaa cgaccgccac gagaccgccg cgctgaagtc gtccctcgga    22716
cccgccgccc acgacgtgcc gatcagttcg atcaagtcga tgatcggcca ttcgctgggc    22776
gccatcgggt cgttggagat cgccgcctgc gccctggcgc tgcgggacga cgtgatcccg    22836
ccgacggcca atctcacccg gccggatccg gaactcgatc tggactacgt gccggtccac    22896
gcgcgcaagc agccgaccaa cagcgtgctc acgaccggaa gcggcttcgg tgggtttcag    22956
agcgccatgt tctcacggga cccggagcat cactc atg acc gca cac atc acc      23009
                                      Met Thr Ala His Ile Thr
                                       110
```

```
ggc atc gac atc gtc tcc ccg ctg ggc ctg tcc cgc gag gaa cac tgg      23057
Gly Ile Asp Ile Val Ser Pro Leu Gly Leu Ser Arg Glu Glu His Trp
115                 120                 125                 130 aag gcc ctc ctc gac gga tgc agc ggt ctg agg gcg acg cag tcg ttc      23105
Lys Ala Leu Leu Asp Gly Cys Ser Gly Leu Arg Ala Thr Gln Ser Phe
                135                 140                 145 gac tcc agc agg tac gac aac ccc atc agc ggg gag gtg ccc cac ttc      23153
Asp Ser Ser Arg Tyr Asp Asn Pro Ile Ser Gly Glu Val Pro His Phe
            150                 155                 160 gcc ccg gag ggc ctg ccc aag cgg ctg ctg ccg gcc acc gac cgg atg      23201
Ala Pro Glu Gly Leu Pro Lys Arg Leu Leu Pro Ala Thr Asp Arg Met
        165                 170                 175 acc cag atg tcg ctg gtc gcc gcg gcg ggg gcg ttc gac gac agc ggt      23249
Thr Gln Met Ser Leu Val Ala Ala Ala Gly Ala Phe Asp Asp Ser Gly
    180                 185                 190 gtc gac acg agc cgg gtc gac ccc ctc gga gtc ggt gtc atg acg gcg      23297
Val Asp Thr Ser Arg Val Asp Pro Leu Gly Val Gly Val Met Thr Ala
195                 200                 205                 210 tcc acc gcg ggg ggt tac gcg ttc ggg cag aag gag ctg cag aac ctg      23345
Ser Thr Ala Gly Gly Tyr Ala Phe Gly Gln Lys Glu Leu Gln Asn Leu
                215                 220                 225 tgg tcc aag ggg ccc agg tac gtc agc acc cat cag tcc tac gcc tgg      23393
Trp Ser Lys Gly Pro Arg Tyr Val Ser Thr His Gln Ser Tyr Ala Trp
            230                 235                 240 ttc tac gcg gtc aac acc ggt cag atc tcc atc cgg cac ggc tgc cag      23441
Phe Tyr Ala Val Asn Thr Gly Gln Ile Ser Ile Arg His Gly Cys Gln
        245                 250                 255 ggc cac agc gga gtg atc gtc gcg gac gac gcc ggc ggg ctc gac gcg      23489
Gly His Ser Gly Val Ile Val Ala Asp Asp Ala Gly Gly Leu Asp Ala
    260                 265                 270 atc tcc ttc gcc gcc cgc cgt ctg gcg cgc ggc aac cgc gtc atg ctc      23537
Ile Ser Phe Ala Ala Arg Arg Leu Ala Arg Gly Asn Arg Val Met Leu
275                 280                 285                 290 acc ggg tcg gtg gac agc acg atg tgt ccc tgg ggg cgg gtc gcg cac      23585
Thr Gly Ser Val Asp Ser Thr Met Cys Pro Trp Gly Arg Val Ala His
                295                 300                 305 acc tcg acc ggc atg ctc tcg gca tcc acc gac gcg cgg gcc gcg tac      23633
Thr Ser Thr Gly Met Leu Ser Ala Ser Thr Asp Ala Arg Ala Ala Tyr
            310                 315                 320 ctt ccg ttc gac gca cga gcc aac ggg tgg gtc aac ggc gaa ggc ggc      23681
Leu Pro Phe Asp Ala Arg Ala Asn Gly Trp Val Asn Gly Glu Gly Gly
        325                 330                 335 gcg cac ctc gtg ctg cag acc cac agt gac ggc cgc tac gcg gcg gtg      23729
Ala His Leu Val Leu Gln Thr His Ser Asp Gly Arg Tyr Ala Ala Val
    340                 345                 350 ctc ggt cac ggt gcg acc atg gac gat ccc cgc gcc gcc ccg ggc acg      23777
Leu Gly His Gly Ala Thr Met Asp Asp Pro Arg Ala Ala Pro Gly Thr
355                 360                 365                 370 ggc ctc gtc cgg gcg atc cac ctc gcg ctc ggc gcg gcg cgg ctg cgc      23825
Gly Leu Val Arg Ala Ile His Leu Ala Leu Gly Ala Ala Arg Leu Arg
                375                 380                 385 ccc ggc gac atc agt gtg gtg ttc gcc gac gcg gcc ggc acc cgg gag      23873
Pro Gly Asp Ile Ser Val Val Phe Ala Asp Ala Ala Gly Thr Arg Glu
            390                 395                 400 gcg gac acc gcc gag gcc gcc gcc ctc gcc gag gtc ttc ggg ccg gat      23921
Ala Asp Thr Ala Glu Ala Ala Ala Leu Ala Glu Val Phe Gly Pro Asp
        405                 410                 415 tcc gtc ccc gtc acc gcg ccc aag gcg gcg acc ggc cgg atg ggc tgc      23969
Ser Val Pro Val Thr Ala Pro Lys Ala Ala Thr Gly Arg Met Gly Cys
    420                 425                 430
```

| | |
|---|---|
| ggg acg gcc gca ctc gac gtc gcg acg gcg gtg ctc gcc ctc cgc gac<br>Gly Thr Ala Ala Leu Asp Val Ala Thr Ala Val Leu Ala Leu Arg Asp<br>435                     440                     445                   450 | 24017 |
| cag acg att ccc ccc acc gtc aac gtc cag gcc gac gcg tcc ctg ggg<br>Gln Thr Ile Pro Pro Thr Val Asn Val Gln Ala Asp Ala Ser Leu Gly<br>                         455                     460                   465 | 24065 |
| gtc aac ctg tgc agc gtc gcc aca cac cac ccc ctc acc aac gtc ctg<br>Val Asn Leu Cys Ser Val Ala Thr His His Pro Leu Thr Asn Val Leu<br>        470                     475                     480 | 24113 |
| gtc ctg gcc cgg ggc gtc ggt ggg ttc aac tcg gcc ctg atc gtc ggg<br>Val Leu Ala Arg Gly Val Gly Gly Phe Asn Ser Ala Leu Ile Val Gly<br>        485                     490                     495 | 24161 |
| aaa tgagagaagg agcaaggaat gtccgcacgc gtcaccatgg acgatctcag<br>Lys | 24214 |
| gcgagccctc gaggagggct ccggtgtcga cgagggcgtc gatcttgaca ccgacctcga | 24274 |
| aaccatggcg ttctccgagc tggggtacga ctccctggcg gtgctggaga ccggcctgcg | 24334 |
| cctcggccgc gagaacgaca tcgagctcga cgactcggtg ttcgccgacc tcgacacgcc | 24394 |
| tcagcagatg ctggacgcgg tcaacgatgc cctcgcgcgt caggcggcgg catc gtg<br>                                                                                Val<br>                                                                                500 | 24451 |
| acc tct ccc cgt cat gcc ctg gtc acc ggc ggt tcc agc ggc ata gga<br>Thr Ser Pro Arg His Ala Leu Val Thr Gly Gly Ser Ser Gly Ile Gly<br>                       505                     510                     515 | 24499 |
| aag tcc gtc gca cgg cgc ctg gcc tcg gcc ggc cac acc gtc acg atc<br>Lys Ser Val Ala Arg Arg Leu Ala Ser Ala Gly His Thr Val Thr Ile<br>                520                     525                     530 | 24547 |
| tgc ggt cgt gac tcc gaa agg ctc cag cag gcc gcc aag gaa ctg tcg<br>Cys Gly Arg Asp Ser Glu Arg Leu Gln Gln Ala Ala Lys Glu Leu Ser<br>        535                     540                     545 | 24595 |
| gag cag ggt gca ccc gtc acc tcg ctg atc gcc gac gtc agc aag ccc<br>Glu Gln Gly Ala Pro Val Thr Ser Leu Ile Ala Asp Val Ser Lys Pro<br>550                     555                     560 | 24643 |
| cgc cag gtg ggc gat ctg gtc cgc gag gcc gtg gag acg aac ggt ccc<br>Arg Gln Val Gly Asp Leu Val Arg Glu Ala Val Glu Thr Asn Gly Pro<br>565                     570                     575                   580 | 24691 |
| ctc ggg atc ctc gtc aac aac gcg ggc agg aac gga ggc ggc cgg acc<br>Leu Gly Ile Leu Val Asn Asn Ala Gly Arg Asn Gly Gly Gly Arg Thr<br>                       585                     590                     595 | 24739 |
| gcg gag ctg agc gac gag ctg tgg cgg gag gta ctg agc acc aac ctc<br>Ala Glu Leu Ser Asp Glu Leu Trp Arg Glu Val Leu Ser Thr Asn Leu<br>                600                     605                     610 | 24787 |
| gac agc gtt ttc tac gtc acg cgg gag gtg ctg gcc cgt ggc ggc atc<br>Asp Ser Val Phe Tyr Val Thr Arg Glu Val Leu Ala Arg Gly Gly Ile<br>                615                     620                     625 | 24835 |
| ggc gag gtg gac cac gcc cgg atc atc aac atc gcc tcc acc gcg ggg<br>Gly Glu Val Asp His Ala Arg Ile Ile Asn Ile Ala Ser Thr Ala Gly<br>630                     635                     640 | 24883 |
| aag cag gga gtt ctg ctg gcc gcc ccg tac tcc gcc tcc aag cac ggt<br>Lys Gln Gly Val Leu Leu Ala Ala Pro Tyr Ser Ala Ser Lys His Gly<br>645                     650                     655                     660 | 24931 |
| gtc gtc ggc ttc acc aag gcg gtg ggc aag gag ctg gcc cct cag ggg<br>Val Val Gly Phe Thr Lys Ala Val Gly Lys Glu Leu Ala Pro Gln Gly<br>                       665                     670                     675 | 24979 |
| atc acc gtg aac gcc gtc tgc ccg ggc tac gtg gag acc ccg atg gcc<br>Ile Thr Val Asn Ala Val Cys Pro Gly Tyr Val Glu Thr Pro Met Ala<br>        680                     685                     690 | 25027 |

| | | |
|---|---|---|
| tca cgg gtc cgg cag gcc tac gca gac gcc tgg gag acc acg gag gcc<br>Ser Arg Val Arg Gln Ala Tyr Ala Asp Ala Trp Glu Thr Thr Glu Ala<br>                     695                    700                  705 | 25075 |
| gag gtg ctg tcc gcc ttc gag gcg aag atc ccg ctc ggc cgg tac agc<br>Glu Val Leu Ser Ala Phe Glu Ala Lys Ile Pro Leu Gly Arg Tyr Ser<br>710                   715                    720 | 25123 |
| acg ccc gac gag gtc gcc tcg ctg gtc gag tac ctc acg acc gaa gga<br>Thr Pro Asp Glu Val Ala Ser Leu Val Glu Tyr Leu Thr Thr Glu Gly<br>725                 730                  735                  740 | 25171 |
| gcc gcc tcg atc acg gct cag gcg ttc aac gtg tgc ggc ggc ctc ggc<br>Ala Ala Ser Ile Thr Ala Gln Ala Phe Asn Val Cys Gly Gly Leu Gly<br>                     745                    750                  755 | 25219 |
| aac ttc taggagatga ttcacatggc cgatccggct cgcacagacc tgcactccgc<br>Asn Phe | 25275 |
| cacgatcacc ggcagcgccg acgcggtgta ccgccgtctg gaggacgtcg ggcagtggtc | 25335 |
| ccagatgttc gaaccgacca tccacggcgc ggaactggcc cgggacggga acaggcagac | 25395 |
| gatccagctg tgggccaccg ccaacggaga acccaaggcc tgggtctccg agcgtgagct | 25455 |
| cgaccccgtc gcgcgcacca tccgcttcgc gcagaccgtc acctcctcgc cgtcgccga | 25515 |
| gatgtccggc gcgtggcagg tgctgcccct gtccgaggac acctgccggg tcgaactcac | 25575 |
| gcacacctac cgtgcggaga acgactcggg ggagtcgctc acatggatcg cccgagccgt | 25635 |
| ggagaccaac agcacgaagg agctctcggc gctcaagttc gcctgcgaac gggacgccga | 25695 |
| cagcgaggcc agtcccttca ccttcaccga tgcggtggac accacggtcg accccgtcct | 25755 |
| gctgttctcg ttcctggacc gcggtgagct gtgggcggga cgcctggagc acgtcgccga | 25815 |
| ggccgagatg agggagttct ccgacggcct gcagttcctc cggatgcgga cgcgcacccc | 25875 |
| ggacggtgac acgcacgtca ccgagtccta ccgggtgtcg cagagcccgg cccggctgct | 25935 |
| gtacaagcag gtgacgctgc ccgcgctgct gtcgctgcac accggcgagt ggaccatcac | 25995 |
| cccggccggg gagagctggc gggtcacgtc gaagcacacc gtggcgatcg atcccgacgc | 26055 |
| ggtgcacaag gtcctcggtg ccgacgcgac ggtctcggac gccaagcggc tcgcccggcg | 26115 |
| caacctggga aacaacagcc tgcggaccct cgaagcagcg gtccggtggg ccggcaccgc | 26175 |
| cgtgtcgcag aggtgagtgg ggacatgacg gagcccgaga cctcggacgt tctcgtcgtc | 26235 |
| ggcgccgggc ccagcggact gctcctggcc gggatcctcg ccggggcggg tgcgcgggtc | 26295 |
| acggtgctgg aggcgcggga cgcgcccagc ccgcagaccc gcgcctccac cttgcacgcc | 26355 |
| cgtgccaggg agatcctcga ccaccacgga gtggagttct ccccggagct gccctggagt | 26415 |
| gcccacggac actacggcgg cctgcgcgtg acctctcccc gggtcgactc cgggcgggcc | 26475 |
| ggtgtctgga agtgccccca gccggaactg gtacggacgc tgaccggctg ggcccgcggg | 26535 |
| cacggcgcgc ggctgctcca cggggagcac gtggagtccg tccgcgagca gggcgggcgc | 26595 |
| tgtctggtgc gtacccgggc cggcaccacg ttcagcggga ccctgctggt cgcggcggac | 26655 |
| ggccggcgga gcacggtgcg gtcgctgctg ggcatcgggt gcggggtgc gccggccacg | 26715 |
| cgcgtactgg tgcaggccga tgtccacggc gacgggctgg cggggcggcg cttcgagcga | 26775 |
| cacgggcggt acaccgtgac cgccgcaccg atcagccccg ggatcacccg ggtgatgctg | 26835 |
| cacgatccgc gctggcccgc gggcgaggaa cgcacgctgg aggacctccg tagagcctgg | 26895 |
| aaggagtcca ccgccgagac cctgccggcc gagccgtcgt ggtcacggac cttcagcgac | 26955 |
| gacacgacag tggcacaccc gctggtcaag ggccgtgtcg tgctgtgcgg cgacgccgcc | 27015 |
| cacccctcg tccccatcgg cggccaggcg ctgaacacgt cgttgatgga cgccgaggcg | 27075 |

-continued

```
ctgggctggc gggtcctggg gtatctggac gacggggacc ggcaaggcct cctcgactac    27135
caggacgagc ggttctcgtg gctgaccgtt ctcgcgggga gactgcgcgc ccaggcacgt    27195
ctgctgttcg acaccgacgc ggcggccacg gaacgcaagg cgctggtcgc cgcgagactg    27255
gccggggacg cggactaccg gcgcaggatc gccgacgccc tggccggtgt cgacgtgtgc    27315
tacctgacgc ccggcggcgc ggtccgccgg cgtctgtccc cggccccggct ccgggagacc    27375 ggagtgaacc ccggcgcccg ccgcgtgcag cgggcgctcg tccccgacga cggaacgcgc    27435
acggacgcct ggatccgtcc cgatcaccac tggtacccgg tggcccgcga cggggcccgg    27495
caggactggg acgacgcggt gcgcctccac gacgacttgg aacccgaggt gacgcg gtg    27554
                                                                Val
```

```
aga gcg ttc ctg ttc ccc ggt cag ggg acc cag aag atc ggc atg ggc    27602
Arg Ala Phe Leu Phe Pro Gly Gln Gly Thr Gln Lys Ile Gly Met Gly
760             765                 770                 775 acc tac ctg cga gaa cgg tac ccc cac ctg atc gcg ccg ttg tgg cgg    27650
Thr Tyr Leu Arg Glu Arg Tyr Pro His Leu Ile Ala Pro Leu Trp Arg
                780                 785                 790 gag gcg gac gac gtc ctg ggt ttc ccc ctc acc cgc ctc tgc gag gaa    27698
Glu Ala Asp Asp Val Leu Gly Phe Pro Leu Thr Arg Leu Cys Glu Glu
            795                 800                 805 ggc ccc ggc gag aag ctc cgc cac atg ccg gtc acc cag ccc gcc gtc    27746
Gly Pro Gly Glu Lys Leu Arg His Met Pro Val Thr Gln Pro Ala Val
810                 815                 820 ttc ctg tgc agt tac gcc gcg ctc gtc gcc gcg cag gcg aac ggc gcg    27794
Phe Leu Cys Ser Tyr Ala Ala Leu Val Ala Ala Gln Ala Asn Gly Ala
825                 830                 835 gag ccg gac gtc atc gcg ggc cac agt ctg ggc gag tac tcg gcg ctg    27842
Glu Pro Asp Val Ile Ala Gly His Ser Leu Gly Glu Tyr Ser Ala Leu
840                 845                 850                 855 gcg gcg gcc ggc gtc ctc acc tgg cag gag gtc ctt cag ctc gtc cac    27890
Ala Ala Ala Gly Val Leu Thr Trp Gln Glu Val Leu Gln Leu Val His
                860                 865                 870 cgc cgc ggt cag ctc atg gcg gag gtg cag cac aag gtg gac ggg aag    27938
Arg Arg Gly Gln Leu Met Ala Glu Val Gln His Lys Val Asp Gly Lys
            875                 880                 885 atg gcg gcc gtc atc ggt ctc gcc atc ggg cag gtc gag gag atc tgc    27986
Met Ala Ala Val Ile Gly Leu Ala Ile Gly Gln Val Glu Glu Ile Cys
890                 895                 900 gag cag gtg cgg tcc gag acc ggt gag gtg gtc gag gtg gcc aac cac    28034
Glu Gln Val Arg Ser Glu Thr Gly Glu Val Val Glu Val Ala Asn His
905                 910                 915 aac gag ccc ctc cag gtc gtc gtc tcc ggc cag tgc gct gcc ata gac    28082
Asn Glu Pro Leu Gln Val Val Val Ser Gly Gln Cys Ala Ala Ile Asp
920                 925                 930                 935 ctc ctg gtc cag cgc gtc gcg acg gcg acc gac gtc cgc acg tcc gtc    28130
Leu Leu Val Gln Arg Val Ala Thr Ala Thr Asp Val Arg Thr Ser Val
                940                 945                 950 ctg agg atc ggt ggc ccg gcc cac tcc agt ctc atg ggc agc gtc gcg    28178
Leu Arg Ile Gly Gly Pro Ala His Ser Ser Leu Met Gly Ser Val Ala
            955                 960                 965 ggg gac ttc gtg gag tac ctc cgg cgc ttc gac ttc tgc acg ccc aag    28226
Gly Asp Phe Val Glu Tyr Leu Arg Arg Phe Asp Phe Cys Thr Pro Lys
970                 975                 980 acg atg ctg atc tcc ggg tcg acc gcc gag ccc tac gcg agt gcg gag    28274
Thr Met Leu Ile Ser Gly Ser Thr Ala Glu Pro Tyr Ala Ser Ala Glu
985                 990                 995
```

-continued

| | | |
|---|---|---|
| gag atc agg cac cag ctc ggc agg cag ctg gtg cac cgg gtg cgg<br>Glu Ile Arg His Gln Leu Gly Arg Gln Leu Val His Arg Val Arg<br>1000                                     1005                           1010 | | 28319 |
| tgg gtg gac gtg atg gcg cag ctc gag agg ctg ggg gtc gca cag<br>Trp Val Asp Val Met Ala Gln Leu Glu Arg Leu Gly Val Ala Gln<br>1015                                     1020                           1025 | | 28364 |
| acc tgg gag ctg ggg ccg ggc aag gtc ctc tcg gga ttc gta cag<br>Thr Trp Glu Leu Gly Pro Gly Lys Val Leu Ser Gly Phe Val Gln<br>1030                                     1035                           1040 | | 28409 |
| cgg tcg ctg cct cag gtg cgg acg tac cgc gcg aat gat ctg ccg<br>Arg Ser Leu Pro Gln Val Arg Thr Tyr Arg Ala Asn Asp Leu Pro<br>1045                                   1050                           1055 | | 28454 |
| tcc ttc ctg gcc ggc gtg acg ggc tgg tgagccggtg aagcacgcag<br>Ser Phe Leu Ala Gly Val Thr Gly Trp<br>1060                                   1065 | | 28501 |

```
tgccgcatca ggcaaccggc gccgctcccg acggaggggg gtccgcgccc cggtccctcg    28561
tgctgatgct ccccggccag gggtcgcagt tcgctgccat gggagtcccg ctctacgagt    28621
ccgacgcccg gttcaggaag gcgctcgacg acttcttcga cgcgttcggc accggtgccg    28681
agcggctccg gcgcgagtgg ctgcacggtt cggcccaggg catcgaacgt gggtccttcg    28741
cgcagccgat gctgttcggc ctcgactacg cggcgggcgc ggtgtggctg aggagctca    28801
agggtgtcga cgtgacgctg gtcggtcaca cgtgggcga ctggcggcg ccaccctcg    28861
cggggccctt cgacctcgag ctggcggggg cactcctggc cgagcgggcc cggctcctcg    28921
acgccgcccc ccggggaggg atgatcgcgt gccgcgcgac ggaggagtcg ctgcgggagc    28981
atctcgacgc cctgggcgga cgcgccgtca tcgcggcgga gaacgcggac aaccagtgcg    29041
tcgtgagctg tgccgaggaa gacctcccgg acacgatgcg gtacctcggc tcgcacggtg    29101
tgacgtgcct gcgcgtcgcc tcgaccgaac cgttccactc cccctcctc gccccgccg    29161
ccgcccggtt cgaggagttc ctggcccggc gcggtcatcg tctgtccacg acggaactgc    29221
ccatggtctc ggcctactcg gcgcggagga tcagcggccg ggagatcatg cccgcctcgt    29281
tctggacgcg tcagatggct gagaaggtgc gtttctggga ggcgctccgc acaacttcg    29341
actccggtcc ccgcacgttc gtggaaatcg gcccaggac cgtcctctcc ctggccgcac    29401
gtcggctgcc gtccgtacgg gcccggcgtt ccacggtgat ctccacgatg ccgcgtcatc    29461
ggccccaccc ggagcactgg gaatcggcca tacatgaggt cgccgaggaa ttctgttgac    29521
cattgcacta cgtgcaacgc gcaaggccgc ccatgggtgt cccccgagtt cccgggaggc    29581
acccatggcc ttgtcggtga aatgttcaac caaatgaacc acctctcgag ggcgccccgg    29641
atcaaagatg ttcaccgatt tgcatagtcg aaaaaatacg gacagcaacg gaagcggagt    29701
gttatcctgc aatctgcacg caacggggga acggggggag gattccaagt gcaggacccg    29761
gtggaccgga cctcggggaa ctccagaggc gcaagcaccg tcggacccga gcagtcccgc    29821
aaagacgcgg ggcactcctg tcgccgaaga gggcccggta ccgtcacgca gcagttttcg    29881
ccgaccctcc accatttctt caccgtcacg agatctcttc gggccgacgg ggaccacacg    29941
ggcagagact gaaggaccgg cgctcgacct cgccggctcc cgcccctcca cccttcccc    30001
gcgttgcccc tgaccgcatg gcggcatct cggtgccgcg tttcttccgc gcctggcgcg    30061
agggagatc tccatcaag gggggccttt caaggccctc tcgcctcgag gcaccgcac    30121
gccgaagacc gatcacaaaa gtatccgaac ggctccgacc gaggtcatat ctgagactga    30181
tcgaatatcc aacggggaga tgtgatgggt ttcatccggt ttgacgttct gggcccgctc    30241
agggtccggt gcgacgacac cctgcttcaa ttgaccgggc gcaagtaccg caccgtggtt    30301
```

```
tcgtatctcg ctcttcaacc cgagtattcg gtggcgatag aggacctcgt ccgagccgct    30361
tggagcgaca agcgcccgtc cagcgcgcac caccaggtcc gtaagatggt ctccgcactc    30421
cggaccagcc tggaccagga ctgggacctg gtggcgacgt cccaggacgg ctacatgctg    30481
aagttgccgc ccaagcagtc cgacgtatcc gaattctgcc gcctcttcga ccaggtgatg    30541
tcgggtcccc tgacgagcga cgacgacctg tcggccgcgt attcggcgct ggcgctctgg    30601
cgcggacgcc cttgcgaagg gtccgagccc catgggcagg agcgccggat ctctcaattg    30661
gtggaacagc accgcgtcct cttgaacaag accgttcagg gattcggcga caggggcagg    30721
tccgatgaac tcgcctcgat actgcacgtc gcatcgaaga ttcacggaca gccggtcacc    30781
gctcgctccg gtgtcgccgt tcccgcgccc gctgtttcgt acgcgggcac gacacaagtc    30841
cccgaacctt cggggtcgac caccctcccc cacgccccg ctccccgt cggtccgcgc    30901 tgcctgccac gggatctgca ggacttcggc ggccgcgaac gcgaaatcaa tgagctgcag    30961
aaactgttga ccgcggaagg accccaccca cagttggtgg cgaccgttca cggaatgagc    31021
ggcgtgggta aaaccgccgt cgccgtccgc ctggcgcaca gactagccca tcactatccg    31081 gacgccagc tctttgtatc cctggacggc ttttcttcgg cctccaccgc caccgtgtcg    31141
aatgcgctgg gaatactcct cagacagaaa ggcctggcgg acgaggacat ttcaccttcg    31201
gaagacggcc gcctcgcaca atggcggacc atcaccgccg acagaagct gctcgtcgtg    31261 ctcgacgacg tgtgcgacat cgagcaagta gaaccctca tcccgccctc gagcgaaagc    31321
gcctgcatca tcacgtcgcg catcatcctc aatggcatcg acggcgctca tcacatctca    31381
ctcgaagtac cggacgagga cgaatgtctg gagatactca gttgcatgat cggcagacgc    31441
ttcgacgacg aggagacgaa ggacgcccgc gcgctgatcc agcagtgcgc caatctgccg    31501
ctggcactcc gtctcgccgc cgcccggata tcgacgcgcg acttcctgaa cctccgggaa    31561
ctcagtgagc aactgtcgtc ctcggcttcc atcttcagtg aactggaagt tcccggccgt    31621
agtctggtcg gccggctcat gacgtccttc acgtgcctgg aggacttcga tcacgaccgg    31681
tacctccgat tatcgctgct cccctgcccc gagatcgatg aaacgtcggt cgcggccgtg    31741
ctgggcgtat ccaccgactg ggcacggcgt gcctgcaggc gcttcgcaga ccgcgcgttg    31801
ctgcaacgca cacgatgcgg tacgtaccgg atgcacccgc tgctgctgca ggcggcacag    31861
ctggaagcgc agaagaccat cccgttcgag gagcaacgcc ggctcgtccg cgccgctttc    31921
ctccattaca aggcgtcgaa cggcctcgtg ggagccagcc gcatcagccc ttcccgggtt    31981
cctgacggac acgtggtact gaggaccctc acgcagtccg cgaagctggc cgcgcggctc    32041
ggcctccagg aggagttggc cgatctgtac accgcctgga aggaactgct ccccctcgtg    32101
ctggaccgcc ggcagcagga ggcggtcggg cgacgcgtac tcgccgtttc acagcacctg    32161
gaccggcccg cgtgcgaggg agcaccccac cggaggcgtc cgcggcaggc acgggacatg    32221
ctgcccgagg ggcagcggtg aacgagggcc ggccggagga aggcagtcgg acgatgacga    32281
ccgtttgtcc gtacatcggg agaccggggt gccacgtgaa acatgtgacc cggtcaccgg    32341
atgtccgatc gcagccgcac ccgggggcga actgaccatg gaccgcgttc ttccgtatgc    32401
agccggcagt gaggcactcc tgtcgtcgag agagcacggc cccacggtga gcgagagaac    32461
cgtctcggcg caggagatcg tcgtggggcg cggggtctg ctggggagac acatcctcgg    32521
cgtgctgggc aatcggctca gccggcgggt acgcatcccg tggacgacc acggccgcgc    32581 ctgtgagcag ctctacgcgc tgggcaggga cctggctcag cagccggcgc gctggaacct    32641
```

-continued

```
gtactggtgc gcgggactgg ccgtcttcca caccccgcc gagcaggtgg agcgagaacg    32701
cctccaggtc agcctcctcc tggcgggcat caacgacggg ctcgaacgct cggggggccc    32761
caccggcggc gcgttgttcc tggcctcctc agccggcggc gcgttcgcgg gctcggaaca    32821
cccgccgttc accgagttct ccccgcccgt gcccacgaac ccgtacggcg cgtccaaact    32881
cgccgtcgag gaggaggccg aggttctggc gcgccgttgg cgactgccca cggtgtcggg    32941
tcggatcacg aacctgtacg gccccggcca gaacctcgac aagaaccagg gcctggtcag    33001
tgccctcgtc aaagcgcagc tgaccggtga acccctgcgg ctgcgggccg ccctgggagac   33061 cacgcgcgac tacatctacg cacgggactg cgcccggatg gtcgtctcgg cgatggagac    33121
cgtacggtcc cgcaccccgcg gcacggaccc ccatgtccgc aagatattca gcagcggacg    33181
ccgtctgcgg atcgacgaac tgctccggat cgccgagcgc ctcttcgacc ggccggtacc    33241
cgtcgtccac gagccggtgg cgggaggggc gaacgtcaac ctctcggtcg agtcccgggt    33301
atgggcggac ctcgaatcgt ccccttcct cagcatcgag gaagggatgc gcgccgtccg     33361
ctccgacctc aggtaccgac tcgggcacgg gtgagcgaca cgaacgacaa aagacccagg    33421
ccgcacatca gcgcggcctg ggtccgatga gccgccttcg ggattcgaac ccgagaccta    33481
cgcattacga gtgcgttgct ctggccatct gagctaaggc ggcgtgctgg gtgcacccat    33541
ggtgcgatca gcgacgtcgg taagtctaca cagtttcgag gggtggttcg taccggcccc    33601
ggagcgggcc ggggctgcct ccggtgggcg gggcggctac gagcagcgtg tgccgtcggc    33661
gggcggggtg ccgtcgagga ggtaggtgtt gatggcggag tcgacgcagg cgctgccgcg    33721
gccgtacggg gtgtggccgt cgccgtcgta ggtgaggagg cgggccgtgg cgagctggcc    33781
ggccagaccc tcggcccagc ggtacggggt ggccgggtcc cggg                    33825
```

<210> SEQ ID NO 13
<211> LENGTH: 108
<212> TYPE: PRT
<213> ORGANISM: Streptomyces griseoflavus

<400> SEQUENCE: 13

```
Leu Phe Ser Ser Leu Ile Val Ala Arg Met Asp Thr Gly His Ala Glu
1               5                   10                  15

Ala Val Ala Asp Val Phe Ala Gly Phe Asp Ala Thr Asp Met Pro Ala
            20                  25                  30

Arg Met Gly Thr Arg Arg Glu Leu Phe Arg Tyr Arg Gly Leu Tyr
        35                  40                  45

Phe His Leu Gln Asp Phe Glu Thr Pro Asp Gly Thr Glu Ala Val Glu
    50                  55                  60

Ala Ala Lys Ser Asp Pro Arg Phe Ile Arg Val Ser Asn Asp Leu Arg
65                  70                  75                  80

Pro Tyr Ile Glu Ala Tyr Ala Pro Asp Trp Gln Ser Pro Lys Asp Ala
                85                  90                  95

Met Ala Glu Arg Phe Tyr His Trp Ser Ser Lys Arg
            100                 105
```

<210> SEQ ID NO 14
<211> LENGTH: 391
<212> TYPE: PRT
<213> ORGANISM: Streptomyces griseoflavus

<400> SEQUENCE: 14

```
Met Thr Ala His Ile Thr Gly Ile Asp Ile Val Ser Pro Leu Gly Leu
1               5                   10                  15
Ser Arg Glu Glu His Trp Lys Ala Leu Leu Asp Gly Cys Ser Gly Leu
            20                  25                  30
Arg Ala Thr Gln Ser Phe Asp Ser Ser Arg Tyr Asp Asn Pro Ile Ser
        35                  40                  45
Gly Glu Val Pro His Phe Ala Pro Glu Gly Leu Pro Lys Arg Leu Leu
    50                  55                  60
Pro Ala Thr Asp Arg Met Thr Gln Met Ser Leu Val Ala Ala Ala Gly
65                  70                  75                  80
Ala Phe Asp Asp Ser Gly Val Asp Thr Ser Arg Val Asp Pro Leu Gly
                85                  90                  95
Val Gly Val Met Thr Ala Ser Thr Ala Gly Tyr Ala Phe Gly Gln
            100                 105                 110
Lys Glu Leu Gln Asn Leu Trp Ser Lys Gly Pro Arg Tyr Val Ser Thr
            115                 120                 125
His Gln Ser Tyr Ala Trp Phe Tyr Ala Val Asn Thr Gly Gln Ile Ser
        130                 135                 140
Ile Arg His Gly Cys Gln Gly His Ser Gly Val Ile Val Ala Asp Asp
145                 150                 155                 160
Ala Gly Gly Leu Asp Ala Ile Ser Phe Ala Ala Arg Arg Leu Ala Arg
                165                 170                 175
Gly Asn Arg Val Met Leu Thr Gly Ser Val Asp Ser Thr Met Cys Pro
            180                 185                 190
Trp Gly Arg Val Ala His Thr Ser Thr Gly Met Leu Ser Ala Ser Thr
            195                 200                 205
Asp Ala Arg Ala Ala Tyr Leu Pro Phe Asp Ala Arg Ala Asn Gly Trp
        210                 215                 220
Val Asn Gly Glu Gly Gly Ala His Leu Val Leu Gln Thr His Ser Asp
225                 230                 235                 240
Gly Arg Tyr Ala Ala Val Leu Gly His Gly Ala Thr Met Asp Asp Pro
                245                 250                 255
Arg Ala Ala Pro Gly Thr Gly Leu Val Arg Ala Ile His Leu Ala Leu
            260                 265                 270
Gly Ala Ala Arg Leu Arg Pro Gly Asp Ile Ser Val Val Phe Ala Asp
            275                 280                 285
Ala Ala Gly Thr Arg Glu Ala Asp Thr Ala Glu Ala Ala Leu Ala
        290                 295                 300
Glu Val Phe Gly Pro Asp Ser Val Pro Val Thr Ala Pro Lys Ala Ala
305                 310                 315                 320
Thr Gly Arg Met Gly Cys Gly Thr Ala Ala Leu Asp Val Ala Thr Ala
                325                 330                 335
Val Leu Ala Leu Arg Asp Gln Thr Ile Pro Pro Thr Val Asn Val Gln
            340                 345                 350
Ala Asp Ala Ser Leu Gly Val Asn Leu Cys Ser Val Ala Thr His His
        355                 360                 365
Pro Leu Thr Asn Val Leu Val Leu Ala Arg Gly Val Gly Gly Phe Asn
    370                 375                 380
Ser Ala Leu Ile Val Gly Lys
385                 390
```

<210> SEQ ID NO 15
<211> LENGTH: 259
<212> TYPE: PRT
<213> ORGANISM: Streptomyces griseoflavus

<400> SEQUENCE: 15

Val Thr Ser Pro Arg His Ala Leu Val Thr Gly Gly Ser Ser Gly Ile
1               5                   10                  15

Gly Lys Ser Val Ala Arg Arg Leu Ala Ser Ala Gly His Thr Val Thr
            20                  25                  30

Ile Cys Gly Arg Asp Ser Glu Arg Leu Gln Gln Ala Ala Lys Glu Leu
        35                  40                  45

Ser Glu Gln Gly Ala Pro Val Thr Ser Leu Ile Ala Asp Val Ser Lys
    50                  55                  60

Pro Arg Gln Val Gly Asp Leu Val Arg Glu Ala Val Glu Thr Asn Gly
65                  70                  75                  80

Pro Leu Gly Ile Leu Val Asn Asn Ala Gly Arg Asn Gly Gly Gly Arg
                85                  90                  95

Thr Ala Glu Leu Ser Asp Glu Leu Trp Arg Glu Val Leu Ser Thr Asn
            100                 105                 110

Leu Asp Ser Val Phe Tyr Val Thr Arg Glu Val Leu Ala Arg Gly Gly
        115                 120                 125

Ile Gly Glu Val Asp His Ala Arg Ile Ile Asn Ile Ala Ser Thr Ala
    130                 135                 140

Gly Lys Gln Gly Val Leu Leu Ala Ala Pro Tyr Ser Ala Ser Lys His
145                 150                 155                 160

Gly Val Val Gly Phe Thr Lys Ala Val Gly Lys Glu Leu Ala Pro Gln
                165                 170                 175

Gly Ile Thr Val Asn Ala Val Cys Pro Gly Tyr Val Glu Thr Pro Met
            180                 185                 190

Ala Ser Arg Val Arg Gln Ala Tyr Ala Asp Ala Trp Glu Thr Thr Glu
        195                 200                 205

Ala Glu Val Leu Ser Ala Phe Glu Ala Lys Ile Pro Leu Gly Arg Tyr
    210                 215                 220

Ser Thr Pro Asp Glu Val Ala Ser Leu Val Glu Tyr Leu Thr Thr Glu
225                 230                 235                 240

Gly Ala Ala Ser Ile Thr Ala Gln Ala Phe Asn Val Cys Gly Gly Leu
                245                 250                 255

Gly Asn Phe

<210> SEQ ID NO 16
<211> LENGTH: 310
<212> TYPE: PRT
<213> ORGANISM: Streptomyces griseoflavus

<400> SEQUENCE: 16

Val Arg Ala Phe Leu Phe Pro Gly Gln Gly Thr Gln Lys Ile Gly Met
1               5                   10                  15

Gly Thr Tyr Leu Arg Glu Arg Tyr Pro His Leu Ile Ala Pro Leu Trp
            20                  25                  30

Arg Glu Ala Asp Asp Val Leu Gly Phe Pro Leu Thr Arg Leu Cys Glu
        35                  40                  45

Glu Gly Pro Gly Glu Lys Leu Arg His Met Pro Val Thr Gln Pro Ala
    50                  55                  60

Val Phe Leu Cys Ser Tyr Ala Ala Leu Val Ala Ala Gln Ala Asn Gly
65                  70                  75                  80

-continued

```
Ala Glu Pro Asp Val Ile Ala Gly His Ser Leu Gly Glu Tyr Ser Ala
            85                  90                  95

Leu Ala Ala Ala Gly Val Leu Thr Trp Gln Glu Val Leu Gln Leu Val
            100                 105                 110

His Arg Arg Gly Gln Leu Met Ala Glu Val Gln His Lys Val Asp Gly
            115                 120                 125

Lys Met Ala Ala Val Ile Gly Leu Ala Ile Gly Gln Val Glu Glu Ile
130                 135                 140

Cys Glu Gln Val Arg Ser Glu Thr Gly Glu Val Val Glu Val Ala Asn
145                 150                 155                 160

His Asn Glu Pro Leu Gln Val Val Val Ser Gly Gln Cys Ala Ala Ile
            165                 170                 175

Asp Leu Leu Val Gln Arg Val Ala Thr Ala Thr Asp Val Arg Thr Ser
            180                 185                 190

Val Leu Arg Ile Gly Gly Pro Ala His Ser Ser Leu Met Gly Ser Val
            195                 200                 205

Ala Gly Asp Phe Val Glu Tyr Leu Arg Arg Phe Asp Phe Cys Thr Pro
210                 215                 220

Lys Thr Met Leu Ile Ser Gly Ser Thr Ala Glu Pro Tyr Ala Ser Ala
225                 230                 235                 240

Glu Glu Ile Arg His Gln Leu Gly Arg Gln Leu Val His Arg Val Arg
            245                 250                 255

Trp Val Asp Val Met Ala Gln Leu Glu Arg Leu Gly Val Ala Gln Thr
            260                 265                 270

Trp Glu Leu Gly Pro Gly Lys Val Leu Ser Gly Phe Val Gln Arg Ser
        275                 280                 285

Leu Pro Gln Val Arg Thr Tyr Arg Ala Asn Asp Leu Pro Ser Phe Leu
        290                 295                 300

Ala Gly Val Thr Gly Trp
305                 310
```